United States Patent
Lal et al.

(10) Patent No.: US 8,148,067 B2
(45) Date of Patent: Apr. 3, 2012

(54) METHODS FOR DIAGNOSING AND MONITORING THE STATUS OF SYSTEMIC LUPUS ERYTHEMATOSUS

(75) Inventors: Preeti G. Lal, Santa Clara, CA (US); Gavin E. Williams, Menlo Park, CA (US); Kirk E. Fry, Palo Alto, CA (US); Jingtao Sun, Foster City, CA (US); Russell L. Dedrick, Kensington, CA (US)

(73) Assignee: Xdx, Inc., Brisbane, CA (US)

( * ) Notice: Subject to any disclaimer, the term of this patent is extended or adjusted under 35 U.S.C. 154(b) by 676 days.

(21) Appl. No.: 11/938,227

(22) Filed: Nov. 9, 2007

(65) Prior Publication Data

US 2009/0298060 A1 Dec. 3, 2009

Related U.S. Application Data

(60) Provisional application No. 60/858,147, filed on Nov. 9, 2006.

(51) Int. Cl.
C12Q 1/68 (2006.01)

(52) U.S. Cl. ........................... 435/6.1; 435/6.11

(58) Field of Classification Search .................. None
See application file for complete search history.

(56) References Cited

U.S. PATENT DOCUMENTS

| | | | |
|---|---|---|---|
| 4,190,535 A | 2/1980 | Luderer et al. | |
| 4,215,051 A | 7/1980 | Schroeder et al. | |
| 4,350,593 A | 9/1982 | Kessler | |
| 4,358,535 A | 11/1982 | Falkow et al. | |
| 4,376,110 A | 3/1983 | David | |
| 4,582,789 A | 4/1986 | Sheldon, III et al. | |
| 4,683,195 A | 7/1987 | Mullis et al. | |
| 4,683,202 A | 7/1987 | Mullis | |
| 4,751,001 A | 6/1988 | Saunders | |
| 4,762,780 A | 8/1988 | Spector et al. | |
| 4,789,630 A | 12/1988 | Bloch et al. | |
| 4,800,159 A | 1/1989 | Mullis et al. | |
| 4,818,418 A | 4/1989 | Saunders | |
| 4,843,155 A | 6/1989 | Chomczynski | |
| 4,889,818 A | 12/1989 | Gelfand et al. | |
| 4,908,318 A | 3/1990 | Lerner | |
| 4,946,778 A | 8/1990 | Ladner et al. | |
| 4,946,952 A | 8/1990 | Kiefer | |
| 4,965,188 A | 10/1990 | Mullis et al. | |
| 5,053,134 A | 10/1991 | Luderer et al. | |
| 5,063,162 A | 11/1991 | Kiefer | |
| 5,066,584 A | 11/1991 | Gyllensten et al. | |
| 5,075,216 A | 12/1991 | Innis et al. | |
| 5,079,352 A | 1/1992 | Gelfand et al. | |
| 5,091,310 A | 2/1992 | Innis | |
| 5,120,525 A | 6/1992 | Goldenberg | |
| 5,142,033 A | 8/1992 | Innis | |
| 5,143,854 A | 9/1992 | Pirrung et al. | |
| 5,210,015 A | 5/1993 | Gelfand et al. | |
| 5,212,071 A | 5/1993 | Fearon et al. | |
| 5,215,882 A | 6/1993 | Bahl et al. | |
| 5,219,727 A | 6/1993 | Wang et al. | |
| 5,264,351 A | 11/1993 | Harley | |
| 5,278,043 A | 1/1994 | Bannwarth et al. | |
| 5,310,652 A | 5/1994 | Gelfand et al. | |
| 5,314,809 A | 5/1994 | Erlich et al. | |
| 5,322,770 A | 6/1994 | Gelfand | |
| 5,340,720 A | 8/1994 | Stetler | |
| 5,346,994 A | 9/1994 | Chomczynski | |
| 5,352,600 A | 10/1994 | Gelfand et al. | |
| 5,374,553 A | 12/1994 | Gelfand et al. | |
| 5,385,824 A | 1/1995 | Hoet et al. | |
| 5,389,512 A | 2/1995 | Sninsky et al. | |
| 5,393,672 A | 2/1995 | Van Ness et al. | |
| 5,405,774 A | 4/1995 | Abramson et al. | |
| 5,407,800 A | 4/1995 | Gelfand et al. | |
| 5,411,876 A | 5/1995 | Bloch et al. | |
| 5,418,149 A | 5/1995 | Gelfand et al. | |
| 5,420,029 A | 5/1995 | Gelfand et al. | |
| 5,426,039 A | 6/1995 | Wallace et al. | |
| 5,445,940 A | 8/1995 | Brenner et al. | |
| 5,455,170 A | 10/1995 | Abramson et al. | |
| 5,459,037 A | 10/1995 | Sutcliffe et al. | |
| 5,464,937 A | 11/1995 | Sims et al. | |
| 5,466,591 A | 11/1995 | Abramson et al. | |
| 5,468,613 A | 11/1995 | Erlich et al. | |
| 5,476,774 A | 12/1995 | Wang et al. | |
| 5,487,970 A | 1/1996 | Rowley et al. | |
| 5,487,972 A | 1/1996 | Gelfand et al. | |
| 5,491,063 A | 2/1996 | Fisher et al. | |

(Continued)

FOREIGN PATENT DOCUMENTS

EP 0217992 A2 4/1987

(Continued)

OTHER PUBLICATIONS

Extended European Search Report received for European Patent Application No. 07861283.5, mailed on Dec. 27, 2010, 17 pages.
Notice of Allowance received for U.S. Appl. No. 11/893,236, mailed on Dec. 10, 2010, 18 Pages.
Non Final Office Action received for U.S. Appl. No. 12/628,168, mailed on Dec. 10, 2010, 35 Pages.
Garraway et al., "Array-based approaches to cancer genome analysis", Drug Discovery Today : Disease Mechanisms, vol. 2, No. 2, 2005, pp. 171-177.
Hayashi et al., "Effects of glucocorticoids on gene transcription", European Journal of Pharmacology, vol. 500, 2004, pp. 51-62.

(Continued)

*Primary Examiner* — James Martinell
(74) *Attorney, Agent, or Firm* — Morrison & Foerster LLP

(57) ABSTRACT

The invention presents a method of diagnosing or monitoring the status of systemic lupus erythematosus (SLE) in a subject or patient comprising detecting the expression of all genes of a diagnostic set in the subject or patient wherein the diagnostic set comprises two or more genes having expression correlated with the classification or status of SLE; and diagnosing or monitoring the status of SLE in the subject or patient by applying at least one statistical method to the expression of the genes of the diagnostic set.

16 Claims, 3 Drawing Sheets

U.S. PATENT DOCUMENTS

| | | | |
|---|---|---|---|
| 5,491,086 | A | 2/1996 | Gelfand et al. |
| 5,501,963 | A | 3/1996 | Burckhardt |
| 5,506,145 | A | 4/1996 | Bull et al. |
| 5,512,462 | A | 4/1996 | Cheng |
| 5,514,556 | A | 5/1996 | Shearer et al. |
| 5,538,848 | A | 7/1996 | Livak et al. |
| 5,561,058 | A | 10/1996 | Gelfand et al. |
| 5,565,339 | A | 10/1996 | Bloch et al. |
| 5,569,583 | A | 10/1996 | Greenberg et al. |
| 5,571,673 | A | 11/1996 | Picone |
| 5,573,906 | A | 11/1996 | Bannwarth et al. |
| 5,604,099 | A | 2/1997 | Erlich et al. |
| 5,618,703 | A | 4/1997 | Gelfand et al. |
| 5,618,711 | A | 4/1997 | Gelfand et al. |
| 5,624,833 | A | 4/1997 | Gelfand et al. |
| 5,635,365 | A | 6/1997 | Ansari et al. |
| 5,641,864 | A | 6/1997 | Gelfand |
| 5,658,744 | A | 8/1997 | Ochoa et al. |
| 5,665,551 | A | 9/1997 | Gelfand et al. |
| 5,674,738 | A | 10/1997 | Abramson et al. |
| 5,677,152 | A | 10/1997 | Birch et al. |
| 5,693,517 | A | 12/1997 | Gelfand et al. |
| 5,707,807 | A | 1/1998 | Kato |
| 5,716,787 | A | 2/1998 | Dunn et al. |
| 5,721,351 | A | 2/1998 | Levinson |
| 5,728,822 | A | 3/1998 | Macfarlane |
| 5,766,585 | A | 6/1998 | Evans et al. |
| 5,773,258 | A | 6/1998 | Birch et al. |
| 5,789,224 | A | 8/1998 | Gelfand et al. |
| 5,795,762 | A | 8/1998 | Abramson et al. |
| 5,804,375 | A | 9/1998 | Gelfand et al. |
| 5,807,522 | A | 9/1998 | Brown et al. |
| 5,811,284 | A | 9/1998 | Chang et al. |
| 5,837,832 | A | 11/1998 | Chee et al. |
| 5,939,270 | A | 8/1999 | Haunso et al. |
| 5,939,292 | A | 8/1999 | Gelfand et al. |
| 5,958,342 | A | 9/1999 | Gamble et al. |
| 5,958,688 | A | 9/1999 | Eberwine et al. |
| 5,965,366 | A | 10/1999 | Ochoa et al. |
| 5,968,799 | A | 10/1999 | Gelfand et al. |
| 5,973,137 | A | 10/1999 | Heath |
| 5,981,481 | A | 11/1999 | Fearon et al. |
| 5,994,056 | A | 11/1999 | Higuchi |
| 5,994,076 | A | 11/1999 | Chenchik et al. |
| 6,001,611 | A | 12/1999 | Will |
| 6,004,755 | A | 12/1999 | Wang |
| 6,010,853 | A | 1/2000 | Kanteti et al. |
| 6,020,186 | A | 2/2000 | Henco et al. |
| 6,033,860 | A | 3/2000 | Lockhart et al. |
| 6,040,138 | A | 3/2000 | Lockhart et al. |
| 6,040,166 | A | 3/2000 | Erlich et al. |
| 6,045,996 | A | 4/2000 | Cronin et al. |
| 6,048,695 | A | 4/2000 | Bradley et al. |
| 6,048,709 | A | 4/2000 | Falb |
| 6,060,240 | A | 5/2000 | Kamb et al. |
| 6,066,322 | A | 5/2000 | Levinson |
| 6,066,498 | A | 5/2000 | Levinson |
| 6,084,083 | A | 7/2000 | Levinson |
| 6,087,112 | A | 7/2000 | Dale |
| 6,087,477 | A | 7/2000 | Falb et al. |
| 6,090,556 | A | 7/2000 | Kato et al. |
| 6,099,823 | A | 8/2000 | Falb |
| 6,124,433 | A | 9/2000 | Falb et al. |
| 6,127,155 | A | 10/2000 | Gelfand et al. |
| 6,132,997 | A | 10/2000 | Shannon |
| 6,146,828 | A | 11/2000 | Lapidus et al. |
| 6,150,121 | A | 11/2000 | Hamawy et al. |
| 6,156,887 | A | 12/2000 | Levinson |
| 6,162,604 | A | 12/2000 | Jacob |
| 6,168,933 | B1 | 1/2001 | Kaser et al. |
| 6,171,785 | B1 | 1/2001 | Higuchi |
| 6,177,254 | B1 | 1/2001 | Rattner et al. |
| 6,187,534 | B1 | 2/2001 | Strom et al. |
| 6,190,857 | B1 | 2/2001 | Ralph et al. |
| 6,190,872 | B1 | 2/2001 | Slotman |
| 6,194,158 | B1 | 2/2001 | Kroes et al. |
| 6,197,563 | B1 | 3/2001 | Erlich et al. |
| 6,203,987 | B1 | 3/2001 | Friend et al. |
| 6,204,371 | B1 | 3/2001 | Levinson |
| 6,214,979 | B1 | 4/2001 | Gelfand et al. |
| 6,218,122 | B1 | 4/2001 | Friend et al. |
| 6,222,093 | B1 | 4/2001 | Marton et al. |
| 6,225,084 | B1 | 5/2001 | Falb et al. |
| 6,225,093 | B1 | 5/2001 | Grant et al. |
| 6,228,628 | B1 | 5/2001 | Gelfand et al. |
| 6,242,185 | B1 | 6/2001 | Kaser et al. |
| 6,245,334 | B1 | 6/2001 | Seilhammer et al. |
| 6,245,526 | B1 | 6/2001 | Yue et al. |
| 6,245,527 | B1 | 6/2001 | Busfield et al. |
| 6,248,527 | B1 | 6/2001 | Chen et al. |
| 6,248,528 | B1 | 6/2001 | Chen et al. |
| 6,251,597 | B1 | 6/2001 | Shyjan |
| 6,262,244 | B1 | 7/2001 | Houchins et al. |
| 6,274,312 | B1 | 8/2001 | Gish et al. |
| 6,280,941 | B1 | 8/2001 | Tsao et al. |
| 6,303,321 | B1 | 10/2001 | Tracey et al. |
| 6,306,602 | B1 | 10/2001 | Sillekens et al. |
| 6,365,352 | B1 | 4/2002 | Yerramilli et al. |
| 6,403,304 | B1 | 6/2002 | Stashenko et al. |
| 6,410,319 | B1 | 6/2002 | Raubitschek et al. |
| 6,797,263 | B2 | 9/2004 | Strom et al. |
| 6,811,973 | B1 | 11/2004 | Reich |
| 6,900,015 | B2 | 5/2005 | Avihingsanon et al. |
| 6,905,827 | B2 | 6/2005 | Wohlgemuth et al. |
| 6,964,850 | B2 | 11/2005 | Bevilacqua et al. |
| 7,026,121 | B1 | 4/2006 | Wohlgemuth et al. |
| 7,118,865 | B2 | 10/2006 | Behrens et al. |
| 7,235,358 | B2 | 6/2007 | Wohlgemuth et al. |
| 7,514,209 | B2 | 4/2009 | Dai et al. |
| 2001/0021700 | A1 | 9/2001 | Moore et al. |
| 2002/0042386 | A1 | 4/2002 | Rosen et al. |
| 2003/0139466 | A1 | 7/2003 | Peritt et al. |
| 2003/0224426 | A1 | 12/2003 | Li |
| 2003/0225526 | A1 | 12/2003 | Golub et al. |
| 2004/0023246 | A1 | 2/2004 | Meuer et al. |
| 2004/0072181 | A1 | 4/2004 | Whitehead et al. |
| 2004/0197786 | A1 | 10/2004 | Sugita et al. |
| 2005/0281815 | A1 | 12/2005 | Eshel et al. |
| 2006/0051803 | A1 | 3/2006 | Wohlgemuth et al. |
| 2006/0088836 | A1 | 4/2006 | Wohlgemuth et al. |
| 2006/0216707 | A1 | 9/2006 | Stuhlmuller et al. |
| 2006/0263813 | A1 | 11/2006 | Rosenberg et al. |
| 2007/0037144 | A1 | 2/2007 | Wohlgemuth et al. |
| 2007/0037166 | A1 | 2/2007 | Wohlgemuth et al. |
| 2007/0037167 | A1 | 2/2007 | Wohlgemuth et al. |
| 2007/0248978 | A1 | 10/2007 | Lal et al. |
| 2008/0038746 | A1 | 2/2008 | Rosenberg et al. |

FOREIGN PATENT DOCUMENTS

| | | |
|---|---|---|
| EP | 0217102 B1 | 1/1992 |
| EP | 1077254 A2 | 2/2001 |
| EP | 1162276 A2 | 12/2001 |
| WO | WO-91/18626 A1 | 12/1991 |
| WO | 93/06864 A1 | 4/1993 |
| WO | WO-94/23023 A1 | 10/1994 |
| WO | WO-95/17506 A1 | 6/1995 |
| WO | WO-96/39536 A1 | 12/1996 |
| WO | WO-97/16568 A1 | 5/1997 |
| WO | WO-97/30065 A1 | 8/1997 |
| WO | WO-98/24935 A1 | 6/1998 |
| WO | WO-99/04251 A1 | 1/1999 |
| WO | WO-99/10536 A1 | 3/1999 |
| WO | WO-99/11782 A1 | 3/1999 |
| WO | WO-99/11822 A1 | 3/1999 |
| WO | WO-99/15700 A1 | 4/1999 |
| WO | WO-99/52541 A2 | 10/1999 |
| WO | WO-99/57130 A1 | 11/1999 |
| WO | WO-00/04191 A1 | 1/2000 |
| WO | WO-00/12753 A1 | 3/2000 |
| WO | WO-0023573 A2 | 4/2000 |
| WO | WO-00/29574 A2 | 5/2000 |
| WO | WO-00/46372 A2 | 8/2000 |
| WO | WO-00/52209 A1 | 9/2000 |
| WO | WO-00/55375 A1 | 9/2000 |
| WO | WO-00/58473 A2 | 10/2000 |
| WO | WO-00/63372 A1 | 10/2000 |
| WO | WO-00/73498 A1 | 12/2000 |

| | | | |
|---|---|---|---|
| WO | WO-00/78808 A1 | 12/2000 | |
| WO | WO-01/14557 A1 | 3/2001 | |
| WO | WO-01/20004 A2 | 3/2001 | |
| WO | WO-01/23426 A2 | 4/2001 | |
| WO | WO-01/23564 A1 | 4/2001 | |
| WO | WO-01/25473 A1 | 4/2001 | |
| WO | WO-01/29269 A2 | 4/2001 | |
| WO | WO-01/32927 A2 | 5/2001 | |
| WO | WO-01/40302 A2 | 6/2001 | |
| WO | WO-01/47944 A2 | 7/2001 | |
| WO | WO-01/54733 A1 | 8/2001 | |
| WO | WO-01/55164 A1 | 8/2001 | |
| WO | WO-01/55201 A1 | 8/2001 | |
| WO | WO-01/55203 A1 | 8/2001 | |
| WO | WO-01/55205 A1 | 8/2001 | |
| WO | WO-01/55328 A2 | 8/2001 | |
| WO | WO-01/55368 A1 | 8/2001 | |
| WO | WO-01/57182 A2 | 8/2001 | |
| WO | WO-01/60860 A2 | 8/2001 | |
| WO | WO-01/71005 A2 | 9/2001 | |
| WO | WO-01/81916 A2 | 11/2001 | |
| WO | WO-01/86003 A2 | 11/2001 | |
| WO | WO-02/00677 A1 | 1/2002 | |
| WO | WO-02/00928 A2 | 1/2002 | |
| WO | WO-02/28999 A2 | 4/2002 | |
| WO | WO-02/057414 A2 | 7/2002 | |
| WO | 03004612 A2 | 1/2003 | |
| WO | WO-03/072035 A2 | 9/2003 | |
| WO | WO-03/090694 A2 | 11/2003 | |
| WO | WO-2004/042346 A2 | 5/2004 | |
| WO | WO-2004/074815 A | 9/2004 | |
| WO | WO-2004/108899 A2 | 12/2004 | |
| WO | 2006/122295 A2 | 11/2006 | |

OTHER PUBLICATIONS

Keshavjee et al., "100: Immunoregulatory Influences on Peripheral Blood Gene Expression in Lung Transplant Patients: The Lung Allograft Rejection Gene Expression Observational (Largo) Study", The Journal of Heart and Lung Transplantation, Feb. 2006, p. S78 (Abstract).

Mehra et al., "131: Gene Expression and Prediction of Early Cardiac Allograft Rejection: Discovery of a Gene-Based Corticosteroid Efficacy Measure", The Journal of Heart and Lung Transplantation, Feb. 2007, pp. S106-S107 (Abstract).

Mehra et al., "The Role of IL1R2 and FLT3 Gene Expression in Cardiac Allograft Rejection: A Precise Measure of Corticosteroid Effect?", Circulation, vol. 114, No. II, 2006, pp. 1-2 (Abstract).

Mehra et al., "Transcriptional Signals of T-cell and Corticosteroid-sensitive Genes Are Associated With Future Acute Cellular Rejection in Cardiac Allografts", The Journal of Heart and Lung Transplantation, vol. 26, No. 12, Dec. 2007, pp. 1255-1263.

Kronick, Mel N., "Creation of the Whole Human Genome Microarray", Expert Rev. Proteomics, vol. 1, No. 1, 2004, pp. 19-28.

Kuehn et al., "Identification of Steroid—Responsive Genes in Organ Cultured Human Eyes", Invest Ophthalmol Vis Sci 2005, 46: E-Abstract 3709, pp. 1-2.

Vermeer et al., "An in Vitro Bioassay to Determine Individual Sensitivity to Glucocorticoids : Induction of FKBP51 mRNA in Peripheral Blood Mononuclear Cells", Molecular and Cellular Endocrinology, vol. 218, 2004, pp. 49-55.

Su et al., "A Gene Atlas of the Mouse and Human Protein-Encoding Transcriptomes", Proceedings National Academy of Sciences, vol. 101, No. 16, Apr. 20, 2004, pp. 6062-6067.

Extended European Search Report received for European Patent Application No. 10157687.4, mailed on Oct. 28, 2010, 9 pages.

Carow et al., "Expression of the Hematopoietic Growth Factor Receptor FLT3 (STK-1/F1k2) in Human Leukemias", Blood, vol. 87, No. 3, 1996, pp. 1089-1096.

Zeigler et al., "Cellular and Molecular Characterization of the Role of the FLK-2/FLT-3 Receptor Tyrosine Kinase in Hematopoietic Stem Cells", Blood, vol. 84, No. 8, 1994, pp. 2422-2430.

Notice of Allowance received for U.S. Appl. No. 12/823,090, mailed on Jan. 25, 2011, 27 pages.

Affymetrix Webstie, Available at: https://www.affymetrix.com/analysis/netaffx/showresults.affx, downloaded Jan. 13, 2011.

Non Final Office Action received for U.S. Appl. No. 12/985,314, mailed on Feb. 22, 2011, 73 pages.

U.S. Office Action mailed Mar. 23, 2010 for U.S. Appl. No. 12/635,438, filed Dec. 10, 2009, 8 pages.

Extended European Search Report received for European Patent Application No. 10183179.0, mailed on Mar. 15, 2011, 10 pages.

Kimball et al., "The paradox of cytokine monitoring-predictor of immunologic activity as well as immunologic silence following cardiac transplantation", Transplantation. vol. 61, No. 6, 1996, pp. 909-915.

Lagoo et al., "Semiquantitative measurement of cytokine messenger RNA in endomyocardium and peripheral blood mononuclear cells from human heart transplant recipients", Journal of Heart and Lung Transplantation, vol. 15, No. 2, 1996, pp. 206-217.

Zhang et al., "Quantitative assessment of cell adhesion molecule gene expression in endomyocardial biopsy specimens from cardiac transplant recipients using competitive polymerase chain reaction", Transplantation, vol. 70, No. 3, 2000, pp. 505-513.

Subar et al., "Acute Leukaemia Following Renal Transplantation", Medical Oncology, vol. 13, No. 1, 1996, pp. 9-13.

Office Action received for European Patent Application No. 03799755.8, mailed on Feb. 24, 2011, 7 pages.

Office Action received for European Patent Application No. 08016970.9, mailed on Feb. 24, 2011, 7 pages.

Non-Final Office Action received for U.S. Appl. No. 11/433,191, mailed on Mar. 31, 2011, 3 pages.

Notice of Allowance receive for U.S. Appl. No. 11/893,236, mailed on Mar. 28, 2011, 11 pages.

Deng, M. C. et al. (Jan. 2006). "Noninvasive discrimination of rejection in cardiac allograft recipients using gene expression profiling," American Journal of Transplantation 6(1):150-160.

European Search Report and Written Opinion mailed Apr. 28, 2010, for EP Application No. 08016970 filed Sep. 26, 2008, 10 pages.

Morgun, A. et al. (Feb. 1, 2001). "Cytokine and TLRC7 MRNA expression during acute rejection in cardiac allograft recipients," Transplantation Proceedings, Orlando, Florida, USA 33:1610-1611.

Nishimura, H. et al. (Aug. 1999). "Development of Lupus-like autoimmune diseases by disruption of the PD-1 gene encoding an ITIM motif-carrying immunoreceptor," Immunity 11(2):141-151.

Abdallah, A. N. et al. (1997). "Evaluation of Plasma Levels of Tumor Necrosis Factor Alpha and Interleukin-6 as Rejection Markers in a Cohort of 142 Heart-Grafted Patients Followed by Endomyocardial Biopsy," European Heart Journal 18:1024-1029.

Ahern, H. (Jul. 24, 1995). "Biochemical, Reagent Kits Offer Scientists Good Return on Investment," The Scientist 9(15):20-24.

Ajjan, R. A. et al. (1996). "Intrathyroidal Cytokine Gene Expression in Hashimoto's Thyroiditis," Clinical and Experimental Immunology 105:523-528.

Akalin, E. et al. (Sep. 2001). "Gene Expression Analysis in Human Renal Allograft Biopsy Samples Using High-Density Oligoarray Technology," Transplantation 72(5):948-953.

Alizadeh, A. A. et al. (2000). "Genomic-Scale Gene Expression Profiling of Normal and Malignant Immune Cells," Current Opinion in Immunology 12:219-225.

Alizadeh, A. A. et al. (Feb. 2000). "Distinct Types of Diffuse Large B-cell Lymphoma Identified by Gene Expression Profiling," Nature 403:503-511.

Alizadeh, A. et al. (1998). "Probing Lymphocyte Biology by Genomic-Scale Gene Expression Analysis," Journal of Clinical Immunology 18(6):373-379.

Alizadeh, A. et al. (1999). "The Lymphochip: A Specialized cDNA Microarray for the Genomic-scale Analysis of Gene Expression in Normal and Malignant Lymphocytes," Cold Spring Harbor Symposia on Quantitative Biology 54:71-78.

Alpert, S. et al. (Dec. 1995). "The Relationship of Granzyme A and Perforin Expression to Cardiac Allograft Rejection and Dysfunction," Transplantation 60(12):1478-1485.

Amaro, A. et al. (1995). "Plasma Leukocyte Elastase Concentration in Angiographically Diagnosed Coronary Artery Disease," European Heart Journal 16:615-622.

Arnett, F. C. et al. (Mar. 1988). "The American Rheumatism Association 1987 Revised Criteria for the Classification of Rheumatoid Arthritis," Arthritis and Rheumatism 31(3):315-324.

Aukrust, P. et al. (1999). "Enhanced Levels of Soluble and Membrane-Bound CD40 Ligand in Patients with Unstable Angina. Possible Reflection of T Lymphocyte and Platelet involvement in the Pathogenesis of Acute Coronary Syndromes," *Circulation* 100:614-620.

Australian Written Opinion and Search Report mailed Oct. 7, 2005, for Singapore Application No. SG 200406287-3 filed Apr. 24, 2003, 12 pages.

Autieri, M. V. et al. (2002). "Allograft Inflammatory Factor-1 Expression Correlates with Cardiac Rejection and Development of Cardiac Allograft Vasculopathy," *Circulation* 106:2218-2223.

Baechler, E. C. et al. (Mar. 2003). "Interferon-Inducible Gene Expression Signature in Peripheral Blood Cells of Patients with Severe Lupus," *Proceedings of the National Academy of Sciences* 100(5):2610-2615.

Bakke, A. C. et al. (2001). "Neutrophil CD64 Expression Distinguishing Acute Inflammatory Autoimmune Disease from Systemic Infections," *Clinical and Applied Immunology Reviews* 1 :267-275.

Bass, C. A. (Oct. 1993). "Clinical Evaluation of a New Polymerase Chain Reaction Assay for Detection of Chlamydia trachomatis in Endocervical Specimens," *Journal of Clinical Microbiology* 31(10):2648-2653.

Bave, U. (2000). "The Combination of Apoptotic U937 Cells and Lupus IgG is a Potent IFN-Alpha Inducer," *The Journal of Immunology* 165:3519-3526.

Bave, U. (2001). "Activation of Natural Interferon-Alpha Producing Cells by Apoptotic U937 Cells Combined with Lupus IgG and its Regulation by Cytokines," *Journal of Autoimmunity* 17:71-80.

Belch, J. J. F. et al. (Apr. 1997). "The White Blood Cell Adhesion Molecule E-Selectin Predicts Restenosis in Patients With Intermittent Claudication Undergoing Percutaneous Transluminal Angioplasty," *Circulation* 95(8):2027-2031.

Bittner, M. et al. (Aug. 2000). "Molecular Classification of Cutaneous Malignant Melanoma By Gene Expression Profiling," *Nature* 406:536-540.

Boelaert, M. et al. (May 1999). "Latent Class Analysis Permits Unbiased Estimates of the Validity of DAT for the Diagnosis of Visceral Leishmaniasis," *Tropical Medicine & International Health* 4(5):395-401.

Bombardier, C. et al. (Jun. 1992). "Derivation of the SLEDAI—A Disease Activity Index for Lupus Patients," *Arthritis and Rheumatism* 35(6):630-640.

Bustin, S. A. (2000). "Absolute Quantification of mRNA Using Real-Time Reverse Transcription Polymerase Chain Reaction Assays," *Journal of Molecular Endocrinology* 25:169-193.

Chang, D. M. et al. (1996). "Cytokines and Cell Surface Markers in Prediction of Cardiac Allograft Rejection," *Immunological Investigations* 25(1&2):13-21.

Chebath, J. et al. (Mar. 1987). "Four Different Forms of Interferon-Induced 2', 5'-Oligo(A) Synthetase Identified by Immunoblotting in Human Cells," *The Journal of Biological Chemistry* 262(8):3852-2857.

Chen, J. et al. (Aug. 1996). "Identification of Differentially Expressed Genes in Rat Aortic Allograft Vasculopathy," *American Journal of Pathology* 149(2):597-611.

Cheung, V. et al. (Mar. 2003). "Natural Variation in Human Gene Expression Assessed in Lymphoblastoid Cells," *Nature Genetics* 33:422-425.

Creemers, P. et al. (2002). "Evaluation of Peripheral Blood CD4 and CD8 Lymphocyte Subsets, CD69 Expression and Histologic Rejection Grade as Diagnostic Markers for the Presence of Cardiac Allograft Rejection," *Transplant Immunology* 10:285-292.

Damas, J. K. et al. (2001). "Enhanced Gene Expression of Chemokines and their Corresponding Receptors in Mononuclear Blood Cells in Chronic Heart Failure—Modulatory Effect of Intravenous Immunoglobin," *Journal of the American College of Cardiology* 38(1):187-193.

Davas, E. M. et al. (1999). "Serum IL-6, TNF-alpha, p55 srTNF-alpha, p75srTNF-alpha, srIL-2-alpha Levels and Disease Activity in Systemic Lupus Erythematosus," *Clinical Rheumatology* 18:17-22.

Deng, M. C. et al. (Nov. 1995). "The Relation of Interleukin-6, Tumor Necrosis Factor-Alpha, IL-2, and IL-2 Receptor Levels to Cellular Rejection, Allograft Dysfunction, and Clinical Events Early After Cardiac Transplantation," *Transplantation* 60(10):1118-1124.

Deuel, T. F. et al. (Jul. 1981). "Platelet Factor 4 is Chemotactic for Neutrophils and Monocytes," *Proceedings of the National Academy of Sciences* 78(7):4584-4587.

Deuel, T. F. et al. (Jun. 1977). "Amino Acid Sequence of Human Platelet Factor 4," *Proceedings of the National Academy of Sciences* 74(6):2256-2258.

Dietz, A. B. et al. (2000). "Maturation of Human Monocyte-Derived Dendritic Cells Studied by Microarray Hybridization," *Biochemical and Biophysical Research Communications* 275:731-738.

Doi, S. et al. (1994). "Polymerase Chain Reaction Quantification of Cytokine Messenger RNA Expression in Peripheral Blood Monoculear Cells of Patients with Acute Exacerbations of Asthma: Effect of Glucocorticoid Therapy," *Clinical and Experimental Allergy* 24:854-867.

Dudek, A. Z. et al. (Jun. 2003). "Platelet Factor 4 Promotes Adhesion of Hematopoietic Progenitor Cells and Binds IL-8: Novel Mechanisms for Modulation of Hematopoiesis," *Blood* 101(12):4687-4694.

Dugre, F. J. (Oct. 2000). "Cytokine and Cytotoxic Molecule Gene Expression Determined in Peripheral Blood Mononuclear Cells in the Diagnosis of Acute Renal Rejection," *Transplantation* 70(7):1074-1080.

Edman, C. F. et al. (1997). "Electric Field Directed Nucleic Acid Hybridization on Microchips," *Nucleic Acids Research* 25(24):4907-4914.

Eisen, M. B. et al. (Dec. 1998). "Cluster Analysis and Display of Genome-Wide Expression Patterns," *Proceedings of the National Academy of Sciences* 95:14863-14868.

EMBL-EBI Accession No. AA053887, last updated Aug. 31, 2006, located at <http://www.ebi.ac.uk/cgi-bin/dbfetch?db=embl&id=AA053887&style=raw> visited on Oct. 31, 2007. (3 pages).

EMBL-EBI Accession No. AAC77576, located at <http://www.ebi.ac.uk/cgi-bin/dbfetch?db=emblcds&id=AAC77576&style=raw> visited on Oct. 31, 2007. (1 page).

EMBL-EBI Accession No. AAK80490, located at <http://www.ebi.ac.uk/cgi-bin/dbfetch?db=emblcds&id=AAK80490&style=raw> visited on Oct. 31, 2007. (1 page).

EMBL-EBI Accession No. AI775145, last updated Jun. 21, 2002, located at <http://www.ebi.ac.uk/cgi-bin/dbfetch?db=embl&id=AI755145&style=raw> visited on Oct. 31, 2007. (2 pages).

EMBL-EBI Accession No. AK000354, last updated Sep. 12, 2006, located at <http://www.ebi.ac.uk/cgi-bin/dbfetch?db=embl&id=AK000354&style=raw> visited on Oct. 31, 2007. (3 pages).

EMBL-EBI Accession No. AV742425, last updated Oct. 10, 2000, located at <http://www.ebi.ac.uk/cgi-bin/dbfetch?db=embl&id=AV742425&style=raw> visited on Oct. 31, 2007. (2 pages).

EMBL-EBI Accession No. AW969353, last updated Jun. 8, 2000, located at <http://www.ebi.ac.uk/cgi-bin/dbfetch?db=embl&id=AW969353&style=raw> visited on Oct. 31, 2007. (1 page).

EMBL-EBI Accession No. G06338, last updated Mar. 4, 2000, located at <http://www.ebi.ac.uk/cgi-bin/dbfetch?db=embl&id=G06338&style=raw> visited on Oct. 31, 2007. (2 pages).

EMBL-EBI Accession No. L26474, last updated Jan. 9, 2007, located at <http://www.ebi.ac.uk/cgi-bin/dbfetch?db=embl&id=L26474&style=raw> visited on Oct. 31, 2007. (6 pages).

EMBL-EBI Accession No. M23068, last updated Nov. 14, 2006, located at <http://www.ebi.ac.uk/cgi-bin/dbfetch?db=embl&id=M23068&style=raw> visited on Oct. 31, 2007. (2 pages).

Le Naour, F. et al. (May 25, 2001). "Profiling Changes in Gene Expression During Differentiation and Maturation of Monocyte-Derived Dendritic Cells Using Both Oligonucleotide Microarrays and Proteomics," *The Journal of Biological Chemistry* 276(21):17920-17931.

Lee, M.-T. et al. (Aug. 29, 2000). "Importance of Replication in Microarray Gene Expression Studies: Statistical Methods and Evidence from Repetitive cDNA Hybridizations," *Proceedings of the National Academy of Sciences* 97(18):9834-9839.

Legros-Maida, S. et al. (1994). "Granzyme B and Perforin Can Be Used as Predictive Markers of Acute Rejection in Heart Transplantation," *European Journal of Immunology* 24:229-233.

Li, B. et al. (Mar. 2001). "Noninvasive Diagnosis of Renal-Allograft Rejection by Measurement of Messenger RNA for Perforin and Granzyme B in Urine," *The New England Journal of Medicine* 344(13):947-954.

Liossis, S.-N. C. (Mar. 2001). "B-cell Kinase Lyn Deficiency in Patients with Systemic Lupus Erythematosus," *Journal of Investigative Medicine* 49(2):157-165.

Loftus, B. J. et al. (1999). "Genome Duplications and Other Features in 12 Mb of DNA sequence from Human Chromosome 16p and 16q," *Genomics* 60:295-308.

Magnusson, M. et al. (2001). "Importance of CpG Dinucleotides in Activation of Natural IFN-Alpha-Producing Cells by a Lupus-Related Oligodeoxynucleotide," *Scandinavian Journal of Immunology* 54:543-550.

Marcelin, A.-G. et al. (Nov. 2001). "Effects of Cyclosporine and Hydrocortisone on Kaposi's Sarcoma-Associated Herpesvirus Genome Replication and Cell Apoptosis Induction," *Transplantation* 72(10):1700-1703.

Marrack, P. et al. (2000). "Genomic-Scale Analysis of Gene Expression in Resting and Activated T Cells," *Current Opinion in Immunology* 12:208-209.

Metler, M. et al. (Nov. 2001). "Expression of the Chemokine Receptor CXCR3 and Its Ligand IP-10 During Human Cardiac Allograft Rejection," *Circulation* 104:2558-2564.

Mohler III, E. R. et al. (Jul. 1997). "Role of Cytokines in the Mechanism of Action of Amlodipine: The PRAISE Heart Failure Trial," *Journal of the American College of Cardiology* 30(1):35-41.

Morita, K. et al. (2001). "Early Chemokine Cascades in Murine Cardiac Grafts Regulate T Cell Recruitment and Progression of Acute Allograft Rejection," *The Journal of Immunology* 167:2979-2984.

Morris, D. L. et al. (Feb. 1997). "Immunophenotyping Analysis of Peripheral Blood, Splenic, and Thymic Lymphocytes in Male and Female Rats," *Journal of Pharmacological and Toxicological Methods* 37(1):37-46.

Neto, E. D. et al. (Mar. 2000). "Shotgun Sequencing of the Human Transcriptome with ORF Expressed Sequences Tags," *Proceedings of the National Academy of Sciences* 97(7):3491-3496.

Newton, M. A. et al. (2001). "On Differential Variability of Expression Ratios: Improving Statistical Inference about Gene Expression Changes from Microarray Data," *Journal of Computational Biology* 8(1):37-52.

Nickel, P. et al. (Sep. 2001). "Cytotoxic Effector Molecule Gene Expression in Acute Renal Allograft Rejection," *Transplantation* 72(6):1158-1161.

Oh, S.-I. et al. (Apr. 2001). "Correlation of Fas and Fas Ligand Expression with Rejection Status of Transplanted Heart in Human," *Transplantation* 71(7):906-909.

Perou, C. M. et al. (Aug. 2000). "Molecular Portraits of Human Breast Tumours," *Nature* 406:747-752.

Pickles, A. et al. (1995). "Latent-Class Analysis of Recurrence Risks for Complex Phenotypes with Selection and Measurement Error: A Twin and Family History Study of Autism," *American Journal of Human Genetics* 57:717-726.

Preble, O. T. et al. (Apr. 1982). "Systemic Lupus Erythematosus: Presence in Human Serum of an Unusual Acid-Labile Leukocyte Interferon," *Science* 216:429-431.

Pruitt, K. D. et al. (Jan. 2000). "Introducing RefSeq and LocusLink: Curated Human Genome Resources at the NCBI," *Trends in Genetics* 16(1):44-47.

Quattrone, A. et al. (1995). "Quantitation of bcl-2 Oncogene in Cultured Lymphoma/Leukemia Cell Lines and in Primary Leukemia B-Cells by a Highly Sensitive RT-PCR Method," *Haematologica* 80:495-504.

Raychaudhuri, S. et al. (May 2001). "Basic Microarray Analysis: Grouping and Feature Reduction," *Trends in Biotechnology* 19(5):189-193.

Rebouillat, D. et al. (Jan. 1999). "The 100-kDa 2',5'-Oligoadenylate Synthase Catalyzing Preferentially the Synthesis of Dimeric pppA2'p5'A Molecules Is Composed of Three Homologous Domains," *The Journal of Biological Chemistry* 274(3):1557-1565.

Ross, S. D. et al. (1999). "Reduced Neutrophil Infiltration Protects Against Lung Reperfusion Injury After Transplantation," *The Annals of Thoracic Surgery* 67:1428-1434.

Rus, V. et al. (Mar. 2002). "Expression of Cytokine- and Chemokine-Related Genes in Peripheral Blood Mononuclear Cells from Lupus Patients by cDNA Array," *Clinical Immunology* 102(3):283-290.

Saiura, A. et al. (Jul. 2001). "A Comparison of Gene Expression in Murine Cardiac Allografts and Isografts by Means DNA Microarray Analysis," *Transplantation* 72(2):320-329.

Salmon, J. E. et al. (Mar. 1996). "Fc-gamma-RIIA Alleles are Heritable Risk Factors for Lupus Nephritis in African Americans," *The Journal of Clinical Investigation* 97(5):1348-1354.

Schena, M. et al. (Oct. 1995). "Quantitative Monitoring of Gene Expression Patterns with a Complementary DNA Microarray," *Science* 270:467-470.

Schena, M. et al. (Oct. 1996). "Parallel Human Genome Analysis: Microarray-based Expression Monitoring of 1000 Genes," *Proceedings of the National Academy of Sciences* 93:10614-10619.

Schowengert, K. O. et al. (May 2000). "Increased Expression of the Lymphocyte Early Activation Marker CD69 in Peripheral Blood Correlates with Histologic Evidence of Cardiac Allograft Rejection," *Transplantation* 69(10):2102-2107.

Sharma, V. K. et al. (Dec. 1996). "Molecular Executors of Cell Death—Differential Intrarenal Expression of Fas Ligand, Fas, Granzyme B, and Perforin During Acute and/or Chronic Rejection of Human Renal Allografts," *Transplantation* 62(12):1860-1866.

Shin, Y. K. et al. (Apr. 2001). "Expression of Leukemia-Associated Antigen, JL1, in Bone Marrow and Thymus," *American Journal of Pathology* 158(4):1473-1480.

Shirali, G. S. et al. (May 2001). "Association of Viral Genome with Graft Loss in Children after Cardiac Transplantation," *The New England Journal of Medicine* 344(20):1498-1503.

Shoker, A. et al. (Aug. 2000). "Heightened CD40 Ligand Gene Expression in Peripheral CD4+ T Cells from Patients with Kidney Allograft Rejection," *Transplantation* 70(3):497-505.

Shou-Nee, S. et al. (1987). "Serum Interferon in Systemic Lupus Erythematosus," *British Journal of Dermatology* 117:155-159.

Shulzhenko, N. et al. (2001). "Monitoring of Intragraft and Peripheral Blood TIRC7 Expression as a Diagnostic Tool for Acute Cardiac Rejection in Humans," *Human Immunology* 62:342-347.

Shulzhenko, N. et al. (Nov. 2001). "Intragraft Activation of Genes Encoding Cytotoxic T Lymphocyte Effector Molecules Precedes the Histological Evidence of Rejection in Human Cardiac Transplantation," *Transplantation* 72(10):1705-1708.

Smith-Norowitz, T. A. et al. (Nov. 1999). "Lymphocyte Activation in Angina Pectoris," *Clinical Immunology* 93(2):168-175.

Staudt, L. M. et al. (2000). "Genomic Views of the Immune System," *Annual Review of Immunology* 18:829-859.

Stellrecht, C. M. et al. (1991). "Expression Pattern of a Hematopoietic Proteoglycan Core Protein Gene During Human Hematopoiesis," *Differentiation* 48:127-135.

Stites, D. P. et al. eds. (1991). *Basic and Clinical Immunology*. 7th Edition, Appleton & Lange: East Norwalk, CT, 6 pages. (Table of Contents).

Strehlau, J. et al. (Jan. 1997). "Quantitative Detection of Immune Activation Transcripts as a Diagnostic Tool in Kidney Transplantation," *Proceedings of the National Academy of Sciences* 94:695-700.

Supplemental Partial European Search Report mailed Jul. 9, 2007, for EP Application No. 01997055.7 filed Oct. 22, 2001, 6 pages.

Supplementary European Search Report mailed Oct. 18, 2007, for EP Application No. 03799755.8 filed Apr. 24, 2003, 17 pages.

Tamayo, P. et al. (Mar. 1999). "Interpreting Patterns of Gene Expression with Self-Organizing Maps: Methods and Application to Hematopoietic Differentiation," *Proceedings of the National Academy of Sciences* 96:2907-2912.

Tan, E. M. et al. (Nov. 1982). "The 1982 Revised Criteria for the Classification of Systemic Lupus Erythematosus," *Arthritis and Rheumatism* 25(2):1271-1277.

Tan, L. et al. (Mar. 2001). "Sequential Monitoring of Peripheral T-Lymphocyte Cytokine Gene Expression in the Early Post Renal Allograft Period," *Transplantation* 71(6):751-759.

Thomas, E. et al. (Jul. 2000). "Subtyping of Juvenile Idiopathic Arthritis Using Latent Class Analysis," *Arthritis & Rheumatism* 43(7):1496-1503.

Tibshirani, R. et al. (May 2002). "Diagnosis of Multiple Cancer Types by Shrunken Centroids of Gene Expression," *Proceedings of the National Academy of Sciences* 99(1):6567-6572.

Non Final Office Action received for U.S. Appl. No. 12/635,438, mailed on May 19, 2011, 18 pages.

Whitehead et al., "Variation in Tissue-Specific Gene Expression Among Natural Populations", Genome Biology, vol. 6, No. 2, Article R13, 2005, pp. R13.1-R13.14.

Benner, S. A. et al. (Jul. 2001). "Evolution, Language and Analogy in Functional Genomics," *Trends in Genetics* 17(7):414-418.

Bennett, L. et al. (Mar. 17, 2003). "Interferon and Granulopoiesis Signatures in Systemic Lupus Erythematosus Blood," *The Journal of Experimental Medicine* 197(6):711-723.

Bergholdt, R. et al. (2000). "Characterization of New Polymorphisms in the 5' UTR of the Human Interleukin-1 Receptor Type 1 (IL1R1) Gene: Linkage to Type 1 Diabetes and Correlation to IL-1RI Plasma Level," *Genes and Immunity* 1:495-500.

Centola, M. et al. (2006). "Genome-Scale Assessment of Molecular Pathology in Systemic Autoimmune Diseases Using Microarray Technology: A Potential Breakthrough Diagnostic and Individualized Therapy-Design Tool," *Scandinavian Journal of Immunology* 64:236-242.

Crow, M. K. et al. (2003). "Microarray Analysis of Gene Expression in Lupus," *Arthritis Research & Therapy* 5(6):279-287.

Dozmorov, M. G. et al. (2007). "5α-Androstane-3α,17β-Diol Selectively Activates the Canonical PI3K/AKT Pathway: A Bioinformatics-Based Evidence for Androgen-Activated Cytoplasmic Signaling," *Genomic Medicine* 1:139-146.

Horwitz, P. A. et al. (2004). "Detection of Cardiac Allograft Rejection and Response to Immunosuppressive Therapy with Peripheral Blood Gene Expression," *Circulation* 110:3815-3821.

Ing, N. H. (2005). "Steroid Hormones Regulate Gene Expression Posttranscriptionally by Altering the Stabilities of Messenger RNAs," *Biology of Reproduction* 72:1290-1296.

International Search Report and Written Opinion mailed Sep. 10, 2008, for PCT Application No. PCT/US07/18135 filed Aug. 14, 2007, 12 pages.

Invitation to Pay Additional Fees mailed Apr. 27, 2009, for PCT Application No. PCT/US2007/023675 filed Nov. 9, 2007, 6 pages.

Kaufman, D. B. et al. (1997). "Functional Significance of Donor Islet Interleukin-1 Receptor Type 1 (IL-1Rt1) Expression in Islet Transplantation," *Transplantation Proceedings* 29:772-773.

Keembiyehetty, C. et al. (Mar. 2006). "Mouse Glucose Transporter 9 Splice Variants Are Expressed in Adult Liver and Kidney and Are Up-regulated in Diabetes," *Molecular Endocrinology* 20(3):686-697.

Kelsen, S. et al. (2004). "The Chemokine Receptor CXCR3 and its Splice Variant are Expressed in Human Airway Epithelial Cells," *American Journal of Physiology—Lung Cellular and Molecular Physiology* 287:L584-L591.

Kirou, K. A. et al. (Dec. 2004). "Coordinate Overexpression of Interferon-?-Induced Genes in Systemic Lupus Erythematosus," *Arthritis & Rheumatism* 50(12):3958-3967.

Mandel, M. et al. (2006). "Gene Expression Studies in Systemic Lupus Erythematosus," *Lupus* 15:451-456.

Seiter, S. et al. (1998). "CD44 Variant Isoform Expression in a Variety of Skin-Associated Autoimmune Diseases," *Clinical Immunology and Immunopathology* 89(1):79-93.

Smith, A. D. et al. eds. (1997). *Oxford Dictionary of Biochemistry and Molecular Biology*. Oxford University Press, Oxford, New York, p. 618.

Tanaka, J. et al. (1995). "Cytokine Receptor Gene Expression in Peripheral Blood Mononuclear Cells During Graft-Versus-Host Disease After Allogeneic Bone Marrow Transplantation," *Leukemia and Lymphoma* 19:281-287.

U.S. Office Action mailed Dec. 4, 2008, for U.S. Appl. No. 11/223,492, filed Sep. 8, 2005, 18 pages.

U.S. Office Action mailed Jul. 18, 2008, for U.S. Appl. No. 10/990,275, filed Nov. 15, 2004, 4 pages.

U.S. Office Action mailed May 29, 2009, for U.S. Appl. No. 11/784,998, filed Apr. 9, 2007, 28 pages.

U.S. Office Action mailed May 29, 2009, for U.S. Appl. No. 11/893,236, filed Aug. 14, 2007, 12 pages.

U.S. Office Action mailed Oct. 8, 2008, for U.S. Appl. No. 10/511,937, filed Jul. 22, 2005, 4 pages.

U.S. Office Action mailed Sep. 19, 2008, for U.S. Appl. No. 10/512,028, filed Jul. 21, 2005, 6 pages.

U.S. Appl. No. 12/235,969, filed Sep. 23, 2008 for Wohlgemuth et al.

Vamvakopoulos, J. et al. (2002). "Genetic Control of IL-1β Bioactivity Through Differential Regulation of the IL-1 Receptor Antagonist," *European Journal of Immunology* 32:2988-2996.

Zhu, H. et al. (Nov. 2005). "The Role of Hyaluronan Receptor CD44 in MSC Migration in The Extracellular Matrix," *Stem Cells Express*, pp. 1-32.

EMBL-EBI Accession No. V00497, last updated Nov. 20, 2004, located at <http://www.ebi.ac.uk/cgi-bin/dbfetch?db=embl&id=V00497&style=raw> visited on Oct. 31, 2007. (5 pages).

Fandrey, J. et al. (Feb. 1, 1993). "In Vivo and In Vitro Regulation of Erythropoietin mRNA: Measurement by Competitive Polymerase Chain Reaction," *Blood* 81(3):617-623.

Felson, D. T. et al. (Jun. 1995). "American College of Rheumatology. Preliminary Definition of Improvement in Rheumatoid Arthritis," *Arthritis and Rheumatism* 38(6):727-735.

Finger, L. R. et al. (1997). "The Human PD-1 Gene: Complete cDNA, Genomic Organization, and Developmentally Regulated Expression in B Cell Progenitors," *Gene* 197:177-187.

Fu, G. et al. (2002). "Representational Difference Analysis in a Lupus-Prone Mouse Strain Results in the Identification of an Unstable Region of the Genome on Chromosome 11," *Nucleic Acids Research* 30(6):1394-1400.

Fullerton, S. M. et al. (Mar. 1994). "Molecular and Population Genetic Analysis of Allelic Sequence Diversity at the Human Beta-Globin Locus," *Proceedings of the National Academy of Sciences* 91:1805-1809.

Gabay, C. et al. (1997). "Circulating Levels of Tumor Necrosis Factor Soluble Receptors in Systemic Lupus Erythematosus are Significantly Higher than in Other Rheumatic Diseases and Correlate with Disease Activity," *The Journal of Rheumatology* 24(2):303-308.

GenBank Accession No. AL591031, located at <http://www.ncbi.nlm.nih.gov/entrez/viewer.fcgi?db=nuccore&id=16073692> visited on Jun. 27, 2007. (41 pages).

GenBank Accession No. Y10376, last updated May 14, 1997, located at <http://www.ncbi.nlm.nih.gov/entrez/viewer.fcgi?db=nuccore&id=2052057> visited on Apr. 8, 2008. (3 pages).

Ghosh, A. et al. (Jul. 2001). "A Specific Isozyme of 2'-5' Oligoadenylate Synthetase is a Dual Function Proapoptotic Protein of the Bcl-2 Family," *The Journal of Biological Chemistry* 276(27):25477-25455.

Glynne, R. et al. (2000). "B-Lymphocyte Quiescence, Tolerance and Activation as Viewed by Global Gene Expression Profiling on Microarrays," *Immunological Reviews* 176:216-246.

Glynne, R. J. et al. (2000). "Genomic-Scale Gene Expression Analysis of Lymphocyte Growth, Tolerance and Malignancy," *Current Opinion in Immunology* 12:210-214.

Golden-Mason, L. et al. (2000). "Differential Expression of Lymphoid and Myeloid Markers on Differentiating Hematopoietic Stem Cells in Normal and Tumor-Bearing Adult Human Liver," *Hepatology* 31 (6):1251-1256.

Golub, T. R. et al. (Oct. 1999). "Molecular Classification of Cancer: Class Discovery and Class Prediction by Gene Expression Monitoring," *Science* 286:531-537.

Gorczynski, R. M. (1996). "Correlation of Peripheral Blood Lymphocyte and Intragraft Cytokine mRNA Expression with Rejection in Orthotopic Liver Transplantation," *Surgery* 120(3):496-502.

Grant, S. C. D. et al. (Aug. 1996). "Serum Cytokines in Human Heart Transplant Recipients," *Transplantation* 62(4):480-491.

Griffiths, G. M. et al. (1991). "Granzyme A and Perforin as Markers for Rejection in Cardiac Transplantation," *European Journal of Immunology* 21:687-692.

Gullestad, L. et al. (1999). "Effect of High- Versus Low-Dose Angiotensin Converting Enzyme Inhibition on Cytokine Levels in Chronic Heart Failure," *Journal of the American College of Cardiology* 34(7):2061-2067.

Harlow, E. et al. (1988). *Antibodies: A Laboratory Manual.* Cold Spring Harbor Laboratory: New York, NY, 9 pages. (Table of Contents).

Hastie, T. et al. (Aug. 2000). "'Gene Shaving' as a Method for Identifying Distinct Sets of Genes with Similar Expression Patterns," *Genome Biology* 1(2):research0003.1-0003.21.

Hastie, T. et al. (Jan. 2001). "Supervised Harvesting of Expression Trees," *Genome Biology* 2(1):research0003.1-0003.12.

Hayward, A. L. et al. (1998). "Modeling and Analysis of Competitive RT-PCR," *Nucleic Acids Research* 26(11):2511-2518.

Hayward-Lester, A. et al. (1995). "Accurate and Absolute Quantitative Measurement of Gene Expression by Single Tube RT-PCR and HPLC," *Genome Research* 5:494-499.

Heller, R. A. et al. (Mar. 1997). "Discovery and Analysis of Inflammatory Disease-Related Genes Using cDNA Microarrays," *Proceedings of the National Academy of Sciences* 94:2150-2155.

Hendricks, D. A. et al. (Nov. 1995). "Quantitation of HBV DNA in Human Serum Using a Branched DNA (bDNA) Signal Amplification Assay," *American Journal of Clinical Pathology* 104 (5):537-546.

Higuchi, K. et al. (1998). "Serum 2'-5' Oligoadenylate Synthetase Activity in Children. 2. Serum 2'-5' Oligoadenylate Synthetase in Childhood Collagen Disease," 342625a, *Chemical Abstracts* 129(26):406.

Hooks, J. J. et al. (1979). "Immune Interferon in the Circulation of Patients with Autoimmune Disease," *The New England Journal of Medicine* 301(1):5-8.

Hooks, J. J. et al. (Apr. 1982). "Multiple Interferons in the Circulation of Patients with Systemic Lupus Erythematosus and Vasculitis," *Arthritis and Rheumatism* 25(4):396-400.

Hsieh, H.-G. et al. (2001). "IL-17 Expression as a Possible Predictive Parameter for Subclinical Renal Allograft Rejection," *Transplant International* 14:287-298.

Iida, K. et al. (May 1982). "Complement Receptor (CR1) Deficiency in Erythrocytes from Patients with Systemic Lupus Erythematosus," *The Journal of Experimental Medicine* 155:1427-1438.

International Search Report and Written Opinion mailed Mar. 27, 2008, for PCT Application No. PCT/US05/31806 filed Sep. 8, 2005, 14 pages.

International Search Report mailed Jul. 18, 2002, for PCT Application No. PCT/US01/47856 filed Oct. 22, 2001, 3 pages.

International Search Report mailed Mar. 1, 2001, for PCT Application No. PCT/US00/17846 filed Jun. 28, 2000, 2 pages.

International Search Report mailed Sep. 23, 2005, for PCT Application No. PCT/US03/12946 filed Apr. 24, 2003, 4 pages.

International Search Report mailed Sep. 30, 2004, for PCT Application No. PCT/US03/13015 filed Apr. 24, 2003, 5 pages.

Jagota, A. (2000). "Nearest Neighbor Classifiers" Chapter 11 *In Data Analysis and Classification for Bioinformatics.* Department of Computer Science, University of California, Santa Cruz, pp. 92-93.

Jardi, M. et al. (1994). "Urokinase Receptor (UPAR) Expression During Hematopoietic Maturation," *Journal of Drug Targeting* 8(Suppl 1):51.

Joulin, V. et al. (Oct. 25, 1988). "Isolation and Characterization of the Human 2,3-Bisphosphoglycerate Mutase Gene," *The Journal of Biological Chemistry* 263(30):15785-15790.

Jude, B. et al. (Oct. 1994). "Evidence for Time-Dependent Activation of Monocytes in the Systemic Circulation in Unstable Angina but Not in Acute Myocardial Infarction or in Stable Angina," *Circulation* 90(4):1662-1668.

Kang, J. J. et al. (2000). "Transcript Quantitation in Total Yeast Cellular RNA Using Kinetic PCR," *Nucleic Acids Research* 28(2):e2, 8 pages.

Kasprzycka, M. et al. (2002). "Expression of FasL Gene in T cells of Renal Allograft Recipients," *Immunology Letters* 80:9-13.

Kassirer, M. et al. (Sep. 1999). "Increased Expression of the CD11b/CD18 Antigen on the Surface of Peripheral White Blood Cells in Patients with Ischemic Heart Disease: Further Evidence for Smoldering Inflammation in Patients with Atherosclerosis," *American Heart Journal* 138(3):555-559.

Katz, M. H. (1999). "Assumptions of Multiple Linear Regression, Multiple Logistic Regression, and Proportional Hazards Analysis" *In Multivariable Analysis: A Practical Guide for Clinicians.* Cambridge University Press: Cambridge, United Kingdom, pp. 36-42.

Kendler, K. S. et al. (Jun. 1998). "The Structure of Psychosis Latent Class Analysis of Probands from the Roscommon Family Study," *Archives of General Psychiatry* 55:492-499.

Khan, J. et al. (Jun. 2001). "Classification and Diagnostic Prediction of Cancers Using Gene Expression Profiling and Artificial Neural Networks," *Nature Medicine* 7(6):673-679.

Kimball, P. et al. (Feb. 1995). "Cytokine Panel Predicts Early Rejection of Therapeutic Response After Cardiac Transplantation," *Transplantation Proceedings* 27(1):1286-1287.

Kobashigawa, J. et al. (Aug. 1998). "A Randomized Active-Controlled Trial of Mycophenolate Mofetil in Heart Transplant Recipients," *Transplantation* 66(4):507-515.

Krause, S. W. (1998). "Carboxypeptidase M as a Marker of Macrophage Maturation," *Immunological Reviews* 161:119-127.

Kumar, R. et al. (Oct. 1994). "Cell Cycle-Dependent Modulation of Alpha-Interferon-Inducible Gene Expression and Activation of Signaling Components in Daudi Cells," *The Journal of Biological Chemistry* 269(41):25437-25441.

Kumar, S. et al. (2000). "Expansion and Molecular Evolution of the Interferon-Induced 2'-5' Oligoadenylate Synthetase Gene Family," *Molecular Biology and Evolution* 17(5):738-750.

Toogood, G. J. et al. (Sep. 1996). "The Immune Response Following Small Bowel Transplantation," *Transplantation* 62(6):851-855.

Toronen, P. et al. (1999). "Analysis of Gene Expression Data Using Self-Organizing Maps," *FEBS Letters* 451:142-146.

Torre-Amione, G. et al. (Apr. 1996). "Proinflammatory Cytokine Levels in Patients with Depressed Left Ventricular Ejection Fraction: A Report from the Studies of Left Ventricular Dysfunction (SOLVD)," *Journal of the American College of Cardiology* 27(5):1201-1206.

Tsutamoto, T. et al. (Mar. 2000). "Angiotensin II Type 1 Receptor Antagonist Decreases Plasma Levels of Tumor Necrosis Factor Alpha, Interleukin-6 and Soluble Adhesion Molecules in Patients with Chronic Heart Failure," *Journal of the American College of Cardiology* 35(3):714-721.

Tusher, V. G. et al. (Apr. 2001). "Significance Analysis of Microarrays Applied to the Ionizing Radiation Response," *Proceedings of the National Academy of Sciences* 98(9):5116-5121.

U.S. Office Action mailed Apr. 1, 2008, for U.S. Appl. No. 10/511,937, filed Jul. 22, 2005, 6 pages.

U.S. Office Action mailed Jun. 15, 2007, for U.S. Appl. No. 11/223,492, filed Sep. 8, 2005, 20 pages.

U.S. Office Action mailed Mar. 5, 2008, for U.S. Appl. No. 11/223,492, filed Sep. 8, 2005, 13 pages.

U.S. Office Action mailed Oct. 3, 2007, for U.S. Appl. No. 10/990,275, filed Nov. 15, 2004, 6 pages.

U.S. Office Action mailed Oct. 5, 2007, for U.S. Appl. No. 10/990,298, filed Nov. 15, 2004, 5 pages.

Umek, R. M. et al. (May 2001). "Electronic Detection of Nucleic Acids: A Versatile Platform for Molecular Diagnostics," *Journal of Molecular Diagnostics* 3(2):74-84.

U.S. Appl. No. 10/512,028, filed Apr. 14, 2006 for Wohlgemuth et al.

Vallin, H. et al. (1999). "Anti-Double-Stranded DNA Antibodies and Immunostimulatory Plasmid DNA in Combination Mimic the Endogenous IFN-Alpha Inducer in Systemic Lupus Erythematosus," *The Journal of Immunology* 163:6306-6313.

Vandevyver, C. et al. (1998). "Cytokine mRNA Profile of Myelin Basic Protein Reactive T-Cell Clones in Patients with Multiple Sclerosis," *Autoimmunity* 28:77-89.

Vasconcellos, L. M. et al. (Sep. 1998). "Cytotoxic Lymphocyte Gene Expression in Peripheral Blood Leukocytes Correlates with Rejecting Renal Allografts," *Transplantation* 66(5):562-566.

Vignali, D. A. A. (2000). "Multiplexed Particle-Based Flow Cytometric Assays," *Journal of Immunological Methods* 243:243-255.

Vincenti, F. et al. (May 2001). "Multicenter Trial Exploring Calcineurin Inhibitors Avoidance in Renal Transplantation," *Transplantation* 71(9):1282-1287.

Vu, H. K. (2000). "A Method for Quantification of Absolute Amounts of Nucleic Acids by (RT)-PCR and a New Mathematical Model for Data Analysis," *Nucleic Acids Research* 28(7):e18, 9 pages.

Watanabe-Fukunaga, R. et al. (Mar. 1992). "Lymphoproliferation Disorder in Mice Explained by Defects in Fas Antigen that Mediates Apoptosis," *Nature* 356:314-317.

Weast, R. C. ed. (1968). *Handbook of Chemistry and Physics*. 49th Edition, The Chemical Rubber Co.: Cleveland, Ohio, p. A-245.

Welsh, J. B. et al. (Jan. 2001). "Analysis of Gene Expression Profiles in Normal and Neoplastic Ovarian Tissue Samples Identifies Candidate Molecular Markers of Epithelial Ovarian Cancer," *Proceedings of the National Academy of Sciences* 98(3):1176-1181.

Westin, L. et al. (Feb. 2000). "Anchored Multiplex Amplification on a Microelectronic Chip Array," *Nature Biotechnology* 18:199-204.

Whitehead, J. (Date Unknown). "An Introduction to Logistic Regression," Department of Economics, East Carolina University, located at <http://arts.uwaterloo.ca/~wnrr/Soc710_421/Whitehead%20Logistic%20Regression.ppt> (48 pages).

Willems, R. et al. (May 29, 1998). "Decrease in Nucleoside Diphosphate Kinase (NDPK/nm23) Expression During Hematopoietic Maturation," *The Journal of Biological Chemistry* 273(22):13663-13668.

Wu, J. et al. (Sep. 1996). "Fas Ligand Mutation in a Patient with Systemic Lupus Erythematosus and Lymphoproliferative Disease," *The Journal of Clinical Investigation* 98(3):1107-1113.

Wu, T. (2001). "Analysing Gene Expression Data from DNA Microarrays to Identify Candidate Genes," *Journal of Pathology* 195:53-65.

Xia, D. et al. (Sep. 2001). "Real-Time Polymerase Chain Reaction Analysis Reveals an Evolution of Cytokine mRNA Production in Allograft Acceptor Mice," *Transplantation* 72(5):907-914.

Yu, F. et al. (Oct. 1999). "Protein Synthesis—Dependent and Independent Induction of p69 2'-5'-Oligoadenylate Synthetase by Interferon-Alpha," *Cytokine* 11(10):744-750.

Zhang, L. et al. (Oct. 1997). "IRFf-7, a New Interferon Regulatory Factor Associated with Epstein-Barr Virus Latency," *Molecular and Cellular Biology* 17(10):5748-5757.

Zucker, S. et al. (1999). "Increased Serum Stromelysin-1 Levels in Systemic Lupus Erythematosus: Lack of Correlation with Disease Activity," *Journal of Rheumatology* 26(1):78-80.

Eitner et al. (1998). "Chemokine Receptor (CXCR4) mRNA-Expressing Leukocytes are Increased in Human Renal Allograft Rejection," *Transplantation* 66(11):1551-1557.

U.S. Office Action mailed Jul. 22, 2010, for U.S. Appl. No. 11/433,191, filed May 11, 2006, 13 pages.

Wang et al. (2004). "Heart, but Not Skin, Allografts from Donors Lackin Flt3 Ligand Exhibit Markedly Prolonged Survival Time," *J Immunol.* 172:5924.

Bertone, P. et al. (Dec. 24, 2004). "Global Identification of Human Transcribed Sequences with Genome Tiling Arrays," *Science* 306:2242-2246.

Flechner, S. M. et al. (2004). "Kidney Transplant Rejection and Tissue Injury by Gene Profiling of Biopsies and Peripherals Blood Lymphocytes," *American Journal of Transplantation* 4:1475-1489.

Galon, J. et al. (Jan. 2002). "Gene Profiling Reveals Unknown Enhancing and Supppressive Actions of Glucocorticoids on Immune Cells," *The FASEB Journal* 16:61-71.

International Search Report and Written Opinion mailed Aug. 25, 2008, for PCT Application No. PCT/US07/08909 filed Apr. 9, 2007, 10 pages.

International Search Report and Written Opinion mailed Jun. 25, 2008, for PCT Application No. PCT/US06/18381 filed May 11, 2006, 8 pages.

Mansfield, E. S. et al. (2004). "Arraying the Orchestration of Allograft Pathology," *American Journal of Transplantation* 4:853-862.

Japanese Notice of Reasons for Rejection mailed on Apr. 27, 2009 for Japanese Patent Application No. 2004-549874 filed on Apr. 24, 2003, 9 pages. [English Translation only].

Japanese Notice of Reasons for Rejection mailed on May 26, 2009 for Japanese Patent Application No. 2003-587333 filed on Apr. 24, 2003, 6 pages. [English Translation, 9 pages].

U.S. Appl. No. 12/329,173, filed Dec. 5, 2008 for Wohlgemuth et al.
U.S. Appl. No. 12/544,182, filed Aug. 19, 2009 for Wohlgemuth et al.
U.S. Appl. No. 12/561,213, filed Sep. 16, 2009 for Wohlgemuth et al.
U.S. Appl. No. 12/584,615, filed Sep. 8, 2009 for Wohlgemuth et al.

Zanders, E. et al. (2000). "Analysis of Immune System Gene Expression in Small Rheumatoid Arthritis Biopsies Using a Combination of Subtractive Hybridization and High-Density cDNA Arrays," *Journal of Immunological Methods* 233(1-2):131-140.

Notice of Allowance received for U.S. Appl. No. 12/584,615, mailed on Sep. 29, 2010, 31 pages.

Final Office Action received for U.S. Appl. No. 12/635,438, mailed on Sep. 27, 2010, 13 pages.

Notice of Allowance received for U.S. Appl. No. 12/855,178, mailed on Sep. 17, 2010, 25 pages.

Office Action received for Japanese Patent Application No. 2004-549874, mailed on Nov. 5, 2010, 13 pages (8 pages of English Translation and 5 pages of office Action).

Michiels et al., "Prediction of cancer outcome with microarrays: a multiple random validation strategy", Lancet, vol. 365, 2005, pp. 488-492.

Schoels et al., "Detection of cardiac allograft rejection by real-time PCR analysis of circulating mononuclear cells", Clinical Transplantation, vol. 18, 2004, pp. 513-517.

European Search Report mailed Dec. 22, 2009, for EP Application No. 06770255.5 filed Dec. 5, 2007, 10 pages.

Japanese Office Action mailed Jan. 15, 2010, for JP Application No. 2003-587333 filed Apr. 24, 2003, English translation 4 pages.

U.S. Appl. No. 12/628,168, filed Nov. 30, 2009 for Lal et al.
U.S. Appl. No. 12/635,438, filed Dec. 10, 2009 for Wohlgemuth et al.

Yeung, K et al. (2004). "From co-expression to co-regulation: how many microarray experiments do we need?," *Genome Biology* 5(7):R48.

Office Action received for European Patent Application No. 10157687.4, mailed on Jul. 6, 2011, 6 pages.

Notice of Allowance received for U.S. Appl. No. 12/958,344, mailed on Sep. 14, 2011, 65 pages.

METHODS FOR DIAGNOSING AND MONITORING THE STATUS OF SYSTEMIC LUPUS ERYTHEMATOSUS

PRIORITY

This application claims the benefit of U.S. Prov. App. No. 60/858,147, filed Nov. 9, 2006, which is incorporated by reference herein in its entirety.

TECHNICAL FIELD

The invention provides for the use of gene expression and statistical analysis to diagnose and monitor the status of systemic lupus erythematosus.

BACKGROUND OF THE INVENTION

Systemic lupus erythematosus (SLE) is an autoimmune rheumatic disease characterized by dysregulation of the immune system and differential expression of genes in immunological pathways. In the United States, SLE affects about 2 million patients and 90% of these patients are female. Targeted tissues and organs include the blood, central nervous system (CNS), joints, kidneys, lungs, skin, and vasculature. Symptoms include abnormal blood panels, arthralgias, atherosclerosis, CNS disorders, infections, joint pain, malaise, rashes, ulcers, and the production of autoantibodies. Since disease severity, symptomology, and response to therapy vary widely, SLE is difficult to diagnose, manage and treat.

As described in USSN 20040033498, SLE clearly involves differential gene expression in SLE patients as compared to normal controls. Two laboratories have reported on the role of the interferon (INF)-α inducible genes in SLE and on high levels of anti-RNA binding protein, anti-Ro antibodies, and renal disease (Baechler et al (2003) PNAS100:2610-2615; Kirou et al (2004) Arthritis and Rheumatism 50:3958-3967). However, low positive correlation between disease activity and IFN-inducible genes, the apparent heterogeneity of SLE patients, and lack of longitudinal studies continue to present challenges for clinicians (Kirou et al. (2005) Arthritis and Rheumatism 52:1491-1503).

These challenges point to a need in the art for better diagnosis, characterization, and follow-up of patients with SLE. To this end, longitudinal data from SLE patients was used with methods for detecting and analyzing gene expression to monitor status, quiescence versus flare, and to classify a patient as having type 1 SLE or type 2 SLE.

SUMMARY

The invention presents methods and compositions for diagnosing and monitoring systemic lupus erythematosus (SLE). The methods use gene expression based on nucleic acid or protein technologies, and statistical methods to classify patients as having type 1 SLE or type 2 SLE and to monitor disease activity, predict flare, and assess the efficacy of treatment administered to the patient.

The invention provides a method of diagnosing or monitoring the status of systemic lupus erythematosus (SLE) in a subject or patient includes detecting the expression of all genes of a diagnostic set in the subject or patient wherein the diagnostic set comprises two or more genes having expression correlated with the classification or status of SLE; and diagnosing or monitoring the status of SLE in the subject or patient by applying at least one statistical method to the expression of the genes of the diagnostic set. In one aspect, the statistical method is a prediction algorithm that produces a number or single value indicative of the status of SLE in the subject or patient. In another aspect, the statistical method further comprises classification of the subject or patient into one of at least two classes of SLE, and is optimized to maximize the separation among longitudinally stable classes of SLE. The method also provides a diagnostic set further comprising at least one gene selected from each of at least two gene clusters selected from cluster 1, cluster 2, cluster 3, cluster 4, cluster 5, cluster 6, cluster 7, cluster 8, cluster 9, cluster 10, cluster 11; cluster 12, cluster 13, cluster 14, and cluster 15 of Table 1. The invention further provides classification of the subject or patient into one of at least two classes of SLE further comprising detecting the expression of two or more gene whose expression correlates with the expression of the IFI27 from about 0.5 to about 1.0 and from about −0.5 to about −1.0 calculated using a Pearson correlation; and classifying a subject or patient as having type 1 or type 2 SLE based on the expression of the two or more genes. In one aspect, one of the two or more genes is selected from Table 2 and the classifying step uses a linear algorithm to produce an interferon response (INFr) score wherein a high IFNr score is correlated with type I SLE and a low IFNr score is correlated with type II SLE. The invention additionally provides at least one linear algorithm producing an IFNr score comprising IFI27+IFI144*(1.1296)+OAS3*(1.8136). The invention still further provides a Pearson correlation that is selected from a range of 0.5, 0.4, 0.3, and 0.2 of the expressed genes.

The invention provides a method of diagnosing or monitoring the status of systemic lupus erythematosus (SLE) in a subject or patient comprising detecting the expression of all genes of a diagnostic set in a subject or patient wherein the diagnostic set includes at least one gene from each of at least two gene clusters selected from cluster 1, cluster 2, cluster 3, cluster 4, cluster 5, cluster 6, cluster 7, cluster 8, cluster 9, cluster 10, cluster 11; cluster 12, cluster 13, cluster 14, and cluster 15 of Table 1; and diagnosing or monitoring the status of SLE in the subject or patient based on expression of the genes in the diagnostic set. In one aspect, the expression of all genes in the diagnostic set is detected using a nucleic acid technology further including hybridization in solution or on a substrate or amplification in a quantitative real-time polymerase chain reaction. In another aspect, expression of all genes is proportional to the amount of RNA isolated from a subject or patient sample further including a body fluid selected from whole blood or a blood fraction, ascites, cerebrospinal fluid, lymph, sputum, and urine or a tissue selected from central nervous system, joints, kidneys, liver, lungs, oral cavity, sinuses, skin, and vasculature obtained by any sampling means selected from aspiration of a body fluid, a biopsy of a tissue or an organ, drawing of peripheral blood, endoscopy, and lavage followed by aspiration.

The invention provides for the use of at least one primer or probe set to detect the expression of each of the genes in the diagnostic set. In one aspect, the primers or probe sets are oligonucleotides selected from natural or synthetic cDNA, genomic DNA, locked nucleic acids, peptide nucleic acids, and RNA and can be used in a diagnostic kit. The invention also provides a method of diagnosing a patient as having a longitudinally stable classification of SLE by detecting the expression of two or more genes whose expression correlates with the expression of the IFI27 from about 0.5 to about 1.0 and from about −0.5 to about −1.0 calculated using Pearson correlation; and diagnosing the patient as having type I or type II SLE based on analyzing the expression of the two or more genes using a statistical method.

The invention further provides for assigning a subject or patient to a clinical trial based on their classification as type I SLE or type 2 SLE.

The invention provides for monitoring the status of SLE in a subject or patient by predicting incipient flare or disease activity, and assessing response to a therapeutic agent administered to the patient or to an immunosuppressant administered to a patient. The invention also provides for screening a subject exhibiting symptoms of a rheumatic disease selected from ankylosing spondylitis, dermatomyositis, autoimmune hepatitis, hepatitis-C (hep-C), polymyalgia rheumatica, polymyositis, rheumatoid arthritis (RA), scleroderma, systemic sclerosis, Sjogren's disease, systemic vasculitis, and Whipple's disease.

The invention provides method of producing a probe set for diagnosing or monitoring SLE in a subject or patient by selecting at least one gene from each of at least two of the gene clusters of Table 1 and at least two genes from Table 2; and producing a probe set consisting of at least one oligonucleotide that detects the expression of each of the selected genes. In one aspect, the probe set is used in a diagnostic kit.

The invention provides a method for predicting flare in a patient diagnosed with SLE by analyzing gene expression in a sample from the patient to produce a gene expression profile wherein a first portion of the analysis includes using expression of at least one gene selected from each of at least two of the clusters 1 through 15 of Table 1 and at least one statistical method to produce a patient expression profile, and a second portion of the analysis includes using expression of at least two genes selected from Table 2 and a linear algorithm to classify the patient as having type 1 SLE or type 2 SLE; and predicting flare by comparing the patient gene expression profile at least one reference profile. In one aspect, the reference profile is selected from at least one normal subject, at least one patient classified as having type 1 SLE with quiescent status, at least one patient classified as having type 1 SLE in flare, at least one patient classified as having type 2 SLE with quiescent status, at least one patient classified as having type 2 SLE in flare.

DESCRIPTION OF THE TABLES

Figure 1:
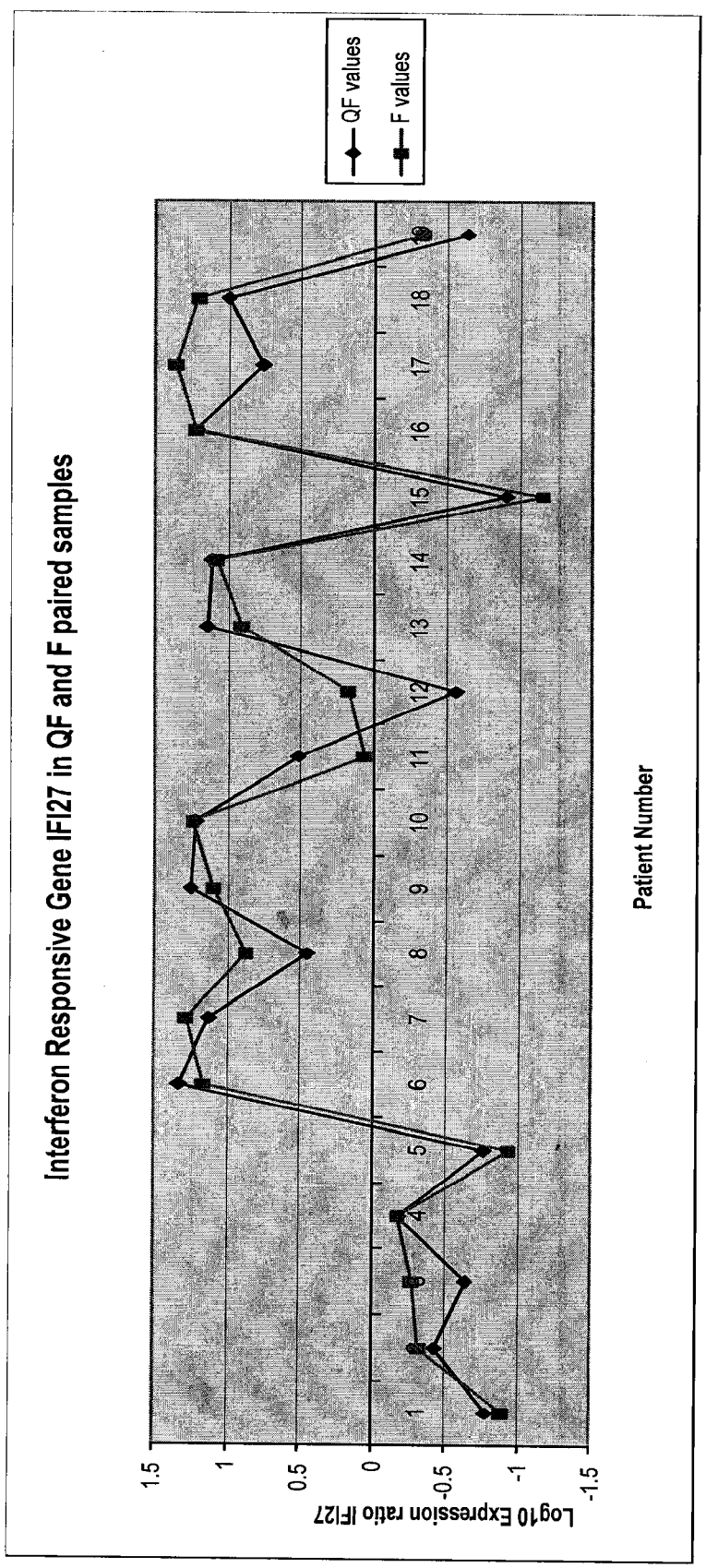
FIG. 1 shows the $Log_{10}$ expression ration for Interferon Responsive Gene IFI27 in QF and F paired samples.

Table 1 shows 15 clusters of correlated genes that are differentially expressed as SLE patients change status from quiescence to flare and can be used with at least one statistical method to predict flare. Cell types corresponding to each cluster are indicated as well as Array ID, Genbank ID, Gene ID, and the source of each gene. 60-mer sequences, which are unique identifiers for the genes, are also displayed in Table 1. The Sequence Listing provides the 60-mer sequences listed in Table 1.

Table 2 lists INFr genes with expression that positively correlates with IFI27 expression and can be used with at least one statistical method to classify a patient as having either type 1 SLE or type 2 SLE. 60-mer sequences, which are unique identifiers for the genes, are also displayed in Table 2.

Table 3 presents longitudinal data for SLE patients showing stability in an individual's INFr score and its lack of correlation with SLEDAI.

DETAILED DESCRIPTION OF THE INVENTION

Definitions

Unless defined otherwise, all scientific and technical terms are understood to have the same meaning as commonly used in the art to which they pertain. In this application, the singular form—"a", "an", and "the"—includes plural references unless the context clearly dictates otherwise. For example, the term "an agent" includes a plurality of agents and mixtures thereof. For the purpose of this invention, the following terms are defined below.

"Amplification" refers to any device, method or technique that can make copies of a nucleic acid. It can be achieved using polymerase chain reaction (PCR) techniques such as linear amplification (cf. U.S. Pat. No. 6,132,997), rolling circle amplification, and the like. Further, amplification and detection can be combined as in TAQMAN Real-Time PCR (RT-PCR) using the TAQMAN protocols and the Prism 7900HT Sequence detection system and software (Applied Biosystems (ABI), Foster City Calif.).

"Array" refers to an ordered arrangement of at least two reagents—antibodies, nucleic acids or proteins—in solution or on a substrate where at least one of the reagents represents a normal control and the other, a sample of diagnostic or prognostic interest. The ordered arrangement insures that the size and signal intensity of each labeled complex, formed between at least one reagent and at least one nucleic acid or protein to which the reagent specifically binds, is individually distinguishable.

The term "diagnostic set" generally refers to a set of two or more genes that, when evaluated for differential expression of their products, collectively yields predictive data. Such predictive data typically relates to diagnosis, prognosis, monitoring of therapeutic outcomes, and the like. In general, the components of a diagnostic set are distinguished from nucleotide sequences that are evaluated by analysis of the DNA to directly determine the genotype of an individual as it correlates with a specified trait or phenotype, such as a disease, in that it is the pattern of expression of the components of the diagnostic set, rather than mutation or polymorphism of the DNA sequence that provides predictive value. It will be understood that a particular component (or member) of a diagnostic set can, in some cases, also present one or more mutations, or polymorphisms that are amenable to direct genotyping by any of a variety of well known analysis methods, e.g., Southern blotting, RFLP, AFLP, SSCP, SNP, and the like.

"cDNA" refers to an isolated polynucleotide, nucleic acid molecule, or any fragment or complement thereof that originated recombinantly or synthetically, is double- or single-stranded, represents coding and noncoding 3' or 5' sequence, and generally lacks introns.

"Classification" refers to the categorization of a subject or patient based on gene expression as having type 1 SLE or type 2 SLE. SLE is considered to be type 1 if it primarily involves Type 1 T helper cells and type 1-linked cytokines, such as interferon-gamma. SLE is considered to be type 2 if there is more involvement of Type 2 helper cells which activate an antibody-driven immune response.

"Expression" refers differential gene expression—an increased (i.e., upregulated) or a decreased (i.e., downregulated) expression as detected by absence, presence, or change in the amount of messenger RNA or protein for a gene in a sample.

"Flare" refers to onset of disease activity in a patient diagnosed with an immune disorder; in SLE, mild flare has been defined by an increase in systemic lupus erythematosus disease activity index (SLEDAI) by ≧four units over a previous score for that patient and severe flare, as an increase in SLEDAI by ≧12 units. SLEDAI represents a composite assessment of disease activity based on 16 clinical manifestations and eight laboratory measures including two immunological tests with a possible range of overall score from 0 to 105.

A "gene expression profile" refers to the identification, characterization, quantification, and representation of a plurality of genes expressed in a sample as measured using nucleic acid or protein technologies. A nucleic acid expression profile is produced using mature mRNA transcript and/or regulatory sequences such as promoters, enhancers, introns, mRNA-processing intermediates, and 3' untranslated regions in nucleic acid technologies. A protein expression profile, although time delayed, mirrors the nucleic acid expression profile and is produced using protein technologies and proteins and/or antibodies to detect protein expression in a sample. Results from subject or patient samples are compared with reference profiles based on normal, diseased, or treated samples.

"Immunosuppressant" refers to any therapeutic agent that suppresses immune response in a patient such as anticoagulents, antimalarials, heart drugs, non-steroidal anti-inflammatory drugs (NSAIDs), and steroids including but not limited to aspirin, azathioprine, chloroquine, corticosteroids, cyclophosphamide, cyclosporin A, dehydroepiandrosterone, deoxyspergualin, dexarnethasone, everolimus, fenoprofen, hydralazine, hydroxychloroquine, immunoglobulin, ibuprofen, indomethacin, leflunomide, ketoprofen, meclophenamate, mepacrine, 6-mercaptopurine, methotrexate, mizoribine, mycophenolate mofetil, naproxen, prednisone, methyprenisone, rapamycin (sirolimus), solumedrol, tacrolimus (FK506), thymoglobulin, tolmetin, tresperimus, triamcinoline, and the like.

"Longitudinally stable" refers to the behavior of one or more interferon response (INFr) genes expressed in samples collected at different time points from an individual or data derived from those samples.

"Diagnosis or monitoring" refers to the detection of gene expression at the nucleic acid or protein level to provide useful information about an individual's medical status, Monitoring status can include determination of prognosis or complication, following progression of a disease, prediction of disease activity or flare, providing information relating to a patient's health over a period of time, selection of a therapeutic agent and/or determining response or resistance to that agent, selecting an individual patient or small subsets of patients most likely to benefit from an experimental therapy or clinical trial, and determining classification of a patient as having a particular disease status.

"Normal" refers to the medical status of an individual, or a sample from an individual, who does not have SLE or any diagnosis or manifestation of an infection or immune disorder and can be used as a negative control.

"Nucleic acid technology" refers to any device, means or system used to detect gene expression or produce a gene expression profile and includes but is not limited to methods using arrays for amplification in PCR, TAQMAN RT-PCR, quantitative RT-PCR, and the like, or hybridization in solution or on a substrate containing cDNAs, genomic DNAs, locked nucleic acids, oligonucleotide primers or probes, peptide nucleic acids, polynucleotides, and RNAs of any length either natural or synthetic, and the like.

"Patient" refers to a human subject who is genetically predisposed to a rheumatic disease or has been diagnosed with a SLE.

"Prediction" refers to the use of gene expression assessed using nucleic acid or protein technologies, algorithms and statistical analyses to provide information about an individual's status; for example, being predisposed to, diagnosed with, or effectively treated for disease activity or flare.

"Protein technology" includes but is not limited to activity assays, affinity antibody or protein arrays, chromatographic separation, calorimetric assays, two-dimensional gel electrophoresis, enzyme-linked immunosorbent assays (ELISA), fluorescent-activated cell sorting (FACS), mass spectrophotometric detection, western analysis, and the like.

A "reference profile" refers to gene expression or gene expression profiles from well-characterized normal, diseased or treated samples taken from at least one subject and giving repeatable results whenever used in or with a particular nucleic acid or protein technology.

A "rheumatic disease" is a condition or disorder selected from ankylosing spondylitis, dermatomyositis, autoimmune hepatitis, hepatitis-C (hep-C), polymyalgia rheumatica, polymyositis, rheumatoid arthritis (RA), scleroderma, systemic sclerosis, Sjogren's disease, systemic vasculitis, Whipple's disease and the like.

"Sample" is used in its broadest sense and refers to any biological material used to obtain histological information or to measure gene expression obtained by any means from a subject. A sample can be a body fluid such as ascites, bile, blood, cerebrospinal fluid, synovial fluid, lymph, pus, semen, sputum, urine; the soluble fraction of a cell preparation, an aliquot of media in which cells were grown; a chromosome, an organelle, or membrane isolated or extracted from a cell; cDNA, genomic DNA, or RNA in solution or bound to a substrate; a cell; a tissue biopsy, and the like, Preferred samples for diagnosis, prognosis, or monitoring of SLE patients are leukocytes or serum derived from whole blood, biopsies of the central nervous system (CNS), joints, kidneys, liver, lungs, oral cavity, sinuses, skin, vasculature, and any other tissues or organs affected by SLE.

"Sampling means" refers to aspiration, biopsy, endoscopy, lavage, needle aspiration or biopsy, puncturing with a lancet; bleeding, ejaculating, expectorating, seeping, or urinating into or onto a collection device, container, substrate, and the like.

"Status" refers to the deterioration, improvement, progression, remission, or stability of a patient with SLE, as determined from analyzing one or more samples from that patient. Status, or a change therein, can be used to evaluate the need for administration of a therapeutic agent, to adjust dosage of such an agent, to change or use another agent or treatment regime, and the like.

"Statistical methods" include but are not limited to analysis of variance, classification algorithms, classification and regression trees, Fisher's Exact Test, linear algorithm, linear discriminatory analysis, linear regression, logistic algorithm, multiple regression, nearest shrunken centroids classifier, Pearson correlation, prediction algorithm, significance analysis of microarrays, one-tailed T-tests, two-tailed T-tests, voting algorithm, Wilcoxon's signed ranks test, and the like.

"Substrate" refers to any rigid or semi-rigid support to which antibodies, nucleic acids or proteins are bound and includes magnetic or nonmagnetic beads, capillaries or other tubing, chips, fibers, filters, gels, membranes, microparticles, plates, polymers, slides, and wafers with a variety of surface forms including channels, columns, pins, pores, trenches, wells and the like.

"Therapeutic agent" refers to any pharmaceutical molecule or compound that will bind specifically to a polynucleotide or to an epitope of a protein and stabilize or modulate the activity of the polynucleotide or protein. It can be composed of inorganic and/or organic substances including minerals, cofactors, nucleic acids, proteins, carbohydrates, fats, and lipids and includes but is not limited to Ace inhibitors, aspirin, azathioprine, B7RP-1-fc, β-blockers, brequinar sodium, campath-1H, celecoxib, chloroquine, corticosteroids, coumadin, cyclophosphamide, cyclosporin A, dehydroepiandrosterone, deoxyspergualin, dexamethasone, diclofenac, dolobid, etodolac, everolimus, FK778, feldene, fenoprofen, flurbiprofen, heparin, hydralazine, hydroxychloroquine, CTLA-4 or LFA3 immunoglobulin, ibuprofen, indomethacin, ISAtx-247, ketoprofen, ketorolac, leflunomide, meclophenamate, mefenamic acid, mepacrine, 6-mercaptopurine, meloxicam, methotrexate, mizoribine, mycophenolate mofetil, naproxen, oxaprozin, Plaquenil, NOX-100, prednisone, methyprenisone, rapamycin (sirolimus), sulindac, tacrolimus (FK506), thymoglobulin, tolmetin, tresperimus, U0126, and antibodies including but not limited to alpha lymphocyte antibodies, adalimumab, anti-CD3, anti-CD25, anti-CD52 anti-IL2R, and anti-TAC antibodies, basiliximab, daclizumab, etanercept, hu5C8, infliximab, OKT4, natalizumab and the like.

DETAILED DESCRIPTION OF THE INVENTION

Description

Microarray experiments have been used to find genes that are differentially expressed in patients diagnosed with systemic lupus erythrematosus (SLE). These genes were described in U.S. Pat. No. 6,905,827 and U.S. Ser. No. 10/990,298, each incorporated by reference herein in its entirety.

The invention provides methods of diagnosing or monitoring the status of SLE in a subject or patient by detecting the expression of all genes of a diagnostic set in the subject or patient wherein the diagnostic set has two or more genes having expression correlated with the classification or status of SLE; and diagnosing or monitoring the status of SLE in the subject or patient by applying at least one statistical method to the expression of the genes of the diagnostic set.

The methods of the invention also include classifying the subject or patient as having type 1 SLE or type 2 SLE, predicting flare, and monitoring disease activity and treatment efficacy.

Diagnostic Genes of the Invention

The invention provides diagnostic sets containing genes that can be used to diagnosis and monitor SLE disease status. The diagnostic sets can also be used to predict occurrence and future complication of the disease.

Diagnostic genes were identified and validated for use in diagnosing and monitoring of SLE status by identifying genes for which a correlation exists between the SLE status of an individual as determined based on various disease criteria and the individual's expression of RNA or protein products corresponding to the gene. Disease criteria may include clinical data such as symptom rash, joint pain, malaise, rashes, blood counts (white and red), tests of renal function (e.g. creatinine, blood urea nitrogen, creative clearance), data obtained from laboratory tests, including complete blood counts with differentials, CRP, ESR, ANA, Serum IL6, Soluble CD40 ligand, LDL, HDL, Anti-DNA antibodies, rheumatoid factor, C3, C4, serum creatinine and any medication levels, the need for pain medications, cumulative doses or immunosuppressive therapy, symptoms or any manifestation of carotid atherosclerosis (e.g. ultrasound diagnosis or any other manifestations of the disease), data from surgical procedures such as gross operative findings and pathological evaluation of resected tissues and biopsies (e.g., renal, CNS), information on pharmacological therapy and treatment changes, clinical diagnoses of disease "flare", hospitalizations, death, response to medications, quantitative joint exams, results from health assessment questionnaires (HAQs), and other clinical measures of patient symptoms and disability. Disease criteria also include the clinical score known as SLEDAI (Bombadier C, Gladman D D, Urowitz M B, Caron D, Chang C H and the Committee on Prognosis Studies in SLE: Derivation of the SLEDAI for Lupus Patients. Arthritis Rheum 35:630-640, 1992.).

The diagnostic genes of this invention include sequences corresponding those provided by the accession numbers and Unigene numbers provided in Table 1 and 2. The 60-mer sequences provided in the Tables are unique identifiers for the diagnostic genes of this invention. Therefore, the diagnostic genes of this invention also include sequences containing the 60-mer sequence provided in the Tables. In other words, the diagnostic genes may be partially or totally contained in (or derived from) the full-length gene sequences referenced in Tables 1 and 2.

In certain embodiments, the diagnostic genes of this invention include any sequences whose expression correlates with the expression of all genes which correlate with IFI27, such as the sequences provided by the accession numbers and Unigene numbers provided in Table 2.

Homologs and variants of the nucleic acid molecules in Table 1 and Table 2 may also be part of the diagnostic gene set. Homologs and variants of these nucleic acid molecules will possess a relatively high degree of sequence identity when aligned using standard methods. The sequences encompassed by the invention have at least 40-50, 50-60, 70-80, 80-85, 85-90, 90-95, or 95-100% sequence identity to the sequences disclosed herein.

The diagnostic gene set may also include other genes that are coexpressed with the correlated sequence or full-length gene. Genes may share expression patterns because they are regulated in the same molecular pathway or in the same cell type. Because of the similarity of expression behavior, these genes are identified as surrogates in that they can substitute for a diagnostic gene in a diagnostic gene set.

In some embodiments, diagnostic genes of the invention are used as a diagnostic gene set in combination with genes that are known to be associated with a disease state ("known markers"). The use of the diagnostic genes in combination with the known markers can provide information that is not obtainable through the known markers alone.

Gene Clusters

In some embodiments, the diagnostic genes of this invention are segregrated into "clusters". In preferred embodiments the diagnostic genes of this invention are sorted into clusters as indicated in Table 1 and diagnostic gene sets of this invention include at least one gene from each of at least two of gene clusters 1 through 15.

As used herein the term "gene cluster" or "cluster" refers to a group of genes related by expression pattern. In other words, a cluster of genes is a group of genes with similar regulation across different conditions, such as a patient having SLE or a patient without SLE. The expression profile for each gene in a cluster should be correlated with the expression profile of at least one other gene in that cluster. Correlation may be evaluated using a variety of statistical methods.

As used herein the term "surrogate" refers to a gene with an expression profile such that is so highly correlated with gene expression of another gene that it can substitute for a diagnostic gene in a diagnostic assay. Such genes are typically members of the same gene cluster as the diagnostic gene. For each member of a diagnostic gene set, a set of potential surrogates can be identified through identification of genes with similar expression patterns as described below.

Many statistical analyses produce a correlation coefficient to describe the relatedness between two gene expression patterns. Patterns may be considered correlated if the correlation coefficient is greater than or equal to 0.8. In preferred embodiments, the correlation coefficient should be greater than 0.85, 0.9 or 0.95. Other statistical methods produce a measure of mutual information to describe the relatedness between two gene expression patterns. Patterns may be considered correlated if the normalized mutual information value is greater than or equal to 0.7. In preferred embodiments, the normalized mutual information value should be greater than 0.8, 0.9 or 0.95. Patterns may also be considered similar if they cluster closely upon hierarchical clustering of gene expression data (Eisen et al. 1998). Similar patterns may be those genes that are among the 1, 2, 5, 10, 20, 50 or 100 nearest neighbors in a hierarchical clustering or have a similarity score (Eisen et al. 1998) of >0.5, 0.7, 0.8, 0.9, 0.95 or 0.99. Similar patterns may also be identified as those genes found to be surrogates in a classification tree by CART (Breiman et al. 1994).

Often, but not always, members of a gene cluster have similar biological functions in addition to similar gene expression patterns. For example, all genes in a particular cluster may be associated with a particular biological pathway or cell type. Representative cell types associated with diagnostic genes of this invention include granulocytes, NK cells, red blood cells, and platelets. Is is expected that the expression pattern of other genes in the same pathway or cell type will also be part of the same cluster and may be useful as surrogates.

Correlated genes, clusters and surrogates are all useful as diagnostic genes of the invention. These surrogates may be used as diagnostic genes in an assay instead of, or in addition to, the diagnostic genes for which they are surrogates.

Clusters also provide a means to ensure that the diagnostic gene sets do not contain redundant information. Diagnostic gene sets of the invention therefore preferably include genes from different clusters. For example, diagnostic gene sets of the invention preferably include at least one gene from at least two gene clusters.

Primer and Probe Sets

The invention further provides methods for producing diagnostic primer sets or probe sets. It is understood that a probe includes any reagent capable of specifically identifying genes in diagnostic setss, and include but are not limited to DNA, RNA, cDNA, splice variants, primers, probe sets, peptide nucleic acids, locked nucleic acids, amplicons, synthetic oligonucleotide, and partial or full-length nucleic acid sequences. In addition, the probe may identify the protein product of a diagnostic gene, and include, for example, antibodies and other affinity reagents. In some applications, a probe set may include one or more oligonucleotide that detects the expression of one or more of the selected genes for the diagnostic set.

It is also understood that each probe can correspond to one gene, or multiple probes can correspond to one gene, or both, or one probe can correspond to more than one gene.

In some embodiments, a diagnostic probe set is immobilized on an array. The array may be a chip array, a plate array, a bead array, a pin array, a membrane array, a solid surface array, a liquid array, an oligonucleotide array, a polynucleotide array or a cDNA array, a microtiter plate, a pin array, a bead array, a membrane or a chip.

Obtaining DNA, RNA and Protein Samples for Detection of Expression

Gene expression can be evaluated at the level of DNA, or RNA or protein products. A variety of techniques are available for the isolation of DNA, RNA and protein from bodily fluids.

A variety of techniques are available for the isolation of RNA from samples. Any technique that allows isolation of mRNA from cells (in the presence or absence of rRNA and tRNA) can be utilized. For example, by means of aspiration of body fluid, biopsy of a tissue or organ, drawing of peripheral blood, endoscopy, and lavage followed by aspiration, RNA can be isolated from ascites, bile, blood, cerebronspinal fluid, lymph, sputum, and/or urine. By the same methods, RNA can also be isolated from the central nervous system, joints, kidneys, liver, lungs, oral cavity, sinuses, skin, and vasculature.

Methods for Obtaining Expression Data

Numerous methods for obtaining expression data are known, and any one or more of these techniques, singly or in combination, are suitable for detecting expression in the context of the present invention.

For example, expression patterns can be evaluated by northern analysis, PCR, RT-PCR, Taq Man analysis, FRET detection, monitoring one or more molecular beacons, hybridization to an oligonucleotide array, hybridization to a cDNA array, hybridization to a polynucleotide array, hybridization to a liquid microarray, hybridization to a microelectric array, cDNA sequencing, clone hybridization, cDNA fragment fingerprinting, serial analysis of gene expression (SAGE), subtractive hybridization, differential display and/ or differential screening (see, e.g., Lockhart and Winzeler (2000) Nature 405:827-836, and references cited therein). Oligonucleotide hybridization may occur in solution or on substrates including, but not limited to magnetic or nonmagnetic beads, chips, fibers, filters, gels, membranes, microparticles, plates, polymers, slides, capillary tubing, and wafers with surface features selected from channels, columns, pins, pores, trenches, and wells.

It is understood that for detection of gene expression, variations in the disclosed sequences will still permit detection of gene expression. The degree of sequence identity required to detect gene expression varies depending on the length of the oligomer. For a 60 mer, 6-8 random mutations or 6-8 random deletions in a 60 mer do not affect gene expression detection. Hughes, T R, et al. "Expression profiling using microarrays fabricated by an ink-jet oligonucleotide synthesizer. Nature Biotechnology, 19:343-347 (2001). As the length of the DNA sequence is increased, the number of mutations or deletions permitted while still allowing the detection of gene expression is increased.

Alternatively, expression at the level of protein products of gene expression can be performed. For example, protein expression in a disease patient can be evaluated by one or more methods including, but not limited to Western analysis, two-dimensional gel analysis, chromatographic separation, mass spectrometric detection, protein-fusion reporter constructs, calorimetric assays, binding to a protein array and characterization of polysomal mRNA. One particularly favored approach involves binding of labeled protein expression products to an array of antibodies specific for members of the candidate library. Methods for producing and evaluating antibodies are widespread in the art, see, e.g., Coligan, supra; and Harlow and Lane (1989) Antibodies: A Laboratory Manual, Cold Spring Harbor Press, NY ("Harlow and Lane"). Additional details regarding a variety of immunological and immunoassay procedures adaptable to the present invention by selection of antibody reagents specific for the products of candidate nucleotide sequences can be found in, e.g., Stites and Terr (eds.)(1991) Basic and Clinical Immunology, 7.sup.th ed., and Paul, supra. Another approach uses systems for performing desorption spectrometry. Commercially available systems, e.g., from Ciphergen Biosystems, Inc. (Fremont, Calif.) are particularly well suited to quantitative analysis of protein expression. Indeed, Protein Chip® arrays (see, e.g., the website, ciphergen.com) used in desorption spectrometry approaches provide arrays for detection of protein expression. Alternatively, affinity reagents (e.g., antibodies, small molecules, etc.) are developed that recognize epitopes of the protein product. Affinity assays are used in protein array assays, e.g. to detect the presence or absence of particular proteins. Alternatively, affinity reagents are used to detect expression using the methods described above. In the case of a protein that is expressed on the cell surface of leukocytes, labeled affinity reagents are bound to populations of leukocytes, and leukocytes expressing the protein are identified and counted using fluorescent activated cell sorting (FACS).

Expression Profiles

Expression patterns, or profiles, of a plurality of genes corresponding to members of the diagnostic set are evaluated in one or more SLE patients. These expression patterns constitute a set of relative or absolute expression values for some number of RNA or protein products corresponding to the plurality of genes evaluated, which is referred to herein as the subject's "expression profile" for those genes. While expression patterns for as few as one independent member of the diagnostic set can be obtained, it is generally preferable to obtain expression patterns corresponding to a larger number of genes, e.g., about 2, about 5, about 10, about 20, about 50, about 100, about 200, about 500, or about 1000, or more. The expression pattern for each differentially expressed component member of the set provides a finite specificity and sensitivity with respect to predictive value, e.g., for diagnosis, prognosis, monitoring, and the like.

Evaluation of Expression Data and Profiles

Expression profiles can be evaluated by qualitative and/or quantitative measures. Certain techniques for evaluating gene expression (as RNA or protein products) yield data that are predominantly qualitative in nature. That is, the methods detect differences in expression that classify expression into distinct modes without providing significant information regarding quantitative aspects of expression. For example, a technique can be described as a qualitative technique if it detects the presence or absence of expression of a diagnostic nucleotide sequence, i.e., an on/off pattern of expression. Alternatively, a qualitative technique measures the presence (and/or absence) of different alleles, or variants, of a gene product.

In contrast, some methods provide data that characterizes expression in a quantitative manner. That is, the methods relate expression on a numerical scale. It will be understood that the numerical, and symbolic examples provided are arbitrary, and that any graduated scale (or any symbolic representation of a graduated scale) can be employed in the context of the present invention to describe quantitative differences in nucleotide sequence expression. Typically, such methods yield information corresponding to a relative increase or decrease in expression.

Any method that yields either quantitative or qualitative expression data is suitable for evaluating expression of diagnostic nucleotide sequence in a SLE subject or patient. In some cases, e.g., when multiple methods are employed to determine expression patterns for a plurality of diagnostic nucleotide sequences, the recovered data, e.g., the expression profile for the nucleotide sequences is a combination of quantitative and qualitative data.

In some applications, expression of the plurality of diagnostic nucleotide sequences is evaluated sequentially. This is typically the case for methods that can be characterized as low- to moderate-throughput. In contrast, as the throughput of the elected assay increases, expression for the plurality of diagnostic nucleotide sequences in a sample or multiple samples of SLE subjects or patients is assayed simultaneously. Again, the methods (and throughput) are largely determined by the individual practitioner, although, typically, it is preferable to employ methods that permit rapid, e.g. automated or partially automated, preparation and detection, on a scale that is time-efficient and cost-effective.

In one some embodiments, once expression levels for a diagnostic set of genes are determined, a diagnostic classifier (a mathematical function that assigns samples to diagnostic categories based on expression data) is applied to unknown sample expression levels in order to diagnose or monitor the status of the SLE in a subject or patient.

The diagnostic classifier is typically derived from a prediction algorithm derived from statistical methods including, but not limited to, analysis of variance, classification algorithms, classification and regression trees, Fisher's Exact Test, linear algorithm. linear discriminatory analysis, linear regression, logistic algorithm, multiple regression, nearest shrunken centroids classifier, Pearson correlation, prediction algorithm, significance analysis of microarrays, one-tailed T-test, two tailed T-tests, voting algorithm, Wilcoxon's signed ranks test and the like.

Expression Reference Standards

In other embodiments, comparison of patient gene expression with reference profiles is used to evaluate expression data and to monitor the status of SLE, to predict flare, and to assess treatment efficacy.

For example, expression profiles derived from a patient (i.e., subjects diagnosed with, or exhibiting symptoms of, or exhibiting a disease criterion, or under a doctor's care for a disease) sample are compared to a control or standard expression RNA to facilitate comparison of expression profiles (e.g. of a set of candidate nucleotide sequences) from a group of patients relative to each other (i.e., from one patient in the group to other patients in the group, or to patients in another group).

The reference RNA used should have desirable features of low cost and simplicity of production on a large scale. Additionally, the reference RNA should contain measurable amounts of as many of the genes of the candidate library as possible.

For example, in one approach to identifying diagnostic gene sets and evaluating expression data, expression profiles derived from patient samples are compared to an expression reference "standard." Standard expression reference can be derived from samples from at least one normal subject and from at least one patient diagnosed with SLE and include but are not limited to a gene expression from one or more patients with quiescent type 1 SLE, from one or more patients with quiescent type 2 SLE, from one or more patients with type 1 SLE showing increased disease activity or flare, from one or more patients with type 2 SLE showing increased disease activity or flare, from one or more patients with type 1 SLE that had been treated with an immunosuppressant, from one or more patients with type 2 SLE that had been treated with an immunosuppressant, from one or more patients with type 1 SLE that had been treated with a therapeutic agent, and from one or more patients with type 2 SLE that had been treated with a therapeutic agent.

Use of an expression reference standard is particularly useful when the expression of large numbers of nucleotide sequences is assayed, e.g. in an array, and in certain other applications, e.g. qualitative PCR, RT-PCR, etc., where it is desirable to compare a sample profile to a standard profile, and/or when large numbers of expression profiles, e.g. a patient population, are to be compared. Generally, an expression reference standard should be available in large quantities, should be a good substrate for amplification and labeling reactions, and should be capable of detecting a large percentage of candidate nucleic acids using suitable expression profiling technology.

Alternatively, the expression reference standard can be derived from any subject or class of subjects including healthy subjects or subjects diagnosed with the same or a different disease or disease criterion. Expression profiles from subjects in two distinct classes are compared to determine which subset of genes in the diagnostic set best distinguish between the two subject classes. It will be appreciated that in the present context, the term "distinct classes" is relevant to at least one distinguishable criterion relevant to a disease of interest, a "disease criterion." The classes can, of course, demonstrate significant overlap (or identity) with respect to other disease criteria, or with respect to disease diagnoses, prognoses, or the like. The mode of discovery involves, e.g., comparing the molecular signature of different subject classes to each other (such as patient to control, patients with a first diagnosis to patients with a second diagnosis, etc.) or by comparing the molecular signatures of a single individual taken at different time points. The invention can be applied to a broad range of diseases, disease criteria, conditions and other clinical and/or epidemiological questions, as further discussed above/below.

In some applications, when a single patient sample is obtained, it may still be desirable to compare the expression profile of that sample to some reference expression profile. In this case, one can determine the change of expression between the patient's sample and a reference expression profile that is appropriate for that patient and the medical condition in question. For example, a reference expression profile can be determined for all patients without the disease criterion in question who have similar characteristics, such as age, sex, race, diagnoses, etc.

Classification of SLE Patients into Longitudinally Stable Classes of SLE

In some embodiments, the invention provides methods for diagnosis of a patient as having a longitudinally stable classification of SLE by detecting the expression of genes whose expression correlates with the expression of IFI27. In some embodiments, the method is practiced as part of a method to diagnose or monitor the status of SLE in a patient.

In preferred embodiments, a subject is classified into one of at least two classes of SLE by detecting the expression of at least two genes whose expression corrrelates with the expression of IFI27 from about 0.5 to about 1.0 and from about –0.5 to about –1.0 calculated using Pearson correlation and classifying the subject as having type I or type II SLE based on the expression of these two genes. In preferred embodiments, the genes are provided in Table 2.

Pharmacogenomics

Pharmocogenomics is the study of the individual propensity to respond to a particular drug therapy (combination of therapies). In this context, response can mean whether a particular drug will work on a particular patient, e.g. some patients respond to one drug but not to another drug. Response can also refer to the likelihood of successful treatment or the assessment of progress in treatment. Titration of drug therapy to a particular patient is also included in this description, e.g. different patients can respond to different doses of a given medication. This aspect may be important when drugs with side-effects or interactions with other drug therapies are contemplated.

Diagnostic gene sets are developed and validated for use in assessing whether a patient will respond to a particular therapy and/or monitoring response of a patient to drug therapy (therapies). Disease criteria correspond to presence or absence of clinical symptoms or clinical endpoints, presence of side-effects or interaction with other drug(s). The diagnostic nucleotide set may further include nucleotide sequences that are targets of drug treatment or markers of active disease.

Example 1 describes the SLE patients, criteria for their diagnosis, and collection and characterization of blood and tissue samples from normal subjects and patients in periods of quiescence and flare. Although analyses determined that expression profiles contained a subset of genes, designated interferon response genes (INFr), whose expression generally correlated with disease severity, but not with change in patient status from quiescence to flare. Based on this fact, subject and patient samples can be queried for expression of the subset of INFr genes.

Example 2 describes the analysis of gene expression in samples from SLE patients. Pearson correlation was used to identify 15 different, pathway or cell-type specific, gene clusters that were differentially expressed in patient samples during periods of disease quiescence versus periods when that patient was converting from quiescence to flare. These clusters are also shown and described in Table 1. Column 1 shows the number of the cluster; column 2, the array ID; column 3, the GenBank ID; column 4, the gene ID; and column 5, a short description of the gene.

To diagnose and monitor the status of a subject or patient, a sample from the subject or patient is analyzed for differential expression of at least one gene selected from each of at least two different gene clusters shown in Table 1. Comparison of patient gene expression with reference profiles can also serve to monitor the status of SLE, to predict flare, and to assess treatment efficacy.

Prediction algorithms were developed using gene expression representing quiescent (QQ) versus flare (QF) samples. Multiple regression analysis was used to associate gene expression with flare, and linear regression was used to examine individual genes. In general, prediction algorithms were trained using 90% of the samples; and cross-validated, using 10% of samples in 100 iterations as explained in Example 3. Prediction algorithms can be also used to assess patient prognosis—presence or likelihood of developing premature carotid atherosclerosis or progressing to end-stage organ damage—and to monitor treatment of SLE patients. Of particular interest are samples and expression profiles from patients who responded to a given steroid or immunosuppressant treatment regime versus samples or profiles from those same patients where the medication stopped working or from different patients who did not respond or were resistant to a specific medication or treatment regime.

Gene expression was analyzed using at least one statistical method selected from analysis of variance, classification algorithms, classification and regression trees, Fisher's Exact Test, linear algorithm, linear discriminatory analysis, linear regression, logistic algorithm, multiple regression, nearest shrunken centroids classifier, Pearson correlation, prediction algorithm, significance analysis of microarrays, one-tailed T-tests, two-tailed T-tests, voting algorithm, Wilcoxon's signed ranks test and the like. One or more of these methods were used to process and evaluate the normal and patient samples and to choose those samples used as reference profiles.

Example 4 describes the classification of SLE patients into type 1 SLE and type 2 SLE is based on IFNr score. A linear algorithm was used in the analysis of the expression of at least two INFr genes selected from Table 2. Expression of IFI27 was chosen as the basis to which all of other genes expressed in SLE were compared, and Table 2 shows the 190 features (probes on a microarray) that represent those INFr genes positively correlated with IFI27 (cutoff of $\geq 0.5$ or $<-0.5$ using Pearson correlation). Column 1 of Table 2 shows the feature ID on the Human Genome CGH 44A microarrays (Agilent Technologies, Palo Alto Calif.) array; column 2, the name of probe; column 3, symbol or identifier for the gene; column 5, description of the gene; and column 6, correlation with IFI27. For purposes of demonstration, IFI27 and the two other INFr genes highlighted in Table 2 were used to develop an exemplary algorithm, IFI27+IFI144*(1.1296)+OAS3* (1.8136), that can be used to produce an INFr score.

The analysis and validation of data from paired, longitudinal samples as described in Example 4 are summarized in Table 3. Exemplary data is shown for the first 25 of 81 patients. The data shows lack of correlation with SLEDAI and the stability of IFNr score in individual patients during periods of quiescence and flare. Regardless of disease activity or flare, a high INFr score classified a patient as having type 1 SLE, a condition characterized by more severe SLE symptoms such as increased organ involvement and dysfunction, low complement levels, and high titer of anti-double-stranded DNA (dsDNA) antibodies; and a low INFr score classified a patient as having type 2 SLE which is generally characterized by less severe symptoms. It is contemplated that many combinations of at least two INFr genes and algorithms developed using them can be used to classify SLE patients.

Examples 5-8 describe how normal and patient samples were purified and handled. Examples 9-11 describe the nucleic acid technologies (microarray and polymerase chain reaction) used to detect gene expression and produce gene expression patient and reference profiles.

Methods are presented for screening subjects for SLE, for classifying a patient already diagnosed with SLE as having type 1 SLE or type 2 SLE, for predicting disease activity or flare, for selecting an effective immunosuppressant and/or therapeutic agent for treatment of SLE, and for identifying subjects with SLE from subjects with other rheumatic diseases.

Useful reference profiles were derived from samples from at least one normal subject and from at least one patient diagnosed with SLE and include but are not limited to a gene expression from one or more patients with quiescent type 1 SLE, from one or more patients with quiescent type 2 SLE, from one or more patients with type I SLE showing increased disease activity or flare, from one or more patients with type 2 SLE showing increased disease activity or flare, from one or more patients with type I SLE that had been treated with an immunosuppressant, from one or more patients with type 2 SLE that had been treated with an immunosuppressant, from one or more patients with type 1 SLE that had been treated with a therapeutic agent, and from one or more patients with type 2 SLE that had been treated with a therapeutic agent.

Reagents used to establish a gene expression profile include but are not limited to:
1) genes and their splice variants, primers, probe sets, peptide nucleic acids, locked nucleic acids and amplicons that can be used in nucleic acid technologies including but not limited to hybridization on arrays and amplification using quantitative RT-PCR; and 2) proteins and their fragments, antibodies, and affinity reagents that can be used in protein technologies including but not limited to protein or antibody arrays and enzyme-linked immunosorbent assays (ELISAs). These reagents can be used in assays or diagnostic kits to screen subjects for SLE.

Assays or diagnostic kits based on the primers and probe sets as described in Example 9 can be used with a sample from a subject with symptoms of a rheumatic disease to diagnose, classify or rule out SLE; and with a sample from a patient diagnosed with type 1 SLE or type 2 SLE to select a clinical trial, to predict flare, to detect immunosuppressant responsiveness, to determine efficacy of a therapeutic agent, to design treatment regimes, to monitor the status of the patient or treatment regime. In one alternative, the diagnostic kit includes an array of nucleic acid molecules or antibodies; in another, the diagnostic kit includes probe sets for use in quantitative RT-PCR.

Pharmacogenomics is the study of an individual's response to a particular therapeutic agent, immunosuppressant or combinations of agents. In this context, response refers to whether a particular agent or drug will work better for a particular type 1 SLE or type 2 SLE patient. The methods disclosed provide for assigning a patient to a clinical trial based on classification as type 1 SLE or type 2 SLE and disease status (quiescent or flare).

Pharmacogenomics is also important in determining the dosage of a therapeutic agent based on classification and disease status of the patient. It is contemplated that a patient diagnosed with type 1 SLE will respond differently to a particular immunosuppressant or therapeutic agent than a patient diagnosed with type 2 SLE. Individual response must also be taken into account relative to the side-effects or interactions of various immunosuppressant or therapeutic agents. Some potentially useful therapeutic agents and immunosuppressants are listed in the definitions and claims.

The present invention contains many preferred embodiments and includes material from patents, patent applications and other publications incorporated by reference in their entirety for all purposes, but especially for details in practicing the invention and known to those in the art.

EXAMPLES

Example 1

Characterization of Patients and Samples

Patients who met the American College of Rheumatology (ACR) criteria for the diagnosis of SLE (malar rash, discoid rash, photosensitivity, oral ulcers, arthritis, serositis, renal disorder, neurologic disorder, hematologic disorder, immunologic disorder, and antinuclear antibody) were identified (cf. Tan et al (1982) Arthritis Rheum 25:1271-7). After institutional review and approval, patients gave informed consent and were included in the Lupus Disease Activity Monitoring and Risk Stratification Archive Discovery Microarray Study.

The samples and clinical data were available via the Autoimmune Biomarkers Collaborative Network (ABCoN).

Blood and/or tissue samples and clinical data have been collected from patients managed at Johns Hopkins Medical Center (JHMC) within the Hopkins Lupus Cohort. In this cohort, all SLE patients have been followed according to protocol with visits at a minimum of every 3 months. The table below has self-explanatory columns that show demographic information for the patients in the SLE cohort.

|  | Number (% of total cohort) |
|---|---|
| Age at Entry into cohort (yrs) |  |
| <30 | 304 (32%) |
| 30 to 49 | 511 (53%) |
| 50+ | 148 (15%) |
| Female | 888 (92%) |
| Race |  |
| White | 529 (55%) |
| Black | 403 (42%) |
| Other | 31 (3%) |
| Education |  |
| <12 yrs | 124 (14%) |
| High School | 281 (31%) |
| Some College | 497 (55%) |
| Years in cohort |  |
| 0 | 191 (19%) |
| 1 to 3 | 409 (41%) |
| 4+ | 391 (40%) |
| Number of cohort visits |  |
| 1 | 78 (8%) |
| 2 to 8 | 320 (32%) |
| 9 to 44 | 492 (50%) |
| 45+ | 101 (10%) |
| Years with SLE prior to cohort entry |  |
| 0 | 304 (31%) |
| 1 to 4 | 325 (33%) |
| 5+ | 362 (36%) |

As seen above, the cohort was more or less racially balanced, and its individuals represented a broad socioeconomic spectrum. The patient samples and clinical data used in this investigation were from SLE patients who had been in the cohort for more than one year. In total, these patients visited the clinic 1782 times (an average of 5.9 quarterly visits for each patient). In the alternative, samples for training and validating prediction algorithms were obtained from the Autoimmune Disease Registry of the Hospital for Special Surgery (HSS; New York City N.Y.).

Clinical data were examined for each patient in order to select samples for use in training or validation studies. Whereas additional samples can be added to the training set, a completely unique set must be used for validation. Both clinical and existing expression data were analyzed for 81 of the first 100 patients in the cohort and a subset of these patients was used for the training study. For the training study, the following classes of samples (Q=quiescent, F=flare) were defined as follows:

QF1: primary QF quiescent sample that proceeds to flare within 150 days
No prior flare within 60 day
1 primary pair per patient only
SLEDAI ≧4
QF4: second QF1

A second, unique QF1|F from the same patient
QF4 precedes a distinct F from the QF1
Can be combined with QF1 for analysis
QF5: earliest baseline additional, earlier QF for a given QF1|F
F: high current disease activity SLEDAI increases ≧4 from previous visit
PGA (Physician's Global Assessment) = rating of disease activity as high or increasing
QQ: primary quiescent and stable SLEDAI ≦4 and no flares in next 150 days or more Sample Characteristics The table below shows the comparison between the various classes. Column one lists the QF, F and QQ classes as defined above; column two, the groups within the class; column three, the number of patients in the class or group; column four, the average (avg) days (da) to flare; column five, the median days to flare; column six, the average (avg) increase in SLEDAI; column seven, the median (med) increase in SLEDAI; column eight, the average increase in SLEDAI at flare; and column nine, the number of visits prior to flare.

| Class | Group | No. | Avg da to F | Med da to F | SLEDAI avg | SLEDAI med | F SLEDAI | Visits to F |
|---|---|---|---|---|---|---|---|---|
| QF | 1 | 30 | 87 | 87 | 5.7 | 4 | 7.6 | 1.1 |
|  | 4 | 3 | 78 | 84 | 6.7 | 4 | 8 | 1 |
|  | 5 | 12 | 227 | 186 |  |  |  |  |
| F |  | 37 |  |  | 7.7 |  |  |  |
| QQ |  | 34 | 357 | 340 |  |  |  |  |

Sample Matching

One of the most important class comparisons was QQ vs. QF. Molecular characterization of the samples that do not progress in disease activity or proceed to flare were particularly important for assessing risk and efficacy of treatment regime, determining prognosis, and the like. A typical subset of patients was characterized in the table below. In that the patients have similar clinical data, their samples showed that observed difference in class was due to activation at the molecular level (measured by gene expression) and not due to observable differences. Column one shows class or T-test; column two, number of patients (No), column three, physician's global assessment (PGA); column four, SLEDAI score, column five, prednisone treatment (Pred); column six, percent of patients on immunosuppressant treatment (Immuno); column seven, percent of patients on intravenous treatment (IVS); and column seven, percent of the patients who are female.

|  | No | PGA | SLEDAI | Pred | Immuno | IVS | % Female |
|---|---|---|---|---|---|---|---|
| QF1 | 30 | 0.79 | 1.87 | 6.96 | 47% | 17% | 97 |
| QQ | 34 | 0.58 | 1.65 | 5.33 | 44% | 12% | 88 |
| T-test |  | 0.14 | 0.60 | 0.41 | 0.84 | 0.58 | 0.22 |
| QF1 + 4 | 33 | 0.78 | 1.82 | 7.75 | 45% | 45% | 97% |
| QQ | 34 | 0.58 | 1.65 | 5.33 | 44% | 12% | 88% |
| T-test |  | 0.17 | 0.68 | 0.26 | 0.91 | 0.69 | 0.18 |

Although none of the clinical variables was statistically significant between classes, there was a slight trend towards more severe disease in the QF group. It must be noted that this trend was not clinically relevant; and as samples are added to the study, it is expected that even this slight trend will disappear.

The normal control sample was a pooled blood sample taken from equal numbers of male and female Expression Genetics employees. These donors were healthy at the time the sample was collected, and none had obvious disease symptoms or diagnosis of SLE or any other rheumatic disease.

Example 2

Analyses of Gene Expression Profiles of SLE Patients Proceeding to Flare

The basis for diagnosing and monitoring the status of SLE in patients involved detecting differential gene expression between quiescence (QQ) and flare (QF) samples. K-means clustering of gene using GeneSpring GX 7.3 were done with the following criteria Number of clusters 15, Number of iterations 200, Similarity Measure Pearson Correlation and genes in which half of the samples did not have data were not used Genes shown in Table 1 were defined as those with a p-value≦0.05 and a fold change ≧1.2. The genes were clustered to group genes which represented a particular pathway or cell type. The table below shows the number of the cluster as presented in Table 1, the average Radius between the clusters and an all clusters average. Average Radius is calculated by the root mean square of the Euclidean distances between each gene and the centroid.

| Cluster No | Cell Type | Average Radius |
|---|---|---|
| 1 | Granulocytes & B cells | 5.15 |
| 2 | NK cells | 6.02 |
| 3 | Granulocytes | 7.23 |
| 4 | Granulocytes | 6.82 |
| 5 | Platelet | 6.31 |
| 6 | All Cell Types | 6.32 |
| 7 | B cells | 4.39 |
| 8 | All Cell Types | 6.85 |
| 9 | B cells | 5.88 |
| 10 | All Cell Types | 8.81 |
| 11 | All Cell Types | 8.34 |
| 12 | All Cell Types | 3.67 |
| 13 | Red Blood Cells | 6.87 |
| 14 | Red Blood Cells | 4.98 |
| 15 | All Cell Types | 2.19 |
| All Clusters Ave |  | 5.99 |

The genes shown in Table 1 were used with the statistical methods described below to diagnose and monitor the status of SLE patients, to predict flare and to assess treatment efficacy.

The various analyses were carried out using classification and prediction algorithms, software and programs including, but not limited to, analysis of variance, classification and regression trees (Brieman et al. (1984) *Classification and Regression Trees*, Wadsworth, Belmont Calif.), linear discriminatory analysis (Statsoft, Tulsa Okla.), multiple additive regression trees (Friedman (2002) Stanford University, Stanford Calif.), nearest shrunken centroids classifier (Tibshirani et al. (2002) PNAS 99:6567-6572), significance analysis of microarrays (Tusher et al. (2001) PNAS 98:5116-5121), one and two tailed T-tests, Wilcoxon's signed ranks test, and the like. The statistical analyses applied to both array and PCR expression data were also described in the Detailed Description of the Invention and in Example 5 of U.S. Pat. No. 6,905,827 incorporated by reference herein in its entirety.

In addition to expression data, any piece of clinical data collected from patients can be used in a correlation or classification analysis. Continuous variables including but not limited to albumin, autoantibodies, hemoglobin or other measures of organ function that contribute to SLEDAI score can be used for correlation analysis. In some cases, the logarithm of the values was used for the analysis. When these variables were included in the analysis, they were treated as another "gene". For example, samples from kidney biopsies can be used to divide SLE patients into groups with or without renal disease. From the analyses of clinical manifestations carried out in this study and differences in clinical manifestations reported by others, it is contemplated that categorical variables such gender, ethnicity and socioeconomic status can also contribute to classification, prediction of flare, and selection or modulation of effective therapeutics.

Example 3

Prediction Algorithms

After all the expression and clinical data were placed in a relational database, these data were used to build prediction algorithms. The prediction algorithms were applied to gene expression profiles from SLE patients converting from quiescence to flare to identify sets of differentially expressed genes for monitoring the status of SLE, specifically for predicting flare or disease activity and effective treatment regimes.

Once a set of genes and expression criteria for those genes have been established for classification, cross-validation was done. Validation of the algorithm by these means yielded an estimate of the predictive value of the algorithm on the target population. For example, a 10-fold cross-validation analysis excluded 10% of the training samples from the analysis, and the classification algorithm was built with the remaining 90%. The 10% of the samples that were initially excluded were then used as a test set for the algorithm. The process was repeated 10 times with 10% of the samples being used as a test set each time. Through this analysis, it was possible to derive a cross-validation error which helped estimate the robustness of the algorithm for use on previously untested samples (i.e., samples that were not included in the training analysis). Untested samples came from the JHMC or HSS archives In the alternative, the samples can come from a new clinical study.

Example 4

Classification of Patients as Type 1 SLE and Type 2 SLE

Another step toward better monitoring the status of SLE patients was to classify them as having either type 1 SLE or type 2 SLE. A number of comparisons of data in the relational database were made and validated as described below.

Gene Expression Patterns

One of the comparisons of gene expression patterns was to analyze genes that were differentially expressed between paired QF1 and F samples from the same patient taken from about two to about six months apart. The first sample was from a time period when the patient's disease activity was low (SLEDAI 0-4), but the second sample from the same patient showed increased disease activity and a SLEDAI≧4. In this process, examination of some of the genes known to be expressed in inflammation or immune disorders showed nearly parallel expression patterns in paired quiescent/flare (QF) and flare (F) patient. The expression of one of those genes, IFI27, is shown in FIG. 1.

The x-axis of FIG. 1 represents patient number and the y-axis, the $Log_{10}$ expression ratio for IFI27, FIG. 1 demonstrates that IFI27 was not differentially expressed according to disease activity or flare. Further examination of longitudinal data showed that expression of INFr genes placed SLE patients into at least two different groups.

INFr score

The relational database of SLE data was searched for genes whose expression correlated with IFI27≧0.5 or ≦−0.5 using Pearson correlation; these designated INFr genes are listed in Table 2. Longitudinal data from an initial group of 81 patients covering a period of up to two years (including extra time points available in the QF4 and QF5 classes) was used to examine IFNr gene expression.

Although many different algorithms were contemplated, one exemplary algorithm was developed to demonstrate how to use three INFr genes to calculate an IFNr score. The genes that encode IFI27, IFI44 and OAS3, highlighted in Table 2, were used to develop the algorithm. The INFr score based on these three genes reflects the $Log_{10}$ ratio of patient sample expression over reference sample expression on the microarray after normalization using Feature Extraction v 7.5 software (Agilent Technologies). The standard deviation for each gene was normalized so that each of the genes would have the same influence on IFNr score. The exemplary algorithm is: IFI27+IFI144*(1.1296)+OAS3*(1.8136).

The genes used to derive INFr score are described as follows: 1) IFI27 (also known as ISG12 and p27) maps to chromosome 14q32, the location of the serine protease inhibitor gene cluster. IFI27 is induced by alpha interferon and localizes to the nuclear membrane. Since IFI27 is expressed in breast, head and neck carcinomas, it has been used to predict patient sensitivity to cisplatin and paclitaxel; 2) IFI44 (also known as MTAP44) is induced by α and β interferons, but not by γ interferon and aggregates to form microtubular-like structures in hepatitus-C infected cells; and 3) OAS3 maps to chromosome 12q24.2 and is an interferon-induced protein that catalyzes the synthesis of 2'-5' oligomers of adenosine.

Table 3 presents longitudinal data for patients with SLE. Column one shows patient number; column two, ABCoN ID followed by sample number; column three, sample designated as quiescent (QF) or flare (F); column four, date sample taken; column five, SLEDAI score; column six, IFNr score (high or low); column seven, days from first sample; and INFr score. The cutoff for distinguishing between high IFNr and low IFNr scores was the average of all INFr scores. Table 3 demonstrated: 1) longitudinal stability of INFr score in an individual over time, 2) the existence of at least two types of SLE as defined by high and low expression of IFNr genes, and 3) lack of correlation between SLEDAI and IFNr scores as shown for patients 2, 4, 6, 9, and 15.

The change from high to low INFr score or from high to low to high INFr score as seen in the data for patients 10 and 13, respectively, were further analyzed. A Fisher's Exact Test was used to calculate a p-value for hypothesized random discordant results. The conversion of one high to low and one low to high produced the p-value=0.000034 that the events happened at random.

Figure 2:
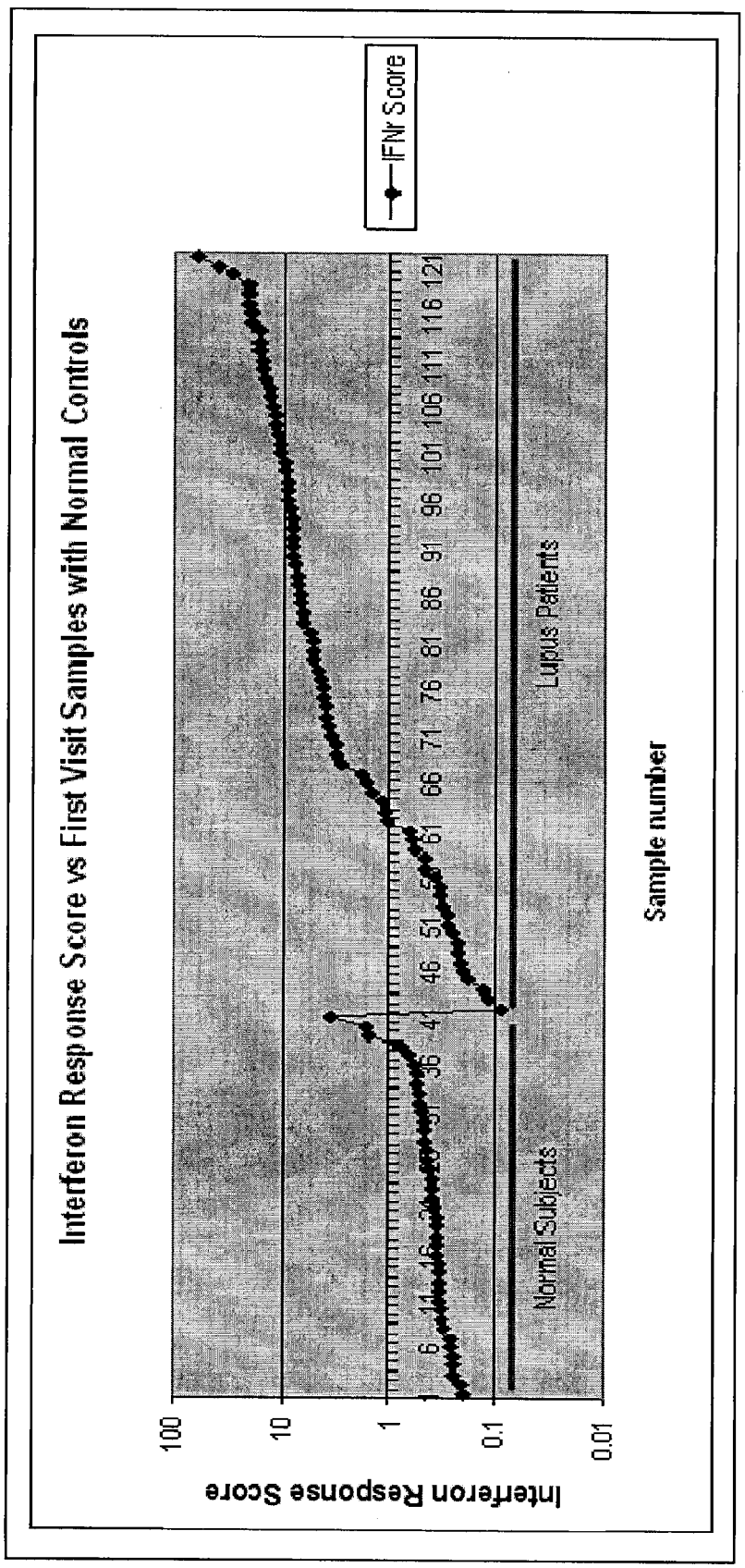
FIG. 2 shows the Interferon Response (INFr) score for normal controls and SLE patient.

Another way to look at IFNr score was to compare normal control and first visit patient samples. In FIG. 2, all samples were sorted low to high and plotted according to INFr score. The normal subjects are presented on the left side of the graph, and the 81 SLE (lupus) patients are presented on the right.

The x-axis shows the number assigned each normal subject or SLE patient, and the y-axis shows INFr score where the scale is fold. As shown on this graph, INFr scores varied by as much as 500-fold. Although they appeared healthy at the time of sampling, three of the normal subjects had slightly elevated IFNr scores that were attributed to infection, allergies, or other sub-acute, non-SLE conditions.

Figure 3:
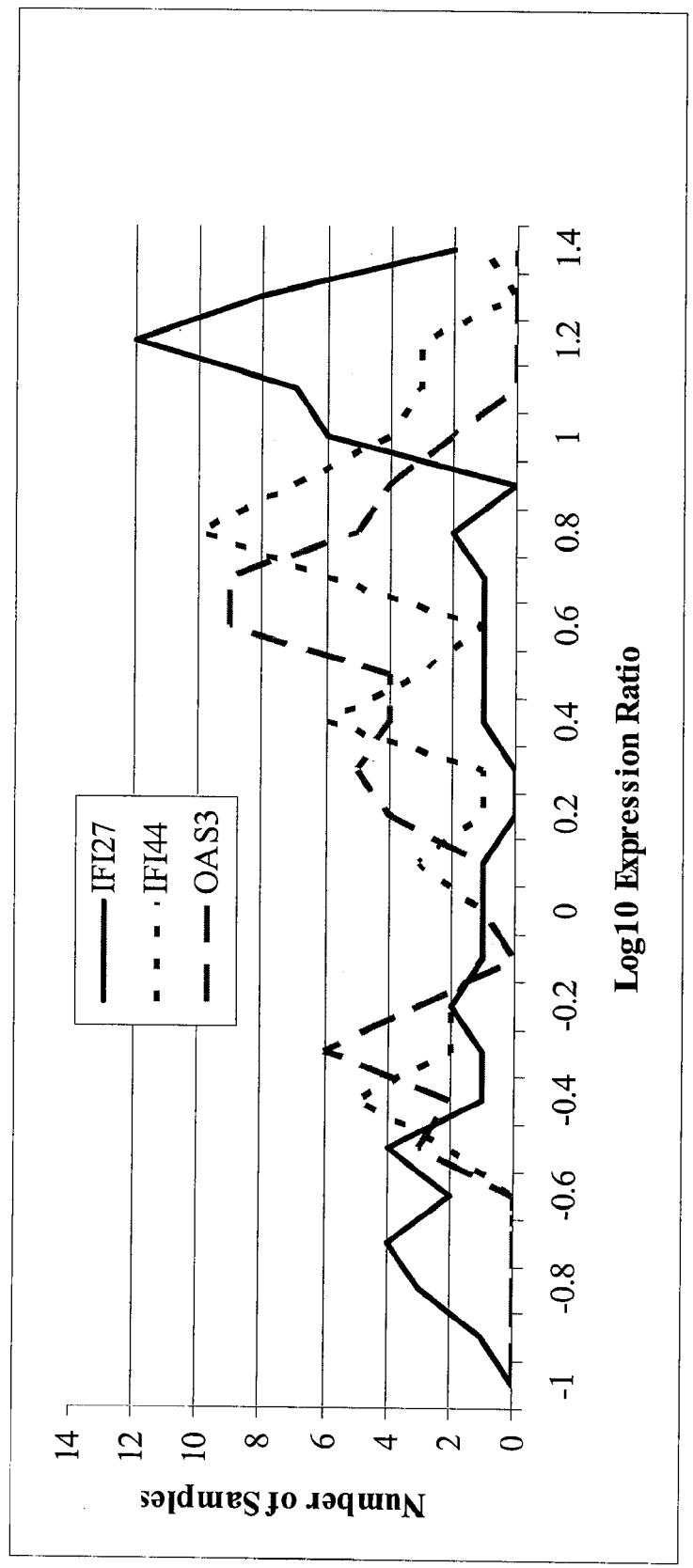
FIG. 3 shows the bimodal distribution for IFI27, IFI44, and OAS3 of SLE patients.

Since the INFr scores of the SLE patients appeared as a continuous slope in the graph above, the data was parsed. The graph for IFI27, IFI44, and OAS3 (FIG. 3) clearly showed the bimodal distribution of SLE patients (type 2 SLE to the left of zero and type I SLE to the right, on the x-axis) when number of samples was graphed against $log_{10}$ of the expression ratio.

Similar graphs or histograms can be plotted for any of the other INFr genes shown in Table 2, and any of these INFr genes can be used to develop an algorithm to classify SLE patients as type 1 SLE or type 2 SLE.

In further support of the stability of type 1 and type 2 SLE classification, a Fisher's Exact Test was applied to the hypothesis, "Do the highs stay high and the lows stay low?" The data presented in the table below produces a p-value=8.01e-13 that further demonstrates the validity of the bimodal distribution and the presence of at least two groups, type I SLE and type 2 SLE.

|  |  | First high | First low |
|---|---|---|---|
| Second | high | 48 | 4 |
| Second | low | 4 | 25 |

Although SLEDAI scores are on average higher in type 1 SLE patients (who generally show more severe symptoms), SLEDAI did not correlate with high or low INFr score. The clinical manifestations that did associate with type 1 SLE included low serum complement levels, high anti-double stranded DNA antibodies, and more renal disease.

Example 5

Harvesting and Preparation of Blood Samples

One or more of the methods and/or procedures below were used to prepare samples from SLE patients and normal control subjects. In the first method, two tubes of blood were drawn from each patient or normal control subject using either a peripheral venous blood draw or directly from a large-bore intra-arterial or intravenous catheter inserted in the femoral artery or vein, subclavian vein or internal jugular vein. Care was taken to avoid sample contamination with heparin since it interferes with RNA preparation.

In the second method, 8 ml of blood was drawn into a VACUTAINER CPT tube (BD Biosciences (BD), San Jose Calif.) containing the anticoagulant sodium citrate, Ficoll Hypaque density fluid, and a thixotropic polyester gel barrier permeable upon centrifugation to red blood cells (RBCs) and granulocytes but not to mononuclear cells. The blood was mixed with the anticoagulant in the tube by inverting the tube 5-10 times. Then, mononuclear cells and plasma were separated using the following procedures.

In one procedure, the mononuclear cells and plasma moved to the top of the tube while the RBCs and the granulocytes were trapped beneath the gel barrier when the tube was centrifuged in a swinging bucket rotor at 1750×g for 20 min at room temperature. After, the mononuclear cells and plasma were decanted into a 15 ml tube, 5 nil of phosphate-buffered saline (PBS) were added. The tubes was inverted 5 times and centrifuged for 5 min at 1750×g to pellet the cells; the supernatant was discarded.

In a second procedure, the clear plasma layer that formed above the mononuclear cell layer during centrifugation was aspirated and discarded. Then the mononuclear cell layer was aspirated, and all of the mononuclear cells were washed from the surface of the gel barrier with PBS. Approximately 2 mls of mononuclear cell suspension were transferred to a microcentrifuge tube and centrifuged in a microcentrifuge for 3 min at 16,000 rpm to pellet the cells; the supernatant was discarded.

Following each of the methods and/or procedures above, 1.8 ml of RLT lysis buffer (Qiagen, Chatsworth Calif.) was added to the pellet, the cells and lysis buffer were pipetted up and down to ensure complete lysis. Cell lysate was frozen and stored at −80° C. until total RNA was isolated.

Example 6

RNA Preparation

RNA was prepared from the RNA samples from SLE patients or normal controls using one of the following protocols. In the first protocol: 1) samples were thawed, 2) 4 ml of chloroform were added to each tube, 3) tubes were vortexed prior to centrifugation at 2000×g for 5 min, and 5) the aqueous layer was moved to new tube and processed using the RNeasy Maxi kit (Qiagen) according to the manufacturer's instructions. RNA quality was assessed using spectrophotometry, A260/A280 spectrophotometric ratios were considered to be acceptable when they ranged between 1.6 and 2.0, and/or gel electrophoresis, when 2 µl of each sample were run on an agarose gel in the presence of ethidium bromide and no degradation of RNA and no DNA contamination were visible.

In the second protocol: 1) samples were thawed and held at room temperature for 5 min, 2) after adding 5 ml of chloroform, the samples were vortexed and incubated at room temperature for 3 min, 3) the aqueous layer was transferred to a new 50 ml tube and purified using the RNeasy Maxi kit (Qiagen), and 4) the columns were eluted twice with 1 ml RNAse free water and incubated for one min before each spin. RNAs isolated using the first and second protocols were combined when the normal control cell preparations demonstrated reproducibility. The RNAs were mixed in a 50 ml tube, aliquoted into two 15 ml storage or 1.5 ml microcentrifuge tubes (100 µl per), and stored at −80° C.

In the third protocol: total RNA was purified using the RNeasy Miniprep kit (Qiagen) according to the protocol provided. Cells were homogenized and DNAse treated on a QIASHREDDER columns (Qiagen) and purified RNA was eluted in 50 µl of water.

After the last two protocols, RNA using the Agilent 2100 bioanalyzer and RNA 6000 microfluidics chips (Agilent Technologies).

Example 7 cDNA Synthesis cDNA was synthesized from RNA using reverse transcription with OLIGO-dT primers/random hexamers (Invitrogen, Carlsbad Calif.) at a final concentration of 0.5 ng/µl and 3 ng/µl, respectively.

For the first strand reaction, 0.5 µg of mononuclear RNA or 2 µg of whole blood RNA and 1 µl of the OLIGO-dT/random hexamers (Invitrogen) were added to water in a reaction tube to a final volume of 11.5 µl. The tube was incubated at 70° C. for 10 min, chilled on ice, centrifuged, and 88.5 µl of first strand buffer mix (Invitrogen) was added to the tube.

The first strand buffer mix contained 1×first strand buffer, 10 mM DTT (Invitrogen), 0.5 mM dATP (New England Biolabs (NEB), Beverly Mass.), 0.5 mM dGTP (NEB), 0.5 mM dTTP (NEB), 0.5 mM dCTP (NEB), 200 U of SUPER-SCRIPT RNAse H reverse transcriptase (Invitrogen), and 18 U of RNAGUARD inhibitor (GE Healthcare (GEH), Piscataway N.J.). After the reaction was incubated at 42° C. for 90 min, the enzyme was heat-inactivated at 70° C. for 15 min. After adding 2 U of RNAse H (NEB) to the reaction tube, it was incubated at 37° C. for 20 min.

For second strand synthesis, 40 U of $E.$ $coli$ DNA polymerase (Invitrogen) and 2 U RNaseH (Invitrogen) were added to the previous reaction to bring the final volume to 150 µl Salts and nucleotides were added to a final concentration of 20 mM Tris-HCl (pH 7.0; Fisher Scientific, Pittsburgh Pa.), 90 mM KCl (Teknova, Half Moon Bay Calif.), 4.6 mM $MgCl_2$ (Teknova), 10 mM $(NH_4)_2SO_4$ (Fisher Scientific), 1×second strand buffer (Invitrogen), 0.266 mM dGTP, 0.266 mM dATP, 0.266 mM dTTP, and 0.266 mM dCTP.

After second strand synthesis for 150 min at 16° C., the cDNA was purified away from the enzymes, dNTPs, and buffers using phenol-chloroform extraction followed by ethanol precipitation in the presence of glycogen. Alternatively, the cDNA was purified on a QIAQUICK silica-gel column (Qiagen) followed by ethanol precipitation in the presence of glycogen. The cDNA was centrifuged at >10,000×g for 30 min; and after the supernatant was aspirated, the pellet was washed with 150 µl of 70% ethanol. Following recentrifugation, the supernatant was removed, and residual ethanol was evaporated at room temperature. Alternatively, the volume of column purified cDNA was reduced in a vacuum evaporator to 7.4 µl.

Example 8

Arrays

Arrays were used to produce a gene expression profile for diagnosing and monitoring the status of SLE in a patient. In one format, the array contains reagents specific for at least two genes or proteins, one that binds to a gene or protein of the invention, and one that binds to a control gene or protein.

Nucleic Acid Arrays

Human Genome CGH 44A microarrays (Agilent Technologies) were used to determine differential gene expression. These $Cy_3/Cy_5$ chips contained 41,675 probes (60-mers) that represented most the genes found in REFSEQ database (NCBI); additional genes on the chip represented various controls. The chips were run as recommended by the manufacturer and scanned using an Agilent DNA microarray scanner. The data was extracted using Feature Extraction v 7.5 software (Agilent Technologies).

In the alternative, Affymetrix U133A Human GeneChips (Affymetrix, Santa Clara Calif.) with probe sets representing about 14,500 full length genes and 22,000 features were used according to the manuals and product inserts supplied by the manufacturer. Affymetrix Microarray Suite (MAS) v 5.0 software was used to generate expression values for each gene. To correct for slight differences in overall chip hybridization intensity and allow for comparison between samples, each chip was scaled to an overall intensity of 1500.

In one alternative, the PAXgene Blood RNA system (Pre-Analytix GmbH, Hombrechtikon Switzerland) was used for whole blood collection, stabilization, and RNA isolation from patient and/or normal samples. Five μg of total RNA was used to prepare biotinylated cRNA for hybridization using a standard protocol (Expression Analysis Technical Manual, Affymetrix). For samples with low RNA yields, two or more rounds of amplification were performed. Fifteen micrograms of each labeled cRNA was hybridized to Affymetrix U133A Human GeneChips.

In another alternative, a low density array containing amplicons produced using probe sets for genes selected from Table 1 and Table 2 are harvested from PCR reactions, purified using Sephacryl-400 beads (GEH) and arrayed on a membrane. The membrane is UV irradiated, washed in 0.2% SDS at room temperature and rinsed three times in distilled water, Non-specific binding sites on the array are blocked by incubation in 0.2% casein in PBS for 30 min at 60° C., and the arrays are washed in 0.2% SDS and rinsed in distilled water.

In another alternative, purified amplicons are robotically arranged and immobilized on polymer-coated glass slides using the procedure described in U.S. Pat. No. 5,807,522 (which is hereby incorporated in its entirety). Polymer-coated slides are prepared by cleaning glass microscope slides (Corning Life Sciences, Corning N.Y.) ultrasonically in 0.1% SDS and acetone, etching in 4% hydrofluoric acid (VWR Scientific Products, West Chester Pa.), coating with 0.05% aminopropyl silane (Sigma-Aldrich) in 95% ethanol, and curing in a 110° C. oven. The slides are washed extensively with distilled water between and after treatments.

Antibody Arrays

Monoclonal antibodies specific to at least two IFNr proteins and at least two proteins selected from the clusters of Table 1 are immobilized on a membrane, slide or dipstick or added to the wells of an ELISA plate using methods well known in the art. The array is incubated in the presence of serum or cell lysate until protein:antibody complexes are formed. The proteins encoded by genes or their splice variants are identified by the known position and labeling of the antibody that binds an epitope of that protein on the array. Quantification is normalized using the antibody:protein complex of various controls.

Example 9

Designing and Selecting Primers and Probe Sets

Primers and probe sets were designed and selected for each gene having utility in the diagnosis and monitoring of SLE using the PRIMER3 program (Whitehead Research Institute (WRI), Cambridge Mass.). Default values were used for all parameters but melting temperature (Tm). Tm was set between 71.7 and 73.7° C.; amplicon size, between 50 and 150 bases in length (optimum, about 100 bases); and primers or probes were allowed to be 36 nucleotides in length. Salt concentration, a critical parameter affecting the Tm of the probes and primers, was used at the default concentration, 50 mM.

The C source code for the PRIMER3 program was downloaded from the WRI website and complied on a Sun Enterprise 250 server (Sun Microsystems, Palo Alto Calif.) using the GCC compiler (Free Software Foundation, Boston Mass.). A subsequent version was compiled for machines running the Windows operating system (Microsoft, Redmond Wash.). The program was run from the command line which also dictated the use of an input file that contained the sequences and the parameters for primer design as described in the help files that accompanied the software. A script was written to input a number of sequences and automatically generate a number of potential primers. The following batch approach was used to design primers for the genes.

The first step in designing primers was to mask out repetitive sequences in the mRNA using the REPEATMASKER program (Institute for Systems Biology, University of Washington, Seattle Wash.). The second step was to mask out all known SNPs for the genes as annotated in the SNP database at NCBI (Bethesda Md.) that have an allelic heterozygosity higher than 1%. The masked sequence was submitted to PRIMER3 using parameters as outlined above, and the top eight sequences were selected. Alternatively, the Primer3 program was used on the MIT website (Massachusetts Institute of Technology, Cambridge Mass.) to examine a specific region on the mRNA of a particular gene. The final step was to test several of the top pairs of primers for correct size and efficiency.

Primers were ordered from Integrated DNA Technologies (Coralville Iowa) or an alternative commercial source.

Example 10

Testing of Primers and Probe Sets for RT-PCR

Control genes: With both microarrays and RT-PCR, variation was monitored by adding one or more genes from bacteria, plants, or animals in one or more wells. Although human β-actin and β-GUS were used to validate the control RNAs, several other genes were also tested for variability between samples, for expression in mononuclear and whole blood RNA from control subjects and SLE patients, on samples prepared using various protocols, and in the RT-PCR assays.

Based on criteria of low variability between control and patient samples and high expression across samples, β-actin, β-GUS, 18s ribosomal subunit, GAPDH, and β2-microglobulin were selected as the control genes and used in the various assays.

Primer Testing: Primers were tested once using RT-PCR protocol (without Rox and Sybr green dyes) to see whether they produced an amplicon of the correct size without amplifying non-specific sequences. Each primer pair/probe set was tested on cDNA made from mononuclear cell control RNA described in Example 2. The PCR reaction contained 1×RealTime-PCR buffer (Ambion, Austin Tex.), 2 mM $MgCl_2$ (ABI), 0.2 mM dATP (NEB), 0.2 mM dTTP (NEB), 0.2 mM dCTP (NEB), 0.2 mM dGTP (NEB), 0.625 U AMPLITAQ Gold enzyme (ABI), 0.3 μM of each primer to be used (Sigma Genosys, The Woodlands Tex.), 5 µl of the reverse transcription reaction, and water added to a final volume of 19 µl.

Following 40 cycles of PCR, 10 l of each product were combined with Sybr Green dye at a final dilution of 1:72,000. Melt curves for each PCR product were determined on a PRISM 7900HT Sequence detection system (ABI), and primer pairs yielding a product with one clean peak were chosen for further analysis. One µl of product from each probe set assay was examined by agarose gel electrophoresis or using a DNA 1000 chip kit and an Agilent 2100 bioanalyzer (Agilent Technologies). From primer design and the genomic sequence, the expected size of the amplicon was known. Only primer pairs showing amplification of the single desired product, and minimal amplification of contaminants, were used in assays.

Primers were tested a second time to determine their efficiency in an RT-PCR reactions. cDNA was synthesized as described above. A set of 5 serial dilutions of cDNA in water: 1:10, 1:20, 1:40, 1:80, and 1:160 was tested using RT-PCR.

Example 11

RT-PCR Assays and Analysis

TAQMAN: PCR reactions were performed using the TAQMAN Universal PCR Master mix (ABI). The master mix was aliquoted into light tight tubes, one for each gene. The primer pair for each gene was added to the tube of PCR master mix labeled for that gene. A FAM/TAMRA dual labeled TAQMAN probe (Biosearch Technologies, Novato Calif.) was added to each tube. Alternatively, different combinations of commercially available fluorescent reporter dyes and quenchers were used such that the absorption wavelength for the quencher matches the emission wavelength for the reporter.

In one alternative, a Sybr green RT-PCR reaction can be performed using the TAQMAN PCR reagent kit (ABI). In the alternative, Universal ProbeLibrary (LNAs; Roche Diagnostics, Pleasanton Calif.), were substituted for Taqman probes.

RT-PCR Assays and Analysis: 18 µl of master mix were dispensed into each well of a 384 well plate (ABI), and 2 µl of the template sample were dispensed into triplicate wells for each primer pair. The final concentration of each reagent was: 1×TAQMAN Universal PCR Master Mix, 300 nM each primer, 0.25 nM TAQMAN probe, and 21 µl of 1:10 diluted template. PCR reactions were run on the PRISM 7900HT Sequence Detection system (ABI) with the following conditions: 10 min at 95° C.; 40 cycles of 95° C. for 15 sec, 60° C. for 1 min.

Sequence detection system v2.0 software (ABI) was used to analyze the fluorescent signal from each reaction. Standard deviation (Stdev) and coefficient of variation (CV) were calculated for triplicate wells. If the CV was greater than 2, an outlier among the three wells was identified and deleted; and the average was recalculated. In each plate, the difference in CT (ΔCT) was calculated for each gene and control combination by subtracting the average CT of the gene from the average CT of the control. The expression relative to the control was calculated by taking two to the power of the ΔCT of the gene.

In each case, all plates were run in duplicate and analyzed in the same manner. The percent variation was determined for each sample and gene combination (relative expression, RE) by taking the absolute value of the RE for the second plate from the RE for the first plate, and dividing that by the average. If more than a quarter of the variation calculations on a plate were greater than 50%, then a third plate was run. The cycle number at which each amplification curve crossed CT was recorded, and the file was transferred to MS Excel for further analysis. CT values for triplicate wells were averaged, and data were plotted as a function of the $\log_{10}$ of the calculated starting concentration of RNA. The starting RNA concentration for each cDNA dilution was determined based on the original amount of RNA used in the reverse transcription reaction, the dilution of the reverse transcription reaction, and the amount used in the RT-PCR reaction (usually 5 µl). For each gene, a linear regression line was plotted through all points of the dilution series. The slope of the line was used to calculate efficiency of the reaction for each primer set using the equation, $E=10^{(-1/slope)}-1$. This efficiency equation was used to compare the expression of primers or probe sets for each gene, and a primer pair was considered successful if the efficiency was reproducibly determined to be 0.85-1.2.

Since variation of RT-PCR assays can arise from unequal amounts of RNA starting material, probe sets for control genes can be run in the same reaction as the probe set for the diagnostic gene to reduce variation. Different fluorescent dyes were used to amplify the control, differentiating their expression from that of the diagnostic gene.

Quantitative RT-PCR: RT-PCR was used to compare the expression of each gene using the primers described above. cDNA was synthesized from normal control, patient, and reference samples. Ten µl RT-PCR reactions were performed using a PRISM 7900 Sequence Detection system (ABI) using FAM-TAMRA labeled probes and the standard TAQMAN protocols described above. RT-PCR amplification product was measured as CT (threshold cycle=the point at which an amplification curve crosses a threshold fluorescence value) during the PCR reaction to observe amplification before any reagent became rate limiting. Threshold was set to a point where all of the reactions were in their linear phase of amplification. A lower CT indicated a higher amount of starting material (greater expression in the sample) since an earlier cycle number meant the threshold was crossed more quickly. A CT of less than 30 based on appropriate cDNA dilutions provided linear results for the blood samples from SLE patients.

In the alternative, other labeling moieties or technologies can be used to measure amplification product in RT-PCR. Molecular beacons (Invitrogen) use FRET technology, and fluorescence is measured when a hairpin structure is relaxed by the specific probe binding to the amplicon.

Other labeling moieties can be used for detection of an antibody, nucleic acid or protein in any of the assays or diagnostic kits described herein. These labeling moieties include fluorescent, chemiluminescent, or chromogenic agents, cofactors, enzymes, inhibitors, magnetic particles, radionuclides, reporters/quenchers, substrates and the like that can be attached to or incorporated into the antibody, nucleic acid or protein. Visible labels and dyes include but are not limited to anthocyanins, avidin-biotin, β glucuronidase, biotin, BIODIPY, Coomassie blue, Cy3 and Cy5, 4,6-diamidino-2-phenylindole (DAPI), digoxigenin, ethidium bromide, FAM/TAMRA, FITC, fluorescein, gold, green fluorescent protein, horseradish peroxidase, lissamine, luciferase, phycoerythrin, reporter/quencher pairs (HEX/TAMRA, JOE/TAMRA, ROX/BHQ2, TAMRA/BHQ2, TET/BHQ1, VIC/BHQ1, and the like), rhodamine, spyro red, silver, streptavidin, and the like. Radioactive markers include radioactive forms of hydrogen, iodine, phosphorous, sulfur, and the like.

Example 12

Protein Expression

Adapter sequences for subcloning are added at either end of a coding region specific to a gene or a portion thereof and amplified using PCR. An epitope or affinity tag (6×his) or sequences for secretion from a cell can be added to the adapter sequence to facilitate purification and/or detection of the protein. The amplified cDNA is inserted into a shuttle or expression vector that can replicate in bacteria, insect, yeast, plant, or mammalian cells. Such vectors typically contain a promoter that operably links to the coding region, replication start sites, and antibiotic resistance or metabolite selection sequences.

The expression vector can be used in an in vitro translation system or to transfect cells. For example, *Spodoptera frugiperda* (Sf9) insect cells are infected with recombinant *Autographica californica* nuclear polyhedrosis virus (baculovirus). The polyhedrin gene is replaced with the cDNA by homologous recombination, and the polyhedrin promoter drives transcription. The protein is synthesized as a fusion protein with an affinity tag that enables purification.

Clones of transformed cells are analyzed to ensure that the inserted sequence is expressed. Once expression is verified, the cells are grown under selective conditions; and the protein is isolated from cells, or if secreted, from the growth media using chromatography, size exclusion chromatography, immunoaffinity chromatography, or other methods including cell fractionation, ion exchange, or selective precipitation.

The isolated and purified protein is then used as a reagent on an array or as an antigen to produce specific antibodies.

Example 13

Antibody Production and Testing

If antibodies are to be used as reagents, the sequence of the gene or splice variant is analyzed to determine regions of high immunogenicity (LASERGENE software; DNASTAR, Madison Wis.), and an appropriate oligopeptide is synthesized and conjugated to keyhole lympet hemocyanin (KLH; Sigma-Aldrich, St Louis Mo.).

Immunization

Rabbits are injected with the oligopeptide-KLH complexes in complete Freund's adjuvant, and the resulting antisera is tested for specific recognition of the protein or fragments thereof. Antisera that react positively with the protein are affinity purified on a column containing beaded agarose resin to which the synthetic oligopeptide has been conjugated (SULFOLINK kit; Pierce Chemical, Rockford Ill.). The column is equilibrated using 12 ml IMMUNOPURE Gentle Binding buffer (Pierce Chemical). Three ml of rabbit antisera is combined with one ml of binding buffer and poured into the column. The column is capped (on the top and bottom), and antisera is allowed to bind with the oligopeptide by gentle shaking at room temperature for 30 min. The column is allowed to settle for 30 min, drained by gravity flow, and washed with 16 ml binding buffer (4×4 ml additions of buffer). The antibody is eluted in one ml fractions with IMMUNOPURE Gentle Elution buffer (Pierce Chemical), and absorbance at 280 nm is determined. Peak fractions are pooled and dialyzed against 50 mM Tris, pH 7.4, 100 mM NaCl, and 10% glycerol. After dialysis, the concentration of the purified antibody is determined using the BCA assay (Pierce Chemical), aliquoted, and frozen.

Electrophoresis and Blotting

Samples containing protein are mixed in 2×loading buffer, heated to 95° C. for 3-5 min, and loaded on 4-12% NUPAGE Bis-Tris precast gel (Invitrogen). Unless indicated, equal amounts of total protein are loaded into each well. The gel is electrophoresed in 1×MES or MOPS running buffer (Invitrogen) at 200 V for approximately 45 min on an XCELL II apparatus (Invitrogen) until the RAINBOW marker (GEH) resolves and the dye front approaches the bottom of the gel. The gel is soaked in 1×transfer buffer (Invitrogen) with 10% methanol for a few minutes; and a PVDF membrane (Millipore, Billerica Mass.) is soaked in 100% methanol for a few seconds to activate it. The membrane, the gel, and supports are placed on the TRANSBLOT SD transfer apparatus (Biorad, Hercules Calif.) and a constant current of 350 mA is applied for 90 min.

Conjugation with Antibody and Visualization

After the proteins are transferred to the membrane, it is blocked in 5% (w/v) non-fat dry milk in 1×phosphate buffered saline (PBS) with 0.1% Tween 20 detergent (blocking buffer) on a rotary shaker for at least 1 hr at room temperature or at 4° C. overnight. After blocking, the buffer is removed, and 10 ml of primary antibody in blocking buffer is added and incubated on the rotary shaker for 1 hr at room temperature or overnight at 4° C. The membrane is washed 3 times for 10 min each with PBS-Tween (PBST), and secondary antibody, conjugated to horseradish peroxidase, is added at a 1:3000 dilution in 10 ml blocking buffer. The membrane and solution are shaken for 30 min at room temperature and washed three times for 10 min with PBST.

The wash solution is carefully removed, and the membrane is moistened with ECL+chemiluminescent detection system (GEH) and incubated for approximately 5 min. The membrane, protein side down, is placed on x-ray film (Eastman Kodak, Rochester N.Y.) and developed for approximately 30 seconds. Antibody:protein complexes are visualized and/or scanned and quantified.

TABLE 1

| Cluster | Ratio cell type to all cells | cell Type | Array ID | Genbank ID | Gene ID | Description | Sequence |
|---|---|---|---|---|---|---|---|
| 1 | | Granulocytes and B cells | | | | | |
| 1 | | | A_23_P113258 | NM_005739 | RASGRP1 | Homo sapiens RAS guanyl releasing protein 1 (calcium and DAG-regulated) (RASGRP1), mRNA | AGAGAAATAGATCCCTCCAGCTTGAAAAA AGCAATCATGTCTTAGCTCAAATGGAGC (SEQ ID NO: 1) |
| 1 | | | A_23_P117599 | NM_012111 | AHSA1 | Homo sapiens AHA1, activator of heat shock 90 kDa protein ATPase homolog 1 (yeast) (AHSA1), mRNA | ATTAGTGTGAGCCTTGCCAAAGATGAGCTGA CACAAATCTCGTGGCCTTAATGAAGGAA (SEQ ID NO: 2) |
| 1 | | | A_23_P128230 | NM_002135 | NR4A1 | Homo sapiens nuclear receptor subfamily 4, group A, member 1 (NR4A1), transcript variant 1, mRNA | AATGACAGATTCTGACATTTATATTTGTATTT TCCTGGATTTATATGTATGTGACTTTT (SEQ ID NO: 3) |
| 1 | | | A_23_P134078 | NM_004824 | CDYL | Homo sapiens chromodomain protein, Y-like (CDYL), transcript variant 1, mRNA | AGGTACAGATACCTTCAGATTCGGGAAACTCAA AATCAAAGACTTAGCTTCTAGGATAAA (SEQ ID NO: 4) |
| 1 | | | A_23_P251686 | NM_005160 | ADRBK2 | Homo sapiens adrenergic, beta, receptor kinase 2 (ADRBK2), mRNA | GTCAAAATGGGTTAACTGTGTATATTGACTTTC ATGTCGTCATGCATCTGTCATGAATGA (SEQ ID NO: 5) |
| 1 | | | A_23_P43580 | NM_007018 | CEP1 | Homo sapiens centrosomal protein 1 (CEP1), mRNA | AACCTAGAAGGAGAATTGAAAGCTTGAAGA GAACCTTCCATTTACCATGAATGAGGGA (SEQ ID NO: 6) |
| 1 | | | A_23_P46781 | NM_003638 | ITGA8 | Homo sapiens integrin, alpha 8 (ITGA8), mRNA | CCCATTATGGGTAATAATACTAGCAATACTTCT TGGATTGTTGGTTCTCGCCATTTTAAC (SEQ ID NO: 7) |
| 1 | | | A_23_P54170 | NM_005466 | MED6 | Homo sapiens mediator of RNA polymerase II transcription, subunit 6 homolog (yeast) (MED6), mRNA | AGGCACCAGACTTGGGATCAGTTATAAACTCT AGAGTGCTTACTGCAGTGCATGGTATTC (SEQ ID NO: 8) |
| 1 | | | A_23_P64689 | NM_014871 | USP52 | Homo sapiens ubiquitin specific peptidase 52 (USP52), mRNA | CCAGATGGAAAGTAATTGGTATTCTTAATATCC TGGGTGACTAATATCCAGGCAGAGAAG (SEQ ID NO: 9) |
| 1 | | | A_24_P115932 | NM_004778 | GPR44 | Homo sapiens G protein-coupled receptor 44 (GPR44), mRNA | TGATGAAATGTCAGTGAAGAAGCAGATGAG AAACTCTTGAGATCTTGGTCCTGTGTTT (SEQ ID NO: 10) |
| 1 | 3 | Granulocyte | A_24_P227585 | NM_018559 | KIAA1704 | Homo sapiens KIAA1704 (KIAA1704), mRNA | TGATGACACATCTGGAGATCGATCAATCTGGA CAGATACTCCAGCTGATAGGGAAGGAA (SEQ ID NO: 11) |

TABLE 1-continued

| Cluster | Ratio cell type to all cells | cell Type | Array ID | Genbank ID | Gene ID | Description | Sequence |
|---|---|---|---|---|---|---|---|
| 1 | | | A_24_P229658 | | | | GAAGGGCGTAGTCACAGAACTCGAAGTAGA GCCGAGATAAATCCATAGGCATAAAAA (SEQ ID NO: 12) |
| 1 | | | A_24_P312692 | NM_006595 | API5 | Homo sapiens apoptosis inhibitor 5 (API5), mRNA | TTGCTATTCAAATCAACTGCCTGAATGACATTT CTAGTAGTCTGATGTATTTTTCTGAGG (SEQ ID NO: 13) |
| 1 | | | A_24_P341489 | AC003043 | | Homo sapiens chromosome 17, clone HRPC1067M6, complete sequence. | ATCTGAAGTCTGTCCAGGAACTCATTTTGAAAC ATGACAAGCCAAGATAAGGAATAAGA (SEQ ID NO: 14) |
| 1 | 3 | B cells | A_24_P359165 | AC026250 | | Homo sapiens chromosome 11, clone RP11-540A21, complete sequence. | TGGATAATTGAAGCCAGTGGTTTTTAACCAAT GTTATGTATCAGAATCACCTCACAAAG (SEQ ID NO: 15) |
| 1 | | | A_24_P4426 | NM_014937 | INPP5F | Homo sapiens inositol polyphosphate-5-phosphatase F (INPP5F), transcript variant 1, mRNA | TCTCATTTGATCCTAATTTTCCCGTATTCTAC TTGAACACATTAAAAATACTCTGCTGC (SEQ ID NO: 16) |
| 1 | | | A_24_P8140 | AK124166 | | Homo sapiens cDNA FLJ42172 fis, clone THYMU2029676. | AGTACTTAGGGTGAGCCTGCCTTCTTCCATT CTATCCGAGTCTCTTCTAAAGTTGCGG (SEQ ID NO: 17) |
| 1 | | | A_24_P861009 | NM_001007246 | BRWD1 | Homo sapiens bromodomain and WD repeat domain containing 1 (BRWD1), transcript variant 3, mRNA | AGTCACAGATCCTACGTATGTGCTCTTCAGTA GAGGATTTTCTGTGATCCTACAATGAAG (SEQ ID NO: 18) |
| 1 | | | A_24_P865672 | AC018347 | | Homo sapiens chromosome 15 clone RP11-410F2, complete sequence. | AAAGCACCCGTGAAGAAATCTATAAAGATGCT CCAGCCGAAATGCACAGAAGTCAAATC (SEQ ID NO: 19) |
| 1 | | | A_32_P90551 | NM_014230 | SRP68 | Homo sapiens signal recognition particle 68 kDa (SRP68), mRNA | GACTTACATCAAGCTGTCAATGGCAATCAAGC GTAATGAGAGCATGGCCAAAGGTCTGCA (SEQ ID NO: 20) |
| 1 | | | A_32_P98683 | AC006449 | | Homo sapiens chromosome 17, clone hCIT.58_E_17, complete sequence. | TGAGGGGTGCCTTCATTCCCTTTGTTCACTT TCTCCAGCTCAACTTGGGACTTGGGTGG (SEQ ID NO: 21) |
| 2 | | NK cells | | | | | |
| 2 | | | A_23_P10025 | NM_006159 | NELL2 | Homo sapiens NEL-like 2 (chicken) (NELL2), mRNA | ACATCACCATGTAGAAGAATGGCGTACAGTA TATACCGTGACATCCTGACCCTGGATA (SEQ ID NO: 22) |

TABLE 1-continued

| Cluster | Ratio cell type to all cells | cell Type | Array ID | Genbank ID | Gene ID | Description | Sequence |
|---|---|---|---|---|---|---|---|
| 2 | | | A_23_P103765 | NM_002001 | FCER1A | Homo sapiens Fc fragment of IgE, high affinity I, receptor for, alpha polypeptide (FCER1A), mRNA | AGCTCCGCTGAGAAGTACTGGCTACAATTT TTATCCCATTGTTGGTGTGATTCTGTT (SEQ ID NO: 23) |
| 2 | | | A_23_P103775 | NM_032270 | LRRC8C | Homo sapiens leucine rich repeat containing 8 family, member C (LRRC8C), mRNA | AAACTCTGAAGATTGGAAAAAACAGCCTATCT GTACTTTCACCGAAAATTGGAAATTTGC (SEQ ID NO: 24) |
| 2 | | | A_23_P107283 | NM_002145 | HOXB2 | Homo sapiens homeo box B2 (HOXB2), mRNA | ATTAAACTCTAGGGGACTTTCTTAAAATAAC TAGAGGGACCTATTTTCCTCTTTTTA (SEQ ID NO: 25) |
| 2 | | | A_23_P117662 | NM_002112 | HDC | Homo sapiens histidine decarboxylase (HDC), mRNA | CCGAGGGTAGACAGGCAGCTTCTGTGGTTCA GCTTGTGACATGATATATAACACAGAAAT (SEQ ID NO: 26) |
| 2 | | | A_23_P119418 | NM_003796 | C19orf2 | Homo sapiens chromosome 19 open reading frame 2 (C19orf2), transcript variant 1, mRNA | TCGCAAATCCATCCTGAAGTCTCGAAGTAGAG AGAATAGTGTGTAGCGACACTAGTGA (SEQ ID NO: 27) |
| 2 | | | A_23_P12572 | NM_001227 | CASP7 | Homo sapiens caspase 7, apoptosis-related cysteine peptidase (CASP7), transcript variant alpha, mRNA | AGTTCTATAAGTGAGGAAGAGTTTATGCAAA GATTTTGGGACTTTGTTTTCAAGATGG (SEQ ID NO: 28) |
| 2 | | | A_23_P126057 | NM_001007099 | SCP2 | Homo sapiens sterol carrier protein 2 (SCP2), transcript variant 3, mRNA | ACATTGCAAATAGCGTGGGATAGATTGTTT CTTAATGGTGTGACCAATCCTGTTTTT (SEQ ID NO: 29) |
| 2 | | | A_23_P127676 | NM_014633 | CTR9 | Homo sapiens SH2 domain binding protein 1 (tetratricopeptide repeat containing) (SH2BP1), mRNA | TAAACCCAGATGCTAAATCATTCCTACAAGGT TTGACTGAAACTGTGGCAGATGTCTCA (SEQ ID NO: 30) |
| 2 | | | A_23_P129128 | NM_152334 | TARSL2 | Homo sapiens threonyl-tRNA synthetase-like 2 (TARSL2), mRNA | TGACCCTTAAAAATGTATTTTCTTAACATGTTA GTACTTCTACGACTTTGGAGCCACTG (SEQ ID NO: 31) |
| 2 | | | A_23_P133543 | NM_017415 | KLHL3 | Homo sapiens kelch-like 3 (Drosophila) (KLHL3), mRNA | TGGCTGTGTTAGGGACTGTATATCTTGTAAAGA ACACTTGTCACATGCTTGATCAGTTACA (SEQ ID NO: 32) |
| 2 | | | A_23_P135857 | NM_004836 | EIF2AK3 | Homo sapiens eukaryotic translation initiation factor 2-alpha kinase 3 (EIF2AK3), mRNA | CCTCCAATAAAGGGAAAATGAAGCTTTTTATGT AAATTGGTTGAAAGGTCTAGTTTTGGG (SEQ ID NO: 33) |
| 2 | | | A_23_P14543 | NM_006020 | ALKBH | Homo sapiens alkB, alkylation repair homolog (E. coli) (ALKBH), mRNA | TTGGCTGTAATGTATGTTGAGAGTCAGTCCA AGGAGGTATGTTCTTCCAACACGCCTT (SEQ ID NO: 34) |

TABLE 1-continued

| Cluster | Ratio cell type to all cells | cell Type | Array ID | Genbank ID | Gene ID | Description | Sequence |
|---|---|---|---|---|---|---|---|
| 2 | | | A_23_P14804 | NM_005724 | TSPAN3 | Homo sapiens tetraspanin 3 (TSPAN3), transcript variant 1, mRNA | GGCTTTATAGGAGGAGTATAATGTATGCACTA CTGTTTAAAGAATTAGTGTGAGTGTG (SEQ ID NO: 35) |
| 2 | | | A_23_P152353 | NM_133451 | KIAA1970 | Homo sapiens KIAA1970 protein (KIAA1970), mRNA | TGGCCAATCTTGTCTGAGTTCTTTGATGGCGA CACATGAACTACAGCCGTTTTGTTGTTG (SEQ ID NO: 36) |
| 2 | | | A_23_P200015 | NM_012093 | AK5 | Homo sapiens adenylate kinase 5 (AK5), transcript variant 2, mRNA | AATGCAGAGGGAACACCAGAGGACGTTTTCT TCAACTCTGCACAGCTATTGACTCTATT (SEQ ID NO: 37) |
| 2 | | | A_23_P208477 | NM_001419 | ELAVL1 | Homo sapiens ELAV (embryonic lethal, abnormal vision, Drosophila)-like 1 (Hu antigen R) (ELAVL1), mRNA | GGAGGCGTAAAATGCTCTGTATTTAATAAC ACAGAAACATTTGAGCATTGTATTTCTC (SEQ ID NO: 38) |
| 2 | | | A_23_P213045 | NM_016269 | LEF1 | Homo sapiens lymphoid enhancer-binding factor 1 (LEF1), mRNA | AGCAGGAGCCAAAAGACCTCACATTAAGAAG CCTCTGAATGCTTTTATGTTATACATGA (SEQ ID NO: 39) |
| 2 | | | A_23_P214882 | NM_019041 | MTRF1L | Homo sapiens mitochondrial translational release factor 1-like (MTRF1L), mRNA | CATAAAGTCAAAAAATCCTAAAACATAAGTGG TGACCATCGTAATCATGATGTGTGG (SEQ ID NO: 40) |
| 2 | | | A_23_P215566 | NM_001621 | AHR | Homo sapiens aryl hydrocarbon receptor (AHR), mRNA | AATGGCTTCGGACACAAAATATCTCTGAGTTCTGT GTATTTCAGTCAAAACTTTAAACCTG (SEQ ID NO: 41) |
| 2 | | | A_23_P215956 | NM_002467 | MYC | Homo sapiens v-myc myelocytomatosis viral oncogene homolog (avian) (MYC), mRNA | TTCAAATGCATGATCAAATGCAACCTCACAACC TTGGCTGAGTCTTGAGACTGAAAGATT (SEQ ID NO: 42) |
| 2 | | | A_23_P217187 | HS333E23 | | Human DNA sequence from clone RP3-333E23 on chromosome Xq21.1 Contains the P2RY10 gene for purinergic receptor P2Y G-protein coupled 10, complete sequence. | TTTTTCTAACAGGCAAGACAGTGTGAAGAATT GAAGCAATATGTGCATAAATTTCAGGAC (SEQ ID NO: 43) |
| 2 | | | A_23_P25566 | NM_004951 | EBI2 | Homo sapiens Epstein-Barr virus induced gene 2 (lymphocyte-specific G protein-coupled receptor) (EBI2), mRNA | CTGAAACGGCAAGTCAGTGTATCGATTCTAG TGCTGTGAAGTCAGCCCCTGAAGAAAAT (SEQ ID NO: 44) |
| 2 | 3 | NK | A_23_P302018 | NM_003328 | TXK | Homo sapiens TXK tyrosine kinase (TXK), mRNA | GCTGAGAGTGCTTCCTTCTTGAAGACGAGTGT CATTCATCCACTTCAGTGATCCATGCATA (SEQ ID NO: 45) |

TABLE 1-continued

| Cluster | Ratio cell type to all cells | cell Type | Array ID | Genbank ID | Gene ID | Description | Sequence |
|---|---|---|---|---|---|---|---|
| 2 | | | A_23_P31376 | NM_018334 | LRRN3 | Homo sapiens leucine rich repeat neuronal 3 (LRRN3), mRNA | GCCTCTCCAGAAATGAACTGTGATGGTGA CACAGCTATGTGAGGAATTACTTACAGA (SEQ ID NO: 46) |
| 2 | | | A_23_P33643 | XM_937367 | IL7R | PREDICTED: Homo sapiens interleukin 7 receptor (IL7R), mRNA | GCAATGAGTGAACTGACTGTGGCTACATTCTT GAGATATACGGGAGAGACGTATTATTA (SEQ ID NO: 47) |
| 2 | | | A_23_P338919 | NM_005876 | APEG1 | Homo sapiens aortic preferentially expressed gene 1 (APEG1), mRNA | GCAGGGGCCACTGTAGTGAGCGTGGAGAAA TTTGGAACACCTATTTCTTAACTCAAAT (SEQ ID NO: 48) |
| 2 | | | A_23_P343398 | NM_001838 | CCR7 | Homo sapiens chemokine (C-C motif) receptor 7 (CCR7), mRNA | AAGAGAGCAACATTTTACCCACACACAGATAA AGTTTTCCCTTGAGGAAACAACAAGCTTT (SEQ ID NO: 49) |
| 2 | | | A_23_P345460 | NM_015432 | PLEKHG4 | Homo sapiens pleckstrin homology domain containing, family G (with RhoGef domain) member 4 (PLEKHG4), mRNA | GACTTGATGCTCTTTTGAATAACTTTCAATAGAA TTGTCTAAAATTATCTTACTGGTTGTT (SEQ ID NO: 50) |
| 2 | | | A_23_P354151 | NM_005546 | ITK | Homo sapiens IL2-inducible T-cell kinase (ITK), mRNA | TTGACACTTCATGAGGAGGACATTCCCTGA TATAAGAGAGGATGGTGTTGCAATTGGC (SEQ ID NO: 51) |
| 2 | | | A_23_P384085 | NM_014635 | GCC2 | Homo sapiens GRIP and coiled-coil domain containing 2 (GCC2), transcript variant 2, mRNA | TCTCTTAAGCCTTCAGTTTATACTCTTAATTAA TTTTCTTTCTGAGCTGGAGAACTGGC (SEQ ID NO: 52) |
| 2 | | | A_23_P404481 | NM_001400 | EDG1 | Homo sapiens endothelial differentiation, sphingolipid G-protein-coupled receptor, 1 (EDG1), mRNA | GCTGAGGCCAAAGTTTCCATGTAAGCGGATC CGTTTTTTGGAATTTGGTTGAAGTCACT (SEQ ID NO: 53) |
| 2 | | | A_23_P436117 | NM_018200 | HMG20A | Homo sapiens high-mobility group 20A (HMG20A), mRNA | CACTTGACAGTGACTTGAAACATTTGCATATTC AGGAATGCATGAGATTTCAAGAGAGCC (SEQ ID NO: 54) |
| 2 | | | A_23_P45726 | NM_005826 | HNRPR | Homo sapiens heterogeneous nuclear ribonucleoprotein R (HNRPR), mRNA | GGGATAGATTACATAGGAGTATGAGTATGCT GTAAATAAAAATACAAGCTAGTGCTTTG (SEQ ID NO: 55) |
| 2 | | | A_23_P55682 | NM_023926 | ZNF447 | Homo sapiens zinc finger protein 447 (ZNF447), mRNA | GCAAGTGGTCACCAGCATTACACAGCAATGAA GCAGAATAAGTAGGCCAGAATGCATCA (SEQ ID NO: 56) |

TABLE 1-continued

| Cluster | Ratio cell type to all cells cell Type | Array ID | Genbank ID | Gene ID | Description | Sequence |
|---|---|---|---|---|---|---|
| 2 | | A_23_P68198 | NM_015677 | SH3YL1 | Homo sapiens SH3 domain containing, Ysc84-like 1 (S. cerevisiae) (SH3YL1), mRNA | TGGAGACAGAATCACAGTTATATCAAAAACAG ATTCACATTTTGATTGGTGGGAAGGAAA (SEQ ID NO: 57) |
| 2 | | A_23_P78268 | NM_016080 | C17orf25 | Homo sapiens chromosome 17 open reading frame 25 (C17orf25), mRNA | TAATCCCGACAGAACATCATGTGAGATTTCTT AAAATGGATTAAACGATTTCTTCAGCC (SEQ ID NO: 58) |
| 2 | | A_23_P83931 | NM_005863 | NET1 | Homo sapiens neuroepithelial cell transforming gene 1 (NET1), mRNA | TCTTTGAAAGGGGGAGGAGGAGTAAAAGCC CGATTATAATGGTGATCAATTCAAGTCAG (SEQ ID NO: 59) |
| 2 | | A_23_P91991 | NM_138381 | MGC15763 | Homo sapiens hypothetical protein BC008322 (MGC15763), mRNA | ATGTACCCAAAGAACACATTTGCTTTGAGAAGT GGTGGTAGGAGGCAGACAAAGGCAGAA (SEQ ID NO: 60) |
| 2 | | A_23_P94889 | AC103817 | | Homo sapiens chromosome 8, clone CTD-3083F21, complete sequence. | TAAGTTTTGTAAAAAGGAGCATCTTGAATCCAC TTAGATAAAGACAGACTGTGTGTTAG (SEQ ID NO: 61) |
| 2 | | A_24_P108291 | NM_018439 | IMPACT | Homo sapiens Impact homolog (mouse) (IMPACT), mRNA | AGAGCCTTTCTGAAGAGAATTATATCAAACTAA TTACAACCAAGAATAATAGTATGAAG (SEQ ID NO: 62) |
| 2 | | A_24_P117528 | NM_002765 | PRPS2 | mRNA | CAAGGCCTAAAGCCAACTGACTTAAAGGTAAT CATTTCAGCTAAGATTAAATTTAAAGCC (SEQ ID NO: 63) |
| 2 | | A_24_P12521 | NM_138811 | C7orf31 | Homo sapiens chromosome 7 open reading frame 31 (C7orf31), mRNA | GGTGCACAAAAGCGTTTCCATAAATCAATTCTA GAAGACCATAAAGACCTCAGGGATAAT (SEQ ID NO: 64) |
| 2 | | A_24_P136438 | NM_014915 | ANKRD26 | Homo sapiens ankyrin repeat domain 26 (ANKRD26), mRNA | ATGTTGATGAAGTGCACAAAAATAATAGAAGTG ATATGATGTCCGCATTAGGATTAGGAC (SEQ ID NO: 65) |
| 2 | | A_24_P157424 | NM_007362 | NCBP2 | Homo sapiens nuclear cap binding protein subunit 2, 20 kDA (NCBP2), mRNA | CCCGTTAAACTGAGTGTGTAGAAATCTGAATTTTT AAAAGAGCTGTAACTAGTTGTAAGTGC (SEQ ID NO: 66) |
| 2 | | A_24_P16361 | | | | ACCAAAAATTCATGAGAGATCCAATTAATTCT GGTGAAAAGGATTGACCCTTGAAGGA (SEQ ID NO: 67) |

TABLE 1-continued

| Cluster | Ratio cell type to all cells | cell Type | Array ID | Genbank ID | Gene ID | Description | Sequence |
|---|---|---|---|---|---|---|---|
| 2 | | | A_24_P170103 | | | | AAGGACAACAGAAAACAATCTTATTCCAAGTC ATTCCAGTAACTTTTTGGGTACGTAC (SEQ ID NO: 68) |
| 2 | | | A_24_P170186 | AL589796 | | Human DNA sequence from clone RP13-469O16 on chromosome 6 Contains a nucleophosmin (nucleolar phosphoprotein B23, numatrin) (NPM1) (B23, NPM) pseudogene and a CpG island, complete sequence. | ATGCACAAAAGTCAAATCAGAATGGAGACTCA AACCATCAAAGCTAAGATCAAAAGGTC (SEQ ID NO: 69) |
| 2 | | | A_24_P202555 | NM_015073 | SIPA1L3 | Homo sapiens signal-induced proliferation-associated 1 like 3 (SIPA1L3), mRNA | TGCAAAAACAGATCTATTTAATTTGAGGTTGAT GTTCTATCCAATGGCCGAAGATAGCAG (SEQ ID NO: 70) |
| 2 | | | A_24_P208345 | NM_033102 | SLC45A3 | Homo sapiens solute carrier family 45, member 3 (SLC45A3), mRNA | GTGCCGTTTGCAATAAATGTCGTCTTATTTATTT AGCGGGGTGAATATTTTATACTGTAAG (SEQ ID NO: 71) |
| 2 | | | A_24_P212596 | AC019288 | | Homo sapiens chromosome 15, clone RP11-139F4, complete sequence. | TTTTCAACAGTACAGAAAAATTGAAAAAAGGGG CTTTGCCTTTGTAACCTTTGATGACCA (SEQ ID NO: 72) |
| 2 | | | A_24_P218970 | NM_001417 | EIF4B | Homo sapiens eukaryotic translation initiation factor 4B (EIF4B), mRNA | TTTTTAAGCTTCCCTTGAGAGAATAAATGGTAA TGGAGAGAACTATTTAACAAGGTCCTG (SEQ ID NO: 73) |
| 2 | | | A_24_P234921 | NM_004367 | CCR6 | Homo sapiens chemokine (C-C motif) receptor 6 (CCR6), transcript variant 1, mRNA | AAGCTTAACTATATCTCTCTTTAAAATGCAAAA TAATGTCTTAAGATTCAAAGTCTGTA (SEQ ID NO: 74) |
| 2 | | | A_24_P251381 | NM_024782 | XLF | Homo sapiens XRCC4-like factor (XLF), mRNA | ACCTTGAAAGAAGCTTACATGGCAGCAATATTT CTAAAATAGTGATACAGTCAGAGGCCT (SEQ ID NO: 75) |
| 2 | | | A_24_P26073 | NM_133259 | LRPPRC | Homo sapiens leucine-rich PPR-motif containing (LRPPRC), mRNA | AGAGAAAGATGTCACATCTGCTAAAGCACTGT ATGAACATTTGACTGCAAAGAATACAAA (SEQ ID NO: 76) |
| 2 | | | A_24_P299911 | NM_015148 | PASK | Homo sapiens PAS domain containing serine/threonine kinase (PASK), mRNA | ATCTTGCTGACTATACATGGAAGAGGTGTTT CGAGTAACAAGCCAGAAGTGGAGAGTTC (SEQ ID NO: 77) |
| 2 | | | A_24_P302506 | AL355145 | | Human DNA sequence from clone RP5-831G13 on chromosome 1 | AATTGGAGAATTGAATAATCAGATATGTAAGC GCACTAGAACCCTGTGTTGAAAACTGC (SEQ ID NO: 78) |

TABLE 1-continued

| Cluster | Ratio cell type to all cells cell Type | Array ID | Genbank ID | Gene ID | Description | Sequence |
|---|---|---|---|---|---|---|
| 2 | | A_24_P307384 | XM_927265 | LOC643288 | PREDICTED: Homo sapiens similar to 60 kDa heat shock protein, mitochondrial precursor (Hsp60) (60 kDa chaperonin) (CPN60) (Heat shock protein 60) (HSP-60) (Mitochondrial matrix protein P1) (P60 lymphocyte protein) (HuCHA60) (LOC643288), mRNA | CTAGTGAATATGAAAAGGAAAAACTGAATGAA CTGGCAAAACTTTCAGATGGAGTAGCTG (SEQ ID NO: 79) |
| 2 | | A_24_P354451 | AC104825 | | Homo sapiens BAC clone RP11-77403 from 4, complete sequence. | CATAACCTTATTAATTTGCACATAGATCATCTG AATGTCGTGTTTAAGACTTAAGGAGG (SEQ ID NO: 80) |
| 2 | | A_24_P366465 | | | | GGATAAGATTGTCATTCAGAAATACCATCCTAA TGGCTACACTTTGAAGTAAGAAAAGC (SEQ ID NO: 81) |
| 2 | | A_24_P382113 | NM_006107 | CROP | Homo sapiens cisplatin resistance-associated overexpressed protein (CROP), transcript variant 2, mRNA | GCAGAGTGAAGACACAACACTGAATCGAAGG AAAGTGATACTAAGAATGAGGTCAATGG (SEQ ID NO: 82) |
| 2 | | A_24_P385341 | NM_014388 | C1orf107 | Homo sapiens chromosome 1 open reading frame 107 (C1orf107), mRNA | TTTCTATGAACTGCCGACATATCCACACTTTTA CAGTGAAATCTGTAATATGCTGAGAGC (SEQ ID NO: 83) |
| 2 | | A_24_P388528 | NM_003032 | ST6GAL1 | Homo sapiens ST6 beta-galactosamide alpha-2,6-sialytransferase 1 (ST6GAL1), transcript variant 2, mRNA | ATGCAAATAATGATATGGACGTTATCATTGGTC TGGTGAGATGTTTCATATTTGTGACAG (SEQ ID NO: 84) |
| 2 | | A_24_P393838 | NM_014765 | TOMM20 | Homo sapiens translocase of outer mitochondrial membrane 20 homolog (yeast) (TOMM20), mRNA | CTAGCTGTGTCGAGTTAAGAAAAAATCAGCA GTTTTTTCTCCCAGAAATGTAATTGCCA (SEQ ID NO: 85) |
| 2 | | A_24_P402690 | NM_001012514 | ITM2C | Homo sapiens integral membrane protein 2C (ITM2C), transcript variant 3, mRNA | ACTCTTAAATGCTTTGTATATTTTCTCAATTAGA TCTCTTTTCAGAAGTGTCTATAGAAC (SEQ ID NO: 86) |
| 2 | | A_24_P419300 | AC010442 | | Homo sapiens chromosome 5 clone CTD-2228K2, complete sequence. | TTACAGAGTTCAATATACTGTGTACCATTGATC TTCTATTGTGAAAGCAAAGAATTTCAT (SEQ ID NO: 87) |
| 2 | | A_24_P472455 | HSM801157 | | Homo sapiens mRNA; cDNA DKFZp564M0264 (from clone DKFZp564M0264). | ACCCTCATGTTAAATCTTAAATGTAGTATTTCT AACTTGTGAAGACAGATTGGTAGGCAG (SEQ ID NO: 88) |
| 2 | | A_24_P4877 | NM_033114 | ZCRB1 | Homo sapiens zinc finger CCHC-type and RNA binding motif 1 (ZCRB1), mRNA | GAAAAATTAATAATCATCATGTTAATACTATTATT GTCATCCCAAGAAAAGATATTTTA (SEQ ID NO: 89) |

TABLE 1-continued

| Cluster | Ratio cell type to all cells cell Type | Array ID | Genbank ID | Gene ID | Description | Sequence |
|---|---|---|---|---|---|---|
| 2 | | A_24_P542375 | NM_002823 | PTMA | Homo sapiens prothymosin, alpha (gene sequence 28) (PTMA), mRNA | ACTATAAGTAGTTGGTTGTTGTATGAGATGGTTAA AAAGGCCAAAGATAAAAGTTTCTTT (SEQ ID NO: 90) |
| 2 | | A_24_P579826 | AC090419 | | Homo sapiens chromosome 17, clone CTD-2107B16, complete sequence. | GAAGAAAGTATAGAGAGTTGCTAGTGTGACA ATCTCAAGACTTTTCAACCACTACAAAT (SEQ ID NO: 91) |
| 2 | | A_24_P59239 | | | | CATCATCACACACCAAAAAGGACAAGAATCCTT CAAAACAGGAAAAAACTCCTAAAACAC (SEQ ID NO: 92) |
| 2 | | A_24_P595460 | AK097398 | | Homo sapiens cDNA FLJ40079 fis, clone TESTI2001498, highly similar to DNA-BINDING PROTEIN NEFA PRECURSOR. | AAATTGTATGTGATATTCAACAGCAAGTTGGA TGCAATGTGTCATAAAAATGACCTCAG (SEQ ID NO: 93) |
| 2 | | A_24_P6725 | NM_001010914 | LOC400986 | Homo sapiens protein immuno-reactive with anti-PTH polyclonal antibodies (LOC400986), mRNA | AATCTGGGACAGTGCTCTCTCAGAAACAATCA GCCTGGAAGTTATATTTAAAAAGAAAG (SEQ ID NO: 94) |
| 2 | | A_24_P686992 | NM_001010914 | LOC400986 | Homo sapiens protein immuno-reactive with anti-PTH polyclonal antibodies (LOC400986), mRNA | TCCAGGAAAGTGCTCTTCTCAGAAACAACCAG CTGAGAAGGCTACAAGTGACGACAAGA (SEQ ID NO: 95) |
| 2 | | A_24_P736638 | NM_002156 | HSPD1 | K (LOC646447), mRNA | GTTGAGAAAATTATGCAAAGTTCCTCAGAAGTT GGTTATGATACTATGTTAGGAGATGTC (SEQ ID NO: 96) |
| 2 | | A_24_P808100 | AC011890 | | Homo sapiens PAC clone RP4-655L22 from Xq23, complete sequence. | TAAAAGTCAGGTTGCAGTTTCCATTGCATTCAA GAAAATCAGAAATAAATACAACTTT (SEQ ID NO: 97) |
| 2 | | A_24_P82142 | NM_003205 | TCF12 | Homo sapiens transcription factor 12 (HTF4, helix-loop-helix transcription factors 4) (TCF12), transcript variant 3, mRNA | TCAGGATGATTCCTAACACAGTCAGTCATTGTG AACTTAGTGGACTTTTTGGTTACTTTA (SEQ ID NO: 98) |
| 2 | | A_24_P832113 | NM_001004419 | CLEC2D | Homo sapiens C-type lectin domain family 2, member D (CLEC2D), transcript variant 2, mRNA | CTTTGAAATAACACCACCAGTAGTCTTACGGTT GAAGTGTGTTCAGGGCCAGTGCATAT (SEQ ID NO: 99) |
| 2 | | A_24_P883109 | AC073089 | | Homo sapiens BAC clone RP11-324F21 from 7, complete sequence. | GGGCAACTAGTCATCTACTAGTAGCTTAGTA AGCTAAGCATTAAATCTAAGAAATAGCA (SEQ ID NO: 100) |
| 2 | | A_24_P927189 | NM_138381 | OXNAD1 | oxidoreductase NAD-binding domain containing 1 | AGTGTGTTGTCGTTATTAATTGCTATTCCTTG TCCTATTCAGAAAGGATTTCAAGAGGC (SEQ ID NO: 101) |

TABLE 1-continued

| Cluster | Ratio cell type to all cells | cell Type | Array ID | Genbank ID | Gene ID | Description | Sequence |
|---|---|---|---|---|---|---|---|
| 2 | | | A_24_P930963 | AC009041 | | Homo sapiens chromosome 16 clone RP11-161M6, complete sequence. | GCCCCATTTCAAGTATAACCAGGAGGGAAAAT GGTGCTTGAAATAAGCATGCCACAAAGG (SEQ ID NO: 102) |
| 2 | | | A_24_P941188 | XM_375697 | OTUD3 | PREDICTED: Homo sapiens OTU domain containing 3 (OTUD3), mRNA | CCACGGATTGTGTTCATCTGAACCATTTTATTT TTTATTTACCAAGTACTGTACTTGGC (SEQ ID NO: 103) |
| 2 | | | A_24_P943263 | NM_006989 | RASA4 | Homo sapiens RAS p21 protein activator 4 (RASA4), mRNA | TCCTGCATAGTCTATCTTTGTATATCTTTGAAC TTTTCAAGAATAAAAAGCTTAAAAG (SEQ ID NO: 104) |
| 2 | | | A_32_P119604 | AC090948 | | Homo sapiens chromosome 3 clone RP11-415F23 map 3p, complete sequence. | CAGAACTTCACTTCAGCAGACACTCAACTCAA AAAGACTGCAAATGGACATGTATTTAC (SEQ ID NO: 105) |
| 2 | | | A_32_P133213 | AC006480 | | Homo sapiens BAC clone RP11-16604 from 7, complete sequence. | TCAAGAGAGATCCTAAAGAAGCAAAATCACT GTGGACTGAAATGAGCAGACAAGTTTT (SEQ ID NO: 106) |
| 2 | | | A_32_P149492 | XM_496391 | NBPF9 | PREDICTED: Homo sapiens neuroblastoma breakpoint family, member 9, transcript variant 1 (NBPF9), mRNA | TTCTGGATTGTTTTTACATTCAGTGTTATAATA TTTGATTATGCTGATTGGTTTTGGTG (SEQ ID NO: 107) |
| 2 | | | A_32_P155506 | NM_152653 | UBE2E2 | Homo sapiens ubiquitin-conjugating enzyme E2E 2 (UBC4/5 homolog, yeast) (UBE2E2), mRNA | TGCAAACAATGTTGGAGCTGTAAATAGTAAGAG CTTTCTTACAAAGCTTTGTTATTACTGTG (SEQ ID NO: 108) |
| 2 | | | A_32_P159787 | NM_005520 | HNRPH1 | Homo sapiens heterogeneous nuclear ribonucleoprotein H1 (H) (HNRPH1), mRNA | AAATAAAAGCATGTCTTTCAACATGCATCCAAA ACAGTGTTCAATTTAACGTGGCAAAGG (SEQ ID NO: 109) |
| 2 | | | A_32_P162306 | NM_001004419 | CLEC2D | Homo sapiens C-type lectin domain family 2, member D (CLEC2D), transcript variant 2, mRNA | GCTGACAAAGATGATCACTTAAGGTGGATAA TGATGAAAATGAGCACCAGTTATCTTTA (SEQ ID NO: 110) |
| 2 | | | A_32_P181548 | AC087407 | | Homo sapiens 3 BAC CTC-269B10 (CalTech Clone Library C) complete sequence. | ATATTCTTCCAATATGTAGGGGAAAAGACATAT GAATAAGACAAATGAAAATTGCATAT (SEQ ID NO: 111) |
| 2 | | | A_32_P187009 | AC010260 | | Homo sapiens chromosome 5 clone CTC-45812, complete sequence. | ATTCACATGAGTAAATGATGAAGAACTCTTT AAGGTAATCTTTGGGATAAAGGATCC (SEQ ID NO: 112) |

TABLE 1-continued

| Cluster | Ratio cell type to all cells | cell Type | Array ID | Genbank ID | Gene ID | Description | Sequence |
|---|---|---|---|---|---|---|---|
| 2 | | | A_32_P193646 | NM_002139 | RBMX | *Homo sapiens* RNA binding motif protein, X-linked (RBMX), mRNA | GACTTGTACTGGTGTTGTAACTTTCCAAGTAAA AGTATCCCTAAAGGCCACTTCCTATCT (SEQ ID NO: 113) |
| 2 | | | A_32_P217510 | NM_032168 | WDR75 | *Homo sapiens* WD repeat domain 75 (WDR75), mRNA | TTACCGAAAAAGTCCAGATACAAGTAACACA GGTTTAGGAGAAGACATTATACATCAGT (SEQ ID NO: 114) |
| 2 | | | A_32_P225604 | NM_000969 | RPL5 | *Homo sapiens* ribosomal protein L5 (RPL5), mRNA | AAGCACTTCATGGGCCAGAATGTTGCAGATTA CATGCGCTACTTAATGGAAGAAGATGAC (SEQ ID NO: 115) |
| 2 | | | A_32_P34149 | NM_005520 | HNRPH1 | *Homo sapiens* heterogeneous nuclear ribonucleoprotein H1 (H) (HNRPH1), mRNA | TGAAGACTTAAGGCCCAGTATTTTTAATAGAA TACTCATCTAGGATGTAACAGTGAAGC (SEQ ID NO: 116) |
| 2 | | | A_32_P49423 | NM_002520 | NPM1 | *Homo sapiens* nucleophosmin (nucleolar phosphoprotein B23, numatrin) (NPM1), transcript variant 1, mRNA | AAACAGGAAAAAACTCCTAAAACACCTAAAAG GACCTAGTTCTGTAGAAGACATTAAAGC (SEQ ID NO: 117) |
| 2 | | | A_32_P63013 | HUMYY74A12 | | *Homo sapiens* full length insert cDNA clone YY74A12. | CCCGGGAGTGTTGCAAGTTAAACTGATGAAAA GACGTTTAGTATTTAATTGCTCCTCATG (SEQ ID NO: 118) |
| 2 | | | A_32_P80068 | NM_001004419 | CLEC2D | *Homo sapiens* C-type lectin domain family 2, member D (CLEC2D), transcript variant 2, mRNA | TGAACTGCACATTGTTGAAGCAGAGGCCATGA ATTACGAAGGCAGTCCAATTAAAGTAAC (SEQ ID NO: 119) |
| 3 | | Granulocytes | | | | | |
| 3 | | | A_23_P11926 | XR_001410 | FLJ21272 | PREDICTED: *Homo sapiens* hypothetical protein FLJ21272 (FLJ21272), misc RNA | ATCTTCCTAATCTCGTGGGATCACAAATATGAAT AACAAGGATGAACATAAGACACATCTG (SEQ ID NO: 120) |
| 3 | | | A_23_P135769 | NM_001101 | ACTB | *Homo sapiens* actin, beta (ACTB), mRNA | TTTAAAACTGGAACGGTGAAGGTGACAGCAG TCGGTTGGAGCGAGCATCCCCCAAAGTT (SEQ ID NO: 121) |
| 3 | | | A_23_P19590 | NM_003379 | VIL2 | *Homo sapiens* villin 2 (ezrin) (VIL2), mRNA | GATTATTCTCGAATCACCTCCTGTGTTGTGCT GGGAGCAGGACTGATTGAATTACGGAAA (SEQ ID NO: 122) |
| 3 | | | A_23_P20894 | NM_024757 | EHMT1 | *Homo sapiens* euchromatic histone-lysine N-methyltransferase 1 (EHMT1), mRNA | TGATTTCAGACTCAGAAGCCGACTTCGAGAG GAAGATTCTTACCTCTTTGATCTCGACA (SEQ ID NO: 123) |

TABLE 1-continued

| Cluster | Ratio cell type to all cells | cell Type | Array ID | Genbank ID | Gene ID | Description | Sequence |
|---|---|---|---|---|---|---|---|
| 3 | | | A_23_P257503 | NM_003922 | HERC1 | Homo sapiens hect (homologous to the E6-AP (UBE3A) carboxyl terminus) domain and RCC1 (CHC1)-like domain (RLD) 1 (HERC1), mRNA | TTTGGTCACTTTTGATAAGTTTCATGAAACCATTTTGGTGCATTTTTAGTTGGGAATGG (SEQ ID NO: 124) |
| 3 | | | A_23_P259901 | NM_012253 | TKTL1 | Homo sapiens transketolase-like 1 (TKTL1), mRNA | GATCCTGTGCTGCTGTGATGAGAGCCTCCACACTGTACTGTTCAAGTCAATGTTAAT (SEQ ID NO: 125) |
| 3 | | | A_23_P26759 | NM_138793 | CANT1 | Homo sapiens calcium activated nucleotidase 1 (CANT1), mRNA | AATTGCCTTTTCTAGAACTGTCAGAAATCCTCATGCCTTTCAAGACTTCTGTGAAT (SEQ ID NO: 126) |
| 3 | | | A_23_P31686 | NM_021174 | KIAA1967 | Homo sapiens KIAA1967 (KIAA1967), transcript variant 1, mRNA | AGAAAAGGCTTTTCGAGTGTGGGACAAGGTCTGATGTCAGTGAACGGAATTGAAGAGCA (SEQ ID NO: 127) |
| 3 | | | A_23_P319895 | XM_037523 | KIAA1076 | PREDICTED: Homo sapiens KIAA1076 protein (KIAA1076), mRNA | TGCAACTGAGGAGAAATAATTATTTTCACATGAGGAAATGCGTAGCTTGTAGAGACGGCT (SEQ ID NO: 128) |
| 3 | | | A_23_P332190 | NM_002163 | IRF8 | Homo sapiens interferon regulatory factor 8 (IRF8), mRNA | GGGATGCCTTACTTTGCACTTAATTAATAAGGGCATTCTCGAGGAGTAGACGTTTAAT (SEQ ID NO: 129) |
| 3 | | | A_23_P359430 | NM_015383 | NBPF14 | Homo sapiens neuroblastoma breakpoint family, member 14 (NBPF14), mRNA | ACCCTGGTTTCAATGAACCTAACCTCATTCTTTGTGTCTTCAGTGTTGGCTTGTTTTAGC (SEQ ID NO: 130) |
| 3 | | | A_23_P388681 | NM_001419 | ELAVL1 | Homo sapiens ELAV (embryonic lethal, abnormal vision, Drosophila)-like 1 (Hu antigen R) (ELAVL1), mRNA | AGATAATTAAGAGTGAAGGAGTTGAAACTTTCTTGTTAGTGTACAACTCATTTTGCGCC (SEQ ID NO: 131) |
| 3 | | | A_23_P406330 | NM_022733 | SMAP1L | Homo sapiens stromal membrane-associated protein 1-like (SMAP1L), mRNA | CAGCAGCCTAAAACTGTGTGTTTTTCTTATGGTTTAAAAACGCCATGTCATTGATAAC (SEQ ID NO: 132) |
| 3 | | | A_23_P416434 | NM_015288 | PHF15 | Homo sapiens PHD finger protein 15 (PHF15), mRNA | ATATATTGAAAAGACAATTTAAATATTTTTGGCTTATGTTGCAATATTTATTTCTT (SEQ ID NO: 133) |
| 3 | | | A_23_P417200 | NM_005652 | TERF2 | Homo sapiens telomeric repeat binding factor 2 (TERF2), mRNA | TCCCTGGTAATCTGTAGAACCTCTCCTAGGAAATGGTGAAGTCTATTAGAGCCACTTG (SEQ ID NO: 134) |
| 3 | | | A_23_P44581 | NM_001004060 | NOMO2 | Homo sapiens NODAL modulator 2 (NOMO2), transcript variant 1, mRNA | AATGTGATCACTTCCTCCTGAATACCTTCCTACATTATGGGTCAAGCTTTACAAAAGCGAA (SEQ ID NO: 135) |

TABLE 1-continued

| Cluster | Ratio cell type to all cells | cell Type | Array ID | Genbank ID | Gene ID | Description | Sequence |
|---|---|---|---|---|---|---|---|
| 3 | | | A_23_P44734 | NM_032557 | USP38 | Homo sapiens ubiquitin specific peptidase 38 (USP38), mRNA | GGATGCTATAACAAAGACAATAAACTATATTT ACAGGAACAAGAGTTGAATGCTCGAGC (SEQ ID NO: 136) |
| 3 | | | A_23_P60354 | NM_003070 | SMARCA2 | Homo sapiens SWI/SNF related, matrix associated, actin dependent regulator of chromatin, subfamily a, member 2 (SMARCA2), transcript variant 1, mRNA | TATCATCATCGTCTATAAACTAGCTTTAGGATA GTGCCAGACAAACATATGATATATCATGG (SEQ ID NO: 137) |
| 3 | | | A_23_P73593 | NM_002444 | MSN | Homo sapiens moesin (MSN), mRNA | GAAGCTTTCAGTATTAGTGATGTCATCTGTCAC TATAGGTCATACAATCCATTCTTAAAG (SEQ ID NO: 138) |
| 3 | | | A_23_P97770 | NM_020216 | RNPEP | Homo sapiens arginyl aminopeptidase (aminopeptidase B) (RNPEP), mRNA | ACCAGGAAGATTTCTGGAAAGTGAAGGAGTTC CTGCATAACCAGGGGAAGCAGAAGTATA (SEQ ID NO: 139) |
| 3 | | | A_24_P174257 | NM_019044 | CCDC93 | coiled-coil domain containing 93 | AAAGAGAGGGAAGAACTACACTAATGTTAGAG ATAGGTATGTTTTGGCTCAAAATGTGT (SEQ ID NO: 140) |
| 3 | | | A_24_P18190 | NM_005347 | HSPA5 | Homo sapiens heat shock 70 kDa protein 5 (glucose-regulated protein, 78 kDa) (HSPA5), mRNA | TTCTACAGCTTCTGATAATCAACCAACTGTTAC AATCAAGTCTATGAAGGTGAAAGACC (SEQ ID NO: 141) |
| 3 | | | A_24_P186030 | NM_002760 | PRKY | Homo sapiens protein kinase, Y-linked (PRKY), mRNA | CCAGTTTCTCTGTACCTGTGTGTATAGAAATA GATCAGAGCACAGTTGAAATTCATGGA (SEQ ID NO: 142) |
| 3 | | | A_24_P187626 | AC055811 | | Homo sapiens chromosome 17, clone RP11-45M22, complete sequence. | GAAGTGTGATGTGGACATCTGCAAAGACTTAT ATGCCAACGTGCTGTCTGCGGCACCAC (SEQ ID NO: 143) |
| 3 | | | A_24_P222599 | NM_002613 | PDPK1 | Homo sapiens 3-phosphoinositide dependent protein kinase-1 (PDPK1), transcript variant 1, mRNA | GCTGGTAAAAGCCTCTATTACGACTGTAAGTA AGTTGGATGTTGGCAAATTAAATTGTT (SEQ ID NO: 144) |
| 3 | | | A_24_P225325 | NM_022733 | SMAP1L | Homo sapiens stromal membrane-associated protein 1-like (SMAP1L), mRNA | CATGTTCTCATGATTTATGGAATGAAGCAAGT ACTGAAATCAAATTAAATACTCCCTGG (SEQ ID NO: 145) |
| 3 | | | A_24_P226037 | NM_001003810 | HNRPD | Homo sapiens heterogeneous nuclear ribonucleoprotein D (AU-rich element RNA binding protein 1, 37 kDa) (HNRPD), transcript variant 4, mRNA | AGAAATACCACAATGTTGGTCTTAGTAAATGTG AATAAAAGTAGCCATGTCGAAGGAAC (SEQ ID NO: 146) |

TABLE 1-continued

| Cluster | Ratio cell type to all cells cell Type | Array ID | Genbank ID | Gene ID | Description | Sequence |
|---|---|---|---|---|---|---|
| 3 | | A_24_P226554 | NM_001101 | ACTB | Homo sapiens actin, beta (ACTB), mRNA | GCACCCAGCACAATGAAGATCAAGATCATTGC TCCTCCTGAGCGCAAGTACTCCGTGTGG (SEQ ID NO: 147) |
| 3 | | A_24_P238744 | XM_292982 | LOC653269 | PREDICTED: Homo sapiens similar to protein expressed in prostate, ovary, testis, and placenta 15, transcript variant 1 (LOC653269), mRNA | TGTGCATCCACGAGAACTACCTTCAACTCCAT CATGAAGTCGGATGTGGACATCTACAAA (SEQ ID NO: 148) |
| 3 | | A_24_P255786 | AL359844 | | Human DNA sequence from clone RP11-314J18 on chromosome 10 | GTCCTCCTGGGAGAGAGCTATGAGCTGTCA GATGGCCAGGTCATCACCAGCAGCAACAA (SEQ ID NO: 149) |
| 3 | | A_24_P261169 | NM_006378 | SEMA4D | Homo sapiens sema domain, immunoglobulin domain (Ig), transmembrane domain (TM) and short cytoplasmic domain, (semaphorin) 4D (SEMA4D), mRNA | AACTTCCTTTTGCTAAATGCATTCTTTCTGCTTT TAGAAATGTAGACATAAACACTCCCC (SEQ ID NO: 150) |
| 3 | | A_24_P273666 | NM_000516 | GNAS | Homo sapiens GNAS complex locus (GNAS), transcript variant 1, mRNA | CCCCGAGTGATTTTGCGAAACCCCTTTTCCC TTCAGCTTGCTTAGATGTTCCAAATTTA (SEQ ID NO: 151) |
| 3 | | A_24_P287272 | XM_498427 | NBPF1 | PREDICTED: Homo sapiens neuroblastoma breakpoint family, member 1, transcript variant 1 (NBPF1), mRNA | ACCTAACCTCATTCTTTGTATCTTCAGTGTTGA ATGTTTTAGCTGATCCATCTTTAACG (SEQ ID NO: 152) |
| 3 | | A_24_P325333 | NM_002600 | PDE4B | Homo sapiens phosphodiesterase 4B, cAMP-specific (phosphodiesterase E4 dunce homolog, Drosophila) (PDE4B), mRNA | ACTTCTACACAGATAAGCTTTCAAAGTTGACAA ACTTTTTTGACTCTTTCTGGAAAAGGG (SEQ ID NO: 153) |
| 3 | | A_24_P331998 | NM_203447 | DOCK8 | Homo sapiens dedicator of cytokinesis 8 (DOCK8), mRNA | CCTACATACAGATCACTTTTGTGGAGCCCTAC TTTGATGAGTATGAGATGAAAGACAGGG (SEQ ID NO: 154) |
| 3 | | A_24_P354724 | NM_054114 | TAGAP | Homo sapiens T-cell activation GTPase activating protein (TAGAP), transcript variant 2, mRNA | GGCCATACGCCATGCCATAGCTTGTGTCTATCT GTAAATATGAGACTTGTAAAGAACTGCC (SEQ ID NO: 155) |
| 3 | | A_24_P369154 | NM_002721 | PPP6C | Homo sapiens protein phosphatase 6, catalytic subunit (PPP6C), mRNA | AATATTGCTTCGATCATGGTCTTCAAAGATGTA AATACAAGAGAACCAAAGTTATTCCGG (SEQ ID NO: 156) |
| 3 | | A_24_P375076 | AL390237 | | Human DNA sequence from clone RP11-278J20 on chromosome 6 Contains a retinoblastoma binding protein 4 (RBBP4) pseudogene and a KIAA0797 pseudogene, complete sequence. | GACAATATTATGCAAGTGTGGCAAATGGCAGA GAACATTTACAACATGAAGAACCCTGAA (SEQ ID NO: 157) |

TABLE 1-continued

| Cluster | Ratio cell type to all cells | cell Type | Array ID | Genbank ID | Gene ID | Description | Sequence |
|---|---|---|---|---|---|---|---|
| 3 | | | A_24_P383901 | HSBA12M9 | | Human DNA sequence from clone RP11-12M9 on chromosome 22, complete sequence. | CATGTACCCTGGCATCACCAACAGGATGCAGA AGAAGATCACCGCCCTAGCACCCAGCAT (SEQ ID NO: 158) |
| 3 | | | A_24_P391568 | NM_001668 | ARNT | Homo sapiens aryl hydrocarbon receptor nuclear translocator (ARNT), transcript variant 1, mRNA | GGCTTTGGCCAGTAGCTAAAGTGCAAGACTGA ATTAATGAGAAGATATATTAAATGTAGT (SEQ ID NO: 159) |
| 3 | | | A_24_P393151 | AC009892 | | Homo sapiens chromosome 19 clone CTB-83J4, complete sequence. | AAGAAATCTTATCATTCGCCATTCACCCTGTAG AATAAAGAAATCTTATCATTCACCGTC (SEQ ID NO: 160) |
| 3 | | | A_24_P401090 | AL354702 | | Human DNA sequence from clone RP11-334L9 on chromosome 1 Contains a heat shock 70 kDa protein 5 (glucose-regulated protein, 78 kDa) (HSPA5) pseudogene, complete sequence. | TTTTCTACAGCTTTTGATAATCAAGTTACAATC AAGGTCTATGAAGGTAAACAACCCCTG (SEQ ID NO: 161) |
| 3 | | | A_24_P408424 | NM_002473 | MYH9 | Homo sapiens myosin, heavy polypeptide 9, non-muscle (MYH9), mRNA | CTGGTCTCACTGGTTGCCGAATTTACTTGTAT TCCTAACTGTTTTGTATATGCTGCATT (SEQ ID NO: 162) |
| 3 | | | A_24_P410017 | NM_001017421 | FKSG30 | Homo sapiens actin-like protein (FKSG30), mRNA | ATGAAACTACCTTCAACTCCATCATGAAGCTG ATGTGGACATCCGCAAAGACCCTGTACA (SEQ ID NO: 163) |
| 3 | | | A_24_P42517 | NM_006854 | KDELR2 | Homo sapiens KDEL (Lys-Asp-Glu-Leu) endoplasmic reticulum protein retention receptor 2 (KDELR2), mRNA | CATCCTATACTGTGACTTCTTCTACTTGTACAT TACAAAGTACTCAAGGGAAAGAAGCT (SEQ ID NO: 164) |
| 3 | | | A_24_P47182 | NM_003373 | VCL | Homo sapiens vinculin (VCL), transcript variant 2, mRNA | ATGGGGTTCAAGAGAGTAATGGGTTTCATATT TCTTATCACCACAGTAAGTTCCTACTAG (SEQ ID NO: 165) |
| 3 | | | A_24_P475115 | AC097103 | | Homo sapiens 3 BAC RP11-319G6 (Roswell Park Cancer Institute Human BAC Library) complete sequence | ACTGACTACTTCATGAAGATCCTCATGGAGTG CAGCTACCCGTTTCACCACCATGGCTGAG (SEQ ID NO: 166) |
| 3 | | | A_24_P63118 | NM_013374 | PDCD6IP | Homo sapiens programmed cell death 6 interacting protein (PDCD6IP), mRNA | TAGTTTTTGCACGAAGACAGAAAGAGATGAA CTCTTAAAGGACTTGCAACAAAGCATTG (SEQ ID NO: 167) |
| 3 | 3 | Granulocyte | A_24_P63136 | NM_023914 | P2RY13 | Homo sapiens purinergic receptor P2Y, G-protein coupled, 13 (P2RY13), transcript variant 1, mRNA | ATGCCAGATTTCTTGGTATCTCCATAATACG ACCTACAGTCCATGCTCTACAGATGTT (SEQ ID NO: 168) |

TABLE 1-continued

| Cluster | Ratio cell type to all cells | cell Type | Array ID | Genbank ID | Gene ID | Description | Sequence |
|---|---|---|---|---|---|---|---|
| 3 | | | A_24_P63827 | NM_005494 | DNAJB6 | Homo sapiens DnaJ (Hsp40) homolog, subfamily B, member 6 (DNAJB6), transcript variant 2, mRNA | CAACTTCAACTAAAATGGTTAATGGCAGAAAAA TCACTACAAGAGAATTGTCGAGAACG (SEQ ID NO: 169) |
| 3 | | | A_24_P643587 | NM_024095 | ASB8 | Homo sapiens ankyrin repeat and SOCS box-containing 8 (ASB8), mRNA | GCTCTGTAATAACAGTAATAAATAGCTCTGAAA TAACAGTCCTAAGACTCCTAAAGTCC (SEQ ID NO: 170) |
| 3 | | | A_24_P681011 | HSM807522 | | Homo sapiens mRNA; cDNA DKFZp686K02111 (from clone DKFZp686K02111). | GTGTTAATCCATGTTAATCTGTGTGAAAATTAT TGCGTGCAACAGTATTTCTCGTGTAC (SEQ ID NO: 171) |
| 3 | | | A_24_P68649 | NM_020216 | RNPEP | Homo sapiens arginyl aminopeptidase (aminopeptidase B) (RNPEP), mRNA | GCAACAGGAGAGAAGCTTTTTGGACCTTATGT TTGGGAAGGTATGACTTGCTCTTTCATG (SEQ ID NO: 172) |
| 3 | | | A_24_P693321 | | | | ATCACAACTATGCCAAATAATCAATCCTACAAT GTCCAAATTTTACTTTAAAACTGGAA (SEQ ID NO: 173) |
| 3 | | | A_24_P714134 | XR_019310 | LOC646447 | PREDICTED: Homo sapiens similar to heterogeneous nuclear ribonucleoprotein | AGAGTGCATAAAATATCCTTGATCTTATATCT GAGTCTCCTACAGAGAATGTGCACAGA (SEQ ID NO: 174) |
| 3 | | | A_24_P787897 | XM_001125986 | LOC283824 | PREDICTED: Homo sapiens hypothetical protein LOC283824 | TGAACTATCTGAAATTGACCAGTAATCAAGTT CCAATCATCTGAATGCTTTTCCTTGAG (SEQ ID NO: 175) |
| 3 | | | A_24_P79617 | NM_014656 | KIAA0040 | Homo sapiens KIAA0040 (KIAA0040), mRNA | TGAAAATGAAAAGTCTTGATGTAGTCAGATGG TTACTCTCTTAACATTAGGTATTACCCC (SEQ ID NO: 176) |
| 3 | | | A_24_P7974 | AF161369 | | Homo sapiens HSPC106 mRNA, partial cds. | GTTGCTTTATGTAGCAAATTCTCCGTTTGGAG CTTTTAAAATAGGATTATTTGCCAGAAC (SEQ ID NO: 177) |
| 3 | | | A_24_P808534 | NM_001357 | DHX9 | Homo sapiens DEAH (Asp-Glu-Ala-His) box polypeptide 9 (DHX9), transcript variant 1, mRNA | GGAAAAGACAAAGATTCTCCACCACTGAAGGT GTAATGCACTTATCCACAAATCATCTGT (SEQ ID NO: 178) |
| 3 | | | A_24_P940059 | NM_015553 | PIP3-E | Homo sapiens phosphoinositide-binding protein PIP3-E (PIP3-E), mRNA | CCCAGGGTTTGTAATAACATAATTGAAAATAAA AGTCCCTGAAACTAAATGTTTGCAGCC (SEQ ID NO: 179) |

TABLE 1-continued

| Cluster | Ratio cell type to all cells | cell Type | Array ID | Genbank ID | Gene ID | Description | Sequence |
|---|---|---|---|---|---|---|---|
| 3 | | | A_32_P11359 | | | | AACTAAAAAGCATTAATTAAAAAGTACTTAACTCAGAAATTATAAAAATAGGAGACATCA (SEQ ID NO: 180) |
| 3 | | | A_32_P144920 | NM_015509 | NECAP1 | Homo sapiens NECAP endocytosis associated 1 (NECAP1), mRNA | TTGAGTTTGAATTGTGTAACATCTTTGATCAGTGGGTGTATCTGTAATGAAGGAGGTTCA (SEQ ID NO: 181) |
| 3 | | | A_32_P155776 | NM_001017421 | FKSG30 | Homo sapiens actin-like protein (FKSG30), mRNA | ATAGTGAAGTCTGATGTGGACATCCGCAAAGACCTGTACACCAACACAGTGCTGTCTGGC (SEQ ID NO: 182) |
| 3 | | | A_32_P221958 | NM_133446 | CTGLF1 | Homo sapiens centaurin, gamma-like family, member 1 (CTGLF1), mRNA | ATGGGAAAAATAAGGATAACTCAGAATTTCAAAAGGAAATCACAAATTCAGCTAGTAATA (SEQ ID NO: 183) |
| 3 | | | A_32_P60551 | HS661I20 | | Human DNA sequence from clone RP4-661I20 on chromosome 20q11.23-12 Contains the RPL12L2 gene for ribosomal protein L12-like 2 pseudogene, the 5' end of the CHD6 gene for chromodomain helicase DNA binding protein 6 and two CpG islands, complete sequence. | GCAGAAGTACAAGCTTTAGGTGTATCTATTCATCTATTCCTAGTACATAAAATTTAGCC (SEQ ID NO: 184) |
| 3 | | | A_32_P79434 | NM_002847 | PTPRN2 | Homo sapiens protein tyrosine phosphatase, receptor type, N polypeptide 2 (PTPRN2), transcript variant 1, mRNA | TCTTCTACATGGTATTGTAATGAATATCTGCTTTAATATAGCTATCATTTCTTTTCCAAAA (SEQ ID NO: 185) |
| 3 | | | A_32_P8666 | NM_002140 | HNRPK | Homo sapiens heterogeneous nuclear ribonucleoprotein K (HNRPK), transcript variant 1, mRNA | GGTCTGCAGATTAAACAAATCCGTCATGAGTCGGGAGCTTCGATCAAAATTGATGAGCCT (SEQ ID NO: 186) |
| 4 | Granulocytes | | A_23_P113762 | | | | AGACCCTGGACGAAGATGGGGATGGGAGTGTGACTTCCAGGAGTTTAATGGCCTTCGTCT (SEQ ID NO: 187) |
| 4 | | | A_23_P117992 | NM_014861 | KIAA0703 | Homo sapiens KIAA0703 gene product (KIAA0703), mRNA | TCCATCACCGGATCAGTTTTCCTCTTAGGAAAGCTGCAGGAACCTCGTGGGCTCCAGGG (SEQ ID NO: 188) |
| 4 | | | A_23_P119222 | NM_020415 | RETN | Homo sapiens resistin (RETN), mRNA | CAATAAGCAGCATTGGCCTGGAGTGCCAGAGCGTCACCTCCAGGGGACCTGGCTACTT (SEQ ID NO: 189) |

TABLE 1-continued

| Cluster | Ratio cell type to all cells | cell Type | Array ID | Genbank ID | Gene ID | Description | Sequence |
|---|---|---|---|---|---|---|---|
| 4 | 2 | Granulocyte | A_23_P121622 | NM_014465 | SULT1B1 | Homo sapiens sulfotransferase family, cytosolic, 1B, member 1 (SULT1B1), mRNA | GAAATAGAGATTGTCTGTAGTTGATTGAAACG AGGGCAGTTATGAATTGATTTGGGCAAT (SEQ ID NO: 190) |
| 4 | 8 | Granulocyte | A_23_P121716 | NM_005139 | ANXA3 | Homo sapiens annexin A3 (ANXA3), mRNA | TGGACATTCGAACAGAGTTCAAGAGAGCATTAT GGCTATTCCCTATATTCAGCAATTAAAT (SEQ ID NO: 191) |
| 4 | | | A_23_P122924 | NM_002192 | INHBA | Homo sapiens inhibin, beta A (activin A, activin AB alpha polypeptide) (INHBA), mRNA | AAACATCATCAAAAAGGACATTCAGAACATGAT CGTGGAGAGTGTGGGTGCTCATAGAG (SEQ ID NO: 192) |
| 4 | | | A_23_P123645 | | | | AATGGTTTTGTGCAGTGAACAACACATGGCGA GGTACTAACTGAGAACTTTTCATGCT (SEQ ID NO: 193) |
| 4 | | | A_23_P126278 | NM_003465 | CHIT1 | Homo sapiens chitinase 1 (chitotriosidase) (CHIT1), mRNA | GGGCCACCAAACAGAGAATCCAGGATCAGAA GGTGCCCTACATCTTCCGGGACAACCAGT (SEQ ID NO: 194) |
| 4 | | | A_23_P130961 | NM_001972 | ELA2 | Homo sapiens elastase 2, neutrophil (ELA2), mRNA | AACGGCTACGACCCCGTAAACTTGCTCAACGA CATCGTGATTCTCCAGCTCAACGGGTCG (SEQ ID NO: 195) |
| 4 | 4 | Granulocyte | A_23_P131785 | NM_001725 | BPI | Homo sapiens bactericidal/permeability-increasing protein (BPI), mRNA | GACTCAGATTCAGAAATGATCTAAACACGAGG AAACATTATTCATTGGAAAAGTGCATGG (SEQ ID NO: 196) |
| 4 | | | A_23_P140384 | NM_001911 | CTSG | Homo sapiens cathepsin C (CTSG), mRNA | TGTGACTGACTCTTCTTCTGGGGACACAGGC CAGCTCCACAGTGTTGCCAGAGCCTTAA (SEQ ID NO: 197) |
| 4 | | | A_23_P141173 | NM_000250 | MPO | Homo sapiens myeloperoxidase (MPO), nuclear gene encoding mitochondrial protein, mRNA | CCTGTTCTCGGGTGCAGCTGAGAGAAAATGAGTGA CTAGACGTTCATTTGTGTCTCATGTAT (SEQ ID NO: 198) |
| 4 | | | A_23_P149301 | NM_002105 | H2AFX | Homo sapiens H2A histone family, member X (H2AFX), mRNA | GGGCCGCGACAACAAGAAGACGCGCATCATC CCGCCGCCACCTGCCACCTGGCCATCCGCAA (SEQ ID NO: 199) |
| 4 | | | A_23_P151637 | NM_002934 | RNASE2 | Homo sapiens ribonuclease, RNase A family, 2 (liver, eosinophil-derived neurotoxin) (RNASE2), mRNA | GTGTAACCCAAATAATGACCTGTCCTAGTAAC AAAACTCGAAAAATTGTCACCACAGTG (SEQ ID NO: 200) |

TABLE 1-continued

| Cluster | Ratio cell type to all cells | cell Type | Array ID | Genbank ID | Gene ID | Description | Sequence |
|---|---|---|---|---|---|---|---|
| 4 | 3 | Granulocyte | A_23_P156180 | NM_003059 | SLC22A4 | Homo sapiens solute carrier family 22 (organic cation transporter), member 4 (SLC22A4), mRNA | AAACAAGAGACTCAATGAGACAGAAGAAAAT CCCAAGGTTCTAATAACTGCATTCTGAA (SEQ ID NO: 201) |
| 4 | | | A_23_P161428 | NM_144590 | ANKRD22 | Homo sapiens ankyrin repeat domain 22 (ANKRD22), mRNA | AATCCTTGTGACCACCACCGATGAGAGATACAGA AAAAGTTAACGACTGGATTCTATCTTCA (SEQ ID NO: 202) |
| 4 | | | A_23_P163025 | NM_002934 | RNASE2 | Homo sapiens ribonuclease, RNase A family, 2 (liver, eosinophil-derived neurotoxin) (RNASE2), mRNA | AGCCACAGCTCAGAGACTGGGAAACATGGTTC CAAAACTGTTCACTTCCCAAATTTGTCT (SEQ ID NO: 203) |
| 4 | | | A_23_P166848 | NM_002343 | LTF | Homo sapiens lactotransferrin (LTF), mRNA | ATATTTGGGACCACCAGTATGTCGCAGGCATTA CTAATCTGAAAAAGTGCTCAACCTCCCC (SEQ ID NO: 204) |
| 4 | 4 | Granulocyte | A_23_P168014 | NM_003509 | HIST1H2AI | Homo sapiens histone 1, H2ai (HIST1H2AI), mRNA | TGAGGAGCTCAACAAGCTTCTGGGCAAACTCA CCATCGCACAGGGTGGCGTTCCTGCCCAA (SEQ ID NO: 205) |
| 4 | | | A_23_P169437 | NM_005564 | LCN2 | Homo sapiens lipocalin 2 (oncogene 24p3) (LCN2), mRNA | GCTATGGTGTTCTTCAAGAAAGTTTCTCAAAC AGGGAGTACTTCAAGATCACCCCTCTAC (SEQ ID NO: 206) |
| 4 | | | A_23_P170233 | NM_005213 | CSTA | Homo sapiens cystatin A (stefin A) (CSTA), mRNA | AACTGGCTACTGACTGAGTCATGATCCTTGCTGATA AATATAACCATCAATAAAGAAGCATTCT (SEQ ID NO: 207) |
| 4 | | | A_23_P19543 | NM_003137 | SRPK1 | Homo sapiens SFRS protein kinase 1 (SRPK1), mRNA | CTGTCAAATTGCCACGATCTCACTAAAGGATTT CTATTTGCTGTCAGTTAAAATAAAGC (SEQ ID NO: 208) |
| 4 | | | A_23_P200507 | NM_014184 | CNIH4 | Homo sapiens cornichon homolog 4 (Drosophila) (CNIH4), mRNA | TGGTTGAAGTCAGCCTACACTACAGTGCACAG TTGAGGAGCCAGAGACTTAAATCAT (SEQ ID NO: 209) |
| 4 | | | A_23_P206760 | NM_005143 | HP | Homo sapiens haptoglobin (HP), mRNA | GATAAGATGTGGTTTGAAGCTGATGGGTGCCA GCCCTGCATTGCTGAGTCAATCAATAAA (SEQ ID NO: 210) |
| 4 | 3 | Granulocyte | A_23_P218442 | NM_002483 | CEACAM6 | Homo sapiens carcinoembryonic antigen-related cell adhesion molecule 6 (non-specific cross reacting antigen) (CEACAM6), mRNA | ACACTCATCTGACTCATTCTTTATTCTATTTAG TTGGTTTGTATCTTGCCTAAGGTGCG (SEQ ID NO: 211) |

TABLE 1-continued

| Cluster | Ratio cell type to all cells | cell Type | Array ID | Genbank ID | Gene ID | Description | Sequence |
|---|---|---|---|---|---|---|---|
| 4 | | | A_23_P23048 | NM_002965 | S100A9 | Homo sapiens S100 calcium binding protein A9 (calgranulin B) (S100A9), mRNA | GAGCTGGTGCGAAAAGATCTGCAAAATTTCT CAAGAAGGAGAATAAGAATTGAAAAGGTC (SEQ ID NO: 212) |
| 4 | | | A_23_P25235 | NM_080387 | CLEC4D | Homo sapiens C-type lectin domain family 4, member D (CLEC4D), mRNA | CATTTAACCCACGCAGAGTATTCTGGCATAAG AATGAACCCGACAACTCTCAGGAGAAA (SEQ ID NO: 213) |
| 4 | 18 | Granulocyte | A_23_P253791 | NM_004345 | CAMP | Homo sapiens cathelicidin antimicrobial peptide (CAMP), mRNA | GAATTGTCCAGAGAATCAAGGATTTTTGCGG AATCTTGTACCCAGGACGAGTCCTAGT (SEQ ID NO: 214) |
| 4 | | | A_23_P258493 | NM_005573 | LMNB1 | Homo sapiens lamin B1 (LMNB1), mRNA | AATATTAACCTAATCACCATGTAAGCACTCTGG ATGATGGATTCCACAAAACTTGGTTTT (SEQ ID NO: 215) |
| 4 | 3 | Granulocyte | A_23_P259506 | NM_032412 | ORF1-FL49 | Homo sapiens putative nuclear protein ORF1-FL49 (ORF1-FL49), mRNA | TGGGATTCTAGATTAATGGGGGTTGCTACTGT TTAATTCAGTGACTTGATCTTTTTAATG (SEQ ID NO: 216) |
| 4 | | | A_23_P302470 | NM_014465 | SULT1B1 | Homo sapiens sulfotransferase family, cytosolic, 1B, member 1 (SULT1B1), mRNA | TGTCTAAGTCACAAATCTGAAGAAATAAGAGAT TGTCTGTAGTTGATTGAAACGAGGGCA (SEQ ID NO: 217) |
| 4 | | | A_23_P306941 | NM_153615 | Rgr | Homo sapiens Ral-GDS related protein Rgr (Rgr), mRNA | CCATGGGACTTTTGTGAGTCAGGCGGAGAC CATTTTATGTTTATTTCTTTAGTGTATA (SEQ ID NO: 218) |
| 4 | 2 | Granulocyte | A_23_P309381 | NM_003516 | HIST2H2AA | Homo sapiens histone 2, H2aa (HIST2H2AA), mRNA | CGACTTTCCCGATCGCCAGGCAGGAGTTTCTC TCGGTGACTACTATCGCTGTCATGTCTG (SEQ ID NO: 219) |
| 4 | | | A_23_P312932 | NM_175857 | KRTAP8-1 | Homo sapiens keratin associated protein 8-1 (KRTAP8-1), mRNA | GGCTATGGCTTCGGCTATGGCTACAACGCT GTGGGGCTTTCGGCTACAGGAGATACTCG (SEQ ID NO: 220) |
| 4 | 24 | Granulocyte | A_23_P31816 | NM_004084 | DEFA1 | Homo sapiens defensin, alpha 1 (DEFA1), mRNA | GAGAACGTCGCTATGGAACCTGCATCTACCAG GGAAGACTCTGGGCATTCTGCTGCTGAG (SEQ ID NO: 221) |
| 4 | 13 | Granulocyte | A_23_P326080 | NM_001925 | DEFA4 | Homo sapiens defensin, alpha 4, corticostatin (DEFA4), mRNA | AGAGCTACAGGAAATGGTGTTCTTCCTATACT TGTCCTTAACATTTTCTTGATCCTA (SEQ ID NO: 222) |

TABLE 1-continued

| Cluster | Ratio cell type to all cells | cell Type | Array ID | Genbank ID | Gene ID | Description | Sequence |
|---|---|---|---|---|---|---|---|
| 4 | | | A_23_P330561 | NM_174918 | MCEMP1 | Homo sapiens mast cell-expressed membrane protein 1 (MCEMP1), mRNA | CTGTCTCCCTGTTTGTGTAAACATACTAGAGTA TACTGCGGCGTGTTTTCTGTCTACCCA (SEQ ID NO: 223) |
| 4 | | | A_23_P332042 | NM_004259 | RECQL5 | Homo sapiens RecQ protein-like 5 (RECQL5), transcript variant 1, mRNA | CTTTCTGCTTGCAAAGCCTATAGACCCTTCTCA GAGCGGTCCTCATGGCTGGGTTTTCTG (SEQ ID NO: 224) |
| 4 | | | A_23_P344973 | NM_021019 | MYL6 | Homo sapiens myosin, light polypeptide 6, alkali, smooth muscle and non-muscle (MYL6), transcript variant 1, mRNA | CCTATGAGGATTATGTCGAAGGACTTCGGGTG TTTGACAGGAAGAAATGGCACCGTCA (SEQ ID NO: 225) |
| 4 | | | A_23_P370635 | NM_138799 | OACT2 | Homo sapiens O-acyltransferase (membrane bound) domain containing 2 (OACT2), mRNA | TTGTTCCTAAATGGTATTTTCAAGTGTAATATT GTGAGAAGCTACTGCAGTAGTTGATG (SEQ ID NO: 226) |
| 4 | | | A_23_P371495 | XM_928461 | LOC653626 | PREDICTED: Homo sapiens similar to ARG99 protein (LOC653626), mRNA | ACCAGACTAAGTGCCAGTATATATGACTGAT ATTTTCGTGACTCATAGAAGGTGTCCA (SEQ ID NO: 227) |
| 4 | | | A_23_P380240 | NM_001816 | CEACAM8 | Homo sapiens carcinoembryonic antigen-related cell adhesion molecule 8 (CEACAM8), mRNA | TAGTCCACCCAATGCTGACAGTAACAGCATC TTTAACACAACTCTTTGTTCAAATGTAC (SEQ ID NO: 228) |
| 4 | | | A_23_P395438 | NM_053044 | HTRA3 | Homo sapiens HtrA serine peptidase 3 (HTRA3), mRNA | AAGGGGCATTTGTGAGCTTTGCTGTAAATGGA TTCCCAGTGTGCTTGTACTGTATGTTT (SEQ ID NO: 229) |
| 4 | | | A_23_P4096 | NM_000717 | CA4 | Homo sapiens carbonic anhydrase IV (CA4), mRNA | TAATATCCCCAAACCTGAGATGAGCACTACGA TGGCAGAGAGCAGCCTGTTGGACCTGCT (SEQ ID NO: 230) |
| 4 | | | A_23_P41114 | NM_005213 | CSTA | Homo sapiens cystatin A (stefin A) (CSTA), mRNA | AACAAATGAGACTTATGAAATTGGAAGCT GTGCAGTATAAAACTCAAGTTGTTGCTG (SEQ ID NO: 231) |
| 4 | | | A_23_P421493 | NM_020995 | HPR | Homo sapiens haptoglobin-related protein (HPR), mRNA | GGGGACAAAGTGACAACTTTAAACTTACTGAC CATCTGAAGTATGTCATGCTGCCTGTGG (SEQ ID NO: 232) |
| 4 | | | A_23_P434809 | NM_002964 | S100A8 | Homo sapiens S100 calcium binding protein A8 (calgranulin A) (S100A8), mRNA | AAAGCCATGAAGAAGAAGCCACAAAGAGTAGCTG AGTTACTGGCCCCAGAGGCTGGGCCCT (SEQ ID NO: 233) |
| 4 | 2 | Granulocyte | | | | | |
| 4 | 5 | Granulocyte | | | | | |

(Note: Granulocyte cell type entries correspond to rows RECQL5 and CEACAM8 respectively based on column alignment.)

TABLE 1-continued

| Cluster | Ratio cell type to all cells | cell Type | Array ID | Genbank ID | Gene ID | Description | Sequence |
|---|---|---|---|---|---|---|---|
| 4 | | | A_23_P60248 | NM_003329 | TXN | Homo sapiens thioredoxin (TXN), mRNA | GGACAAAAGGTGGTGAATTTCTGGAGCCAA TAAGGAAAAGCTTGAAGCCACCATTAAT (SEQ ID NO: 234) |
| 4 | | | A_23_P63390 | NM_000566 | FCGR1A | Homo sapiens Fc fragment of IgG, high affinity Ia, receptor (CD64) (FCGR1A), mRNA | TTTAGTGAACACTGTTCTCTGGTGACAATAC GTAAAGAACTGAAAGAAGAAGAAAAGTG (SEQ ID NO: 235) |
| 4 | 4 | Granulocyte | A_23_P67847 | NM_024572 | GALNT14 | Homo sapiens UDP-N-acetyl-alpha-D-galactosamine:polypeptide N-acetylgalactosaminyltransferase 14 (GalNAc-T14) (GALNT14), mRNA | AAGCCTTCTTTTTCACTAGGCCAGGACTACATT GAGAGATGAAGAATGGAGGTTGTTTCC (SEQ ID NO: 236) |
| 4 | | | A_23_P74001 | NM_005621 | S100A12 | Homo sapiens S100 calcium binding protein A12 (calgranulin C) (S100A12), mRNA | TGAAGGCTTTTTACCCAGCAATGTCCTCAATG AGGGTCTTTTCTTTCCCTCCACCAAAACC (SEQ ID NO: 237) |
| 4 | 3 | B cells | A_23_P85250 | NM_013230 | CD24 | Homo sapiens CD24 antigen (small cell lung carcinoma cluster 4 antigen) (CD24), mRNA | CTGCCTGCACACACATAAACCTTTTTAAAAATA GACACTCCCCGAAGTCTTTTGTTTGTA (SEQ ID NO: 238) |
| 4 | | | A_23_P85903 | NM_003268 | TLR5 | Homo sapiens toll-like receptor 5 (TLR5), mRNA | AACAGTAGAAAGATCGTTTGTCTTGTGAGCAG ACACTTCCTTAGAGATGGCTGGTGCCTT (SEQ ID NO: 239) |
| 4 | | | A_23_P94230 | NM_015364 | LY96 | Homo sapiens lymphocyte antigen 96 (LY96), mRNA | TGAAGCTATTTCTGGGAGCCAGAAGAAATGC TCTTTTGTTGGAGTTTGTCATCCTACA (SEQ ID NO: 240) |
| 4 | 3 | Granulocyte | A_23_P99253 | NM_004664 | LIN7A | Homo sapiens lin-7 homolog A (C. elegans) (LIN7A), mRNA | TTGAGGGAAAGCTACTTGATCAAACATCCGAT AGTCACAAATTTGAAACCGTGCTTCAGA (SEQ ID NO: 241) |
| 4 | | | A_24_P145066 | NM_183416 | KIF1B | Homo sapiens kinesin family member 1B (KIF1B), transcript variant 2, mRNA | TAGCTAGAACAGTTGAAGTCTTCAACTGAGGT TTATAGCAGATTAGACATGGGTAAATG (SEQ ID NO: 242) |
| 4 | 33 | Granulocyte | A_24_P181254 | NM_006418 | OLFM4 | Homo sapiens olfactomedin 4 (OLFM4), mRNA | TTTTTCCTTTGATGTTCAAGTCCTAGTCTATAG GATTGGCAGTTTAAATGCTTTACTCCC (SEQ ID NO: 243) |
| 4 | | | A_24_P252996 | NM_000804 | FOLR3 | Homo sapiens folate receptor 3 (gamma) (FOLR3), mRNA | CCTGCAAAAGCAACTGGCACAAAGGCTGAAT TGGACCTCCAGGGATTAATGAGTGTCCGG (SEQ ID NO: 244) |

TABLE 1-continued

| Cluster | Ratio cell type to all cells | cell Type | Array ID | Genbank ID | Gene ID | Description | Sequence |
|---|---|---|---|---|---|---|---|
| 4 | | | A_24_P273143 | NM_052871 | MGC4677 | Homo sapiens hypothetical protein MGC4677 (MGC4677), mRNA | ACAGGAAGCTCTATGACACACTTGATCGAATA TGACAGACACCGAAAATCACGACTCAGC (SEQ ID NO: 245) |
| 4 | | | A_24_P52004 | NM_015200 | SCC-112 | Homo sapiens SCC-112 protein (SCC-112), mRNA | TGCATTGATAGGGACCTTTGTCTTCCTTCCTCCC TTTGATTAATTGCCCGGCATCACAGTTT (SEQ ID NO: 246) |
| 4 | | | A_24_P649624 | BC063684 | | Homo sapiens cDNA clone IMAGE: 4395035, partial cds. | CTGTTAGAGCCAAAATTGTGATGAGCAATACT GATAATTGTCCAGTTTATGTCATCTTTC (SEQ ID NO: 247) |
| 4 | | | A_24_P6921 | NM_052871 | MGC4677 | Homo sapiens hypothetical protein MGC4677 (MGC4677), mRNA | CAGGAAGCTCTATGACACACTTGATCGAATAT GACAGACACTGAAAATCACGACTCATCC (SEQ ID NO: 248) |
| 4 | | | A_24_P759747 | CNS01RGE | | Human chromosome 14 DNA sequence BAC R-300J18 of library RPCI-11 from chromosome 14 of Homo sapiens (Human), complete sequence. | GGAGGAGCCCCACCTTCTGCTACTATTATGTT CTTCAGATGAGTAGAAGAGAGTGGGGAG (SEQ ID NO: 249) |
| 4 | | | A_24_P8151 | AK098403 | | Homo sapiens cDNA FLJ25537 fis, clone CBR09136. | ATCTAGCAGGCGACTGAGTGCCGAGAAAATAC CTGGCAGAGGTGGGCACAAGGCGGGGTC (SEQ ID NO: 250) |
| 4 | | | A_24_P86389 | NM_003514 | HIST1H2AM | Homo sapiens histone 1, H2am (HIST1H2AM), mRNA | CTTGTAAAGTTACCATCGCTCAGGCGGTGT TCTGCCTAACATCCAGGCCGTACTGCTC (SEQ ID NO: 251) |
| 4 | | | A_32_P112452 | NM_002965 | S100A9 | Homo sapiens S100 calcium binding protein A9 (calgranulin B) (S100A9), mRNA | CGTGGAGGTGTTGATGATGGTCTCTATGTTG CGTTCCAGCTGCGACATTTTGCAAGTCA (SEQ ID NO: 252) |
| 4 | | | A_32_P113646 | NM_005544 | IRS1 | Homo sapiens insulin receptor substrate 1 (IRS1), mRNA | CAGTCTCTTCCTCTCTCGGGAGCTGGCTGAG CTGGGATGGACACCTGACAGAAGAGAAATT (SEQ ID NO: 253) |
| 4 | | | A_32_P143589 | AC018758 | CD177 | Homo sapiens chromosome 19, BAC CTB-6117 (BC52850), complete sequence. | AGCTTGGATGGTAGCAGAGACTTCAGGGTGC TCCAGCCAAACGTATTTGGGCATCACCAT (SEQ ID NO: 254) |
| 4 | | | A_32_P146815 | AC007528 | | Homo sapiens 12 BAC RP11-473N11 (Roswell Park Cancer Institute Human BAC Library) complete sequence. | TACCTTTGCATATGCTTTTCTTGGCCTTAGGA TAGTACTGAACTTTGTTGTCCCTCTGCT (SEQ ID NO: 255) |

TABLE 1-continued

| Cluster | Ratio cell type to all cells | cell Type | Array ID | Genbank ID | Gene ID | Description | Sequence |
|---|---|---|---|---|---|---|---|
| 4 | 2 | Granulocyte | A_32_P198223 | AC022784 | | Homo sapiens chromosome 8, clone RP11-10A14, complete sequence. | CAGGAATCACGGGAGTGAATCACATTCCAGAC ACTTGCTTGGACTTCATCACATCCTCAG (SEQ ID NO: 256) |
| 4 | 26 | Granulocyte | A_32_P228455 | AC073172 | | Homo sapiens chromosome 11, clone RP11-531H8, complete sequence. | AGTTACTTGCCTCCAGATATCTTGGTGTGTGA GAACATTAAATCTGTATGTGTCTAAATC (SEQ ID NO: 257) |
| 4 | | | A_32_P41604 | HS86F14 | | Human DNA sequence from clone RP1-86F14 on chromosome 1q23-24 Contains the F5 gene for coagulation factor V (proaccelerin labile factor) and the 3' end of the SELP gene for selectin P (granule membrane protein 140 kDa antigen CD62), complete sequence. | GATCTGGAAAATACTTGTTTGGGGATCAATAAT ATGTTTGGGCTATTATCTAATGCTGTG (SEQ ID NO: 258) |
| 4 | | | A_32_P47754 | HSM803756 | | Homo sapiens mRNA; cDNA DKFZp434F1129 (from clone DKFZp434F1129). | TTCACGTCAACTTCTGGCTCCTCAGTTTGGCA GTAAGGCAGGGAAGTTGTTTTCCTATTT (SEQ ID NO: 259) |
| 4 | | | A_32_P9753 | AC004686 | | Homo sapiens chromosome 17, clone hRPC.1073_F_15, complete sequence. | ATTGGATAGGAAGAGGAATAAAATATAAAAATC AGAGAACTGCTGAAATTCTGACCCCC (SEQ ID NO: 260) |
| 5 | | Platelet | A_23_P104624 | XM_290546 | KIAA0830 | PREDICTED: Homo sapiens KIAA0830 protein, transcript variant 1 (KIAA0830), mRNA | GGAGAGAACACATGTACAATCGTAACACATG AAGGACAAGTAAGTGCTGCAGTAAAGGT (SEQ ID NO: 261) |
| 5 | | | A_23_P118313 | NM_007285 | GABARAPL2 | Homo sapiens GABA(A) receptor-associated protein-like 2 (GABARAPL2), mRNA | TGAGGTAGGTGCGGTATTAAAGTGAAAGGGAA GGTGATGCATTATTCTGGGTTATGCTT (SEQ ID NO: 262) |
| 5 | | | A_23_P131646 | NM_144563 | RPIA | Homo sapiens ribose 5-phosphate isomerase A (ribose 5-phosphate epimerase) (RPIA), mRNA | ACTTTTGCTAAGATCTGGGGTTTCTTCATATT CCTGCTGTTGGAAGCAGTTGACCAGAA (SEQ ID NO: 263) |
| 5 | | | A_23_P134925 | NM_004331 | BNIP3L | Homo sapiens BCL2/adenovirus E1B 19 kDa interacting protein 3-like (BNIP3L), mRNA | ATTTGGGACAAAAAGGCAGGCTTCATTTTTC ATATGTTTGATGAAAACTGGCTCAAGAT (SEQ ID NO: 264) |
| 5 | | | A_23_P137434 | NM_014372 | RNF11 | Homo sapiens ring finger protein 11 (RNF11), mRNA | TGTAGTATCCATATGTTGCTTAAATTCCTTAT GAGCCCCATGATGAAAGACTTAAAGA (SEQ ID NO: 265) |

TABLE 1-continued

| Cluster | Ratio cell type to all cells | cell Type | Array ID | Genbank ID | Gene ID | Description | Sequence |
|---|---|---|---|---|---|---|---|
| 5 | | | A_23_P140256 | NM_000270 | NP | Homo sapiens nucleoside phosphorylase (NP), mRNA | CTACTAGCTCTTTGAGATAATATACATTCCGAGG GGCTCAGTTCTGCCTTATCTAAATCACC (SEQ ID NO: 266) |
| 5 | | | A_23_P141764 | NM_003826 | NAPG | Homo sapiens N-ethylmaleimide-sensitive factor attachment protein, gamma (NAPG), mRNA | CATGCCATTTCAAGGACTTGGGAATAGATTAG GGATATCCGTACTTCATTACAGTCATGA (SEQ ID NO: 267) |
| 5 | | | A_23_P144145 | AC092953 | | Homo sapiens 3 BAC RP11-531F16 (Roswell Park Cancer Institute Human BAC Library) complete sequence. | TCTTTAGTGAATATCATCTGCATATCTCTGTAA GTTCAATTGTGTTTCTTACAGTCCCTG (SEQ ID NO: 268) |
| 5 | | | A_23_P145114 | NM_001498 | GCLC | Homo sapiens glutamate-cysteine ligase, catalytic subunit (GCLC), mRNA | AGAATGCCGTTTTCGTTTGCATTTCTTGT GTAAATCAGGTTGTAAAAGGCAGATA (SEQ ID NO: 269) |
| 5 | 2 | Platelet | A_23_P157795 | NM_003798 | CTNNAL1 | Homo sapiens catenin (cadherin-associated protein), alpha-like 1 (CTNNAL1), mRNA | GGATAGTAAACTTGAGAGCTTTTGGGGTCA GATCTGGAACATCATGTGATGAAGCT (SEQ ID NO: 270) |
| 5 | | | A_23_P160359 | NM_004437 | EPB41 | Homo sapiens erythrocyte membrane protein band 4.1 (elliptocytosis 1, RH-linked) (EPB41), transcript variant 3, mRNA | AGAGCAAGACAGTATGAAGTACCATCCGAT TCAAACTTCCCAGTTACCGAGCAGCTAA (SEQ ID NO: 271) |
| 5 | | | A_23_P203558 | NM_000518 | HBB | Homo sapiens hemoglobin, beta (HBB), mRNA | GTCCAACTACTAAACTGGGGGATATTATGAAG GGCCTTGAGCATCTGGATTCTGCCTAAT (SEQ ID NO: 272) |
| 5 | | | A_23_P209426 | NM_015049 | TRAK2 | Homo sapiens trafficking protein, kinesin binding 2 (TRAK2), mRNA | AGAAAATGTTGTGCTGTATGTTCTTGATTTGAC ATAAATGAATAGACTTTGGCAAGGGAG (SEQ ID NO: 273) |
| 5 | | | A_23_P21785 | NM_022072 | NSUN3 | Homo sapiens NOL1/NOP2/Sun domain family, member 3 (NSUN3), mRNA | ACGTAAACATCATCGCTTATGGACATTAAAGGA ATAGCAAGACTTGCTCCCACGACTTCA (SEQ ID NO: 274) |
| 5 | | | A_23_P383377 | NM_006563 | KLF1 | Homo sapiens Kruppel-like factor 1 (erythroid) (KLF1), mRNA | GGACCCGGACGTGGGCACTGGACTCGG GGGACTGCGAGAGGATCCAGGTGTGATAGCC (SEQ ID NO: 275) |
| 5 | | | A_23_P38757 | NM_015865 | SLC14A1 | Homo sapiens solute carrier family 14 (urea transporter), member 1 (Kidd blood group) (SLC14A1), mRNA | GTATTAAAAATTAAACCCCATAAACCAACCT AAGCCTATGGAATCCACGTCACACAAAA (SEQ ID NO: 276) |
| 5 | | | A_23_P397999 | NM_003468 | FZD5 | Homo sapiens frizzled homolog 5 (Drosophila) (FZD5), mRNA | GGGGCTTTACAATCCTAAGGTTGCGTTGTAA TGAAGTTCCACTTGGTTCAGGTTTCTTT (SEQ ID NO: 277) |

TABLE 1-continued

| Cluster | Ratio cell type to all cells | cell Type | Array ID | Genbank ID | Gene ID | Description | Sequence |
|---|---|---|---|---|---|---|---|
| 5 | 2 | Platelet | A_23_P45304 | NM_021083 | XK | Homo sapiens X-linked Kx blood group (McLeod syndrome) (XK), mRNA | GCTTTCGTTGACTGCTTCTCGCAGTCGTTGA TGCTAATAAATATTGTCCTGTTTCTTCA (SEQ ID NO: 278) |
| 5 | | | A_23_P55578 | NM_003831 | RIOK3 | Homo sapiens RIO kinase 3 (yeast) (RIOK3), transcript variant 1, mRNA | CTTTAGTGGGTAGAACAAATGGAAATTTGTTT CAGAATGCTGACAGAAATCGACATAA (SEQ ID NO: 279) |
| 5 | | | A_23_P60324 | NM_016172 | UBADC1 | Homo sapiens ubiquitin associated domain containing 1 (UBADC1), mRNA | TTTAGCATCTGACAGGTGTTTACAAAAAGTG GTTGTCGCACTGGGAAGTGGAGTGATGG (SEQ ID NO: 280) |
| 5 | | | A_23_P63547 | XM_931256 | CR1L | PREDICTED: Homo sapiens complement component (3b/4b) receptor 1-like, transcript variant 3 (CR1L), mRNA | AACACCTGTTTGTGACAGTGAGTTGAAATATG CATTCCTATTTCTTTTACCGATACATTC (SEQ ID NO: 281) |
| 5 | | | A_23_P67708 | NM_003200 | TCF3 | Homo sapiens transcription factor 3 (E2A immunoglobulin enhancer binding factors E12/E47) (TCF3), mRNA | CGGAGAAATGGAAACATATCACTCAAGGGGA TGCTGTGAAACCTGGCTTATTCTTCTA (SEQ ID NO: 282) |
| 5 | | | A_23_P69695 | NM_001008388 | LOC493856 | Homo sapiens similar to RIKEN cDNA 1500009M05 gene (LOC493856), mRNA | ATTTGTGTCTTACTAAAGCAGCTTATTGTAGGT GTTGGCGTTCTAAAACGTTTCCTGCCT (SEQ ID NO: 283) |
| 5 | | | A_23_P70843 | NM_001724 | BPGM | Homo sapiens 2,3-bisphosphoglycerate mutase (BPGM), transcript variant 1, mRNA | TAGTAGAATTCCTCTTTGGCCACAAGAATAAG CAGCAAATAAACAACTATGGCTGTTGAG (SEQ ID NO: 284) |
| 5 | | | A_24_P132039 | NM_004290 | RNF14 | Homo sapiens ring finger protein 14 (RNF14), transcript variant 1, mRNA | GGGTGTTAGAACCTAGATTCAAAATGGCTTGT CTTTGCTACTTTTGTTCCACATTCTCTC (SEQ ID NO: 285) |
| 5 | | | A_24_P173823 | HSM800166 | | Homo sapiens mRNA; cDNA DKFZp586J2118 (from clone DKFZp586J2118). | ATGATACTAACACGGTGTAGGTTTTACAGTCTC CTAATTTGTACTGGTAATGCATATTCC (SEQ ID NO: 286) |
| 5 | | | A_24_P285880 | NM_003262 | TLOC1 | Homo sapiens translocation protein 1 (TLOC1), mRNA | AAGTATTTTTCCTTTCCCTCTTACTGATTT TTCAATTTTCAAACCATATGGCCTAGG (SEQ ID NO: 287) |
| 5 | | | A_24_P32790 | NM_018566 | YOD1 | Homo sapiens YOD1 OTU deubiquinating enzyme 1 homolog (yeast) (YOD1), mRNA | CTAGGGATCTAATTAAGGACATTAAAGTACAAT TCTTGAGCTACTAACCATCAGCTCTTC (SEQ ID NO: 288) |

TABLE 1-continued

| Cluster | Ratio cell type to all cells | cell Type | Array ID | Genbank ID | Gene ID | Description | Sequence |
|---|---|---|---|---|---|---|---|
| 5 | | | A_24_P335620 | NM_003486 | SLC7A5 | Homo sapiens solute carrier family 7 (cationic amino acid transporter, y+ system), member 5 (SLC7A5), mRNA | TTTCAGTCGTTGTGCTTTTTGTTTTGTGCTAA CGTCTTACTAATTAAAGATGCTGTCG (SEQ ID NO: 289) |
| 5 | | | A_24_P483083 | NM_007111 | TFDP1 | Homo sapiens transcription factor Dp-1 (TFDP1), mRNA | AAACAGAAACAGTCTCAACTTCAAAACTTATTC TACAGCAAATTGCCTTCAAGAACCTGG (SEQ ID NO: 290) |
| 5 | | | A_24_P503866 | XM_930101 | LOC647087 | PREDICTED: Homo sapiens hypothetical protein LOC647087 (LOC647087), mRNA | TATACCTTTTCACATTAAAAAAGGTATTTATATT ATTACTTTGTAGTGATTGTCTTAAGA (SEQ ID NO: 291) |
| 5 | | | A_24_P570806 | | | | TCTCAGAAGACAGAGGGTTTTCTTTTGAGGTA AATTTGATAGTACATTTTGATATAGTACGG (SEQ ID NO: 292) |
| 5 | | | A_24_P599496 | CNS01DVX | | Human chromosome 14 DNA sequence BAC C-2555C10 of library CalTech-D from chromosome 14 of Homo sapiens (Human), complete sequence. | GGCGGAAAACAAGTTTAGTCACAGAAGACTAC TCCATGTTTGAGCTTCTGTTTCAAGGGA (SEQ ID NO: 293) |
| 5 | | | A_24_P673786 | AL513128 | | Human DNA sequence from clone RP11-301N24 on chromosome 10 | GTCTATAACAAACAGTCTGTTCATTATTCTG TTGATAAACCATTTGGACAGAGTGAGG (SEQ ID NO: 294) |
| 5 | | | A_24_P67946 | NM_019094 | NUDT4 | Homo sapiens nudix (nucleoside diphosphate linked moiety X)-type motif 4 (NUDT4), transcript variant 1, mRNA | GAACTCAGATTTGCAAACCAGGTTTCTGAAAC TTTGGTAAGGTGTATGCTTTTAACTTT (SEQ ID NO: 295) |
| 5 | | | A_24_P886515 | AC124287 | | Homo sapiens chromosome 17, clone RP13-991F5, complete sequence. | CGTTGCCTGTCTTGCTGGATAACTGCATATATT GTGTTCAGTTGTGTATTTGTTTTGCTT (SEQ ID NO: 296) |
| 5 | | | A_24_P926507 | AC087685 | | Homo sapiens chromosome 18, clone RP11-618K16, complete sequence. | GAATAAACAGAAATAGGGAAGTAAACCTACAA ATATTTAGGAGGAGAAGCTCACTTCTTCC (SEQ ID NO: 297) |
| 5 | | | A_24_P935893 | NM_017709 | FAM46C | Homo sapiens family with sequence similarity 46, member C (FAM46C), mRNA | TTCACATGCAAGTTCTAATCTAAAGTTAAGCAG TCTCTTATTTGTTTCGGACTCTGATT (SEQ ID NO: 298) |
| 5 | 4 | Platelet | A_32_P109653 | AF163864 | | Homo sapiens SNCA isoform (SNCA) gene, complete cds, alternatively spliced. | TGTGGTTTGGTATTCCAAGTGGGTCTTTTTC AGAATCTGCACTAGTGTGAGATGCAA (SEQ ID NO: 299) |

TABLE 1-continued

| Cluster | Ratio cell type to all cells cell Type | Array ID | Genbank ID | Gene ID | Description | Sequence |
|---|---|---|---|---|---|---|
| 5 | | A_32_P11181 | AC034102 | | *Homo sapiens* 12 BAC RP11-603J24 (Roswell Park Cancer Institute Human BAC Library) complete sequence. | GGATGCTGTCCCAGGAAACTAGGGCTCCA CTAACTTATGAGGTTTTAAACACATTGA (SEQ ID NO: 300) |
| 5 | | A_32_P122715 | AC025300 | | *Homo sapiens* chromosome 11, clone RP11-573E11, complete sequence. | GAAAGTTCACATACAGGGGAAAGTGTACGATT TCATCTACTGTTTATCTTCTAACCTCAC (SEQ ID NO: 301) |
| 5 | | A_32_P133840 | NM_014858 | TMCC2 | *Homo sapiens* transmembrane and coiled-coil domain family 2 (TMCC2), mRNA | CTTCCATTCCATTTAGCCTTTGGATCATCCTGG CTGGGAGAGTGGGACCGAGCCACCCA (SEQ ID NO: 302) |
| 5 | | A_32_P159651 | NM_003884 | PCAF | *Homo sapiens* p300/CBP-associated factor (PCAF), mRNA | GAGTGGTGTCTAGATTTCTAATGAAGAATCAT GATACAGTTTGGATTAAGTATCTTGGAC (SEQ ID NO: 303) |
| 5 | | A_32_P165297 | HSJ842K24 | | Human DNA sequence from clone RP5-842K24 on chromosome Xq25-26.3 Contains the 3' end of the MBNL3 gene for muscleblind-like 3 (*Drosophila*) and a novel gene, complete sequence. | GAGGGGTATTTAGGGCCACTGTTATTTTGGTG CCACAATTTTCTACATTGTTGGCATTTT (SEQ ID NO: 304) |
| 5 | | A_32_P1712 | NM_002934 | RNASE2 | *Homo sapiens* ribonuclease, RNase A family, 2 (liver, eosinophil-derived neurotoxin) (RNASE2), mRNA | TCCAGGTGCCTTTAATGTACTGTAACCTCACAA CTCCAAGTCCACAGAATATTTCAAACT (SEQ ID NO: 305) |
| 5 | | A_32_P175183 | AC019227 | ZBTB44 | *Homo sapiens* BAC clone RP11-567O18 from 11, complete sequence. | CAGTCAAGCTGTGGATGAAATGACCAGGAACG GAGAATGAAGTATGTAAATCCCAGCTTC (SEQ ID NO: 306) |
| 5 | | A_32_P178945 | NM_018566 | YOD1 | *Homo sapiens* YOD1 OTU deubiquinating enzyme 1 homolog (yeast) (YOD1), mRNA | TTGCCAGCATTTTTTGAAGTAATACACTGCTGC TACCTGGAAGATGTCTAACTTCATTTT (SEQ ID NO: 307) |
| 5 | | A_32_P192480 | HSJ842K24 | | Human DNA sequence from clone RP5-842K24 on chromosome Xq25-26.3 Contains the 3' end of the MBNL3 gene for muscleblind-like 3 (*Drosophila*) and a novel gene, complete sequence. | TAGTGCTGTAGTGCTTGTTTATGTTTAAAAGTG CACATTATGCAGCTCATTTTAGTATGC (SEQ ID NO: 308) |
| 5 | | A_32_P204048 | HSJ842K24 | | Human DNA sequence from clone RP5-842K24 on chromosome Xq25-26.3 Contains the 3' end of the MBNL3 gene for muscleblind-like 3 (*Drosophila*) and a novel gene, complete sequence. | GGGTGGGAAAGCATAAGATGGGACTAAGAC TTTGCCTTTAACCTTTCATGACATGAAGAA (SEQ ID NO: 309) |
| 5 | | A_32_P23795 | XM_929854 | LOC646890 | PREDICTED: *Homo sapiens* hypothetical protein LOC646890 (LOC646890), mRNA | GATGAAGAGATTGCCTTACTTTGTTGTTCGCTC AGTTCCTAAGACTGTGAGTTGTCAAAT (SEQ ID NO: 310) |

TABLE 1-continued

| Cluster | Ratio cell type to all cells | cell Type | Array ID | Genbank ID | Gene ID | Description | Sequence |
|---|---|---|---|---|---|---|---|
| 5 | | | A_32_P36694 | NM_175061 | JAZF1 | Homo sapiens juxtaposed with another zinc finger gene 1 (JAZF1), mRNA | CAGTAAGGATGGGAATATTTGTTATACTGTGTATAGTGAATGTATTGTACTGTGTCTG (SEQ ID NO: 311) |
| 5 | | | A_32_P465742 | NM_001031687 | PIP5K1B | Homo sapiens phosphatidylinositol-4-phosphate 5-kinase, type I, beta (PIP5K1B), transcript variant 1, mRNA | TTCCTATGGACTTTTGCATTATTTCATTGTGCATGCATCCAGTGATTATACATAAGCAAC (SEQ ID NO: 312) |
| 6 | | all cell types | A_23_P109133 | NM_000490 | AVP | Homo sapiens arginine vasopressin (neurophysin II, antidiuretic hormone, diabetes insipidus, neurohypophyseal) (AVP), mRNA | CGAGAGCTGCGTGACCGAGCCCGAGTGCCGCGAGGGCTTTCACCCGCCGCCCGCGCCAG (SEQ ID NO: 313) |
| 6 | | | A_23_P15174 | NM_005949 | MT1F | Homo sapiens metallothionein 1F (functional) (MT1F), mRNA | TGCCAGGACAACCTTTCTCCCAGATGTAAACAGAGAGACATGTACAAACCTGGATTTTTT (SEQ ID NO: 314) |
| 6 | | | A_23_P157943 | NM_016219 | MAN1B1 | Homo sapiens mannosidase, alpha, class 1B, member 1 (MAN1B1), mRNA | AGCTATGACAACAGCAAGAGTTGCGGCCGCGCTCGTGCTGGAGGAAATGGAAGCAACTG (SEQ ID NO: 315) |
| 6 | | | A_23_P159191 | NM_000805 | GAST | Homo sapiens gastrin (GAST), mRNA | AGCCTATGGATGATGGACTTCCGCCGCGCAGTGCTGAGGATGAGAACTAACAATCCTA (SEQ ID NO: 316) |
| 6 | | | A_23_P16483 | NM_000455 | STK11 | Homo sapiens serine/threonine kinase 11 (STK11), mRNA | CCGTGGCCTTCGTGCTCCGCAGGGCGCCCAGCGCCGTCCGGCGGCCCCGCCGCCAGACCAGC (SEQ ID NO: 317) |
| 6 | | | A_23_P208900 | | | | GGGTCTCCCAGGTGCCGGTTAGGAGTTTGAACCCCCCCACTCTGCAGAGGGAAGCGGGG (SEQ ID NO: 318) |
| 6 | | | A_23_P211345 | NM_080647 | TBX1 | Homo sapiens T-box 1 (TBX1), transcript variant C, mRNA | TGTAGATACTGTAGATACTGTAGATACCCCCGGCGGCACTTGATAAACGGTTTCGCC (SEQ ID NO: 319) |
| 6 | | | A_23_P25790 | NM_022478 | CDH24 | Homo sapiens cadherin-like 24 (CDH24), transcript variant 1, mRNA | CGAGACGTGTTGCCCCGGGCCGGTGTCGCGCCAGCCCAGACCCCCGCCCCCCGCCGAC (SEQ ID NO: 320) |
| 6 | | | A_23_P3413 | NM_130901 | OTUD7 | Homo sapiens OTU domain containing 7 (OTUD7), mRNA | GCCGACGCGCCGACCGCGCGCTCGAACGTGAGTGCGGCCGGCCTGGCGCGGGGCCGGTG (SEQ ID NO: 321) |

TABLE 1-continued

| Cluster | Ratio cell type to all cells cell Type | Array ID | Genbank ID | Gene ID | Description | Sequence |
|---|---|---|---|---|---|---|
| 6 | | A_23_P346309 | NM_004324 | BAX | Homo sapiens BCL2-associated X protein (BAX), transcript variant beta, mRNA | CCCGCGCGGACCCGGCGGAGAGGGGCGCG GGAGCGGCCGGTGATGACGGGTCCGGGGAG (SEQ ID NO: 322) |
| 6 | | A_23_P35534 | NM_020999 | NEUROG3 | Homo sapiens neurogenin 3 (NEUROG3), mRNA | CATTCAAAGAATACTAGAATGGTAGCACTACC CGGCCGGAGCGCCCCACCGTCTTGGGTC (SEQ ID NO: 323) |
| 6 | | A_23_P401626 | NM_174919 | LOC201175 | Homo sapiens hypothetical protein LOC201175 (LOC201175), mRNA | GCAGCGACTTCAGAGAACGTCTACGAGTCAT CCAGGACTTGCACGTCCCGCCGCCGAGG (SEQ ID NO: 324) |
| 6 | | A_23_P431346 | NM_175887 | LOC222171 | Homo sapiens hypothetical protein LOC222171 (LOC222171), mRNA | CCCCAAACCAGACAAGTTATACGGGGACAAAT CCGCAGCAGCCGCCGCAATTTGAAGAT (SEQ ID NO: 325) |
| 6 | | A_23_P96072 | NM_000832 | GRIN1 | Homo sapiens glutamate receptor, ionotropic, N-methyl D-aspartate 1 (GRIN1), transcript variant NR1-1, mRNA | CAGGGTGCAGGGCGCGCACCGCCCAACCCCA CCTCCCGGTGTATGCAGTGGTGATGCCTA (SEQ ID NO: 326) |
| 6 | | A_24_P108738 | NM_153334 | SCARF2 | Homo sapiens scavenger receptor class F, member 2 (SCARF2), transcript variant 1, mRNA | CAGGCCGCGTGCAGCTGGCGCTGGCGCCCTCA CCACCGCCGCCAGGCTCCGAGGCCGCGCC (SEQ ID NO: 327) |
| 6 | | A_24_P112803 | NM_005986 | SOX1 | Homo sapiens SRY (sex determining region Y)-box 1 (SOX1), mRNA | GCTGGGCTCTCTGGTGAAGTCGGAGCCCAGC GGCAGCCCGCCCGCCCCAGCGCACTCGCG (SEQ ID NO: 328) |
| 6 | | A_24_P113725 | NM_005634 | SOX3 | Homo sapiens SRY (sex determining region Y)-box 3 (SOX3), mRNA | GCCGCCCGCCATCGCATCGCACTCTCAGCGC GCGTGCCTCGGACCTGCGCGACATGAT (SEQ ID NO: 329) |
| 6 | | A_24_P11737 | XR_015426 | LOC731268 | PREDICTED: Homo sapiens similar to zinc finger protein 499 (LOC731268) | GTGAGAAGTTCTGCAGATGTATGTGGCGCACA GCCTTCTACAGCCGCCGACTTCCGACTCCT (SEQ ID NO: 330) |
| 6 | | A_24_P117782 | NM_033129 | SCRT2 | Homo sapiens scratch homolog 2, zinc finger protein (Drosophila) (SCRT2), mRNA | CTTCAAGCACTACCGCTGCCGCCAGTGCGAC AAGAGCTTCGCGCTCAAGTCTACCTCCA (SEQ ID NO: 331) |
| 6 | | A_24_P127719 | NM_201589 | MAFA | Homo sapiens v-maf musculoaponeurotic fibrosarcoma oncogene homolog A (avian) (MAFA), mRNA | GTTCGAGGTGAAGAAGGAGCCTCCCGAGCC GAGCGCTTCTGCCACCGCCTGCCGCCAGG (SEQ ID NO: 332) |

TABLE 1-continued

| Cluster | Ratio cell type to all cells | cell Type | Array ID | Genbank ID | Gene ID | Description | Sequence |
|---|---|---|---|---|---|---|---|
| 6 | | | A_24_P144465 | NM_022107 | GPSM3 | Homo sapiens G-protein signalling modulator 3 (AGS3-like, C. elegans) (GPSM3), mRNA | CAGACTGAACTCCTTCTGGACCTGGTGGCTGA AGCCCAGTCCCGCCGCCTGGAGGAGCAG (SEQ ID NO: 333) |
| 6 | | | A_24_P253293 | NM_014360 | NKX2-8 | Homo sapiens NK2 transcription factor related, locus 8 (Drosophila) (NKX2-8), mRNA | GCGAGGTGGGAACCGCGGCCCCAGGAGA AGTGCGGCGCCCTCCAGCCGCCGCCTGCC (SEQ ID NO: 334) |
| 6 | | | A_24_P273378 | NM_006549 | CAMKK2 | Homo sapiens calcium/calmodulin-dependent protein kinase kinase 2, beta (CAMKK2), transcript variant 1, mRNA | CCGGGCCGCCCCCCAGGATGAGCTGGGGG TAGGGCAGCAGCAGCAGCCGAAAGCCAGAA (SEQ ID NO: 335) |
| 6 | | | A_24_P280660 | NM_178174 | TREML1 | Homo sapiens triggering receptor expressed on myeloid cells-like 1 (TREML1), mRNA | GAGGGTGCCAGCCCCTGGTGTCCTCAGCTG TGGATCGCAGAGTCCAGCGGGCAGGCGT (SEQ ID NO: 336) |
| 6 | | | A_24_P315500 | NM_014223 | NFYC | Homo sapiens nuclear transcription factor Y, gamma (NFYC), mRNA | TCAGGAGTCCAGGAGAGCAGGAGAGCCGCCC CGCCTCCTACGAGTCGGGCAATGCAGA (SEQ ID NO: 337) |
| 6 | | | A_24_P328846 | NM_016170 | TLX2 | Homo sapiens T-cell leukemia homeobox 2 (TLX2), mRNA | ACGGAGCCTCGGGTACGGTCCCCGCCGGTC ACTTGCCCCGCTGCCCGGCCAGCTCCGGAG (SEQ ID NO: 338) |
| 6 | | | A_24_P376451 | NM_000514 | GDNF | Homo sapiens glial cell derived neurotrophic factor (GDNF), transcript variant 1, mRNA | AACAGCAATGGTGCGCCGCCGGACGGGACT TTAAGATGAAGTTATGGGATGTCGTGGCT (SEQ ID NO: 339) |
| 6 | | | A_24_P37665 | NM_022042 | SLC26A1 | Homo sapiens solute carrier family 26 (sulfate transporter), member 1 (SLC26A1), transcript variant 1, mRNA | TTATTTGAACAAGGGTCCCCGCCATCATGCA GCCTTCCAAGGTGCCAAGAGGACTCCCTA (SEQ ID NO: 340) |
| 6 | | | A_24_P40775 | XM_290842 | LRFN1 | PREDICTED: Homo sapiens leucine rich repeat and fibronectin type III domain containing 1 (LRFN1), mRNA | AGGGGGCGCGCCGCCGGGAGGATGAGACCT GGGCTGGGCTCCCGCCAGGGCGTCCCTGGC (SEQ ID NO: 341) |
| 6 | | | A_24_P416595 | NM_174945 | ZNF575 | Homo sapiens zinc finger protein 575 (ZNF575), mRNA | CAAGCTGCCACCACCGCTTAGCACACGA GGCGCCCGACCCACCCATGCCCAGACTG (SEQ ID NO: 342) |
| 6 | | | A_24_P471099 | | | | TGCAGGTTTTGCCCCGCCGTTGCGGCTGTT TTCCCCCGTCAGCGAGGCTTTTTGTTG (SEQ ID NO: 343) |

TABLE 1-continued

| Cluster | Ratio cell type to all cells | cell Type | Array ID | Genbank ID | Gene ID | Description | Sequence |
|---|---|---|---|---|---|---|---|
| 6 | | | A_24_P535483 | NM_207349 | LOC284739 | Homo sapiens hypothetical protein LOC284739 (LOC284739), mRNA | AGGAGGCCCGCCCTCCACGCGCCGAAGGCCT CAATAAACGGAGCTGGCGCTGCGGGTCCG (SEQ ID NO: 344) |
| 6 | | | A_24_P600087 | | | | GGGGGTTTCCCCCCGGGAGGACCCCCCTG GGGGCCCCCTGTTTGTTACACGGCGGGT (SEQ ID NO: 345) |
| 6 | | | A_24_P75183 | NM_199046 | TEPP | Homo sapiens testis/prostate/placenta-expressed protein, isoform 2 (TEPP), transcript variant 1, mRNA | TCAGCGGCTACGCCGTGCCGTACTTGAAGCC CGACGTGACCCAGACCTGGCGGTACTGCC (SEQ ID NO: 346) |
| 6 | | | A_24_P780709 | | | | AGGCAGCCCCGGCCAGGTCGAGGCCGCC GCCGCCCGGCCAGAGCACGCCAGGAGCAG (SEQ ID NO: 347) |
| 6 | | | A_24_P920135 | | | | CAAGTGGAAAAAATATTAAAAAACTGATAATG GCCTCGGTTGGCCTCAGCGGCGAACT (SEQ ID NO: 348) |
| 6 | | | A_32_P138359 | NM_012331 | MSRA | Homo sapiens methionine sulfoxide reductase A (MSRA), mRNA | TGCGGCTCCGCTGCGGTAGCGCCGTCCCC GGGACCACCCTTCGGCTGCGCCCTCCCA (SEQ ID NO: 349) |
| 6 | | | A_32_P336712 | NM_173573 | C11orf35 | Homo sapiens chromosome 11 open reading frame 35 (C11orf35), mRNA | AGCCCCAAGGGCGAGGTCCTCAGTGAGCACC GGATCCCACGCCGAGACTCCGCCCCG (SEQ ID NO: 350) |
| 6 | | | A_32_P509169 | NM_207322 | NLF1 | Homo sapiens nuclear localized factor 1 (NLF1), mRNA | CCCCGCCTGGCCTTGGCTGCGCTCCGGAATT CTTGGGTCGAAGAAGCAGGGATGGACGAG (SEQ ID NO: 351) |
| 7 | | B cells | | | | | |
| 7 | 4 | B cells | A_23_P158817 | NM_001040070 | ELK2P1 | ELK2, member of ETS oncogene family, pseudogene 1 | ATGCATGAGGCTTCTGCACAACCACTACACGCA GAAGAGCCTTCTCCCTGTCTTCCGGGTAAA (SEQ ID NO: 352) |
| 7 | 4 | B cells | A_23_P158868 | | | | ACACCTTCTACGTATGACGTCTGGGGCCAA GGGACCACGGTCACCGTCTCCTCAGCAT (SEQ ID NO: 353) |
| 7 | | B cells | A_23_P168229 | NM_022085 | TXNDC5 | Homo sapiens thioredoxin domain containing 5 (TXNDC5), transcript variant 2, mRNA | ATACGCAAGGGGATGTGATACTTGGCCAAA GTAACTGGTGGTAGGAATCTTAGAAACA (SEQ ID NO: 354) |

TABLE 1-continued

| Cluster | Ratio cell type to all cells | cell Type | Array ID | Genbank ID | Gene ID | Description | Sequence |
|---|---|---|---|---|---|---|---|
| 7 | 7 | B cells | A_23_P21260 | | | | TAGGAGACAGAGTCACCATCACTTGCCGGGC AAGTCAGACCATTAGCAGCTATTTAAATT (SEQ ID NO: 355) |
| 7 | 4 | B cells | A_23_P350782 | XM_942302 | LOC652694 | PREDICTED: Homo sapiens similar to Ig kappa chain V-I region HK102 precursor (LOC652694), mRNA | GCAGCCTGAGCCTGAAGATATTGCAACATAT TACTGTCAACAGTATGATAATCTCCCTC (SEQ ID NO: 356) |
| 7 | 5 | B cells | A_23_P361654 | AC073416 | | Homo sapiens BAC clone RP11-136K15 from 2, complete sequence. | TCAGGTATTAGCAGCTGGTTAGCCTGGTATC AGCAGAAACCAGAGAAAGCCCCTAAGTC (SEQ ID NO: 357) |
| 7 | 9 | B cells | A_23_P435390 | | | | AGACAGCACTGGTTCTTATTTGCTGTTCGGCG GAGGGACCAAGCTGACCGTCCTAGGTCA (SEQ ID NO: 358) |
| 7 | 3 | B cells | A_23_P44053 | | | | AGCTCCTGATCTACGATGCATCCACTTTGAA ACCGGGGTCCCATCAAGGTTCAGTGCAC (SEQ ID NO: 359) |
| 7 | 7 | B cells | A_23_P61042 | S55735 | | Homo sapiens immunoglobulin A1-A2 lambda hybrid GAU heavy chain mRNA, partial cds. | GAGTTGAAGACCCCACTAACCGCCAACATAC AAAATCCGGAAACACATTCCGGCCCGAG (SEQ ID NO: 360) |
| 7 | 8 | B cells | A_23_P61068 | | | | GCCTGAAGATCTTGCAGTATATTACTGTCAGC AGTATAGTTCCACCTCGGACTTTTGG (SEQ ID NO: 361) |
| 7 | | | A_23_P72330 | | | | AGATGGTGCAGCCACCAGTTCGTTTGATCTCCA GCTCGACCCGCTGCGTGTTTTCCTTTG (SEQ ID NO: 362) |
| 7 | 5 | B cells | A_23_P84596 | NM_016459 | PACAP | Homo sapiens proapoptotic caspase adaptor protein (PACAP), mRNA | GGACATGTTTGCACTACTTGGGGGAGTTTGAA GAAGACCAGATCTATGAAGCCCACCAAC (SEQ ID NO: 363) |
| 7 | 4 | B cells | A_24_P100684 | | | | ATGGTATGATGAAGTAATAAATACTATGCAGA CTCCGTGAAGGGCCGATTCACCATCTC (SEQ ID NO: 364) |
| 7 | 5 | B cells | A_24_P144346 | | | | GTGGCACATATCATGCAGACTCCGTGAAGGG CCGATTCACCATCTCCAGAGACAATGCCA (SEQ ID NO: 365) |
| 7 | 6 | B cells | A_24_P15388 | | | | GCCAAGAACACGCTGTATCTGCAAATGAACAG TCTGAGAGCCGAGGACACGGCTGTGTAT (SEQ ID NO: 366) |

TABLE 1-continued

| Cluster | Ratio cell type to all cells | cell Type | Array ID | Genbank ID | Gene ID | Description | Sequence |
|---|---|---|---|---|---|---|---|
| 7 | 2 | B cells | A_24_P15550 | | | | GCAGGGTGGAGGCTGAGGATGTTGGGGTTTA TTACTGCATGCAAGTACACACTGCCTC (SEQ ID NO: 367) |
| 7 | | | A_24_P169713 | S80758 | | Ig VL = platelet glycoprotein IIIa leucine-33 form-specific antibody light chain variable region [human, plasma, mRNA Partial, 329 nt]. | CATAGTTATAACCAACGTCACTGCTGTT CCAGTGCAGGAGATGGATGCGACTGTC (SEQ ID NO: 368) |
| 7 | 13 | B cells | A_24_P169873 | HSM806780 | | Homo sapiens mRNA; cDNA DKFZp686O16217 (from clone DKFZp686O16217). | GTAAACCCACCCACATCAATGTGTCTGTTGTC ATGCGGAGGCGGATGGGCACCTGCTACT (SEQ ID NO: 369) |
| 7 | | | A_24_P204374 | | | | AGCCTGATGCCTGAACAGTGGAGATCCGCA GCAGCTACAACTGCTGGGCCATGCATAAA (SEQ ID NO: 370) |
| 7 | 4 | B cells | A_24_P204574 | HUMIGLVE | | Homo sapiens Ig germline lambda-chain gene variable region myeloma subgroup I (IGLV), complete exon. | GAGGATGAGGCTGATTATTACTGCAGCATG GGATGACAGCCTGAGTGGTGTCCCACAGTG (SEQ ID NO: 371) |
| 7 | 5 | B cells | A_24_P212024 | | | | TGATCTATGCTGCATCCAGTTTGCAGTCGGGG GTCCCATTCGGTTCAGTGGCAGTGGAT (SEQ ID NO: 372) |
| 7 | 5 | B cells | A_24_P239076 | NM_001013618 | LOC91353 | Homo sapiens similar to omega protein (LOC91353), mRNA | AACAAGGCCACACTGGTGTCTCATGAATGA CTTCTATCTGGGAATCTTGACGGTGACC (SEQ ID NO: 373) |
| 7 | 4 | B cells | A_24_P24371 | | | | CACAAGCCCAGCAACACCAAGGTGGACAAGA GAGTTGAGTCCAAATATGTCCCCATGC (SEQ ID NO: 374) |
| 7 | 7 | B cells | A_24_P272146 | | | | TCACTATCAGCAGCCTGCAGCCTGAAGATTTT GCAACTTACTATTGTCAACAGGCTAACA (SEQ ID NO: 375) |
| 7 | 3 | B cells | A_24_P315854 | | | | ATCAGTAGACACGTCCAAGAACCAGTTCTCCC TGAAGCTGAGCTCTGTGACCGCTGCGGA (SEQ ID NO: 376) |
| 7 | 4 | B cells | A_24_P33341 | XM_370973 | LOC388255 | PREDICTED: Homo sapiens similar to Ig heavy chain V-III region VH26 precursor (LOC388255), mRNA | CCGTATCTGCAAATGAACAGCTTGAGAGCTGA GGACACGGCTGTGTATTACTGTGTGAAA (SEQ ID NO: 377) |

TABLE 1-continued

| Cluster | Ratio cell type cells to all cells | cell Type | Array ID | Genbank ID | Gene ID | Description | Sequence |
|---|---|---|---|---|---|---|---|
| 7 | 7 | B cells | A_24_P357847 | | | | CCATCAGCAGCCTGCAGTCTGAAGATTTTGCA GTTTATTACTGTCAGCAGTATAATAACT (SEQ ID NO: 378) |
| 7 | 4 | B cells | A_24_P465799 | AF063695 | | Homo sapiens clone BCPBLL11 immunoglobulin lambda light chain variable region mRNA, partial cds. | CTGTCAGTGTGGGATAGTACTAGTGATCATT ATGTCTTCGGAACTGGGACCAAGGTCGC (SEQ ID NO: 379) |
| 7 | 6 | B cells | A_24_P488083 | HSA519285 | | Homo sapiens partial mRNA for IgM immunoglobulin heavy chain variable region (IGHV gene), clone ANBPM204. | CAATTCCAAGAACACGCTGTATCTGCAAGTGA ACAGCCTGAGAGTCGAGGACACGGCCCT (SEQ ID NO: 380) |
| 7 | 6 | B cells | A_24_P490109 | | | | AGCAGCCTGCAGTCTGAAGATTTTGCAACCTA TTACTGTCAACAGAGTGACAACACAAGA (SEQ ID NO: 381) |
| 7 | 7 | B cells | A_24_P510357 | S76132 | | Ig V lambda II = IgG rheumatoid factor [human, hybridoma AEE111F, mRNA Partial, 315 nt]. | CATCACTGGTCTCCAGGCTGAGGACGAGGCT GATTATTACTGCAGCTCTATATACAAGCAG (SEQ ID NO: 382) |
| 7 | 9 | B cells | A_24_P605563 | S42404 | | Ig lambda chain = anti-Rh(D) antibody [human, mRNA Partial, 642 nt]. | AAGATAGCAGCCCCGTCAGGCGGAGTGAG ACCACCACCCTCCAAACAAAGCAACAA (SEQ ID NO: 383) |
| 7 | 5 | B cells | A_24_P608268 | | | | CCAGAGATGATTCAAGAACACGCGTATCTG CAAATGAACAGCCTGAAAACCGAGGACA (SEQ ID NO: 384) |
| 7 | 5 | B cells | A_24_P626951 | | | | GACAGAGTCACCATCACTTGTCGGCGAGTCA GGGAATTAGCAATTATTTAGCCTGGTTT (SEQ ID NO: 385) |
| 7 | 3 | B cells | A_24_P66578 | | | | GCAGATTACTCACTCTCCACCATCCGAGCCTGCA GCCTGAAGATTTTGCAAATTATTACTGT (SEQ ID NO: 386) |
| 7 | 6 | B cells | A_24_P702749 | | | | ATGCAGACTCCGTGAAGGGCCGATTCACCATC TCCAGAGACAATTCCAAGAACACCGGTGT (SEQ ID NO: 387) |
| 7 | 4 | B cells | A_24_P76868 | HSZ74662 | | H. sapiens mRNA for immunoglobulin, light chain, V-J region. | TGGGCATCACCGGACTCCAGACTGGGACGA GGCCGATTATTACTGCGGAACATGGAATA (SEQ ID NO: 388) |

TABLE 1-continued

| Cluster | Ratio cell type to all cells | cell Type | Array ID | Genbank ID | Gene ID | Description | Sequence |
|---|---|---|---|---|---|---|---|
| 7 | 6 | B cells | A_24_P83102 | NM_001013618 | LOC91353 | Homo sapiens similar to omega protein (LOC91353), mRNA | TCCAAGCCAACAAGGCTACACTGTGTCTC ATGAATGACTTTATCCGGAATCTTGA (SEQ ID NO: 389) |
| 7 | 3 | B cells | A_24_P852001 | HSA234192 | | Homo sapiens mRNA for Ig heavy chain variable region, clone C2. | AGTTTGGGCTGAGCTGCCTTTTCTTGTGGCT ATTTTAAAGGTGTCCAGTGTGAGGTGC (SEQ ID NO: 390) |
| 7 | 6 | B cells | A_32_P148118 | | | | CAGCAGCCTGCAGCCTGAAGATTTTGCAGCTT ATTACTGTCAACAGAGTGACAGTACCCC (SEQ ID NO: 391) |
| 7 | 3 | B cells | A_32_P157927 | AC096579 | | Homo sapiens BAC clone RP11-601N4 from 2, complete sequence. | GGCCACCATCAACTGCAAGTCCAGCCAGAGT GTTTTATACAGCTCCAAGAATAAGAACTA (SEQ ID NO: 392) |
| 7 | 6 | B cells | A_32_P159192 | | | | AGCAGCCTGCAGCCTGAAGATTTTGCAGTTA TTACTGTCAGCAGGATIATMCTTACCT (SEQ ID NO: 393) |
| 7 | 13 | B cells | A_32_P200144 | XM_939003 | LOC649923 | PREDICTED: Homo sapiens similar to Ig gamma-2 chain C region (LOC649923), mRNA | CGTGAGGATGCTTGGCACGTACCCCGTGTAC ATACTTCCAGGCACCCAGCCATGGAAATA (SEQ ID NO: 394) |
| 7 | 7 | B cells | A_32_P39440 | | | | GTGGGTCTGGGACAGAGTTCACTCTCACCATC AGCAGCCTGCAGTCTGAAGATTTTGCAG (SEQ ID NO: 395) |
| 7 | 4 | B cells | A_32_P43664 | NM_144646 | IGJ | Homo sapiens immunoglobulin J polypeptide, linker protein for immunoglobulin alpha and mu polypeptides (IGJ), mRNA | TCTGTCATAAGTGTAGCAGTCTCTGTAGCAC TGTCTTCATCACAGATATTGCTCTGGGT (SEQ ID NO: 396) |
| 7 | 3 | B cells | A_32_P722809 | XM_940969 | LOC651751 | PREDICTED: Homo sapiens similar to Ig kappa chain V-II region RPMI 6410 precursor (LOC651751), mRNA | GATTTTACACTGAAAATCAGCAGAGTGGAGGC TGAGGATGTTGGGGTTTATTACTGCATG (SEQ ID NO: 397) |
| 8 | | all cell types | | | | | |
| 8 | | | A_23_P148473 | NM_000206 | IL2RG | Homo sapiens interleukin 2 receptor, gamma (severe combined immunodeficiency) (IL2RG), mRNA | CTTTCCTGTTTGCATTGGAAGCCGTGGTTATC TCTGTTGGCTCCATGGGATTGATTATCA (SEQ ID NO: 398) |
| 8 | | | A_23_P21057 | NM_052838 | SEPT1 | Homo sapiens septin 1 (SEPT1), mRNA | ATTTCCTGAACCTGCGACGGATGCTGGTGCAG ACACACCTGCAGGACCTGAAAGAGGTGA (SEQ ID NO: 399) |

TABLE 1-continued

| Cluster | Ratio cell type to all cells | cell Type | Array ID | Genbank ID | Gene ID | Description | Sequence |
|---|---|---|---|---|---|---|---|
| 8 | | | A_23_P213424 | NM_003633 | ENC1 | Homo sapiens ectodermal-neural cortex (with BTB-like domain) (ENC1), mRNA | GTTGGAGGATACTTTGGCATTCAGCGATGCAA GACTTTGGACTGCTACGATCCAACATTA (SEQ ID NO: 400) |
| 8 | | | A_23_P25069 | XM_927026 | LOC440080 | PREDICTED: Homo sapiens similar to cDNA sequence BC048546, transcript variant 2 (LOC440080), mRNA | TTTACTCCAACCATGTCATCCATTGAAGAGCTT GAAAACAAGGGCCAAGTGATGAGAGACT (SEQ ID NO: 401) |
| 8 | | | A_23_P26810 | NM_000546 | TP53 | Homo sapiens tumor protein p53 (Li-Fraumeni syndrome) (TP53), mRNA | CTGTGAGGGATGTTTGGGAGATGTMGAAATG TTCTTGCAGTTAAGGGTTAGTTTACAAT (SEQ ID NO: 402) |
| 8 | | | A_23_P301925 | MIHSXX | | H. sapiens mitochondrial genome. | CTACGTTGTAGCCCACTTCCACTATGTCCTATC AATAGGAGCTGTATTTGCCATCATAGG (SEQ ID NO: 403) |
| 8 | | | A_23_P315252 | HUMMTCG | | Human mitochondrion, complete genome. | CATCGCTGGGTCAATAGTACTTGCCGCAGTAC TCTTAAAACTAGGCGGCTATGGTATAAT (SEQ ID NO: 404) |
| 8 | | | A_23_P337726 | MIHSXX | | H. sapiens mitochondrial genome. | CATGGCCATCCCCTTATGAGCGGGCACAGTG ATTATAGGCTTTCGCTCTAAGATTAAAA (SEQ ID NO: 405) |
| 8 | | | A_23_P402751 | MTHSCOXII | | H. sapiens mitochondrial coxII mRNA for cytochrome C oxidase II subunit. | GACTCCTTGACGTTGACAATCGAGTAGTACTC CCGATTGAAGCCCCATTCGTATAATAA (SEQ ID NO: 406) |
| 8 | | | A_23_P70095 | NM_001025158 | CD74 | Homo sapiens CD74 antigen (invariant polypeptide of major histocompatibility complex, class II antigen-associated) (CD74), transcript variant 3, mRNA | AAGATCAGAAGCCAGTCATGGATGACCAGCG CGACCTTATCTCCAACAATGAGCAACTGC (SEQ ID NO: 407) |
| 8 | | | A_23_P86943 | NM_003139 | SRPR | Homo sapiens signal recognition particle receptor ('docking protein') (SRPR), mRNA | GCTAGGCTGGAGTGATTGTTACAAATGACGA AAGATGAGTCCTTGCTTCCCTCAGAAA (SEQ ID NO: 408) |
| 8 | | | A_23_P98884 | NM_005785 | RNF41 | Homo sapiens ring finger protein 41 (RNF41), transcript variant 1, mRNA | TTCCAGATGAGCTCTTCTTTCCTACAAGTTTTC ATAATTAGGAATGCCAGGGTTTAGGG (SEQ ID NO: 409) |
| 8 | | | A_24_P202319 | NM_005173 | ATP2A3 | Homo sapiens ATPase, Ca++ transporting, ubiquitous (ATP2A3), transcript variant 1, mRNA | CAACTTCTACCAGTGAGGAACTTCCTGAAGT GCTCCGAAGACAACCCGCTCTTTGCCGG (SEQ ID NO: 410) |

TABLE 1-continued

| Cluster | Ratio cell type to all cells | cell Type | Array ID | Genbank ID | Gene ID | Description | Sequence |
|---|---|---|---|---|---|---|---|
| 8 | | | A_24_P204334 | | | | CTAGCCATGGCCATCCCCTTAAGCGGGTGAT TATAGGCTTTCGCTCTAAGATTAAAAAT (SEQ ID NO: 411) |
| 8 | | | A_24_P350200 | | | | AAGGCCACCACACCACCTGTCCAGAAAGG CCTTCGATACGGGATAATCCTATTTATTA (SEQ ID NO: 412) |
| 8 | | | A_24_P381224 | NM_032431 | SYVN1 | Homo sapiens synovial apoptosis inhibitor 1, synoviolin (SYVN1), transcript variant 1, mRNA | AAGTTTAGAATTGGAATTACTTCCTTACTAGTG TCTTTTGGCTTAAATTTGTCTTTTGA (SEQ ID NO: 413) |
| 8 | | | A_24_P416728 | NM_001130 | AES | Homo sapiens amino-terminal enhancer of split (AES), transcript variant 2, mRNA | ACGGCTTGAACATCGAGATGCACAAACAGGCT GAGATCGTCAAAGGCTGAACGGGATTT (SEQ ID NO: 414) |
| 8 | | | A_24_P551842 | | | | CTCCGATCCGTCCCTATTATATCCATCCTCAT (SEQ ID NO: 415) |
| 8 | | | A_24_P700170 | NM_014225 | PPP2R1A | Homo sapiens protein phosphatase 2 (formerly 2A), regulatory subunit A (PR 65), alpha isoform (PPP2R1A), mRNA | ACGGCTGAACATCATCTCTAACCTGGACTGTG TGAACGAGGTGATTGGCATCCGGTCAGC (SEQ ID NO: 416) |
| 8 | | | A_24_P710024 | | | | TTAGCATCATCCCTCCTACTATTTTTAGCCAAA TCAACAACAACCTATTTTAGCTGTTCC (SEQ ID NO: 417) |
| 8 | | | A_24_P713185 | | | | AATATGACTAGCTTACACAATAGCTCACATAGT ACAGATACTCTTTACGGACTCCACTTA (SEQ ID NO: 418) |
| 8 | | | A_24_P910169 | | | | TTACATGGGTTTTCATGATCAGCCGCGAAACT GAGAACGTCAGGTCAGCGAGGAGATTGG (SEQ ID NO: 419) |
| 9 | | B cells | | | | | |
| 9 | 5 | B cells | A_23_P10356 | NM_021777 | ADAM28 | Homo sapiens ADAM metallopeptidase domain 28 (ADAM28), transcript variant 3, mRNA | CTTAGAAGCTTCGAACTGAAAATCATGAAAG GTTTTAAGATTTGAGGTTGGTTTTTAGGG (SEQ ID NO: 420) |
| 9 | 9 | B cells | A_23_P113572 | NM_001770 | CD19 | Homo sapiens CD19 antigen (CD19), mRNA | TACATGCCAGTGACACTTCCAGTCCCCTTTGT ATTCCTTAAATAAACTCAATGAGCTCTT (SEQ ID NO: 421) |

TABLE 1-continued

| Cluster | Ratio cell type to all cells | cell Type | Array ID | Genbank ID | Gene ID | Description | Sequence |
|---|---|---|---|---|---|---|---|
| 9 | 6 | B cells | A_23_P116371 | NM_021950 | MS4A1 | Homo sapiens membrane-spanning 4-domains, subfamily A, member 1 (MS4A1), transcript variant 3, mRNA | GAGCTCACACACCATATATTAACATATACAACT GTGAACCAGCTAATCCCTCTGAGAAAA (SEQ ID NO: 422) |
| 9 | 6 | B cells | A_23_P121657 | NM_005114 | HS3ST1 | Homo sapiens heparan sulfate (glucosamine) 3-O-sulfotransferase 1 (HS3ST1), mRNA | GGCAGAACATTTGACTGGCACTGGTTGCAAT AAGCTAAGCTCAGAAACTTTCCTACTGT (SEQ ID NO: 423) |
| 9 | | | A_23_P125618 | NM_000808 | GABRA3 | Homo sapiens gamma-aminobutyric acid (GABA) A receptor, alpha 3 (GABRA3), mRNA | TGCATGCCTGCCCACTGAAGTTTGGAAGCTAT GCCTATACAACAGCTGAAGTGGTTTATT (SEQ ID NO: 424) |
| 9 | 4 | B cells | A_23_P149368 | NM_052938 | FCRL1 | Homo sapiens Fc receptor-like 1 (FCRL1), mRNA | AAACAAGATGGAATAAAAGAAATTGGGATCTT GGGTTGGAGGGACAGTGAAGCTTAGAGC (SEQ ID NO: 425) |
| 9 | | | A_23_P151166 | NM_032369 | MGC15619 | Homo sapiens hypothetical protein MGC15619 (MGC15619), mRNA | TCTAGAAAGTCTCTTATTTTCAAGCTGTTCTA AATAGCTTCGTCTCAGTTTCCCCAAAA (SEQ ID NO: 426) |
| 9 | 9 | B cells | A_23_P160751 | NM_030764 | FCRL2 | Homo sapiens Fc receptor-like 2 (FCRL2), transcript variant 2, mRNA | GAGGAATCAGAAGGGAAGATCAACAGCAAGG ATGGGCATCATTAAGACTTGCTATAAAA (SEQ ID NO: 427) |
| 9 | 4 | B cells | A_23_P207201 | NM_000626 | CD79B | Homo sapiens CD79B antigen (immunoglobulin-associated beta) (CD79B), transcript variant 1, mRNA | CGCTGAAGGATGGTATCATCATGATCCAGACG CTGCTGATCATCCTCTTCATCATCGTGC (SEQ ID NO: 428) |
| 9 | 7 | B cells | A_23_P209055 | NM_001771 | CD22 | Homo sapiens CD22 antigen (CD22), mRNA | GCCTTCAGGCACACAAGAAAATGTGGACTATGTGA TCCTCAAACATTGACACTGGATGGGCTG (SEQ ID NO: 429) |
| 9 | 4 | B cells | A_23_P250245 | NM_001782 | CD72 | Homo sapiens CD72 antigen (CD72), mRNA | TGCTCAAAGCTCAAAATGTAACAAGGTACATAA AACTTGGTCATGGTGGACACTGGAGTC (SEQ ID NO: 430) |
| 9 | | | A_23_P307382 | NM_080552 | SLC32A1 | Homo sapiens solute carrier family 32 (GABA vesicular transporter), member 1 (SLC32A1), mRNA | CCAGCTTGCCTGCCGGTTTTCAGGAATCTAAA CTCATCTTGTGCAATTTATCAGGTGT (SEQ ID NO: 431) |
| 9 | 5 | B cells | A_23_P31725 | NM_001715 | BLK | Homo sapiens B lymphoid tyrosine kinase (BLK), mRNA | TCGCACGGTCATCCGGAGTACTAAGCACCCAGT AAGTGTTCAGGACTGGTAAGCGACTGT (SEQ ID NO: 432) |
| 9 | 5 | B cells | A_23_P357717 | NM_021966 | TCL1A | Homo sapiens T-cell leukemia/lymphoma 1A (TCL1A), mRNA | TTTCCCCCTTTATAGATGGTCACGCACCTGG GTGTTACAAGTTGTATGTGGCATGAAT (SEQ ID NO: 433) |

TABLE 1-continued

| Cluster | Ratio cell type to all cells | cell Type | Array ID | Genbank ID | Gene ID | Description | Sequence |
|---|---|---|---|---|---|---|---|
| 9 | | | A_23_P398294 | NM_003959 | HIP1R | Homo sapiens huntingtin interacting protein 1 related (HIP1R), mRNA | GTTAGCATTCCTCCTGAAGTGTTCTGTTGGC AATAAATGCACTTTGACTGTTGTTGT (SEQ ID NO: 434) |
| 9 | 2 | B cells | A_23_P76402 | NM_024549 | FLJ21127 | Homo sapiens tectonic (FLJ21127), mRNA | GCTTTGGTTATAGAAGTGAAGTGGACTAAATA CGGATCCCTGCTGAATCCACAGGCCAAA (SEQ ID NO: 435) |
| 9 | 4 | B cells | A_23_P904 | NM_024603 | C1orf165 | Homo sapiens chromosome 1 open reading frame 165 (C1orf165), mRNA | CATCGTCAGAGAGTGTTTGTATGACAGAATAG CACAAGAACTGTGGATGAAACTGAAAT (SEQ ID NO: 436) |
| 9 | 4 | B cells | A_24_P203056 | NM_001024808 | BCL7A | Homo sapiens B-cell CLL/lymphoma 7A (BCL7A), transcript variant 2, mRNA | TCGCCAAGAACCTGGTTAGAGGCATAAAGACC TTTTTTCACCGTTACCTAATTTTTTCCC (SEQ ID NO: 437) |
| 9 | 4 | B cells | A_24_P252945 | NM_001716 | BLR1 | Homo sapiens Burkitt lymphoma receptor 1, GTP binding protein (chemokine (C-X-C motif) receptor 5) (BLR1), transcript variant 1, mRNA | TTTTCTTTTTAATAAAAAGGCACCTATAAACA GGTCAATACAGTACAGGCAGCAGCACAGAG (SEQ ID NO: 438) |
| 9 | | | A_24_P254106 | | | | AACACTATTGTAGGTAGTGATATGTGTTAG GAAAAAATAAGGCCGAGAGAGGGGAGT (SEQ ID NO: 439) |
| 9 | | | A_24_P305067 | NM_024015 | HOXB4 | Homo sapiens Homo box B4 (HOXB4), mRNA | GATCAACTCAAACTATGTCGACCCCAAGTTCC CTCCATGCGAGGAATATTCACAGAGCGA (SEQ ID NO: 440) |
| 9 | 3 | B cells | A_24_P324838 | HSIGCMUDE | | Human immunoglobulin C(mu) and C(delta) heavy chain genes (constant regions). | AGATGGTGCAGTGTTAGAGCTGAGGCTTATC CCACAGAGAACCCTGGCGCCTTGGTCAA (SEQ ID NO: 441) |
| 9 | 4 | B cells | A_24_P413126 | NM_020182 | TMEPAI | Homo sapiens transmembrane, prostate androgen induced RNA (TMEPAI), transcript variant 1, mRNA | AAGAAACTGCTTGTTGTGTATCAGTAATCATTA GTGGCAATGATGACATTCTGAAAAGCT (SEQ ID NO: 442) |
| 9 | 8 | B cells | A_24_P417352 | HSIGCMUS | | Human C mu gene for IgM heavy chain exons CH1 4, secretory. | TGACCACCTATGACAGCGTGACCATCTCCTGG ACCCGCCAGAATGCGAAGCTGTGAAAA (SEQ ID NO: 443) |
| 9 | 8 | B cells | A_24_P621701 | HS250D10 | | Human DNA sequence from clone CTA-250D10 on chromosome 22 | TGGTAAGTTCTCTCTTAGAGACTCCACAA TAAAGTTTTCAACATGGTAAGGTTTTC (SEQ ID NO: 444) |

TABLE 1-continued

| Cluster | Ratio cell type to all cells | cell Type | Array ID | Genbank ID | Gene ID | Description | Sequence |
|---|---|---|---|---|---|---|---|
| 9 | 7 | B cells | A_24_P64344 | NM_013314 | BLNK | Homo sapiens B-cell linker (BLNK), mRNA | TAAGCGAGTATATATAATATTCCTGTGCGATTTAT TGAAGCAACAAAACAATATGCCTTGGG (SEQ ID NO: 445) |
| 9 | | | A_24_P916364 | AC007172 | | Homo sapiens chromosome 9, clone hRPK.538_E_7, complete sequence. | GGGTGAATGTTTGAAAATCATGAATCAGCCAC CATTATTAATTGAAGAGCTGGGAATACC (SEQ ID NO: 446) |
| 9 | 7 | B cells | A_24_P940348 | NM_173544 | BCNP1 | Homo sapiens B-cell novel protein 1 (BCNP1), mRNA | AGACAAGCTTTTACCGACTTCCTCTGCTTGCC AGCAAAGTCATCTGCTAACTGGATATTG (SEQ ID NO: 447) |
| 9 | | | A_24_P95723 | NM_014792 | KIAA0125 | Homo sapiens KIAA0125 (KIAA0125), mRNA | CCATTTTAAAGATGGCTACTTAGGACCATATG GATGTTGTACTGATGTCATTTGACCACG (SEQ ID NO: 448) |
| 9 | | | A_32_P107002 | NM_001012391 | LOC400509 | Homo sapiens similar to FLJ12363 protein (LOC400509), mRNA | TGTGAAAAGCATCGATGATGAAGATGTGGATG AAAACGAAGATGACGTGTATGGAAACTC (SEQ ID NO: 449) |
| 9 | 3 | B cells | A_32_P13337 | AC006230 | | Homo sapiens chromosome 4 clone C0287J14 map 4p16, complete sequence. | ATCCTCCATGGTATCTGAATCCCAGAATCCTA CAATCCTCCATGGTATCTGAAACATACT (SEQ ID NO: 450) |
| 9 | 3 | B cells | A_32_P137819 | AL450344 | | Human DNA sequence from clone RP11-136K14 on chromosome 6 Contains three novel genes, the 5' end of a novel gene (contains FLJ31738 and KIAA1209) and a CpG island, complete sequence. | CTGCAGATCTTTATTACTGGCAAGAAAGTCCC AGAAGTTCTTTTCTCCTAACTTATGACTA (SEQ ID NO: 451) |
| 9 | 4 | B cells | A_32_P356316 | NM_002119 | HLA-DOA | Homo sapiens major histocompatibility complex, class II, DO alpha (HLA-DOA), mRNA | TGGAAAGGTGTTCTCTCATCTCTGTCCTAAG GCTTGATAAAGTCATTAAAATTGTGTTC (SEQ ID NO: 452) |
| 9 | 3 | B cells | A_32_P57013 | NM_018014 | BCL11A | Homo sapiens B-cell CLL/lymphoma 11A (zinc finger protein) (BCL11A), transcript variant 2, mRNA | ATAATACAAAGATGCGCAGGAGGAAGATGAATT GTGGGAGAGCCCGTCATGCCTTTTTTTA (SEQ ID NO: 453) |
| 9 | | | A_32_P64016 | | | | CTCTGAGGCTAAGATTACTGGTGTACTCATTG GGACCAGTTTGGTCTCAGTGACTGAAAA (SEQ ID NO: 454) |
| 9 | 9 | B cells | A_32_P71876 | AL356276 | | Human DNA sequence from clone RP11-36J7 on chromosome 1 | GAAGTTTGAACTTCTTTGTTATTGTATGATCATC CCTTTACCTTAATACTCACATGAAATG (SEQ ID NO: 455) |

TABLE 1-continued

| Cluster | Ratio cell type to all cells | cell Type | Array ID | Genbank ID | Gene ID | Description | Sequence |
|---|---|---|---|---|---|---|---|
| 9 | | | A_32_P8813 | | | | GACGGGACATCATGCTGGGCAACACAGCTAA AATGCGGGTGAAGACCAGATTTCTTGCAC (SEQ ID NO: 456) |
| 10 | | all cell types | A_23_P117480 | CNS06C82 | | Human chromosome 14 DNA sequence BAC C-2335L22 of library CalTech-D from chromosome 14 of Homo sapiens (Human), complete sequence. | ATTGTCGGCATCTTCCATGCTCTGAGTCAGTT AGCATTTACAGTGAATCTGCCCTTCTGT (SEQ ID NO: 457) |
| 10 | | | A_23_P153827 | NM_005934 | MLLT1 | Homo sapiens myeloid/lymphoid or mixed-lineage leukemia (trithorax Homolog, Drosophila); translocated to, 1 (MLLT1), mRNA | TACACCGGAGGCTGATGGCCTGCGGGAGCG CAACGTGCTGCAGCAGATTGTGAATCTGA (SEQ ID NO: 458) |
| 10 | | | A_23_P170464 | NM_031297 | DKFZP761H1 710 | Homo sapiens hypothetical protein DKFZp761H1710 (DKFZP761H1710), mRNA | TGGCCCCAGAGGATGAGGTCATTGTGAATCAG TACTGATTCGGCTGGCCCCTCGGCCT (SEQ ID NO: 459) |
| 10 | | | A_23_P258887 | NM_012190 | ALDH1L1 | Homo sapiens aldehyde dehydrogenase 1 family, member L1 (ALDH1L1), mRNA | TTCGGGCCTGTCATGATCATCTCTGGGTTGC TGATGGGACTTGGATGCCGTGCTGTCT (SEQ ID NO: 460) |
| 10 | | | A_23_P30805 | NM_003541 | HIST1H4K | Homo sapiens histone 1, H4k (HIST1H4K), mRNA | AAGCGCCAGGGCCCGACCCTCTACGGTTTCG GTGGTTGAGCGTCCCTTCTATCAATAAA (SEQ ID NO: 461) |
| 10 | | | A_23_P390504 | NM_001453 | FOXC1 | Homo sapiens forkhead box C1 (FOXC1), mRNA | CCTTCCAGCCAGTCTTCTGTACCGCACGTCCGG AGCTTTCGTCTACGACTGTAGCAAGTTT (SEQ ID NO: 462) |
| 10 | | | A_23_P407695 | NM_147161 | ACOT11 | Homo sapiens acyl-CoA thioesterase 11 (ACOT11), transcript variant 2, mRNA | AGCGGACTTCAGGGCGCGGAGGCTTCCCACCG GGAGGCAGGAAGAAATAAAGGTCTTTGGCT (SEQ ID NO: 463) |
| 10 | | | A_23_P432506 | NM_152757 | FLJ30313 | Homo sapiens hypothetical protein FLJ30313 (FLJ30313), mRNA | GTGGGAGGGTTTCTTGGGTTTCTTGAAGCCA GTATTTCCCATAGTATCTTACGTCCCAG (SEQ ID NO: 464) |
| 10 | | | A_23_P46894 | NM_020549 | CHAT | Homo sapiens choline acetyltransferase (CHAT), transcript variant M, mRNA | TAGCCTCCTCGGCAGAAAAACTTCAACGAATA GTAAAGAACCTTGACTTCATTGTCTATA (SEQ ID NO: 465) |

TABLE 1-continued

| Cluster | Ratio cell type to all cells | cell Type | Array ID | Genbank ID | Gene ID | Description | Sequence |
|---|---|---|---|---|---|---|---|
| 10 | | | A_23_P57089 | NM_020182 | TMEPAI | Homo sapiens transmembrane, prostate androgen induced RNA (TMEPAI), transcript variant 1, mRNA | GCCGGGCTGGGGCTGCGTAGGTGAAAAGCA GAACACTCCGCGCTTCTTAGAAGAGGAGT (SEQ ID NO: 466) |
| 10 | | | A_23_P69652 | NM_080819 | GPR78 | Homo sapiens G protein-coupled receptor 78 (GPR78), mRNA | GCTCGTGCCCTTCGTCACCGTGAACGCCAG TGGGCATCCTCAGCAAGTGCCTGACCTA (SEQ ID NO: 467) |
| 10 | | | A_23_P75283 | NM_006744 | RBP4 | Homo sapiens retinol binding protein 4, plasma (RBP4), mRNA | TCAGTTCCATAAAACCTTCATTACACATAAAG ATACACGTGGGGTCAGTGAATCTGCT (SEQ ID NO: 468) |
| 10 | | | A_23_P93217 | NM_006672 | SLC22A7 | Homo sapiens solute carrier family 22 (organic anion transporter), member 7 (SLC22A7), transcript variant 1, mRNA | AGTGAACTTCTCCTATTACGGCCTGAGTCTGG ATGTGTCGGGGCTGGGGCTGAACGTGTA (SEQ ID NO: 469) |
| 10 | | | A_24_P187539 | | | | ACGAATATGCGTTCGACAAGCCGGTCCCGAAA GACATGGTCATCTGGAATCGTGAACGGG (SEQ ID NO: 470) |
| 10 | | | A_24_P297539 | NM_007019 | UBE2C | Homo sapiens ubiquitin-conjugating enzyme E2C (UBE2C), transcript variant 1, mRNA | TTGTCTTTTAAATTAAGCCTCGGTTGAGCCCTT GTATATTAAATAAATGCATTTTTGTCC (SEQ ID NO: 471) |
| 10 | | | A_24_P302172 | NM_000959 | PTGFR | Homo sapiens prostaglandin F receptor (FP) (PTGFR), mRNA | CCCATTCAAATTGTCCTAGTCTATCAGAAATT AGGGAAGGTAGTCCTGCTTTATAATAG (SEQ ID NO: 472) |
| 10 | | | A_24_P322229 | NM_033315 | RASL10B | Homo sapiens RAS-like, family 10, member B (RASL10B), mRNA | TGGGGAAGGGTCGTGGGTGGGGAATTTATC ACCAACATCCATTGTAGGGGGAATCTATG (SEQ ID NO: 473) |
| 10 | | | A_24_P396489 | HSM807143 | | Homo sapiens mRNA; cDNA DKFZp686E15252 (from clone DKFZp686E15252). | AGCTTTGCTTTGCAAAGATTGATGACAGACTG GTTCCTCAGAGGCCTAGGCTACCCGTCA (SEQ ID NO: 474) |
| 10 | | | A_24_P418176 | NM_001007238 | HRES1 | Homo sapiens HTLV-1 related endogenous sequence (HRES1), mRNA | GCGGGCTGGGCGCTCTGGCGTGTGCGCTG AGGTGGGCAGAGCCGGCAGGTGGGGCGTTG (SEQ ID NO: 475) |
| 10 | | | A_24_P636974 | NM_001013665 | LOC399744 | Homo sapiens hypothetical LOC399744 (LOC399744), mRNA | GTGGGAGGGCCCGTGTGAGGCAAGGCTCA CGCTGACCTCTCTGGCGTGGGAGGGCCG (SEQ ID NO: 476) |

TABLE 1-continued

| Cluster | Ratio cell type to all cells | cell Type | Array ID | Genbank ID | Gene ID | Description | Sequence |
|---|---|---|---|---|---|---|---|
| 10 | | | A_24_P741378 | AC027682 | | Homo sapiens chromosome 16 clone CTD-2012K14, complete sequence. | CACAGAAACATACAAGGAAGGCACCCCCGCTC TGTGGGCCGAGACAAAGCAGCAATCCTCT (SEQ ID NO: 477) |
| 10 | | | A_24_P810084 | AC016394 | | Homo sapiens chromosome 10 clone RP11-152N13, complete sequence. | GGAATTGGCTCTTCCTATTTCCCTACTTCATGA AACTCCAGTAGAAGACCTTAGAACCT (SEQ ID NO: 478) |
| 10 | | | A_24_P8298 | AC026740 | | Homo sapiens chromosome 5 clone CTD-2589H19, complete sequence. | TTTAAACACACGTGGTCCCCGTCTAGAAGCC TCTGCATTTAAGCACACGTGGTCCCCG (SEQ ID NO: 479) |
| 10 | | | A_32_P138032 | NM_006365 | C1orf61 | Homo sapiens chromosome 1 open reading frame 61 (C1orf61), mRNA | ATGGCTAAGTTGGGAGACCAAAAAGAAGAATG TACTTCATCTGGTTGGCTGGATTCCCT (SEQ ID NO: 480) |
| 10 | | | A_32_P187571 | NM_004588 | SCN2B | Homo sapiens sodium channel, voltage-gated, type II, beta (SCN2B), mRNA | TGTGACTCGACTGCTGGGATGTATCTGCTTTT GGGAGCAGACTGAGTTTCTTTTGCAATT (SEQ ID NO: 481) |
| 10 | | | A_32_P219148 | NM_001013725 | LOC441268 | Homo sapiens hypothetical gene supported by BC044942 (LOC441268), mRNA | TCCCCGTCCACGTTACCGCCATTCAGAGCTTGG GTCACCTGGACACTGAACTCAGGTGAAT (SEQ ID NO: 482) |
| 10 | | | A_32_P222149 | XM_499058 | LOC442512 | PREDICTED: Homo sapiens similar to U2 small nuclear ribenucleoprotein A (U2 snRNP-A) (LOC442512), mRNA | TACAGAGCAGTCGCCGGGCAGTTGAAGATCA GCTAAAGATATGTGGCCACGAGGAGGATG (SEQ ID NO: 483) |
| 10 | | | A_32_P52386 | AC004080 | | Homo sapiens PAC clone RP1-170O19 from 7p15-p21, complete sequence. | AAATGTGGCGCTCTCGCCAAGAAAAAGCTTGG GGACTGAATTCTTGAGATTTATGGTGCA (SEQ ID NO: 484) |
| 10 | | | A_32_P71710 | NM_000577 | IL1RN | Homo sapiens interleukin 1 receptor antagonist (IL1RN), transcript variant 3, mRNA | AAGATTTATTGTAAAACAGAGCTGAAGTCACA GGAAGTAGGGAACTTTGCACCCAACAT (SEQ ID NO: 485) |
| 11 | | all cell types | | | | | |
| 11 | | | A_23_P128974 | NM_006399 | BATF | Homo sapiens basic leucine zipper transcription factor, ATF-like (BATF), mRNA | TATTAAGAAAGATGCTCAGTCCCATGGCACA GAGCAAGGCGGGCAGGGAACGCGGTTATTT (SEQ ID NO: 486) |
| 11 | | | A_23_P218731 | NM_005111 | CRYZL1 | Homo sapiens crystallin, zeta (quinone reductase)-like 1 (CRYZL1), transcript variant 1, mRNA | AAGATGATGAACCAGCTGTAAAACTACAACTA CTACCACATAAACATGATGATTCATCACAC (SEQ ID NO: 487) |

TABLE 1-continued

| Cluster | Ratio cell type to all cells | cell Type | Array ID | Genbank ID | Gene ID | Description | Sequence |
|---|---|---|---|---|---|---|---|
| 11 | | | A_23_P42514 | NM_030939 | C6orf62 | Homo sapiens chromosome 6 open reading frame 62 (C6orf62), mRNA | TCCTTTGGAGTAAAACTAGTGCTTACCAGTTTC CAATGTATTTAGCTTCTGGTTGGAAT (SEQ ID NO: 488) |
| 11 | | | A_23_P92967 | NM_004531 | MOCS2 | Homo sapiens molybdenum cofactor synthesis 2 (MOCS2), transcript variant 3, mRNA | AAGCATATCTACCCATGGCGGAAAATGAAGTC AGAAAGATTTGTAGTGACATTAGGCAGA (SEQ ID NO: 489) |
| 11 | | | A_32_P160615 | AC016554 | | Homo sapiens chromosome 5 clone CTC-340H12, complete sequence. | ACTGCAATGAACACATATACATATACATCCAAA CATTCCTCCATTCGTCTATTAATCTGC (SEQ ID NO: 490) |
| 11 | | | A_32_P37461 | | | | CATCAACTGGTAAACAAAAAACTGTGAGAACG GATCCTGAATCTTGCGCTTACCAGGGGA (SEQ ID NO: 491) |
| 12 | | all cell types | | | | | |
| 12 | | | A_23_P100711 | NM_000304 | PMP22 | Homo sapiens peripheral myelin protein 22 (PMP22), transcript variant 1, mRNA | TGTGCCTCCAAGGACTGTCTGGCAATGACTTG TATTGGCCACCAACTGTAGATGTATATA (SEQ ID NO: 492) |
| 12 | | | A_23_P135730 | NM_145295 | ZNF627 | Homo sapiens zinc finger protein 627 (ZNF627), mRNA | ACTCCCCTAGTCTCTGTAGACGGAATTGGCATAC GGTCTAATTGTGTAGTAAGCACCACCTTTG (SEQ ID NO: 493) |
| 12 | | | A_23_P307968 | NM_022124 | CDH23 | Homo sapiens cadherin-like 23 (CDH23), transcript variant 1, mRNA | CCATCTGACGCTACAGTCACCACGACCTTCAA TATCCTGGTTATTGACATCAATGACAAT (SEQ ID NO: 494) |
| 12 | | | A_23_P411162 | NM_003894 | PER2 | Homo sapiens period Homolog 2 (Drosophila) (PER2), transcript variant 2, mRNA | TCCTCCTGAAAAGAGAATTTTACAACCACCCA TACACCAAATTGTTTGTTCCAGGATGT (SEQ ID NO: 495) |
| 12 | | | A_23_P63343 | NM_006786 | UTS2 | Homo sapiens urotensin 2 (UTS2), transcript variant 2, mRNA | AGAATCTGGAAACCATACAAGAAACGTGAGAC TCCTGATTGCTTCTGGAAATACTGTGTC (SEQ ID NO: 496) |
| 12 | | | A_23_P64879 | NM_004982 | KCNJ8 | Homo sapiens potassium inwardly-rectifying channel, subfamily J, member 8 (KCNJ8), mRNA | CTTCCCTCATGGTACCAAAGGTGCAATTTATG ACTCCAGAGGAAATCAAAACACATCGG (SEQ ID NO: 497) |
| 12 | | | A_24_P45620 | NM_006786 | UTS2 | Homo sapiens urotensin 2 (UTS2), transcript variant 2, mRNA | AGAAAGTTTCAGGATTTCTCTGGACAAGATCC TAACATTTTACTGAGTCATCTTTTGGCC (SEQ ID NO: 498) |

TABLE 1-continued

| Cluster | Ratio cell type to all cells | cell Type | Array ID | Genbank ID | Gene ID | Description | Sequence |
|---|---|---|---|---|---|---|---|
| 12 | | | A_24_P614702 | AC091320 | | Homo sapiens BAC clone RP11-447A2 from 7, complete sequence | CCTTCCTCATTTTGGAACTTAAGGTTGTGTACAGAACAGTCTTACAATGACAGTGTTTAG (SEQ ID NO: 499) |
| 12 | | | A_32_P31144 | | | | TTCTATACCTCTAAGCTGTTCTTTTCTGAACCATGAATCGGGAGAATTATTGTCACTCAT (SEQ ID NO: 500) |
| 12 | | | A_32_P427222 | XM_291007 | LOC339766 | PREDICTED: Homo sapiens hypothetical protein LOC339766 (LOC339766), mRNA | TCTCTACCGCTTCTTGCTAGAAACAATGGCCTATGTTAAAATAACTTGTCAAGAATCAG (SEQ ID NO: 501) |
| 13 | | Red Blood cells | | | | | |
| 13 | | | A_23_P109322 | NM_006198 | PCP4 | Homo sapiens Purkinje cell protein 4 (PCP4), mRNA | CCCTCCTAGTCCACCTGAAAACACCAAATTCAACCATCATCTGTCAAGAAATTAAAAGAA (SEQ ID NO: 502) |
| 13 | 3 | RBC | A_23_P11408 | NM_001102758 | PRY2 | Homo sapiens PTPN13-like, Y-linked 2 (PRY2), mRNA | ACCTCCTTCTCTTCTCTGGACATGTCCAGGAGTGGCCGGTTGCTACAAGTCACCTGGTGCTAC (SEQ ID NO: 503) |
| 13 | | | A_23_P135568 | AC026315 | | Homo sapiens 3 BAC RP11-114D6 (Roswell Park Cancer Institute Human BAC library) complete sequence. | AGCAAGATATCCTCCTCATGGTCCTTTAGCTCTCAAAAGCAATGAAAATCCTCCTGTTCT (SEQ ID NO: 504) |
| 13 | | | A_23_P161474 | NM_018518 | MCM10 | Homo sapiens MCM10 minichromosome maintenance deficient 10 (S. cerevisiae) (MCM10), transcript variant 2, mRNA | CCTCCTGTGACTCTGGAAAGCAAAGGATTGGCTGTGTATTGTCCATTGATTCCTGATTGA (SEQ ID NO: 505) |
| 13 | | | A_23_P204998 | NM_005766 | FARP1 | Homo sapiens FERM, RhoGEF (ARHGEF) and pleckstrin domain protein 1 (chondrocyte-derived) (FARP1), transcript variant 1, mRNA | TCCTCCTGCAACTGTGGTTTGAAACTGCCCATTCTCTAGTAGTATATCGTCGCCTGTCT (SEQ ID NO: 506) |
| 13 | 3 | RBC | A_23_P205637 | NM_015163 | TRIM9 | Homo sapiens tripartite motif-containing 9 (TRIM9), transcript variant 1, mRNA | CCTTCCTGACTTAAATAGAAAAAACTTGACATTTTTTATCAACGATGAACAACAAGTCC (SEQ ID NO: 507) |
| 13 | | | A_23_P215549 | NM_000940 | PON3 | Homo sapiens paraoxonase 3 (PON3), mRNA | GCACCTTCGTGGCTTCTGTGTACCATGGAAAATTCTCATAGGCACCGTATTTCACAAAA (SEQ ID NO: 508) |
| 13 | | | A_23_P254626 | NM_003919 | SGCE | Homo sapiens sarcoglycan, epsilon (SGCE), mRNA | ACTGGTCTCTTTTCTAATACTTGCTTATATCATGTGCTGCCGACGGGAAGGCGTGAAAA (SEQ ID NO: 509) |

TABLE 1-continued

| Cluster | Ratio cell type to all cells cell Type | Array ID | Genbank ID | Gene ID | Description | Sequence |
|---|---|---|---|---|---|---|
| 13 | | A_23_P26582 | NM_020988 | GNAO1 | Homo sapiens guanine nucleotide binding protein (G protein), alpha activating activity polypeptide O (GNAO1), transcript variant 1, mRNA | TTGTACTGACCTCTTGTCCTGTATAGCAACCTA TTTGACTGCTTCACGGACTCTTTGCTG (SEQ ID NO: 510) |
| 13 | | A_23_P303803 | NM_152474 | C19orf18 | Homo sapiens chromosome 19 open reading frame 18 (C19orf18), mRNA | CAGCTCGAGTCACTTATAAGAACCTCAGGAT ACCGTTATTAGGGATGAAGAAGAGGGC (SEQ ID NO: 511) |
| 13 | | A_23_P309278 | NM_173158 | NR4A1 | Homo sapiens nuclear receptor subfamily 4, group A, member 1 (NR4A1), transcript variant 3, mRNA | CTCCCTTGCCACCCAAATGTTAGAAAAATAGCT GTGAACAGAGAGCGCTTTTGTCTGCAA (SEQ ID NO: 512) |
| 13 | | A_23_P326844 | NM_174913 | C14orf21 | Homo sapiens chromosome 14 open reading frame 21 (C14orf21), mRNA | ACTCCTGGTCTTGTACTTCGAAGTCTGGGTGC CTTGACGGGACCACCAGCTTCTGTCCCTT (SEQ ID NO: 513) |
| 13 | | A_23_P44648 | NM_030955 | ADAMTS12 | Homo sapiens ADAM metallopeptidase with thrombospondin type 1 motif, 12 (ADAMTS12), mRNA | CAGACCTCCAGAATTCAAAAAATGCAACCAGC AGGCCTGCAAGAAAAGTGCCGATTTACT (SEQ ID NO: 514) |
| 13 | | A_23_P68234 | NM_006794 | GPR75 | Homo sapiens G protein-coupled receptor 75 (GPR75), mRNA | ATCTCCCATCATGAAACAAACTGCCTACAT GTTATCTCCAAAGCCACAGAAGAAATT (SEQ ID NO: 515) |
| 13 | | A_23_P78795 | NM_001009813 | MEIS3 | Homo sapiens Meis1, myeloid ecotropic viral integration site 1 homolog 3 (mouse) (MEIS3), transcript variant 2, mRNA | CCTCCCAGACCAGAATAATATGTGGATTCGAG ACCATGAGGATAGTGGGTCTGTACATTT (SEQ ID NO: 516) |
| 13 | | A_23_P80122 | NM_004627 | WRB | Homo sapiens tryptophan rich basic protein (WRB), mRNA | CCTGGTAGCCTTTCCTACTAGAGTAGCAGGTG GTGTTGGAATTACCTGTTGGATTTTAGT (SEQ ID NO: 517) |
| 13 | | A_24_P126587 | NM_181489 | ZNF445 | Homo sapiens zinc finger protein 445 (ZNF445), mRNA | GCTCCTACAGGAGATGACCTCCAGAGTAAAAC AAACAAATTCATCTTAAATCAGGAACCT (SEQ ID NO: 518) |
| 13 | | A_24_P136299 | AC103975 | | Homo sapiens chromosome 15, clone RP11-1001M11, complete sequence. | TCAATTGCTTCCTCCCTCCAATCTGCAGCCACT GACCTGCAGTTGTGCTAACGCTGCCCT (SEQ ID NO: 519) |
| 13 | | A_24_P200250 | HSU37055 | | Human hepatocyte growth factor-like protein gene, complete cds. | CCTTCCATTAGCAACTACTCTGTACCACCCTTC CCAAGAGTATGTCTGGAGGACTAGTGT (SEQ ID NO: 520) |

TABLE 1-continued

| Cluster | Ratio cell type to all cells | cell Type | Array ID | Genbank ID | Gene ID | Description | Sequence |
|---|---|---|---|---|---|---|---|
| 13 | | | A_24_P312594 | AL133215 | | Human DNA sequence from clone RP11-108L7 on chromosome 10 | TTCTTCCCTCCATACATTTGCTTCCAAGTGAAT TGCATAAGCAGTGCTCAGACTGCACC (SEQ ID NO: 521) |
| 13 | | | A_24_P31875 | NM_152577 | ZNF645 | Homo sapiens zinc finger protein 645 (ZNF645), mRNA | CTCCTTCAACCCTACATGGTCGATCACATCATT CACACCAGAAGACATAGACGTATT (SEQ ID NO: 522) |
| 13 | 2 | RBC | A_24_P341116 | NM_207378 | SERPINA13 | Homo sapiens serpin peptidase inhibitor, clade A (alpha-1 antiproteinase, antitrypsin), member 13 (SERPINA13), mRNA | CTTCCTGGTGATGACTTTCCACACGGAAACAG GAAGCATGCTTTTTCTGGAGAAGATTGT (SEQ ID NO: 523) |
| 13 | | | A_24_P365349 | AC008440 | | Homo sapiens chromosome 19 clone CTC-331H23, complete sequence. | CCTGGCTCTGTTATTTACCGTGTATCATATGTA AATATCGACAGAAACTTCAATAAACTT (SEQ ID NO: 524) |
| 13 | | | A_24_P409451 | NM_018651 | ZNF167 | Homo sapiens zinc finger protein 167 (ZNF167), transcript variant 1, mRNA | AAGAACTATCCTCCTGTCTGCGAAATCTTCCG GCTACACTTCAGGCAATTGTTACCAC (SEQ ID NO: 525) |
| 13 | 4 | RBC | A_24_P59735 | BC041372 | | Homo sapiens similar to seven in absentia 2, mRNA (cDNA clone IMAGE: 5273845), partial cds. | TCCTGGTTTTGAGACTCAACCACTTTGAAAGC ATTTGTTAGCATCACAGTGCTCCAG (SEQ ID NO: 526) |
| 13 | | | A_24_P607751 | HSU91328 | | Human hereditary haemochromatosis region, histone 2A-like protein gene, hereditary haemochromatosis (HLA-H) gene, RoRet gene, and sodium phosphate transporter (NPT3) gene, complete cds. | CCTTCTTGGGTCAGTAGGCCATTGGTTTCTTT TTAAAGGTTTTCAAATTTATTTGCATC (SEQ ID NO: 527) |
| 13 | | | A_24_P666035 | AC055716 | | Homo sapiens 12 BAC RP11-641A6 (Roswell Park Cancer Institute Human BAC Library) complete sequence. | AGTTGTATGTCAAGGGGCAGCATTTCTGGTA TTTCTATATAATAAATTTTTCTGTGATCTC (SEQ ID NO: 528) |
| 13 | | | A_24_P915376 | NM_006757 | TNNT3 | Homo sapiens troponin T type 3 (skeletal, fast) (TNNT3), mRNA | AGAAACCGAGACCCAAACTCACTGCTCTCAAG ATCCCAGAAGGGGAGAAAGTGGACTTCG (SEQ ID NO: 529) |
| 13 | | | A_24_P920555 | NM_198486 | RPL7L1 | Homo sapiens ribosomal protein L7-like 1 (RPL7L1), mRNA | GGCATTCACTGATCCCAGCAGGTCTCCATCTA TTTGTACCAGCCCTCCTCTATTCCTCCCA (SEQ ID NO: 530) |
| 13 | | | A_24_P927404 | AC084033 | | Homo sapiens 12q BAC RP11-58A17 (Roswell Park Cancer Institute Human BAC Library) complete sequence. | GCCCTTTTTGTCACTCACTGTTGTGACAGATC CTCCGATTTCTTACATAAGTTATGCAG (SEQ ID NO: 531) |

TABLE 1-continued

| Cluster | Ratio cell type to all cells | cell Type | Array ID | Genbank ID | Gene ID | Description | Sequence |
|---|---|---|---|---|---|---|---|
| 13 | | | A_32_P114483 | NM_153344 | C6orf141 | Homo sapiens chromosome 6 open reading frame 141 (C6orf141), mRNA | GAGCCCAACTACCCTTCTGTCTTTCAACGAGA AAAGCGAATTTCTGGCAGGCGTGTAGCC (SEQ ID NO: 532) |
| 13 | 3 | RBC | A_32_P133106 | AP005433 | | Homo sapiens genomic DNA, chromosome 18 clone: RP11-945C19, complete sequence. | CTAATGGACTAGATTGCTGACCTTTAATACCT TTGGTTTCATTGAACATACAATCACC (SEQ ID NO: 533) |
| 13 | | | A_32_P181638 | NM_007073 | BVES | Homo sapiens blood vessel epicardial substance (BVES), transcript variant A, mRNA | AATCCTGGTTTCCTAACCTCCTCTTGTAGTAAT TCTCAACTCAACTCAAAGTCCCAAGAA (SEQ ID NO: 534) |
| 13 | | | A_32_P354945 | AC011503 | | Homo sapiens chromosome 19 clone CTB-92J24, complete sequence. | CCCTCCTGATGATGAAGGACCTGTCATTGGAG AATCGACCAAAACTGACAGTGATAACTT (SEQ ID NO: 535) |
| 13 | 2 | RBC | A_32_P5057 | AC010798 | | Homo sapiens , clone RP11-470B24, complete sequence. | CCCTGAACCTACATAGACATTTTATATCAGCAT ACAGAAAGTAAAATCCTCCTTCAGTC (SEQ ID NO: 536) |
| 13 | | | A_32_P51005 | BX629352 | | Human DNA sequence from clone WI2-80267E6 on chromosome 9, complete sequence. | ATTCCTTTCTGGTCTCCATCCTGCTCTGTAGATA TGTAGATCTCTTTGAAACGAAGTAAGC (SEQ ID NO: 537) |
| 13 | | | A_32_P524904 | | | | GGCTGAGCACTCTGCTGAAAACCTTTGAAC CTCACGGTGTCCTGATGAGGAAGCAGA (SEQ ID NO: 538) |
| 14 | | Red Blood cells | | | | | |
| 14 | | | A_23_P153351 | NM_000713 | BLVRB | Homo sapiens biliverdin reductase B (flavin reductase (NADPH)) (BLVRB), mRNA | CAAGGTGCCCCACGACTGCAGGCTGTGACT GATGACCACCATCCGATGCACAAGGTGCT (SEQ ID NO: 539) |
| 14 | 7 | RRC | A_23_P207842 | NM_000964 | RARA | Homo sapiens retinoic acid receptor, alpha (RARA), transcript variant 1, mRNA | AGTTCTCCTCCTCCAGCCTTTTCCTCCTCAGTTT TCTCTTTAAAACTGTGAAGTACTAACT (SEQ ID NO: 540) |
| 14 | 3 | RBC | A_23_P210465 | NM_002638 | PI3 | Homo sapiens peptidase inhibitor 3, skin-derived (SKALP) (PI3), mRNA | TCCTGCCCATTATCTTGATCCGTGCCCAT GTTGAATCCCCCTAACCGGTGCTTGAAA (SEQ ID NO: 541) |
| 14 | 2 | RBC | A_23_P23850 | NM_021080 | DAB1 | Homo sapiens disabled homolog 1 (Drosophila) (DAB1), mRNA | CTCCCTCACCTGTACCTCAGAGGCCTTCCA GTTACTTCAACAAGTCGGGGTGCACA (SEQ ID NO: 542) |

TABLE 1-continued

| Cluster | Ratio cell type to all cells | cell Type | Array ID | Genbank ID | Gene ID | Description | Sequence |
|---|---|---|---|---|---|---|---|
| 14 | | | A_23_P251898 | NM_152743 | C7orf27 | Homo sapiens chromosome 7 open reading frame 27 (C7orf27), mRNA | GGGCAGAAGTCTTGTGACTCCTTCTTCC TGAGGGACAAGATTGCTTCCTACAGCAG (SEQ ID NO: 543) |
| 14 | 6 | RBC | A_23_P332392 | NM_152479 | TTC9B | Homo sapiens tetratricopeptide repeat domain 9B (TTC9B), mRNA | ACTTCCCCTGCAGACACCAATGTCTCCCTA CATCCAGCTGACTCAGCTGAAGATGAAT (SEQ ID NO: 544) |
| 14 | 2 | RBC | A_23_P338168 | NM_019085 | FBXL19 | Homo sapiens F-box and leucine-rich repeat protein 19 (FBXL19), mRNA | TCCTTCCCCCTGACCCTGACTCCTTGACGTC ACTGAAAACGGCAGCTATTGCAAGGAGT (SEQ ID NO: 545) |
| 14 | | | A_23_P362893 | NM_021961 | TEAD1 | Homo sapiens TEA domain family member 1 (SV40 transcriptional enhancer factor) (TEAD1), mRNA | TTTTTTCTCCTTCCCTTTCTTTAAGAGAGGCT GACAGATCTAGGTGTCAATCAATTGGA (SEQ ID NO: 546) |
| 14 | 5 | RBC | A_23_P377717 | NM_0112516 | NOVA2 | Homo sapiens neuro-oncological ventral antigen 2 (NOVA2), mRNA | CCTCCCCTTCTGGTAGTCATAGGCAGGATTGA GTGACGGTTGGGAAGGGGCTCAGAAGC (SEQ ID NO: 547) |
| 14 | 5 | RBC | A_23_P39265 | NM_014400 | LYPD3 | Homo sapiens LY6/PLAUR domain containing 3 (LYPD3), mRNA | TCCCCTACTCCCCGCCATCTTGGGAATCGGT TCCCATATGTCTTCCTTACTAGACTGT (SEQ ID NO: 548) |
| 14 | 5 | RBC | A_23_P62361 | NM_014235 | UBL4A | Homo sapiens ubiquitin-like 4A (UBL4A), mRNA | GCTTCCTGCACCCTGAAGTGACTGAGACAATG GAGAGGGGTTCTCCAAATAGAATTCTC (SEQ ID NO: 549) |
| 14 | 3 | RBC | A_23_P67332 | NM_007121 | NR1H2 | Homo sapiens nuclear receptor subfamily 1, group H, member 2 (NR1H2), mRNA | ACCACCCTCCAGCAGATAGACGCCGGCACCC CTTCCTCTTCCTAGGGTGGAAGGGCCCT (SEQ ID NO: 550) |
| 14 | 4 | RBC | A_23_P79323 | NM_003936 | CDK5R2 | Homo sapiens cyclin-dependent kinase 5, regulatory subunit 2 (p39) (CDK5R2), mRNA | TCCCTTCAGCCATTCCCCTCCGTTTTATCC ATTTCCTTGCCTCCCTTTTTGTGTCTTCA (SEQ ID NO: 551) |
| 14 | | | A_23_P81717 | NM_024919 | FRMD1 | Homo sapiens FERM domain containing 1 (FRMD1), mRNA | AGGTTCCTCCAGACCTGAATCCCTCTCTGCA ACTCCTGTTTGCAAGCGCTGGGCCTGCC (SEQ ID NO: 552) |
| 14 | 2 | RBC | A_24_P102343 | NM_017957 | EPN3 | Homo sapiens epsin 3 (EPN3), mRNA | TCCCTCAGCTTCCTCTTGGTCAACCTTGACT CGTTGGTCAAGGCACCCCAGGTTGCAAA (SEQ ID NO: 553) |
| 14 | | | A_24_P233078 | NM_021093 | PYY2 | Homo sapiens peptide YY, 2 (seminalplasmin) (PYY2), mRNA | GCCCACCCTCATTTACATGTTCATCCCGACCC TGGAAACCCGGATTTCGCCTCCGACAG (SEQ ID NO: 554) |

TABLE 1-continued

| Cluster | Ratio cell type to all cells | cell Type | Array ID | Genbank ID | Gene ID | Description | Sequence |
|---|---|---|---|---|---|---|---|
| 14 | 4 | RBC | A_24_P256083 | HS526I14 | | Human DNA sequence from clone RP3-526I14 on chromosome 22, complete sequence. | ATTTTCACCTCCCCTGGTCCATGCTCAGGAAG TCTGGTCACCCTGGCAAACTGCACCTGA (SEQ ID NO: 555) |
| 14 | 3 | RBC | A_24_P318990 | HS285332 | | H. sapiens Ig lambda light chain variable region gene (22-21SWIA31) rearranged; Ig-Light-Lambda; VLambda. | TCTGACACCTCAGCTCTCCTGGCCATCACTGG ACTCCAGCTGACTGAGGCTGATTAT (SEQ ID NO: 556) |
| 14 | 4 | RBC | A_24_P365523 | NM_021784 | FOXA2 | Homo sapiens forkhead box A2 (FOXA2), transcript variant 1, mRNA | CCTCCTACTACCAGGGGTGTACTCCCGGCC CATTATGAACTCTCTTAAGAAGACGACG (SEQ ID NO: 557) |
| 14 | | RBC | A_24_P493646 | AP002776 | | Homo sapiens genomic DNA, chromosome 11 clone: RP11-126P21, complete sequence. | TCGCCACGCCAGCCCCTTTCCTCAGAACGCC GAGGCCTCAGGAGCGTGTGCGCCGCGGGA (SEQ ID NO: 558) |
| 14 | | RBC | A_24_P911718 | AF240580 | | Homo sapiens clone 17ptel_211lctg.drft sequence. | CTTCCTTCCCCATCTTCTGGATCTCAGCACCCTTTTAGA TCCCGTGCAGATTGTCTTTCTGTTAAA (SEQ ID NO: 559) |
| 14 | 2 | RBC | A_24_P920188 | AY236488 | | Homo sapiens unidentified genomic region, partial sequence. | CTCCTTCCCACTCTCTGTAACACAACCTTTA TTTATTTGTGGGAACCTATTCCCTGT (SEQ ID NO: 560) |
| 14 | 6 | RBC | A_32_P48536 | 2772567 | | 7n93b04.x1 NCI_CGAP_Ov18 Homo sapiens cDNA clone IMAGE: 3571927 3', mRNA sequence | AATTGCCATGCTGCCACTCCCGAAGTGTTA GGAGGTAACATCTCATCGTCTCATCGCA (SEQ ID NO: 561) |
| 15 | | all cell types | | | | | |
| 15 | | | A_23_P101121 | NM_031303 | KATNAL2 | Homo sapiens katanin p60 subunit A-like 2 (KATNAL2), mRNA | TCAGAAGATCTCGTATTGTCTTAGCAGCTTCT AACCTGCCGTGGTAAGAGACCAAGAGA (SEQ ID NO: 562) |
| 15 | | | A_23_P120243 | NM_024501 | HOXD1 | Homo sapiens homeobox D1 (HOXD1), mRNA | TTTTTCTTTAAAAAGCCGGTTCTACCTCTA TGTGCCTGAGTGATGATACAATCGCT (SEQ ID NO: 563) |
| 15 | | | A_23_P133845 | NM_004366 | CLCN2 | Homo sapiens chloride channel 2 (CLCN2), mRNA | TGGGAGTGGACCATGCTTATGTCACCAGTATT GGCAGACTCATTGGAATCGTTACTCTAA (SEQ ID NO: 564) |
| 15 | | | A_23_P15765 | NM_018996 | TNRC6C | Homo sapiens trinucleotide repeat containing 6C (TNRC6C), mRNA | GACATTGTGTTTGCAACATGGGCCTCTTATCA CATTCCACCTGAATCTGACTCAAGGCAA (SEQ ID NO: 565) |

TABLE 1-continued

| Cluster | Ratio cell type to all cells | cell Type | Array ID | Genbank ID | Gene ID | Description | Sequence |
|---|---|---|---|---|---|---|---|
| 15 | | | A_23_P313623 | NM_015198 | COBL | Homo sapiens cordon-bleu homolog (mouse) (COBL), mRNA | GTCTACAGGCCAAAATGGCACAGTTGATTT CGGTGTGTTCCTGTATAACGGCTTGAAA (SEQ ID NO: 566) |
| 15 | | | A_23_P319466 | NM_020377 | CYSLTR2 | Homo sapiens cysteinyl leukotriene receptor 2 (CYSLTR2), mRNA | GGCAAATAGCAAAAGTTGTTGCACTCCTGAAA TTCTATTAACATTTCCGCAGAAGATGAG (SEQ ID NO: 567) |
| 15 | | | A_23_P369994 | NM_004734 | DCAMKL1 | Homo sapiens doublecortin and CaM kinase-like 1 (DCAMKL1), mRNA | AAATGTTTTACCGTAGCCCTCATCTAACTTAC ACGTGGTGCATATTAAAATAAGCAGAG (SEQ ID NO: 568) |
| 15 | | | A_23_P39294 | AC011533 | | Homo sapiens chromosome 19 clone LLNLR-240E6, complete sequence. | CTCCCAGCAGAGTCATCACTACCTTTGGGGCC GCAGGATCACCCAGCTTGGAACTAGATA (SEQ ID NO: 569) |
| 15 | | | A_23_P399797 | AC009014 | | Homo sapiens chromosome 5 clone P1_748D6, complete sequence. | ACAACTGCCCAGAGTGTAATTCCCACGATAA GCGCGGATCCTTATCTTTGAAACACAAA (SEQ ID NO: 570) |
| 15 | | | A_23_P413923 | NM_022160 | DMRTA1 | Homo sapiens DMRT-like family A1 (DMRTA1), mRNA | CTGTACTTCAGACCAAATCAGGACAATCCGTA ATGTATATGCCCATTCTCTCTTTCTGGA (SEQ ID NO: 571) |
| 15 | | | A_23_P45560 | NM_000273 | GPR143 | Homo sapiens G protein-coupled receptor 143 (GPR143), mRNA | ATATTCCTCAGACTCAACAATTCTTGTTCTTTA GAACTGTGTTCTCACCTTCCCAACACT (SEQ ID NO: 572) |
| 15 | | | A_23_P502413 | NM_002974 | SERPINB4 | Homo sapiens serpin peptidase inhibitor, clade B (ovalbumin), member 4 (SERPINB4), mRNA | TCCTCTTCTATGGCAGATTCTCATCCCCATAGA TGCAATTAGTCTGTCACTCCATTTAGA (SEQ ID NO: 573) |
| 15 | | | A_23_P81103 | NM_003013 | SFRP2 | Homo sapiens secreted frizzled-related protein 2 (SFRP2), mRNA | ATAACCTACTACCGAGATACAAAATCATC CTGGAGACCAAGAGACAAGACCATTTAC (SEQ ID NO: 574) |
| 15 | | | A_24_P20091 | NM_153041 | FLJ32955 | Homo sapiens hypothetical protein FLJ32955 (FLJ32955), mRNA | CACAAATTCCTCACTCATCTTGAGAAGCTCC CAGTTTTCAATATTCTCCTAAATGCTGT (SEQ ID NO: 575) |
| 15 | | | A_24_P252780 | NM_198514 | NHLRC2 | Homo sapiens NHL repeat containing 2 (NHLRC2), mRNA | GTTCCTAGTAGAAAAACAGAAGACATTACCCA AACTACCTAAATCTGCTCCAAGCATTAG (SEQ ID NO: 576) |

TABLE 1-continued

| Cluster | Ratio cell type to all cells | cell Type | Array ID | Genbank ID | Gene ID | Description | Sequence |
|---|---|---|---|---|---|---|---|
| 15 | | | A_24_P382187 | NM_001552 | IGFBP4 | Homo sapiens insulin-like growth factor binding protein 4 (IGFBP4), mRNA | GAAAAATCTCATTCCCAGAGTCAGAGGAAAG AGACATGTACCTTGACCATCGTCCTTCC (SEQ ID NO: 577) |
| 15 | | | A_24_P410605 | BC080541 | | Homo sapiens receptor tyrosine kinase-like orphan receptor 1, mRNA (cDNA clone IMAGE: 5477978), complete cds. | GACATCCCAGCTTGCGGTAAATAGAAGTCATT GCCCTAATGTATTCAATCATCTTTAAA (SEQ ID NO: 578) |
| 15 | | | A_24_P499215 | NM_001005751 | LOC387680 | Homo sapiens similar to KIAA0592 protein (LOC387680), mRNA | TCAAAGACAAGAGAGAAGCAAAAGCCTCCAAGC TCTCCAAAAGAAAGCATCTGCCCTGTT (SEQ ID NO: 579) |
| 15 | | | A_24_P744957 | AL353653 | | Human DNA sequence from clone RP11-244L4 on chromosome 20 Contains ESTs, STSs and GSSs, complete sequence. | AGACACAGGATGTTCCTGTTGGTCCAGATACT TGAGCTAAAAGGTGATGGATACCTGGAT (SEQ ID NO: 580) |
| 15 | | | A_24_P82155 | NM_182703 | ANKDD1A | Homo sapiens ankyrin repeat and death domain containing 1A (ANKDD1A), mRNA | CTACTTCCCAAAATAGTATTTCTCAGCAGAT ATTTCTTTGGTACTACCATGTATTGTG (SEQ ID NO: 581) |
| 15 | | | A_24_P91165 | NM_000723 | CACNB1 | Homo sapiens calcium channel, voltage-dependent, beta 1 subunit (CACNB1), transcript variant 1, mRNA | TACTTCAAAGGCTCATCAGTCCCGAGGAAAG TCTCAGTCCAAACACCTCAATGTCCAAA (SEQ ID NO: 582) |
| 15 | | | A_24_P933902 | AY358788 | | Homo sapiens clone DNA129793 AVLL5809 (UNQ5809) mRNA, complete cds. | TCGCGGTGAGACTGAACATTTCATGAGCTCAT GTTGCCTTTGACCACCATTTCTTAAGGA (SEQ ID NO: 583) |
| 15 | | | A_24_P934063 | NM_004978 | KCNC4 | Homo sapiens potassium voltage-gated channel, Shaw-related subfamily, member 4 (KCNC4), transcript variant 1, mRNA | ATGGGAGATTTTCCACCAGTCCTGTGCAAACA AGGATATCTGAGTCTTTCCCAGCCAAAA (SEQ ID NO: 584) |
| 15 | | | A_32_P102383 | HS243L18 | | Human DNA sequence from clone RP1-243L18 on chromosome 1p36.11-36.23 Contains the 5' end of a novel gene (KIAA1026) and a CpG island, complete sequence. | TTTCTTGAGGGTTGAGAGAGTCTGTTTTCCT AAGAATCTGGTTCTCTCCATCAGTCTCT (SEQ ID NO: 585) |
| 15 | | | A_32_P146764 | AC002076 | | Homo sapiens BAC clone GS1-345D13 from 7, complete sequence. | ATGTCTCTTTCAACCATATGATCAATCAGTTGG ACGACTTCGGTTTTCCTGAATAAAT (SEQ ID NO: 586) |
| 15 | | | A_32_P181131 | NM_001005353 | AK3L1 | Homo sapiens adenylate kinase 3-like 1 (AK3L1), nuclear gene encoding mitochondrial protein, transcript variant 1, mRNA | CTCTTCATAGCTCAGTTCTCAGTGCATACAGA GATTCAAATAGCCCCATCGCTCTCAGT (SEQ ID NO: 587) |

TABLE 1-continued

| Cluster | Ratio cell type to all cells | cell Type | Array ID | Genbank ID | Gene ID | Description | Sequence |
|---|---|---|---|---|---|---|---|
| 15 | | | A_32_P221507 | BC066346 | | Homo sapiens cDNA clone IMAGE: 4824446, partial cds. | CATAGAGACAGTTGCTCCCCATTGACACCAAGT AATTCCAGTCCACATTGCCTTTAAGCA (SEQ ID NO: 588) |

TABLE 2

| Feature | Agilent Probe | Gene | Description | Correlation-IFI27 | Sequence |
|---|---|---|---|---|---|
| 2703 | A_23_P48513 | IFI27 | interferon, alpha-inducible protein 27 variant a | 1 | ACCCAGCGAGGAGCCAACTATCCCAAATATACCTGGG GTGAAATATACCAAATTCTGCAT (SEQ ID NO: 589) |
| 40154 | A_23_P48513 | IFI27 | interferon, alpha-inducible protein 27 variant a | 0.999 | ACCCAGCGAGGAGCCAACTATCCCAAATATACCTGGG GTGAAATATACCAAATTCTGCAT (SEQ ID NO: 590) |
| 32566 | A_23_P48513 | IFI27 | interferon, alpha-inducible protein 27 variant a | 0.999 | ACCCAGCGAGGAGCCAACTATCCCAAATATACCTGGG GTGAAATATACCAAATTCTGCAT (SEQ ID NO: 591) |
| 7079 | A_23_P48513 | IFI27 | interferon, alpha-inducible protein 27 variant a | 0.999 | ACCCAGCGAGGAGCCAACTATCCCAAATATACCTGGG GTGAAATATACCAAATTCTGCAT (SEQ ID NO: 592) |
| 508 | A_23_P48513 | IFI27 | interferon, alpha-inducible protein 27 variant a | 0.999 | ACCCAGCGAGGAGCCAACTATCCCAAATATACCTGGG GTGAAATATACCAAATTCTGCAT (SEQ ID NO: 593) |
| 18306 | A_23_P48513 | IFI27 | interferon, alpha-inducible protein 27 variant a | 0.999 | ACCCAGCGAGGAGCCAACTATCCCAAATATACCTGGG GTGAAATATACCAAATTCTGCAT (SEQ ID NO: 594) |
| 5149 | A_23_P48513 | IFI27 | interferon, alpha-inducible protein 27 variant a | 0.999 | ACCCAGCGAGGAGCCAACTATCCCAAATATACCTGGG GTGAAATATACCAAATTCTGCAT (SEQ ID NO: 595) |
| 13333 | A_23_P48513 | IFI27 | interferon, alpha-inducible protein 27 variant a | 0.998 | ACCCAGCGAGGAGCCAACTATCCCAAATATACCTGGG GTGAAATATACCAAATTCTGCAT (SEQ ID NO: 596) |
| 6656 | A_24_P270460 | IFI27 | interferon, alpha-inducible protein variant a | 0.997 | TGAAATATACCAAATTCTGCATCTCCAGAGGAAAATAA GAAATAAAGATGAATTGTTGCA (SEQ ID NO: 597) |
| 16373 | A_23_P48513 | IFI27 | interferon, alpha-inducible protein 27 variant a | 0.996 | ACCCAGCGAGGAGCCAACTATCCCAAATATACCTGGG GTGAAATATACCAAATTCTGCAT (SEQ ID NO: 598) |
| 5290 | A_23_P48513 | IFI27 | interferon, alpha-inducible protein 27 variant a | 0.996 | ACCCAGCGAGGAGCCAACTATCCCAAATATACCTGGG GTGAAATATACCAAATTCTGCAT (SEQ ID NO: 599) |
| 27987 | A_23_P819 | G1P2 | interferon, alpha-inducible protein | 0.911 | CACGGTCCTGCTGGTGGTGGACAAATGCGACGAACCT CTGAGCATCCTGGTGAGGAATAA (SEQ ID NO: 600) |
| 27626 | A_23_P45871 | IFI44L | chromosome 1 ORF 29 (C1orf29) | 0.893 | TTGTTCGTTTTGCCTTCTGTCCTTGGAACAGTCATATCT CAAGTTCAAAGGCCAAAACCT (SEQ ID NO: 601) |
| 11715 | A_32_P132206 | USP18 | ubiquitin specific protease 18 | 0.887 | AGACTTGTATACTGGCTGAATATCAGTGCTGTTTGTAA TTTTTCACTTTGAGAACCAACA (SEQ ID NO: 602) |
| 21005 | A_24_P28722 | RSAD2 | viperin (cig5) | 0.877 | ACTCTGAGTCAGTTGAAATAGGGTACCATCTAGGTCAG TTTAAGAAGAGTCAGCTCAGAG (SEQ ID NO: 603) |
| 30386 | A_24_P261929 | FAM14B | family with sequence similarity 14, member B | 0.868 | TGCAGTCAGTGGGGGCAGCTGGACTCTCTGTGACATC TAAAGTTATCGGGGGCTTTGCTG (SEQ ID NO: 604) |
| 36995 | A_32_P99533 | G1P2 | interferon, alpha-inducible protein | 0.864 | ACCAGGATGTTCAGAGGTTCGTCGCATTTGTCCACCA CCAGCAGGACCGTGCTGCCGGGG (SEQ ID NO: 605) |
| 36654 | A_24_P361896 | MT2A | metallothionein 2A | 0.863 | CGCTCCCAGATGTAAAGAACGCGACTTCCACAAACCT GGATTTTTTATGTACAACCCTGA (SEQ ID NO: 606) |
| 21017 | A_24_P316965 | RSAD2 | viperin (cig5) | 0.861 | ATTCTGGATGAATATATGCGCTTTCTGAACTGTAGAAA GGGACGGAAGGACCCTTCCAAG (SEQ ID NO: 607) |
| 12478 | A_23_P64828 | OAS1 | 2',5'-oligoadenylate synthetase 1 variant E18 | 0.855 | CTCTGCATCTACTGGACAAAGTATTATGACTTTAAAAAC CCCATTATTGAAAAGTACCTG (SEQ ID NO: 608) |
| 36260 | A_23_P106844 | MT2A | metallothionein 2A | 0.854 | CAACCCTGACCGTGACCGTTTGCTATATTCCTTTTTCT ATGAAATAATGTGAATGATAAT (SEQ ID NO: 609) |

TABLE 2-continued

| Feature | Agilent Probe | Gene | Description | Correlation-IFI27 | Sequence |
|---|---|---|---|---|---|
| 16580 | A_23_P23074 | IFI44 | interferon-induced protein 44 | 0.852 | AAGGATGTTCTAATTCTTTCTGCTCTGAGACGAATGCT ATGGGCTGCAGATGACTTCTTA (SEQ ID NO: 610) |
| 22208 | A_23_P252413 | MT2A | metallothionein 2A | 0.850 | CTGACCGTGACCGTTTGCTATATTCCTTTTTCTATGAAA TAATGTGAATAATAATTAAAC (SEQ ID NO: 611) |
| 20525 | A_23_P201459 | G1P3 | interferon, alpha-inducible protein variant | 0.846 | AGTAGCCAGCAGCTCCCAGAACCTCTTCTTCCTTCTTG GCCTAACTCTTCCAGTTAGGAT (SEQ ID NO: 612) |
| 43723 | A_23_P105794 | EPSTI1 | epithelial stromal interaction 1 | 0.846 | AGAAGAGAAGCATTTAGAGAGCATCAGCAATACAAAAC CGCTGAGTTCTTGAGCAAACTG (SEQ ID NO: 613) |
| 16830 | A_24_P316257 | FLJ36208 | hypothetical protein FLJ36208 | 0.839 | TGGGGGAGCTTCCTACAAGGAGAGACTCCTGCTGCTT TGGAAAACTGAGAAAAAATAGGG (SEQ ID NO: 614) |
| 25919 | A_23_P131255 | DNAPTP6 | DNA polymerase-trans-activated protein 6 | 0.836 | CTGAAGATCAGAGGCTCAGTTAGCAACCTGTGTTGTA GCAGTGATGTCAGTCCATTGATT (SEQ ID NO: 615) |
| 41211 | A_32_P227059 | RSAD2 | upsteam 5' end of Gene | 0.835 | CAAAATAATCTGAAACTTTACTGGCCAAAGTGGGACTC CTTTAAAATTCCAAAACTTGCC (SEQ ID NO: 616) |
| 41347 | A_23_P384355 | LOC129607 | thymidylate kinase family LPS-inducible member | 0.834 | ACAGTGGATCTTGGAGTGGGATTTCTTGGGTAAATTAT CTTTGCCCTTTGAAATGTCTCC (SEQ ID NO: 617) |
| 36358 | A_23_P47955 | QAS3 | 2'-5' oligoadenylate synthetase 3 | 0.834 | AGAAGGCAGAGAAAGTGAAGACCAAGTCCAGAACTGA ATCCTAAGAAATGCAGGACTGCA (SEQ ID NO: 618) |
| 14388 | A_24_P335305 | OAS3 | 2'-5' oligoadenylate synthetase 3 | 0.833 | TCTTTGGCAATGGCCACCCTGGTGTTGGCATATTGGC CCCACTGTAACTTTTGGGGGCTT (SEQ ID NO: 619) |
| 19864 | A_24_P943205 | EPSTI1 | downstream from gene | 0.824 | AACCAAATATCTATGTAGGCAGAGGTAACCAGGAGAG AAGCAAGACTTGCTGCCTAAAGG (SEQ ID NO: 620) |
| 3173 | A_23_P132159 | USP18 | ubiquitin specific protease 18 | 0.822 | CTGTCATTTTCCATTTCCGTTCCTGGATCTACGGGAGTC TTCTAAGAGATTTTGCAATGAG (SEQ ID NO: 621) |
| 23814 | A_23_P139786 | OASL | 2'-5'-oligoadenylate synthetase-like variant | 0.821 | GTTTCCAGCCAGTTAGTTTTCTCTGGGAGACTTCTCTG TACATTTCTGCCATGTACTCCA (SEQ ID NO: 622) |
| 28716 | A_24_P557479 | HSXIAPAF1 | XIAP associated factor-1 variant 2 | 0.816 | CAAATAAACCAACGGGAAAAAGAAAGGTTCCAGTTTT GTCTGAAAATTCTGATTAAGCC (SEQ ID NO: 623) |
| 39451 | A_23_P206724 | MT1E | metallothionein 1E | 0.816 | GGCATGGGAGAAGTGCAGCTGCTGTGCCtGATGTGG GAAGAGCTCTTCTCCCAGATGTAA (SEQ ID NO: 624) |
| 632 | A_23_P52266 | IFIT1 | interferon-induced protein variant 2 | 0.815 | ACTTTGAGAACTCTGTGAGACAAGGTCCTTAGGCACC GAGATATCAGCCACTTTCACATT (SEQ ID NO: 625) |
| 7680 | A_23_P427703 | MT1E | 602705675F1 NIH_MGC_43 clone IMAGE: 4842259 5' | 0.813 | CTGCTGTGCCTGATGTGGGGACAGACCTGCTCCCAGG TGTAAACAGAGCAACCTGCACAA (SEQ ID NO: 626) |
| 18216 | A_23_P17663 | MX1 | myxovirus (influenza virus) resistance 1, IFI protein p78 | 0.808 | CAGCTTATTTGCTCATTTTTATAATGTCCCTTCACAAAC CCAGTGTTTTAGGAGCATGAG (SEQ ID NO: 627) |
| 1309 | A_23_P303242 | MT1X | metallothionein 1x | 0.805 | TGCCAAGTGTGCCCAGGGCTGCATCTGCAAAGGGAC GTCAGACAAGtGCAGCTGCTGTGC (SEQ ID NO: 628) |
| 13366 | A_23_P414343 | MT1J | metallothionein 1J | 0.804 | TGTGCCAAGTGTGCCCACGGCTGCATCTGCAAAGGGA CGTCGGAGAAGTGCAGCTGCTGT (SEQ ID NO: 629) |
| 21994 | A_23_P60933 | MT1G | metallothionein 1G | 0.804 | AGCTGCTGTGCCTGATGTCGGGACAGCGCTGCTCCCA AGTACAAATAGAGTGACCCGTAA (SEQ ID NO: 630) |
| 22827 | A_23_P166797 | IFRG28 | 28kD interferon responsive protein | 0.798 | CAAGCAGGATCAAGTTTGTAGAATAAACACTGGTTTCC TAGCCATCCTCTGAAAACAGTA (SEQ ID NO: 631) |
| 34047 | A_24_P317762 | LY6E | lymphocyte antigen 6 complex, locus E | 0.798 | CTACTGCGTGACTGTGTCTGCTAGTGCCGGCATTGGG AATCTCGTGACATTTGGCCACAG (SEQ ID NO: 632) |
| 27981 | A_23_P4286 | HSXIAPAF1 | XIAP associated factor-1 variant 2 | 0.796 | TTTAACAGTGGCATTCCTGCCTACTTGCTGTGGTGGTC TTGTGAAAGGTGATGGGTTTTA (SEQ ID NO: 633) |

TABLE 2-continued

| Feature | Agilent Probe | Gene | Description | Correlation-IFI27 | Sequence |
|---|---|---|---|---|---|
| 41919 | A_24_P917810 | BRCA2 intron | BRCA2 intron | 0.795 | TTTGCACTATGGTAGATTTCAGGAATTTCAAAAGAAATC TGATGTCAGTGCAATTATCCG (SEQ ID NO: 634) |
| 42276 | A_23_P4283 | BIRC4BP | X-linked inhibitor of apoptosis | 0.791 | TCAACTTGACTTCATGTTAAAAACCCTCAACAAACCAG GCGTCGAAGGAACATACCTCAA (SEQ ID NO: 635) |
| 7108 | A_23_P204087 | OAS2 | 2'-5'-oligoadenylate synthetase 2 variant 1 | 0.789 | TCTTCAAAGCAAAGCTCTTTACTTTCCCCTTGGTTCTCA TAACTCTGTGATCTTGCTCTC (SEQ ID NO: 636) |
| 8777 | A_23_P110196 | HERC5 | hect domain and RLD 5 | 0.787 | TGTCCTGAAAGTTGGAATGAAAGAGACCCTATAAGAG CACTGACATGTTTCAGTGTCCTC (SEQ ID NO: 637) |
| 1565 | A_24_P343929 | OAS2 | 2'-5'-oligoadenylate synthetase 2 variant 1 | 0.784 | GGAAGGTCAATTACAACTTTGAAGATGAGACCGTGAG GAAGTTTCTACTGAGCCAGTTGC (SEQ ID NO: 638) |
| 18175 | A_23_P35412 | IFIT4 | IFI protein with tetratricopeptide repeats 4 | 0.779 | ATTCGAATAAAGCTCTTGAGAAGGGACTGAATCCTCTG AATGCATACTCCGATCTCGCTG (SEQ ID NO: 639) |
| 18624 | A_23_P38346 | LGP2 | likely ortholog of mouse D11Igp2 | 0.775 | CATACTGTACTCAGAATCACGACATTCCTTCCCTACCA AGGCCACTTGTATTTTTTGAGG (SEQ ID NO 640) |
| 28011 | A_23_P250353 | HERC6 | hect domain and RLD 6 | 0.764 | TTTCACCTCAGTCTGTAATTGGCTGTGAGTCAGTCTTTC ATTTACATAGGGTGTAACCATC (SEQ ID NO: 641) |
| 24371 | A_23_P37983 | MT1B | metallothionein 1B | 0.761 | TCATCAGAGAAGTGCCGCTGCTGTGCCTGATGTTGGG AGAGCCCTGCTCCCAGACATAAA (SEQ ID NO: 642) |
| 18869 | A_24_P378019 | IRF7 | interferon regulatory factor variant a | 0.760 | CAACAGCCTCTATGACGACATCGAGTGCTTCCTTATGG AGCTGGAGCAGCCCGCCTAGAA (SEQ ID NO: 643) |
| 11320 | A_24_P125096 | MT1X | metallothionein 1X | 0.759 | CCAGGGCTGCATGTGCAAAGGGACGTCAGACAAGTGC AGCTGCTGTGCCTGATGCCAGGA (SEQ ID NO: 644) |
| 20855 | A_23_P152782 | IFI35 | interferon-induced protein 35 | 0.758 | CGGAAGTGCCTAAGTCTTTAGTTTCCAATTTGCGGATC CACTGCCCTCTGCTTGCGGGCT (SEQ ID NO: 645) |
| 33108 | A_32_P15128 | OAS2 | 2'-5'-oligoadenylate synthetase 2 variant 1 | 0.755 | TAAAGAGCTTTGCITGAAGACACAGAGGATTCCTTTT TTAGACTGGAAGGAAAAAGGAG (SEQ ID NO: 646) |
| 40042 | A_24_P30194 | IFIT5 | IFI protein with tetratricopeptide repeats 5 | 0.741 | AATGTGGCTTCTCTAATGTAGTTTCTTTGATTACCGACT ACACAATTATGTACCATCACA (SEQ ID NO: 647) |
| 7065 | A_23_P132388 | SCO2 | SCO cytochrome oxidase deficient homolog 2 | 0.738 | AGTCACAGTTACCGCGTGTACTACAATGCCGGCCCCA AGGATGAGGACCAGGACTACATC (SEQ ID NO: 648) |
| 4620 | A_23_P63668 | IFIT5 | IFI protein with tetratricopeptide repeats 5 | 0.731 | AAGATAGATCCAGAAAATGCAGAATTCCTGACTGCTCT CTGTGAGCTCCGACTTTCCATT (SEQ ID NO: 649) |
| 32013 | A_23_P38894 | FLJ11286 | hypothetical protein FLJ11286 | 0.727 | ATCCCCCCACCAGGATAAAAGTCCTGACCTTTGTTCTC TTGACGGAATAAAAGCTTGCTT (SEQ ID NO: 650) |
| 41755 | A_23_P29773 | LAMP3 | lysosomal-associated membrane protein 3 | 0.726 | ACCATGTTGACTTTCCTCATGTGTTTCCTTATGACTCAG TAAGTTGGCAAGGTCCTGACT (SEQ ID NO: 651) |
| 3171 | A_23_P64343 | TIMM10 | translocase of inner mitochondrial membrane 10 homolog | 0.725 | ATGAGCGGATGGGCAAAAAGTTGACAGAGTTGTCTAT GCAGGATGAAGAGCTGATGAAGA (SEQ ID NO: 652) |
| 35302 | A_23_P39465 | BST2 | bone marrow stromal cell antigen 2 | 0.722 | TGCTCGGCTTTTCGCTTGAACATTCCCTTGATCTCATC AGTTCTGAGCGGGTCATGGGGC (SEQ ID NO 653) |
| 28820 | A_23P_370682 | MGC20410 | hypothetical protein BC012330 | 0.722 | TGGAAGTTCAGTTTTGGTGTCTGCTTCAAGAGGGGGT TTTACACTCTGATTCCAGGACAA (SEQ ID NO: 654) |
| 16269 | A_23_P358944 | PML | promyelocytic leukemia variant 8 | 0.718 | GGACTGGCTATCCCAAGACCTGGCAGATGTGGCTGCT CAATAAACACTTGTTGAACCATC (SEQ ID NO: 655) |
| 13700 | A_23_P142750 | PRKR | protein kinase, IFI double-stranded RNA dependent | 0.717 | AGAACAGATTTCTTCGCAAGACTATGGAAAGGAAGTG GACCTCTACGCTTTGGGGCTAAT (SEQ ID NO: 656) |

TABLE 2-continued

| Feature | Agilent Probe | Gene | Description | Correlation-IFI27 | Sequence |
|---|---|---|---|---|---|
| 26554 | A_23_P259141 | DLM-1 | FLJ46548 fis, THYMU3038347, highly similar to DLM-1 | 0.716 | ATGTTTGAGTCCCAACAAAATTCATATCAAAACATAATC CCAACTGGGTGCAGTGGCTCA (SEQ ID NO: 657) |
| 7372 | A_32_P54553 | USP41 | ubiquitin specific protease 41 | 0.714 | ATATGATCCGGATGAAGGACTCCTTGATTTGCCTTGAC TGTGCCATGGAGAGTAGCAGAA (SEQ ID NO: 658) |
| 22061 | A_24_P334361 | FLJ20035 | hypothetical protein FLJ20035 | 0.712 | GTGAAAATGAAGACGACAACGTTGTCTTAGCCTTTGAA CAACTGAGTACAACTTTTTGGG (SEQ ID NO: 659) |
| 23517 | A_23_P139123 | SERPING1 | serine proteinase inhibitor, clade G member 1 | 0.710 | GACAACATTTGATCCCAAGAAAACCAGAATGGAACCCT TTCACTTCAAAAACTCAGTTAT (SEQ ID NO: 660) |
| 19683 | A_32_P452655 | LGALS9 | lectin, galactoside-binding, soluble, 9 variant | 0.708 | TGACCAGAGTGTTCTCTTCAGGGGACTGGCTCCTTTC CCAGTGTCCTTAAAATAAAGAAA (SEQ ID NO: 661) |
| 28706 | A_23_P218879 | TREX1 | three prime repair exonuclease 1 variant 4 | 0.707 | CAGCCTTGGAGAGAGCAGGGGTACCAAGGATCTTCCT CCAGTGAAGGACCCTGGAGCCCT (SEQ ID NO: 662) |
| 41524 | A_24_P332926 | SFRS14 | splicing factor, arginine/serine-rich 14 | 0.701 | GTGTGTCTCATCCAGGAGCCAAAAGTCCATGAACCAG TTCGAATTGCCTATGACAGGCCT (SEQ ID NO: 663) |
| 3797 | A_23_P20814 | DDX58 | DEAD (Asp-Glu-Ala-Asp) box polypeptide 58 | 0.697 | TGAGTGGGAAGAAACAAACATAGTGGGTATAATCAT GATCGCTTGTACCCCTGTGAAA (SEQ ID NO: 664) |
| 40576 | A_32_P134290 | ZCCHC2 | zinc finger, CCHC domain containing 2 | 0.697 | AATTAATTGTTAAGCTGCAGTTGAGTTGTTCAAGTGAG AGTTTTGATAAGCCACTTATGG (SEQ ID NO: 665) |
| 8270 | A_23P_145874 | C7orf6 | chromosome 7 ORf 6 | 0.695 | CATTGATATCCACTGGTCACATCATAACTGTCTATAGG GCAATAAAATCTGTGTTAAACT (SEQ ID NO: 666) |
| 10995 | A_23_P304054 | LOC400653 | hypothetical LOC400653 | 0.694 | AGTTCTTTACGCTTTCTGATTGAACTGATTTGAAGTTCT TATTTCGTGTGTTGGGGAACA (SEQ ID NO: 667) |
| 23236 | A_23_P68155 | MDA5 | melanoma differentiation associated protein-5 | 0.693 | CTACGTCCTGGTTGCTCACAGTGGTTCAGGAGTTATC GAACGTGAGACAGTTAATGATTT (SEQ ID NO: 668) |
| 40635 | A_23_P206441 | FANCA | Fanconi anemia, complementation group A | 0.685 | ATGAGGGCCTCGTTTATTAAGATCTTTAAACTGCTTTAT ACACTGTCACGTGGCTTCATC (SEQ ID NO: 669) |
| 43149 | A_23_P17481 | SIGLEC1 | lectin-like adhesion molecule | 0.681 | GGAAGAGGTGATCACTCTCACACTAAGACTGAGGAAA TAAAAAAGGTTTGGTGTTTTCCT (SEQ ID NO: 670) |
| 1523 | A_24_P561165 | SERPING1 | serine proteinase inhibitor, clade G member 1 | 0.678 | CGATTTTTCTTCATGACCTTAACCTGTGTGGGCTAACA GAGGACCCAGATCTTACAGGTT (SEQ ID NO: 671) |
| 34907 | A_23_P111804 | ZC3HDC1 | zinc finger CCCH type domain containing 1 | 0.677 | TGATTCGGTTTCTCAGAGTCTCATGGCATCATAGTTTTT CCAGAATGACACAGTAGCCAC (SEQ ID NO: 672) |
| 37561 | A_24_P304071 | IFIT2 | IFI protein with tetratricopeptide repeats 2 | 0.673 | TCTAAGAGAGAATGGAATGTATGGGAAAAGAAAGTTAT TGGAACTAATAGGACACGCTGT (SEQ ID NO: 673) |
| 37323 | A_24_P118892 | IRF7 | interferon regulatory factor 7 variant a | 0.669 | TCAGCCGGGAGCTGTGCTGGCGAGAAGGCCCAGGCA CGGACCAGACTGAGGCAGAGGCCC (SEQ ID NO: 674) |
| 1157 | A_23_P163782 | MT1H | metallothionein 1H | 0.668 | AAGTGCAAATGCACCTCCTGCAAGAAGAGCTGCTGCT CCTGTTGCCCCCTGGGCTGTGCC (SEQ ID NO: 675) |
| 21378 | A_23_P97064 | FBXO6 | F-box protein 6 | 0.665 | CAACAGTGGAACAATGCCACATGGACAGAGGTCTCCT ACACCTTCTCAGACTACCCCCGG (SEQ ID NO: 676) |
| 37891 | A_23_P18604 | LAP3 | leucine aminopeptidase 3 | 0.660 | TTCGTTTCAGTCAAGACAATGCTTAGTTCAGATACTCA AAAATGTCTTCACTCTGTCTTA (SEQ ID NO: 677) |
| 1986 | A_23_P69109 | PLSCR1 | phospholipid scramblase 1 | 0.660 | GTTTAGCTCTTACACTCTATCCTTCCTAGAAAATGGTAA TTGAGATTACTCAGATATTAA (SEQ ID NO: 678) |
| 6936 | A_23_P203498 | TRIM22 | tripartite motif-containing 22 | 0.652 | GTACATAAGAATCTATCACTAAGTAATGTATCCTTCAGA ATGTGTTGGTTTACCAGTGAC (SEQ ID NO: 679) |

TABLE 2-continued

| Feature | Agilent Probe | Gene | Description | Correlation-IFI27 | Sequence |
|---|---|---|---|---|---|
| 17172 | A_23_P120435 | WFDC3 | WAP four-disulfide core domain 3 variant 4 | 0.652 | ACCAGTCCTGCCCCCAAAACTGACCATGAACCCCAAC TGGACTGTGAGGTCTGATTCCGA (SEQ ID NO: 680) |
| 7518 | A_23_P21838 | CNP | 2',3'-cyclic nucleotide 3' phosphodiesterase | 0.651 | TAACAGGGCCTTGCTAATCGGGTTGTCACTCAAC GTGCTTTGGATTTAAGTTACTA (SEQ ID NO: 681) |
| 36793 | A_32_P156746 | STAT2 | signal transducer and activator of transcription 2 | 0.651 | GAGATTGTCCAGAGTCCTATGACAGACCTTCAAGGTTT TAAGTTCCACAGACTTGGACTT (SEQ ID NO: 682) |
| 22443 | A_23_P209995 | IL1RN | interleukin 1 receptor antagonist variant 4 | 0.646 | TATTCCTGCATTTGTGAAATGATGGTGAAAGTAAGTGG TAGCTTTTCCCTTCTTTTTCTT (SEQ ID NO: 683) |
| 23150 | A_23_P161125 | MOV10 | Moloney leukemia virus 10, homolog | 0.642 | TCCCCGTACCGGAAACAGGTGGAGAAAATCCGTTACT GCATCACCAAACTTGACAGGGAG (SEQ ID NO: 684) |
| 17566 | A_24_P395966 | ZBP1 | Z-DNA binding protein 1 | 0.641 | GTCGTCGTCCCGCAGACACACAATCCAGAAGTCACTT TCCTCGAGACATTGGTCAGCCCA (SEQ ID NO: 685) |
| 8222 | A_23_P250358 | HERC6 | hect domain and RLD 6 | 0.639 | CCTTACACCTAAATAATCAAGAGATTAATGAATAGTG GTTAGAAGTAGTTGAGGGAGAG (SEQ ID NO: 686) |
| 41451 | A_24_P172481 | TRIM22 | tripartite motif-containing 22 | 0.639 | TGCCCCTTAAAAGATTGAAGAAAGAGAAACTTGTCAAC TCATATCCACGTTATCTAGCAA (SEQ ID NO: 687) |
| 18011 | A_24_P7040 | IFITM3 | interferon induced transmembrane protein | 0.636 | CGCCAAGCATGTGAACATCTGGGCCCTGACTGTGGGC ATCCTCATGACCATTCTGCTCAT (SEQ ID NO: 688) |
| 15599 | A_24_P117410 | LOC113730 | hypothetical protein BC009980 | 0.635 | GCTCAGGGAAGGGGCTGGGATCGGAACTTCCTGCTCT TGTTTCTGGACAACTTTCCCCTT (SEQ ID NO: 689) |
| 2072 | A_23_P75741 | UBE2L6 | ubiquitin-conjugating enzyme E2L 6 variant 2 | 0.628 | AATAGACCGAATATCAGGGAGCCCCTGCGGATGGACC TCGCTGACCTGCTGACACAGAAT (SEQ ID NO: 690) |
| 37424 | A_23_P71148 | BLVRA | biliverdin reductase A | 0.627 | AGGTGATGTAGCACTTCCAAGATGGCACCAGCATTTG GTTCTTCTCAAGAGTTGACCATT (SEQ ID NO: 691) |
| 28056 | A_24_P45446 | GBP4 | guanylate binding protein 4 | 0.627 | AGGGGACACAGGCTTCTTAAAACAACCCGGCTTCCTC ACCCTATGTCCTTTATTTACAAA (SEQ ID NO: 692) |
| 44249 | A_23_P101025 | LGALS9 | lectin, galactoside-binding, soluble, 9 variant | 0.622 | CCCAGCCTTTCCAACCGTGCCTGGGATCTGGGCTTTA ATGCAGAGGCCATGTCCTTATCT (SEQ ID NO: 693) |
| 24243 | A_23_P91802 | ECGF1 | endothelial cell growth factor 1 | 0.619 | CCGCCTGGGGTGGGCGGAGAGCTGCTGGTCGACGT GGGTCAGAGGCTGCGCCGTGGGAC (SEQ ID NO: 694) |
| 3378 | A_24_P394246 | SCOTIN | scotin | 0.618 | TTCTCTTCCTCACCTGAAATTATGCTTCCTAAAATCTCA AGCCAAACTCAAAGAATGGGG (SEQ ID NO: 695) |
| 17300 | A_23_P428248 | STI2 | TPR domain containing STI2 | 0.617 | GCCATCAACCTACTGAAGTTGTGTGGAGGGATGGAAA GTGGGTCAGTGGAGAAGGGATTC (SEQ ID NO: 696) |
| 9338 | A_23_P24004 | IFIT2 | IFI protein with tetratricopeptide repeats 2 | 0.615 | AGCTGACCCAGCATCAGCCACACTCTGGGTTGGAAAA TGTTTGCCTGTTGGAATTAATTT (SEQ ID NO: 697) |
| 28969 | A_23_P42353 | ETV7 | ets variant gene 7 | 0.611 | TGAGCCCTACATCAAGTGGGAAGACAAGGACGCCAAG ATCTTCCGAGTTGTGGATCCAAA (SEQ ID NO: 698) |
| 18692 | A_23_P70660 | C6orf37 | chromosome 6 ORF 37 | 0.610 | GCTATCCGGGTGTTAGCTGACCAAAATGTCATTCCTAA TGTGGCTAATGTCACTTGCTAT (SEQ ID NO: 699) |
| 13508 | A_23_P212475 | SCOTIN | scotin | 0.610 | ATCTGTTGTGTTTCTGAGTCTAGGGTCTGTACATTGT TTATAATAAATGCAATCGTTTG (SEQ ID NO: 700) |
| 43198 | A_23_P216655 | TRIM14 | tripartite motif-containing 14 variant 1 | 0.609 | ATAGCCAGAAAGCGGCAGTTTCAGTCCATATCAATTGT GTGACCAGGGCTAGTCACTTTT (SEQ ID NO: 701) |
| 8567 | A_23_P72737 | IFITM1 | interferon induced transmembrane protein 1 | 0.594 | ATACAGCAGTTTATACCCACACACCTGTCTACAGTGTC ATTCAATAAAGTGCACGTGCTT (SEQ ID NO: 702) |

TABLE 2-continued

| Feature | Agilent Probe | Gene | Description | Correlation-IFI27 | Sequence |
|---|---|---|---|---|---|
| 24307 | A_24_P161018 | PARP14 | poly (ADP-ribose) polymerase family, member 14 | 0.593 | AAATATTPAGATTTCCCTGGACCATAAGAGACCTTTGAT TAAGGTTTTGGGAATTAGGAG (SEQ ID NO: 703) |
| 15588 | A_23_P140207 | PCK2 | phosphoenolpyruvate carboxykinase 2 | 0.589 | AGGACATAGCACCCTCATCTGGGAATAGGGAAGGCAC CTTGCAGAAAATATGAGCAATTT (SEQ ID NO: 704) |
| 31781 | A_32_P38003 | EIF2AK2 | downstream from gene | 0.589 | AAACTGTGAGGCAAATAAAATGCTTCTCAAATCTGTGT GGCTCTTATGGGGTTAATTTGA (SEQ ID NO: 705) |
| 27401 | A_23_P206441 | FANCA | Fanconi anemia, complementation group A (FANCA) 5503 | 0.587 | ATGAGGGCCTCGTTTATTAAGATCTTTAAACTGCTTTAT ACACTGTCACGTGGCTTCATC (SEQ ID NO: 706) |
| 39922 | A_23_P400378 | GPBAR1 | G protein-coupled bile acid receptor 1 | 0.556 | TGTCGACCTGGACTTGAACTAAAGGAAGGGCCTCTGC TGACTCCTACCAGAGCATCCGTC (SEQ ID NO: 707) |
| 4393 | A_32_P107372 | LOC400760 | similar to Interferon-induced guanylate-binding protein 1 | 0.585 | GGTACTGAGCAGAGTCTTAGGTAAAAGTCTTGGGAAA TATTTGGGCATTGGTCTGGCCAA (SEQ ID NO: 708) |
| 41600 | A_23_P206441 | FANCA | Fanconi anemia, complementation group A | 0.580 | ATGAGGGCCTCGTTTATTAAGATCTTTAAACTGCTTTAT ACACTGTCACGTGGCTTCATC (SEQ ID NO: 709) |
| 24950 | A_23_P121011 | AXUD1 | AXIN1 up-regulated 1 | 0.580 | GCGTGATGTTCCTTAGCCCAAAGACGGTGAGACAGGG CTGAAATCAGGTGGCTTCTGCCA (SEQ ID NO: 710) |
| 37768 | A_23_P206441 | FANCA | Fanconi anemia, complementation group A | 0.577 | ATGAGGGCCTCGTTTATTAAGATCTTTAAACTGCTTTAT ACACTGTCACGTGGCTTCATC (SEQ ID NO: 711) |
| 26191 | A_24_P419286 | DNAH3 | dynein, axonemal, heavy polypeptide 3 | 0.576 | CCCAGAAGATCGTTGCGACCTACCGCCTGTGCTCGGA ACAACTGTCCTCTCAGCATCATT (SEQ ID NO: 712) |
| 10783 | A_23_P206441 | FANCA | Fanconi anemia, complementation group A | 0.576 | ATGAGGGCCTCGTTTATTAAGATCTTTAAACTGCTTTAT ACACTGTCACGTGGCTTCATC (SEQ ID NO: 713) |
| 24951 | A_23_P15174 | MT1F | metallothionein 1F | 0.573 | TGCCAGGACAACCTTTCTCCCAGATGTAAACAGAGAG ACATGTACAAACCTGGATTTTTT (SEQ ID NO: 714) |
| 30864 | A_24_P148717 | CCR1 | chemokine (C-C motif) receptor 1 | 0.569 | CTTTTCAAGTTGGGTGATATGTTGGTAGATTCTAATGG CTTTATIGCAGCGATTAATAAC (SEQ ID NO: 715) |
| 38267 | A_23_P106226 | C14orf123 | chromosome 14 ORF 123 | 0.567 | CTGAGTGGGTATCCTGATAAATCTGGGCTTGTCTTCCT AATGCTACCTTTGTTGGTCCTT (SEQ ID NO: 716) |
| 40688 | A_24_P274270 | STAT1 | signal transducer and activator of transcription 1 variant beta | 0.567 | TTGAACCCTACACGAAGAAAGAACTTTCTGCTGTTACT TTCCCTGACATCATTCGCAATT (SEQ ID NO: 717) |
| 13093 | A_23_P206441 | FANCA | Fanconi anemia, complementation group A | 0.565 | ATGAGGGCCTCGTTTATTAAGATCTTTAAACTGCTTTAT ACACTGTCACGTGGCTTCATC (SEQ ID NO: 718) |
| 30444 | A_24_P344711 | AGPAT3 | 1-acylglycerol-3-phosphate O-acyltransferase 3 | 0.565 | TCCCATAGAAGTTCCCTCCCTTTGAAATTAATATATAAT GTATAAATTCTGCACTGAGCC (SEQ ID NO: 719) |
| 42135 | A_23_P125624 | ACATE2 | ortholog of acyl-Coenzyme A thioesterase 2, mitochondrial | 0.565 | TGAAGACCTGATCGAGTGTATTGATTTAGTATTGCTT CGTGTCCTGCACACAGGAGGAG (SEQ ID NO: 720) |
| 32604 | A_24_P941912 | BBAP | rhysin 2 | 0.564 | TTTATAATAACGGTAGCCCACATTGTAGTAGTTTTCAG CTCTTTACTAAGTCCCACCAA (SEQ ID NO: 721) |
| 31047 | A_24_P207139 | PML | promyelocytic leukemia variant 1 | 0.564 | ACAGTGAATTTGATGCATTTAAAATAAGATTCTGATGC CAGACTGTTAAAACAGGCGCT (SEQ ID NO: 722) |
| 30304 | A_23_P65174 | PHF11 | PHD finger protein 11 | 0.564 | TATGAAGAAATCGGGAGTGCACTTTTTGACTGTAGATT GTTCGAAGACACATTTGTAAAT (SEQ ID NO: 723) |
| 9201 | A_23_P355244 | FLJ20073 | FLJ20073 protein (FLJ20073) 6853 | 0.564 | TCACTGGAGGAAGATTTTCCCTTGCTTCTGCATAAAAT TTTAACTCCATAACTTATAAGC (SEQ ID NO: 724) |
| 41835 | A_23_P69383 | BAL | B aggressive lymphoma gene | 0.561 | TTTTTAGTGGCATGCAGGCTATACCTCAGTATTTGTGG ACATGCACCCAGGAATATGTAC (SEQ ID NO: 725) |

TABLE 2-continued

| Feature | Agilent Probe | Gene | Description | Correlation-IFI27 | Sequence |
|---|---|---|---|---|---|
| 13417 | A_23_P306148 | PML | promyelocytic leukemia variant 11 | 0.560 | AGGCAGAGGAACGCGTTGTGGTGATCAGCAGCTCGG AAGACTCAGATGCCGAAAACTCGT (SEQ ID NO: 726) |
| 37690 | A_23_P123672 | TDRD7 | tudor domain containing 7 | 0.560 | AAATCTTAACTCTGCTACATGGCTCTGACTGCTGTGGG GGATTGAAAAGAATATGCTTAT (SEQ ID NO: 727) |
| 22106 | A_23_P6263 | LOC442209 | FLJ16669 fis, clone THYMU3000306 | 0.555 | TCTGGGTCAAATTCTTCTTTTGTATGTCCAGTCTCCTG CACAGCACCTGCAGCATTGTAA (SEQ ID NO: 728) |
| 33663 | A_23_P12044 | FLJ10199 | hypothetical protein FLJ10199 | 0.554 | GCCTGATGAACGTAGGCACGTGATGCGTAATAGTCTT CAATGGTACACTTAACTAGTCTC (SEQ ID NO: 729) |
| 18942 | A_23_P206441 | FANCA | Fanconi anemia, complementation group A | 0.549 | ATGAGGGCCTCGTTTATTAAGATCTTTAAACTGCTTTAT ACACTGTCACGTGGCTTCATC (SEQ ID NO: 730) |
| 22341 | A_23_P423331 | NTNG2 | netrin G2 | 0.549 | AACTATTTTGTTTGTATTCACTGTCCCCTGCAAGGGG GACGGGCGGGAGCACTGGTCA (SEQ ID NO: 731) |
| 39663 | A_24_P868905 | LOC391020 | similar to IFI transmembrane protein 3 | 0.544 | ATCCTCATGAGCATTCTGCTCATCTTCATCCCAGTGTT GATCTTTCAAGTCTATCAATAG (SEQ ID NO: 732) |
| 22603 | A_32_P92415 | PARP14 | poly (ADP-ribose) polymerase family, member 14 | 0.543 | GAAGGGTTTCACAATGAAGATGTGTAGCAGGCGTTAT CCCATTGTTATCACTGGGCAGAA (SEQ ID NO: 733) |
| 12663 | A_23_P154488 | PNPT1 | polyribonucleotide nucleotidyltransferase 1 | 0.543 | AAATTCAGGTGAAATACTTTGGACGTGACCCAGCCGAT GGAAGAATGAGGCTTTCTCGAA (SEQ ID NO: 734) |
| 38515 | A_24_P15702 | EST | highly conserved region | 0.542 | CCAATGCAGACAAACCACCCCTTTTTGTTGGGAAAGG AATTACCTTTGACAGTGGTGGTA (SEQ ID NO: 735) |
| 37436 | A_32_P53603 | EST | space dust | 0.542 | CTTTTATGTGGTTCCTGCCCCTGAGAATAAAGAAGCCC CAGCGTGGCTGCGAGGCACCAT (SEQ ID NO: 736) |
| 19668 | A_23_P116557 | LGALS9 | lectin, galactoside-binding, soluble, 9 variant | 0.542 | AGTGTGGATCTTGTGTGAAGCTCACTGCCTCAAGGTG GCCGTGGATGGTCAGCACCTGTT (SEQ ID NO: 737) |
| 31202 | A_23_P87545 | IFITM3 | interferon induced transmembrane protein 3 | 0.541 | GGGCCCTGATTCTGGGCATCCTCATGACCATTCTGCT CATCGTCATCCCAGTGCTGATCT (SEQ ID NO: 738) |
| 39745 | A_23_P55564 | ZCCHC2 | zinc finger, CCHC domain containing 2 | 0.540 | GACATCTGACGTAGAGACCTGCGAATGGATCTGAGAT GAGTAGTAACGCAGGTTGTCCGG (SEQ ID NO: 739) |
| 31706 | A_24_P350124 | KIAA1618 | KIAA1618 | 0.540 | GCAGATTCTGAGAACAATAACTCCACAATGGCGTCGG CCTCGGAGGGTGAAATGGAGTGT (SEQ ID NO: 740) |
| 31855 | A_24_P344087 | REC8L1 | REC8-like 1 | 0.539 | TCCTGGTGCTCTCAGCGCAACAGATTCTTCACGTGAAA CAAGAAAAGCCATATGGTCGCC (SEQ ID NO: 741) |
| 27231 | A_23_P75811 | SLC3A2 | solute carrier family 3 member 2 | 0.538 | ATCCTGAGCCTACTCGAATCCAACAAAGACTTGCTGTT GACTAGCTCATACCTGTCTGAT (SEQ ID NO: 742) |
| 35807 | A_23_P138856 | DRAP1 | DR1-associated protein 1 (negative cofactor 2 alpha) | 0.537 | CTTCTGCCCCCAGACCATAGCCCCTTTTAGTTGGTTT TAGTTGCTCTGGGGGAGGAGA (SEQ ID NO: 743) |
| 14385 | A_24_P16124 | IFITM4P | IFI transmembrane protein 4 pseudogene, chromosome 6 | 0.536 | GGGATTCATAGCATTCACCTACTCCCTGAAGTCTAGG GACAGGAAGATGGTTGGAGACCT (SEQ ID NO: 744) |
| 14104 | A_23_P62890 | GBP1 | guanylate binding protein 1, interferon-inducible | 0.536 | CAAAGATGCATTTACCTCTGTATCAACTCAGGAAATCT CATAAGCTGGTACCACTCAGGA (SEQ ID NO: 745) |
| 21955 | A_24_P197964 | TRIM14 | tripartite motif-containing 14 variant 4 | 0.536 | AAATTGCTTGCAGATATTTTTAAATGACAGCAATTTTCT AATATTTGGTTTAATAAAATG (SEQ ID NO: 746) |
| 23148 | A_23_P153372 | HSH2D | hematopoietic SH2 domain containing | 0.536 | GAATCCGAGCCCTTTTCCCATATCATCTGTTTGTTCTG TTGTCTAAAAGCACACTGCAAG (SEQ ID NO: 747) |
| 11424 | A_23_P206441 | FANCA | Fanconi anemia, complementation group A | 0.532 | ATGAGGGCCTCGTTTATTAAGATCTTTAAACTGCTTTAT ACACTGTCACGTGGCTTCATC (SEQ ID NO: 748) |

TABLE 2-continued

| Feature | Agilent Probe | Gene | Description | Correlation-IFI27 | Sequence |
|---|---|---|---|---|---|
| 8658 | A_23_P202964 | PORIMIN | pro-oncosis receptor inducing membrane injury gene | 0.531 | TCTGAAGCAAAGAAAGGATCAAAATTTGATACTGGGAG CTTTGTTGGTGGTATTGTATTA (SEQ ID NO: 749) |
| 34298 | A_24_P259276 | LOC254359 | hypothetical protein LOC254359 | 0.531 | ACTCAGTAAGGAAGTCGGGTTGGACCTTAACATCTGC ATTGGACAACTCCACCCCTTCCT (SEQ ID NO: 750) |
| 26056 | A_23_P98167 | UNC93B1 | unc-93 homolog B1 | 0.531 | TCGCCGGCCTCAGTTTACCACGTCTGAGGTCGGGGG GACCCCCTCCGAGTCCGCGCTGT (SEQ ID NO: 751) |
| 43514 | A_32_P157846 | FLJ31401 | FLJ34941 fis, clone NT2RP7007480 | 0.529 | ACAGTTGTTTTGTCTTCAAGCCACTGACTTCTGGAATTT GCAGATTTTGCAATCCATGCA (SEQ ID NO 752) |
| 23132 | A_24_P50543 | LOC400368 | hypothetical gene supported by BC031266 | 0.527 | AAATCAGCCTCCATCAGTATCACTGCAGTTATATATGA TGTATGCCTTATTGCTCAAGAC (SEQ ID NO: 753) |
| 22246 | A_23_P214080 | EGR1 | early growth response 1 | 0.526 | AAACAAAGTGACTGTTTGGCTTATAAACACATTGAATG CGCTTTATTGCCCATGGGATAT (SEQ ID NO: 754) |
| 3490 | A_23_P206441 | FANCA | Fanconi anemia, complementation group A | 0.523 | ATGAGGGCCTCGTTTATTAAGATCTTTAAACTGCTTTA ACACTGTCACGTGGCTTCATC (SEQ ID NO: 755) |
| 2659 | A_23_P50108 | KNTC2 | kinetochore associated 2 | 0.520 | AAAGTGGGAAATAACTTGCAACGTCTGTTAGAGATGGT TGCTACACATGTTGGGTCTGTA (SEQ ID NO: 756) |
| 21328 | A_24_P382319 | CEACAM1 | carcinoembryonic antigen-related cell adhesion molecule 1 | 0.519 | CCATGCTGTGCTGTGTTATTTAATTTTTCCTGGCTAAGA TCATGTCTGAATTATGTATGA (SEQ ID NO: 757) |
| 33919 | A_23_P255104 | LHFPL2 | lipoma HMGIC fusion partner-like 2 | 0.518 | CCAAAAGAGTTAAAGGCACGACTGGGATTTCTTCTGA GACTGTGGTGAAACTCCTTCCAA (SEQ ID NO: 758) |
| 27245 | A_24_P43588 | MAD2L1BP | MAD2L1 binding protein variant 1 | 0.518 | CCATAAACTGACTGTGACCCTGTCATGTGGCAGACCTT CCATCCGAACCACGGCTTGGGA (SEQ ID NO: 759) |
| 33581 | A_23_P502520 | IL4I1 | interleukin 4 induced 1 variant 2 | 0.517 | CCAGTTATCTCTCCAAAACACGACCCACACGAGGACC TCGCATTAAAGTATTTTCGGAAA (SEQ ID NO: 760) |
| 8566 | A_24_P54879 | SCARB2 | scavenger receptor class B, member 2 | 0.516 | AGTGATGTACCTCAATGAGAGTGTTCACATTGATAAAG AGACGGCGAGTCGACTGAAGTC (SEQ ID NO: 761) |
| 16203 | A_24_P175188 | FLJ20073 | FLJ20073 protein | 0.515 | TGCCAATGTACTGGCAGATTAACATACAACCTATGTTT TGAACAAAACAACCAGCGATA (SEQ ID NO: 762) |
| 11310 | A_23_P34915 | ATF3 | activating transcription factor 3 | 0.513 | GATGTCAATAGCATTGTTTTGTCATGTAGCTGTTTTAA GAAATCTGGCCCAGGGTGTTT (SEQ ID NO: 763) |
| 26089 | A_23_P75769 | MS4A4A | membrane-spanning 4-domains, subfamily A, member 4 variant 2 | 0.511 | CACCAAAAGATCAACAGACAAATGCTCCAGAAATCTAT GCTGACTGTGACACAAGAGCCT (SEQ ID NO: 764) |
| 7745 | A_23_P166459 | LGALS1 | lectin, galactoside-binding, soluble, 1 | 0.511 | CCAGATGGATACGAATTCAAGTTCCCCAACCGCCTCA ACCTGGAGGCCATCAACTACATG SEQ ID NO: 765) |
| 12417 | A_32_P71710 | IL1RN | interleukin 1 receptor antagonist variant 4 | 0.510 | AAGATTTTATTGTAAAACAGAGCTGAAGTCACAGGAAG TAGGGAACTTTGCACCCAACAT (SEQ ID NO: 766) |
| 35164 | A_23_P376488 | TNF | tumor necrosis factor, superfamily member 2 | 0.509 | GGGGTATCCTGGGGGACGCAATGTAGGAGCTGCCTT GGCTCAGACATGTTTTCCGTGAAA (SEQ ID NO: 767) |
| 37407 | A_23_P135123 | FRMD3 | FERM domain containing 3 | 0.509 | CTGGTCTGAAGGGTCACGGGCTGTCAACAGGTGTTC CTTACTCATAATTGATTATTCAA (SEQ ID NO: 768) |
| 32481 | A_23_P59005 | TAP1 | transporter 1, ATP-binding cassette, subfamily B | 0.507 | TCCAGGATGAGTTACTTGAAATTTGCCTTGAGTGTGTT ACCTCCTTTCCAAGCTCCTCGT (SEQ ID NO: 769) |
| 27197 | A_24_P254933 | ATXN2 | ataxin 2 | 0.506 | CCGACCATGTCCTGGTCCCTGTTCAACACCCACTTCAT GAATGCTGCCTGGGCTTCATAG (SEQ ID NO: 770) |
| 29912 | A_24_P326957 | WDR23 | WD repeat domain 23 variant 1 | 0.506 | TGGGTCTTTAGGGTAGGACAGGCTGTGGTATGAGAGG CAGGAGTCTCCACAAGGCTTCAT (SEQ ID NO: 771) |
| 26767 | A_23_P356526 | TRIM5 | tripartite motif-containing 5 variant delta | 0.506 | GAAGCCAGAAACTTTTCCAAAAAATCAAAGGAGAGTGT TTCGAGCTCCTGATCTGAAAGG (SEQ ID NO: 772) |

TABLE 2-continued

| Feature | Agilent Probe | Gene | Description | Correlation-IFI27 | Sequence |
|---|---|---|---|---|---|
| 41790 | A_23_P165636 | CAPG | capping protein (actin filament), gelsolin-like | 0.506 | CTGCTTGCTTGTCTGGCTGCCTGGTCAGTGCAGAGGT GCCCGCTGCAGATGTTCAATAAA (SEQ ID NO: 773) |
| 38573 | A_24_P127641 | LOC441109 | hypothetical gene supported by AL713721 | 0.503 | TATATCGTAGGTGGCTTTAATACGTGTTATTTGCTCATC TGTATTTCTTACTCTTTGCAC (SEQ ID NO: 774) |
| 40160 | A_23_P88234 | C14orf122 | chromosome 14 ORF 122 | 0.503 | GATAAGAACTTAGTGATGTGGAGGGACTGGGAAGAGT CACGGCAGATGGTGGGAGCTCTA (SEQ ID NO: 775) |
| 9098 | A_24_P383523 | SAMD4 | sterile alpha motif domain containing 4 | 0.501 | CCATCTTCAGGGTTGCACAGAATCCTCCAAGATACTTT GCAGCCTTTTTTCCCCCTGGTC (SEQ ID NO: 776) |
| 16598 | A_24_P242391 | MPZL1 | myelin protein zero-like 1 variant 2 | -0.501 | GTGTATGCGGATATCCGAAAGAATTAAGAGAATACGTA GAACATATCCTCAGCAAGAAAC (SEQ ID NO: 777) |
| 39617 | A_32_P109516 | LOC389089 | LOC389089 | -0.507 | TCCGTTTTTACAGCATTCTCGACCTGTGATTCTTGGTG GGGGAAACTAGTTATGTGGATA (SEQ ID NO: 778) |
| 36575 | A_23_P417282 | MGC18216 | hypothetical protein MGC 18216, clone IMAGE: 4156235 | -0.507 | AAATCAAACCAGAAGGCGGGATGGAATGGATGCACCG CAAATAATGCATTTTCTGAGTTT (SEQ ID NO: 779) |
| 34695 | A_23_P403284 | OTX1 | orthodenticle homolog 1 | -0.517 | TTAGTTGCTGTTGGTTGGTTGAACTGAACATATCTTGT CTTAGCACCCAGGAAACAGAAC (SEQ ID NO: 780) |
| 33205 | A_24_P467358 | EEF1G | eukaryotic translation elongation factor 1 gamma | -0.526 | CTGGATGCTTACTTGAAGACGAGGACTTTTCTGGTGG GCGAACGAGTGACATTGGCTGAC (SEQ ID NO: 781) |
| 25932 | A_24_P87763 | EEF2 | eukaryotic translation elongation factor 2 | -0.527 | CATGTTTGTGGTCAAGGCCTATCTGCCCGTCAACGAG TCCTTTGGCTTCACCGCTGACCT (SEQ ID NO: 782) |
| 14152 | A_23_P124252 | CAMK1D | calcium/calmodulin-dependent protein kinase ID | -0.528 | TCCTGTTTGCCAGGCGCTTTCTATACTTAATCCCATGT CATGCGACCCTAGGAC1TTTTT (SEQ ID NO: 783) |
| 35180 | A_24_P177653 | LOC340947 | similar to bA508N22.1 (HSPC025) | -0.528 | CATGAGTATTGATGAGAGCATTCACCTCCAGCGGTGG GATAAATACAGCAACAAGATGCT (SEQ ID NO: 784) |
| 38227 | A_23_P104318 | DDIT4 | DNA-damage-inducible transcript 4 | -0.529 | TCGTGGAGGTGGTTTGTGTATCTTACTGGTCTGAAGG GACCAAGTGTGTTTGTTGTTTGT (SEQ ID NO: 785) |
| 3684 | A_23_P57521 | EIF3S6IP | eukaryotic TIF 3, subunit 6 interacting protein | -0.529 | GAATTTCAGTCAGCCTCAGAGGTTGACTTCTACATTGA TAAGGACATGATCCACATCGCG (SEQ ID NO: 786) |
| 7635 | A_32_P172917 | LOC389832 | similar to chromosome 2 ORF 27 | -0.530 | AACTCAGCAGCAGCACTGCAGAATCTCCATGCCTGCA CCTGCCCAAGGATTTATTCATAG (SEQ ID NO: 787) |
| 39387 | A_32_P76399 | EIF3S6IP | eukaryotic TIF 3, subunit 6 interacting protein | -0.531 | AGGTTGACTTCTACATTGATAAGGACATGATCCACATC GCGGACACCAAGGTCTCCAGGC (SEQ ID NO: 788) |
| 24015 | A_23_P105138 | CAT | catalase | -0.532 | CTCATCACTGGATGAAGATTCTCCTGTGCTAGATGTGC AAATGCAAGCTAGTGGCTTCAA (SEQ ID NO: 789) |
| 15339 | A_24_P8371 | MYBBP1A | MYB binding protein (P160)1a | -0.536 | GCTGCTGATTGTGAATCTCAGAGTCTTAAGAGAGAAG CCAAATATATTCCTCTTGTAAAT (SEQ ID NO: 790) |
| 23589 | A_24_P757154 | ANP32A | acidic (leucine-rich) nuclear phosphoprotein 32 family, member A | -0.536 | ACACTTTGCATGCTGGGTCAGGGAAGATTGTGGAGAG AGGACAGTGCACCTGGTTTCCCC (SEQ ID NO: 791) |
| 19944 | A_24_P32151 | MGC45871 | hypothetical protein MGC45871 | -0.537 | AAGGAAGTAAGGTACACCTCCTTGGTCAAGTACGACT CCGAGAGGCACTTCATCGACGAC (SEQ ID NO: 792) |
| 11244 | A_24_P154037 | IRS2 | insulin receptor substrate 2 | -0.540 | GATGGTTCGTGTTCATACTGCAGCTTAAAACAAGCAAA ATACACAGATGATAATATGCTA (SEQ 10 NO:793) |
| 2728 | A_32_P128258 | SIGLECP3 | sialic acid binding Ig-like lectin, pseudogene 3 | -0.543 | ACTATGTGCCAGCATTTCCGTATGTGCAGAAGTTCATC AATAGATATAGACTCAAAGAGC (SEQ ID NO: 794) |

TABLE 2-continued

| Feature | Agilent Probe | Gene | Description | Correlation-IFI27 | Sequence |
|---|---|---|---|---|---|
| 43581 | A_24_P717462 | LOC651628 | similar to Elongation factor 1-gamma | -0.552 | TGGATGAATGTGAGCAGAGTACCTTTGTGTTGGATAAA TTTCAGTGCAGGTACTCTAAGG (SEQ ID NO: 795) |
| 24821 | A_24_P136641 | NDUFB6 | NADH dehydrogenase (ubiquinone) 1 beta subcomplex, 6 | -0.552 | GCTAAGGAGGAAATACCCAGACAAAATCTTTGGGACG AATGAAAATTTGTAACTCTTCTG (SEQ ID NO: 796) |
| 26400 | A_24_P588235 | EIF3S6IP | eukaryotic TIF 3, subunit 6 interacting protein | -0.561 | TGTGGATCATGTCCTTATCAATGTAGAAGTCAACCTCT GAGGCTGACTGAAATTCACCAT (SEQ ID NO: 797) |
| 40567 | A_23_P50081 | IMPA2 | inositol(myo)-1 (or 4)-monophosphatase 2 | -0.583 | TAGCTGTTTCTCTCTTTAATCTCACGTAGCCTTTTTCAG GTTAGTACGTGTTCTTCTGTC (SEQ ID NO: 798) |
| 10228 | A_24_P299318 | FAM101B | family with sequence similarity 101, member B | -0.598 | ACTTAATTTGAGCGAGTACCTTTTCATTTGACACTTTTC CTGTTTCTAACCTTAGGAAAC (SEQ ID NO: 799) |
| 6063 | A_24_P856176 | EST | highly conserved genomic region | -0.603 | CCAGGCTGTGCAGTGGGTGAACTTTGCTGATGATAGC CAGTACCAGGGTGTTCCCACCTT (SEQ ID NO: 800) |
| 14283 | A_32_P159289 | EST | EST defined by BE677474 | -0.630 | ACTGGCTTTTCTTTCATCTCTGGAGAGAGCTTGATTCG TCATCTTATTGCTTTGTCTGAA (SEQ ID NO: 801) |
| 19711 | A_24_P554408 | EFF1G | eukaryotic translation elongation factor 1 gamma | -0.636 | GGCAATGGCGTTGCTCTCAAACACACAGAATCCATCAT CACCCTCAAATGCTGGGACCTT (SEQ ID NO: 802) |

TABLE 3

| Patient | ABCoN ID | Sample | Date | SLEDAI | INFr | Days from 1st Sample | INFr Score |
|---|---|---|---|---|---|---|---|
| 1 | JHP004-01 | QF1 | Jul. 26, 2006 | 2 | LOW | 0 | -2.813 |
|  | JHP004-02 | F | Oct. 15, 2006 | 6 | LOW | 81 | -1.864 |
| 2 | JHP012-02 | QF1 | Sep. 10, 2006 | 0 | LOW | 0 | -2.21 |
|  | JHP012-04 | F | Nov. 5, 2006 | 8 | LOW | 56 | -2.202 |
| 3 | JHP017-02 | QF1 | Nov. 12, 2006 | 0 | LOW | 0 | -2.44 |
|  | JHP017-03 | F | Feb. 4, 2007 | 4 | LOW | 84 | -2.07 |
| 4 | JHP019-05 | QF5 | Mar. 8, 2007 | 0 | LOW | 0 | 0.255 |
|  | JHP019-06 | QF1 | May 16, 2007 | 2 | LOW | 69 | -0.219 |
|  | JHP019-07 | F | Aug. 26, 2007 | 8 | LOW | 171 | -0.124 |
| 5 | JHP021-02 | F | Oct. 18, 2006 | 4 | HIGH | 0 | 2.882 |
|  | JHP021-04 | QF1 | Dec. 19, 2006 | 0 | HIGH | 62 | 1.878 |
| 6 | JHP023-01 | QF4 | Aug. 30, 2006 | 0 | LOW | 0 | -1.684 |
|  | JHP023-02 | F | Nov. 15, 2006 | 4 | LOW | 77 | -1.404 |
|  | JHP023-03 | QF1 | Feb. 14, 2007 | 0 | LOW | 168 | -1.959 |
|  | JHP023-04 | F | May. 9, 2007 | 8 | LOW | 252 | -1.293 |
| 7 | JHP028-01 | QF5 | Sep. 13, 2006 | 4 | HIGH | 0 | 2.883 |
|  | JHP028-03 | QF1 | Mar. 18, 2007 | 4 | HIGH | 186 | 3.57 |
|  | JHP028-04 | F | Jun. 17, 2007 | 16 | HIGH | 277 | 3.784 |
|  | JHP028-05 | QF4 | Jul. 8, 2007 | 4 | HIGH | 298 | 4.696 |
|  | JHP028-06 | F | Sep. 30, 2007 | 16 | HIGH | 382 | 4.325 |
| 8 | JHP029-01 | QF1 | Sep. 13, 2006 | 4 | HIGH | 0 | 3.463 |
|  | JHP029-03 | F | Mar. 7, 2007 | 9 | HIGH | 175 | 3.867 |
| 9 | JHP030-03 | F | Feb. 4, 2007 | 12 | LOW | 0 | 1.392 |
|  | JHP030-09 | F | Jun. 10, 2007 | 6 | LOW | 126 | 0.815 |
| 10 | JHP033-02 | QF1 | Dec. 17, 2006 | 2 | LOW | 0 | 1.277 |
|  | JHP033-03 | F | Mar. 4, 2007 | 12 | HIGH | 77 | 2.276 |
| 11 | JHP039-02 | QF1 | Jan. 24, 2007 | 4 | HIGH | 0 | 4.707 |
|  | JHP039-03 | F | Mar. 28, 2007 | 12 | HIGH | 63 | 4.281 |
| 12 | JHP068-02 | QF5 | Apr. 8, 2007 | 0 | HIGH | 0 | 3.389 |
|  | JHP068-03 | QF1 | Jul. 1, 2007 | 0 | HIGH | 84 | 3.773 |
|  | JHP068-04 | F | Sep. 30, 2007 | 7 | HIGH | 175 | 3.992 |
| 13 | JHP072-01 | F | Jan. 14, 2007 | 10 | HIGH | 0 | 3.178 |
|  | JHP072-02 | QF5 | Apr. 15, 2007 | 0 | LOW | 91 | 0.155 |
|  | JHP072-03 | QF1 | Jul. 15, 2007 | 0 | HIGH | 182 | 1.794 |
|  | JHP072-04 | F | Oct. 7, 2007 | 8 | HIGH | 266 | 2.377 |
| 14 | JHP074-01 | QF1 | Jan. 14, 2007 | 3 | HIGH | 0 | 3.087 |
|  | JHP074-05 | F | Jan. 13, 2008 | 9 | HIGH | 364 | 4.226 |
| 15 | JHP075-02 | QF1 | Oct. 7, 2007 | 1 | LOW | 0 | -1.516 |
|  | JHP075-03 | F | Jan. 13, 2008 | 11 | LOW | 98 | -0.26 |

TABLE 3-continued

| Patient | ABCoN ID | Sample | Date | SLEDAI | INFr | Days from 1st Sample | INFr Score |
|---|---|---|---|---|---|---|---|
| 16 | JHP078-01 | QF5 | Jan. 14, 2007 | 4 | HIGH | 0 | 3.381 |
|  | JHP078-02 | QF1 | Jul. 22, 2007 | 4 | HIGH | 189 | 4.042 |
|  | JHP078-03 | F | Dec. 12, 2007 | 10 | HIGH | 332 | 4.03 |
| 17 | JHP079-02 | F | Feb. 28, 2007 | 4 | LOW | 0 | −2.02 |
|  | JHP079-03 | QF4 | Apr. 15, 2007 | 0 | LOW | 46 | −2.095 |
|  | JHP079-04 | F | Jul. 15, 2007 | 4 | LOW | 137 | −1.931 |
| 18 | JHP080-03 | QF1 | Jul. 18, 2007 | 4 | HIGH | 0 | 4.606 |
|  | JHP080-04 | F | Sep. 12, 2007 | 8 | HIGH | 56 | 4.35 |
| 19 | JHP081-01 | QF5 | Jan. 17, 2007 | 0 | LOW | 0 | −2.31 |
|  | JHP081-02 | QF1 | May 16, 2007 | 0 | LOW | 119 | 0.595 |
|  | JHP081-03 | F | Jul. 18, 2007 | 4 | LOW | 182 | −1.632 |
|  | JHP081-04 | QQ | Oct. 17, 2007 | 0 | LOW | 273 | −1.729 |
| 20 | JHP100-01 | QF1 | May 16, 2007 | 4 | HIGH | 0 | 3.896 |
|  | JHP100-03 | F | Mar. 26, 2008 | 12 | HIGH | 315 | 3.88 |
| 21 | JHP102-01 | QF5 | May 20, 2007 | 4 | HIGH | 0 | 3.993 |
|  | JHP102-02 | QF1 | Jun. 17, 2007 | 4 | HIGH | 28 | 4.048 |
|  | JHP102-03 | F | Sep. 23, 2007 | 8 | HIGH | 126 | 3.19 |
|  | JHP102-04 | QF4 | Dec. 23, 2007 | 0 | HIGH | 217 | 3.704 |
|  | JHP102-05 | F | Feb. 20, 2008 | 4 | HIGH | 276 | 3.054 |
| 22 | JHP104-01 | QF5 | Jun. 6, 2007 | 4 | HIGH | 0 | 4.508 |
|  | JHP104-02 | QF1 | Sep. 5, 2007 | 4 | HIGH | 91 | 3.259 |
|  | JHP104-04 | F | Feb. 27, 2008 | 12 | HIGH | 266 | 3.59 |
| 23 | JHP111-02 | QQ | Sep. 12, 2007 | 0 | HIGH | 0 | 3.585 |
|  | JHP111-04 | QF1 | Mar. 30, 2008 | 2 | HIGH | 200 | 3.503 |
|  | JHP111-05 | F | Jun. 25, 2008 | 6 | HIGH | 287 | 2.196 |
| 24 | JHP117-02 | QF1 | Sep. 30, 2007 | 0 | LOW | 0 | −0.932 |
|  | JHP117-03 | F | Dec. 19, 2007 | 4 | LOW | 80 | 0.251 |
| 25 | JHP120-04 | QQ | Nov. 11, 2007 | 0 | HIGH | 0 | 3.736 |
|  | JHP120-06 | QF1 | Apr. 27, 2008 | 0 | HIGH | 168 | 2.258 |

We claim:

1. A method of diagnosing a patient as having a longitudinally stable classification of SLE comprising:
    detecting the expression of two or more interferon response (INFr) genes in a sample from the patient; and
    diagnosing the patient as having type 1 or type 2 SLE based on analyzing the expression of the two or more genes using a statistical method, wherein expression of the two or more interferon response genes correlates with the expression of IFI27 from about 0.5 to about 1.0 and from about −0.5 to about −1.0 as calculated using a Pearson correlation.

2. The method of claim 1 wherein at least one of the two or more genes is selected from the group consisting of the genes comprising SEQ ID NOs: 589-802.

3. The method of claim 1 wherein the statistical method comprises a linear algorithm to produce an INFr score.

4. The method of claim 3 wherein the INFr score is determined to be a high INFr score if the score is above an average of INFr scores taken from a plurality of patients, and the INFr score is determined to be a low INFr score if the score is below an average of INFr scores taken from a plurality of patients.

5. The method of claim 4 wherein a high INFr score is correlated with type 1 SLE and a low INFr score is correlated with type 2 SLE.

6. The method of claim 3 wherein the linear algorithm comprises IFI27 +IFI144*(1.1296) +OAS3*(1.8136).

7. The method of claim 1 further comprising assigning the patient to a clinical trial based on the diagnosis of type 1 or type 2 SLE.

8. The method of claim 1 further comprising monitoring the status of the patient based on the diagnosis of type 1 or type 2 SLE.

9. The method of claim 8 wherein the status of the patient is incipient flare or disease activity.

10. The method of claim 8 wherein the status of the patient comprises a response to a therapeutic agent administered to the patient.

11. The method of claim 10 wherein the therapeutic agent is selected from the group consisting of ACE inhibitors, aspirin, azathioprine, B7RP-1-fc,β-blockers, brequinar sodium, campath-1H, celecoxib, chloroquine, corticosteroids, warfarin, cyclophosphamide, cyclosporin A, dehydroepiandrosterone, deoxyspergualin, dexamethasone, diclofenac, diflunisal, etodolac, everolimus, FK778, piroxicam, fenoprofen, flurbiprofen, heparin, hydralazine, hydroxychloroquine, CTLA-4 or LFA3 immunoglobulin, ibuprofen, indomethacin, ISAtx-247, ketoprofen, ketorolac, leflunomide, meclophenamate, mefenamic acid, mepacrine, 6-mercaptopurine, meloxicam, methotrexate, mizoribine, mycophenolate mofetil, naproxen, oxaprozin, hydroxychloroquine, NOX-100, prednisone, methylprednisolone, rapamycin (sirolimus), sulindac, tacrolimus anti-thymocyte globulin, tolmetin, tresperimus, U0126, and antibodies including but not limited to alpha lymphocyte antibodies, adalimumab, anti-CD3, anti-CD25, anti-CD52, anti-IL2R, and anti-TAC antibodies, basiliximab, daclizumab, etanercept, hu5C8, infliximab, OKT4, and natalizumab.

12. The method of claim 8 wherein the status of the patient comprises a response to an immunosuppressant administered to the patient.

13. The method of claim 12 wherein the immunosuppressant is selected from the group consisting of aspirin, azathioprine, chloroquine, corticosteroids, cyclophosphamide, cyclosporin A, dehydroepiandrosterone, deoxyspergualin, dexamethasone, everolimus, fenoprofen, hydralazine, hydroxychloroquine, immunoglobulin, ibuprofen, indomethacin, leflunomide, ketoprofen, meclophenamate, mepacrine, 6-mercaptopurine, methotrexate, mizoribine, mycophenolate mofetil, naproxen, prednisone, methylprednisolone, rapamycin (sirolimus), methylprednisolone sodium succinate, tacrolimus, anti-thymocyte globulin, tolmetin, tresperimus, and triamcinolone.

14. A method for predicting flare in a patient diagnosed with SLE comprising:
   analyzing expression in a sample from the patient to produce a gene expression profile
   wherein a first portion of the analysis comprises using the expression of at least one gene selected from each of at least two of the clusters 1 through 15 of Table 1 and at least one statistical method to produce a patient gene expression profile, and
   a second portion of the analysis comprises using expression of at least two interferon response genes and a linear algorithm to classify the patient as having type 1 SLE or type 2 SLE, wherein expression of the two or more interferon response genes correlates with the expression of IFI27 from about 0.5 to about 1.0 and from about −0.5 to about −1.0 as calculated using a Pearson correlation; and
   predicting flare by comparing the patient gene expression profile to at least one reference profile.

15. The method of claim 14 wherein the at least two INFr genes are selected from the group consisting of the genes comprising SEQ ID NOs: 589-802.

16. The method of claim 14 wherein the at least one reference profile is selected from the group consisting of at least one normal subject, at least one patient classified as having type 1 SLE with quiescent status, at least one patient classified as having type 1 SLE in flare, at least one patient classified as having type 2 SLE with quiescent status, and at least one patient classified as having type 2 SLE in flare.

* * * * *

SEQUENCE LISTING

<160> NUMBER OF SEQ ID NOS: 802

<210> SEQ ID NO 1
<211> LENGTH: 60
<212> TYPE: DNA
<213> ORGANISM: Homo sapiens

<400> SEQUENCE: 1
agaagaaaat agaatccctc cagcttgaaa aaagcaatca tgtcttagct caaatggagc    60

<210> SEQ ID NO 2
<211> LENGTH: 60
<212> TYPE: DNA
<213> ORGANISM: Homo sapiens

<400> SEQUENCE: 2
attagtgtga gccttgccaa agatgagcct gacacaaatc tcgtggcctt aatgaaggaa    60

<210> SEQ ID NO 3
<211> LENGTH: 60
<212> TYPE: DNA
<213> ORGANISM: Homo sapiens

<400> SEQUENCE: 3
aatgacagat tctgacattt atatttgtgt attttcctgg atttatagta tgtgactttt    60

<210> SEQ ID NO 4
<211> LENGTH: 60
<212> TYPE: DNA
<213> ORGANISM: Homo sapiens

<400> SEQUENCE: 4
aggtacagat acctcagatt cgggaaactc aaaatcaaaa gacttagctt ctaggataaa    60

<210> SEQ ID NO 5
<211> LENGTH: 60
<212> TYPE: DNA
<213> ORGANISM: Homo sapiens

<400> SEQUENCE: 5
gtcaaaatgg gttaactgtg tatattgact ttcatgtcgt catgcatctg tcatgaatga    60

<210> SEQ ID NO 6
<211> LENGTH: 60
<212> TYPE: DNA
<213> ORGANISM: Homo sapiens

<400> SEQUENCE: 6
aacctagaag gagaattgga aagcttgaaa gagaaccttc catttaccat gaatgaggga    60

<210> SEQ ID NO 7
<211> LENGTH: 60
<212> TYPE: DNA
<213> ORGANISM: Homo sapiens

<400> SEQUENCE: 7
cccattatgg gtaataatac tagcaatact tcttggattg ttggttctcg ccattttaac    60

<210> SEQ ID NO 8
<211> LENGTH: 60
<212> TYPE: DNA
<213> ORGANISM: Homo sapiens

<400> SEQUENCE: 8
aggcaccaga cttgggatca gttataaact ctagagtgct tactgcagtg catggtattc    60

<210> SEQ ID NO 9
<211> LENGTH: 60
<212> TYPE: DNA
<213> ORGANISM: Homo sapiens

<400> SEQUENCE: 9
ccagatggaa agtaattggt attcttaata tcctgggtga ctaatatcca ggcagagaag    60

<210> SEQ ID NO 10
<211> LENGTH: 60
<212> TYPE: DNA
<213> ORGANISM: Homo sapiens

<400> SEQUENCE: 10
tggatgaaat gtcagtggaa gaagcagatg agaaactctt gagatcttgg tcctgtgttt    60

<210> SEQ ID NO 11
<211> LENGTH: 60
<212> TYPE: DNA
<213> ORGANISM: Homo sapiens

<400> SEQUENCE: 11
tgatgacaca tctggagatc gatcaatctg gacagatact ccagctgata gggaaaggaa    60

<210> SEQ ID NO 12
<211> LENGTH: 60
<212> TYPE: DNA
<213> ORGANISM: Homo sapiens

<400> SEQUENCE: 12
gaagggcgta gtcacagaac tcgaagtagg agccgagata aatcccatag gcataaaaaa    60

```
<210> SEQ ID NO 13
<211> LENGTH: 60
<212> TYPE: DNA
<213> ORGANISM: Homo sapiens

<400> SEQUENCE: 13
ttgctattca aatcaactgc ctgaatgaca tttctagtag tctgatgtat ttttctgagg      60

<210> SEQ ID NO 14
<211> LENGTH: 60
<212> TYPE: DNA
<213> ORGANISM: Homo sapiens

<400> SEQUENCE: 14
atctgaagtc tgtccaggaa ctcattttga aacatggaca agccaagata aggaataaga      60

<210> SEQ ID NO 15
<211> LENGTH: 60
<212> TYPE: DNA
<213> ORGANISM: Homo sapiens

<400> SEQUENCE: 15
tggataattg aagccagtgg ttttttaacc aatgttatgt atcagaatca cctcacaaag      60

<210> SEQ ID NO 16
<211> LENGTH: 60
<212> TYPE: DNA
<213> ORGANISM: Homo sapiens

<400> SEQUENCE: 16
tctcatttga tcctaatttt ccccgtattc tacttgaaca cattaaaaat actctgctgc      60

<210> SEQ ID NO 17
<211> LENGTH: 60
<212> TYPE: DNA
<213> ORGANISM: Homo sapiens

<400> SEQUENCE: 17
agctacttag ggtgagcctg ccttcttcca ttctatccga agtctcttct aaagttgcgg      60

<210> SEQ ID NO 18
<211> LENGTH: 60
<212> TYPE: DNA
<213> ORGANISM: Homo sapiens

<400> SEQUENCE: 18
agtcacagat cctacgtatg tgctcttcag tagaggattt tctgtgatcc tacaatgaag      60

<210> SEQ ID NO 19
<211> LENGTH: 60
<212> TYPE: DNA
<213> ORGANISM: Homo sapiens

<400> SEQUENCE: 19
aaagcaccgg tgaagaaatc tataaagatg ctccagccga aaatgcacag aagtcaaatc      60

<210> SEQ ID NO 20
<211> LENGTH: 60
<212> TYPE: DNA
<213> ORGANISM: Homo sapiens

<400> SEQUENCE: 20
gacttacatc aagctgtcaa tggcaatcaa gcgtaatgag agcatggcca aggtctgca       60
```

<210> SEQ ID NO 21
<211> LENGTH: 60
<212> TYPE: DNA
<213> ORGANISM: Homo sapiens

<400> SEQUENCE: 21 tgagggtgc cttcattccc ctttgttcac tttctccagc tcaacttggg acttgggtgg    60

<210> SEQ ID NO 22
<211> LENGTH: 60
<212> TYPE: DNA
<213> ORGANISM: Homo sapiens

<400> SEQUENCE: 22
acatcaccat gtagaagaat gggcgtacag tatataccgt gacatcctga accctggata    60

<210> SEQ ID NO 23
<211> LENGTH: 60
<212> TYPE: DNA
<213> ORGANISM: Homo sapiens

<400> SEQUENCE: 23
agctccgcgt gagaagtact ggctacaatt ttttatccca ttgttggtgg tgattctgtt    60

<210> SEQ ID NO 24
<211> LENGTH: 60
<212> TYPE: DNA
<213> ORGANISM: Homo sapiens

<400> SEQUENCE: 24
aaactctgaa gattggaaaa aacagcctat ctgtactttc accgaaaatt ggaaatttgc    60

<210> SEQ ID NO 25
<211> LENGTH: 60
<212> TYPE: DNA
<213> ORGANISM: Homo sapiens

<400> SEQUENCE: 25
attaaactct aggggactt tcttaaaaat aactagaggg acctattttc ctcttttta    60

<210> SEQ ID NO 26
<211> LENGTH: 60
<212> TYPE: DNA
<213> ORGANISM: Homo sapiens

<400> SEQUENCE: 26
ccgagggtag acaggcagct tctgtggttc agcttgtgac atgatatata acacagaaat    60

<210> SEQ ID NO 27
<211> LENGTH: 60
<212> TYPE: DNA
<213> ORGANISM: Homo sapiens

<400> SEQUENCE: 27
tcgcaaatcc atcctgaagt ctcgaagtag agagaatagt gtgtgtagcg acactagtga    60

<210> SEQ ID NO 28
<211> LENGTH: 60
<212> TYPE: DNA
<213> ORGANISM: Homo sapiens

<400> SEQUENCE: 28
agttctataa gtgaggaaga gtttatggca aagattttg gcactttgtt ttcaagatgg    60

<210> SEQ ID NO 29
<211> LENGTH: 60
<212> TYPE: DNA
<213> ORGANISM: Homo sapiens

<400> SEQUENCE: 29
acattggcaa atagcgtggg atagatttgt ttcttaatgg gtgtgaccaa tcctgttttt    60

<210> SEQ ID NO 30
<211> LENGTH: 60
<212> TYPE: DNA
<213> ORGANISM: Homo sapiens

<400> SEQUENCE: 30
taaacccaga tgctaaatca ttcctacaaa ggtttgactg aaactgtggc agatgtctca    60

<210> SEQ ID NO 31
<211> LENGTH: 60
<212> TYPE: DNA
<213> ORGANISM: Homo sapiens

<400> SEQUENCE: 31
tgacccttaa aaatgtattt ttcttaacat gttagtactt ctacgactttt ggagccactg   60

<210> SEQ ID NO 32
<211> LENGTH: 60
<212> TYPE: DNA
<213> ORGANISM: Homo sapiens

<400> SEQUENCE: 32
tggctgttag ggactgtata tcttgtaaaa gaacacttgt cacatgcttg atcagttaca    60

<210> SEQ ID NO 33
<211> LENGTH: 60
<212> TYPE: DNA
<213> ORGANISM: Homo sapiens

<400> SEQUENCE: 33
cctccaataa agggaaaatg aagcttttta tgtaaattgg ttgaaaggtc tagttttggg    60

<210> SEQ ID NO 34
<211> LENGTH: 60
<212> TYPE: DNA
<213> ORGANISM: Homo sapiens

<400> SEQUENCE: 34
ttggctgtaa tgtatgttga gaagtcagtc caaggaggta tgttcttcca caacagcctt    60

<210> SEQ ID NO 35
<211> LENGTH: 60
<212> TYPE: DNA
<213> ORGANISM: Homo sapiens

<400> SEQUENCE: 35
ggctttatag gaggagtata atgtatgcac tactgtttta aaagaattag tgtgagtgtg    60

<210> SEQ ID NO 36
<211> LENGTH: 60
<212> TYPE: DNA
<213> ORGANISM: Homo sapiens

<400> SEQUENCE: 36
tggccaatct tgtctgagtt ctttgatggc gacacatgaa ctacagccgt tttgttgttg    60

```
<210> SEQ ID NO 37
<211> LENGTH: 60
<212> TYPE: DNA
<213> ORGANISM: Homo sapiens

<400> SEQUENCE: 37
aatgcagagg gaacaccaga ggacgttttt cttcaactct gcacagctat tgactctatt      60

<210> SEQ ID NO 38
<211> LENGTH: 60
<212> TYPE: DNA
<213> ORGANISM: Homo sapiens

<400> SEQUENCE: 38
ggaggcgtaa aatggctctg tattttaata acacagaaac atttgagcat tgtatttctc      60

<210> SEQ ID NO 39
<211> LENGTH: 60
<212> TYPE: DNA
<213> ORGANISM: Homo sapiens

<400> SEQUENCE: 39
agcaggagcc aaaaagacct cacattaaga agcctctgaa tgcttttatg ttatacatga      60

<210> SEQ ID NO 40
<211> LENGTH: 60
<212> TYPE: DNA
<213> ORGANISM: Homo sapiens

<400> SEQUENCE: 40
cataaagtca aaaatccta aaacataagt tggtgaccat ctgtaatcat gatgtggtgg       60

<210> SEQ ID NO 41
<211> LENGTH: 60
<212> TYPE: DNA
<213> ORGANISM: Homo sapiens

<400> SEQUENCE: 41
aatggcttcg gacaaaatat ctctgagttc tgtgtatttt cagtcaaaac tttaaacctg      60

<210> SEQ ID NO 42
<211> LENGTH: 60
<212> TYPE: DNA
<213> ORGANISM: Homo sapiens

<400> SEQUENCE: 42
ttcaaatgca tgatcaaatg caacctcaca accttggctg agtcttgaga ctgaaagatt      60

<210> SEQ ID NO 43
<211> LENGTH: 60
<212> TYPE: DNA
<213> ORGANISM: Homo sapiens

<400> SEQUENCE: 43
tttttctaac aggcaagaca gtgtgaagaa ttgaagcaat atgtgcataa atttcaggac      60

<210> SEQ ID NO 44
<211> LENGTH: 60
<212> TYPE: DNA
<213> ORGANISM: Homo sapiens

<400> SEQUENCE: 44
ctgaaacggc aagtcagtgt atcgatttct agtgctgtga agtcagcccc tgaagaaaat      60
```

<210> SEQ ID NO 45
<211> LENGTH: 60
<212> TYPE: DNA
<213> ORGANISM: Homo sapiens

<400> SEQUENCE: 45
gctgagagtg cttccttctt gaagacgagt gtcattcatc acttcagtga tccatgcata        60

<210> SEQ ID NO 46
<211> LENGTH: 60
<212> TYPE: DNA
<213> ORGANISM: Homo sapiens

<400> SEQUENCE: 46
gcctctctcc agaaatgaac tgtgatggtg acacagcta tgtgaggaat tacttacaga         60

<210> SEQ ID NO 47
<211> LENGTH: 60
<212> TYPE: DNA
<213> ORGANISM: Homo sapiens

<400> SEQUENCE: 47
gcaatgagtg aactgactgt ggctacattc ttgaagatat acgggagaga cgtattatta        60

<210> SEQ ID NO 48
<211> LENGTH: 60
<212> TYPE: DNA
<213> ORGANISM: Homo sapiens

<400> SEQUENCE: 48 gcaggggcc actgtagtga gcgtggagaa atttggaaac acctatttct taactcaaat         60

<210> SEQ ID NO 49
<211> LENGTH: 60
<212> TYPE: DNA
<213> ORGANISM: Homo sapiens

<400> SEQUENCE: 49
aagagagcaa cattttaccc acacacagat aaagttttcc cttgaggaaa caacagcttt        60

<210> SEQ ID NO 50
<211> LENGTH: 60
<212> TYPE: DNA
<213> ORGANISM: Homo sapiens

<400> SEQUENCE: 50
gacttgatgc cttttgaata actttcaata gaattgtcta aaattatctt actggttgtt        60

<210> SEQ ID NO 51
<211> LENGTH: 60
<212> TYPE: DNA
<213> ORGANISM: Homo sapiens

<400> SEQUENCE: 51
ttgaacactt catgaggagg gacattccct gatataagag aggatggtgt tgcaattggc        60

<210> SEQ ID NO 52
<211> LENGTH: 60
<212> TYPE: DNA
<213> ORGANISM: Homo sapiens

<400> SEQUENCE: 52
tctcttaagc cttcagttta tactcttaat ttaatttct ttctgagctg gagaactggc        60

```
<210> SEQ ID NO 53
<211> LENGTH: 60
<212> TYPE: DNA
<213> ORGANISM: Homo sapiens

<400> SEQUENCE: 53
gctgaggcca aagtttccat gtaagcggga tccgtttttt ggaatttggt tgaagtcact      60

<210> SEQ ID NO 54
<211> LENGTH: 60
<212> TYPE: DNA
<213> ORGANISM: Homo sapiens

<400> SEQUENCE: 54
cacttgacag tgacttgaaa catttgcata ttcaggaatg catgagattt caagagagcc      60

<210> SEQ ID NO 55
<211> LENGTH: 60
<212> TYPE: DNA
<213> ORGANISM: Homo sapiens

<400> SEQUENCE: 55
gggatagatt acataggagt atggagtatg ctgtaaataa aaatacaagc tagtgctttg      60

<210> SEQ ID NO 56
<211> LENGTH: 60
<212> TYPE: DNA
<213> ORGANISM: Homo sapiens

<400> SEQUENCE: 56
gcaagtggtc accagcatta cacagcaatg aagcagaata agtaggcca gaatgcatca       60

<210> SEQ ID NO 57
<211> LENGTH: 60
<212> TYPE: DNA
<213> ORGANISM: Homo sapiens

<400> SEQUENCE: 57
tggagacaga atcacagtta tatcaaaaac agattcacat tttgattggt gggaaggaaa      60

<210> SEQ ID NO 58
<211> LENGTH: 60
<212> TYPE: DNA
<213> ORGANISM: Homo sapiens

<400> SEQUENCE: 58
taatcccgac agaacatcat gtgagatttc tttaaaatgg attaaacgat ttcttcagcc      60

<210> SEQ ID NO 59
<211> LENGTH: 60
<212> TYPE: DNA
<213> ORGANISM: Homo sapiens

<400> SEQUENCE: 59
tctttgaaag gggggaggag gagtaaaagc ccgattataa tggtgatcaa ttcaagtcag      60

<210> SEQ ID NO 60
<211> LENGTH: 60
<212> TYPE: DNA
<213> ORGANISM: Homo sapiens

<400> SEQUENCE: 60
atgtacccaa agaacacatt tgctttgaga agtggtggta ggaggcagac aaaggcagaa      60
```

```
<210> SEQ ID NO 61
<211> LENGTH: 60
<212> TYPE: DNA
<213> ORGANISM: Homo sapiens

<400> SEQUENCE: 61
taagttttgt aaaaaggagc atcttgaatc cacttagata agacagact gtgtgtgtag      60

<210> SEQ ID NO 62
<211> LENGTH: 60
<212> TYPE: DNA
<213> ORGANISM: Homo sapiens

<400> SEQUENCE: 62
agagcctttc tgaagagaat tatatcaaac taattacaac caagaaataa tagtatgaag      60

<210> SEQ ID NO 63
<211> LENGTH: 60
<212> TYPE: DNA
<213> ORGANISM: Homo sapiens

<400> SEQUENCE: 63
caaggcctaa agccaactga cttaaaggta atcatttcag ctaagattaa atttaaagcc      60

<210> SEQ ID NO 64
<211> LENGTH: 60
<212> TYPE: DNA
<213> ORGANISM: Homo sapiens

<400> SEQUENCE: 64
ggtgcacaaa agcgtttcca taaatcaatt ctagaagacc ataaagacct cagggataat      60

<210> SEQ ID NO 65
<211> LENGTH: 60
<212> TYPE: DNA
<213> ORGANISM: Homo sapiens

<400> SEQUENCE: 65
atgttgatga agtgcacaaa aataatagaa gtgatatgat gtccgcatta ggattaggac      60

<210> SEQ ID NO 66
<211> LENGTH: 60
<212> TYPE: DNA
<213> ORGANISM: Homo sapiens

<400> SEQUENCE: 66
cccgttaaac tgagtgtaga aatctgaatt tttaaaagag ctgtaactag ttgtaagtgc      60

<210> SEQ ID NO 67
<211> LENGTH: 60
<212> TYPE: DNA
<213> ORGANISM: Homo sapiens

<400> SEQUENCE: 67
accaaaaaat tcatgagaga tccaattaat tctggtgaaa aaggattgac ccttgaagga      60

<210> SEQ ID NO 68
<211> LENGTH: 60
<212> TYPE: DNA
<213> ORGANISM: Homo sapiens

<400> SEQUENCE: 68
aacgacaaca gaaaacaat cttattccaa gtcattccag taactttttt gggtacgtac       60
```

<210> SEQ ID NO 69
<211> LENGTH: 60
<212> TYPE: DNA
<213> ORGANISM: Homo sapiens

<400> SEQUENCE: 69
atgcacaaaa gtcaaatcag aatggagact caaaaccatc aaagctaaga tcaaaaggtc    60

<210> SEQ ID NO 70
<211> LENGTH: 60
<212> TYPE: DNA
<213> ORGANISM: Homo sapiens

<400> SEQUENCE: 70
tgcaaaaaca gatctattta atttgaggtt gatgttctat ccaatggccg aagatagcag    60

<210> SEQ ID NO 71
<211> LENGTH: 60
<212> TYPE: DNA
<213> ORGANISM: Homo sapiens

<400> SEQUENCE: 71
gtgccgtttg caataatgtc gtcttattta tttagcgggg tgaatatttt atactgtaag    60

<210> SEQ ID NO 72
<211> LENGTH: 60
<212> TYPE: DNA
<213> ORGANISM: Homo sapiens

<400> SEQUENCE: 72
ttttcaacag tacagaaaaa ttgaaaaaag gggctttgcc tttgtaacct tgatgacca    60

<210> SEQ ID NO 73
<211> LENGTH: 60
<212> TYPE: DNA
<213> ORGANISM: Homo sapiens

<400> SEQUENCE: 73
tttttaagct tcccttgaga gaataaatgg taatggagag aactatttaa caaggtcctg    60

<210> SEQ ID NO 74
<211> LENGTH: 60
<212> TYPE: DNA
<213> ORGANISM: Homo sapiens

<400> SEQUENCE: 74
aagctttaac tatatctctc tttaaaatgc aaataatgt cttaagattc aaagtctgta    60

<210> SEQ ID NO 75
<211> LENGTH: 60
<212> TYPE: DNA
<213> ORGANISM: Homo sapiens

<400> SEQUENCE: 75
accttgaaag aagcttacat ggcagcaata tttctaaaat agtgatacag tcagaggcct    60

<210> SEQ ID NO 76
<211> LENGTH: 60
<212> TYPE: DNA
<213> ORGANISM: Homo sapiens

<400> SEQUENCE: 76
agagaaagat gtcacatctg ctaaagcact gtatgaacat ttgactgcaa agaatacaaa    60

```
<210> SEQ ID NO 77
<211> LENGTH: 60
<212> TYPE: DNA
<213> ORGANISM: Homo sapiens

<400> SEQUENCE: 77
atcttgctga ctatacatgg gaagaggtgt ttcgagtaaa caagccagaa agtggagttc    60

<210> SEQ ID NO 78
<211> LENGTH: 60
<212> TYPE: DNA
<213> ORGANISM: Homo sapiens

<400> SEQUENCE: 78
aattggagaa ttgaataatc agcatatgta agcgcactag aaccctgtgt tgaaaactgc    60

<210> SEQ ID NO 79
<211> LENGTH: 60
<212> TYPE: DNA
<213> ORGANISM: Homo sapiens

<400> SEQUENCE: 79
ctagtgaata tgaaaaggaa aaactgaatg aactggcaaa actttcagat ggagtagctg    60

<210> SEQ ID NO 80
<211> LENGTH: 60
<212> TYPE: DNA
<213> ORGANISM: Homo sapiens

<400> SEQUENCE: 80
cataacctta ttaatttgca catagatcat ctgaatgtcg tggtttaaga cttaaggagg    60

<210> SEQ ID NO 81
<211> LENGTH: 60
<212> TYPE: DNA
<213> ORGANISM: Homo sapiens

<400> SEQUENCE: 81
ggataagatt gtcattcaga ataccatcc taatggctac aactttgaag taagaaaagc     60

<210> SEQ ID NO 82
<211> LENGTH: 60
<212> TYPE: DNA
<213> ORGANISM: Homo sapiens

<400> SEQUENCE: 82
gcagagtgaa gacacaaaca ctgaatcgaa ggaaagtgat actaagaatg aggtcaatgg    60

<210> SEQ ID NO 83
<211> LENGTH: 60
<212> TYPE: DNA
<213> ORGANISM: Homo sapiens

<400> SEQUENCE: 83
tttctatgaa ctgccgacat atccacactt ttacagtgaa atctgtaata tgctgagagc    60

<210> SEQ ID NO 84
<211> LENGTH: 60
<212> TYPE: DNA
<213> ORGANISM: Homo sapiens

<400> SEQUENCE: 84
atgcaaatta tgatatggac gttatcattg gtctggtgag atgtttcata tttgtgacag    60
```

<210> SEQ ID NO 85
<211> LENGTH: 60
<212> TYPE: DNA
<213> ORGANISM: Homo sapiens

<400> SEQUENCE: 85
ctagctgtgt cgagttaaag aaaaaatcag cagttttttc tcccagaaat gtaattgcca    60

<210> SEQ ID NO 86
<211> LENGTH: 60
<212> TYPE: DNA
<213> ORGANISM: Homo sapiens

<400> SEQUENCE: 86
actcttaaat gctttgtata ttttctcaat tagatctctt ttcagaagtg tctatagaac    60

<210> SEQ ID NO 87
<211> LENGTH: 60
<212> TYPE: DNA
<213> ORGANISM: Homo sapiens

<400> SEQUENCE: 87
ttacagagtt caatatactg tgtaccattg atcttctatt gtgaaagcaa agaatttcat    60

<210> SEQ ID NO 88
<211> LENGTH: 60
<212> TYPE: DNA
<213> ORGANISM: Homo sapiens

<400> SEQUENCE: 88
accctcatgt taaatcttaa atgtagtatt tctaacttgt gaagacagat tggtaggcag    60

<210> SEQ ID NO 89
<211> LENGTH: 60
<212> TYPE: DNA
<213> ORGANISM: Homo sapiens

<400> SEQUENCE: 89
gaaaaattaa tactatcatg ttaatactat tattgtcatc ccaagaaaaa agatatttta    60

<210> SEQ ID NO 90
<211> LENGTH: 60
<212> TYPE: DNA
<213> ORGANISM: Homo sapiens

<400> SEQUENCE: 90
actataagta gttggtttgt atgagatggt taaaaggcc aaagataaaa ggtttcttt    60

<210> SEQ ID NO 91
<211> LENGTH: 60
<212> TYPE: DNA
<213> ORGANISM: Homo sapiens

<400> SEQUENCE: 91
gaagaaaagt ataagagttg ctaggtgtga caatctcaag acttttcaac cactacaaat    60

<210> SEQ ID NO 92
<211> LENGTH: 60
<212> TYPE: DNA
<213> ORGANISM: Homo sapiens

<400> SEQUENCE: 92
catcatcaac accaaaaaag gacaagaatc cttcaaaaca ggaaaaaact cctaaaacac    60

<210> SEQ ID NO 93
<211> LENGTH: 60
<212> TYPE: DNA
<213> ORGANISM: Homo sapiens

<400> SEQUENCE: 93
aaattgtatg tgatattcca acagcaagtt ggatgcaatg tgtcataaaa atgacctcag    60

<210> SEQ ID NO 94
<211> LENGTH: 60
<212> TYPE: DNA
<213> ORGANISM: Homo sapiens

<400> SEQUENCE: 94
aatctgggac agtgtctcct cagaaacaat cagcctggaa ggttatattt aaaaagaaag    60

<210> SEQ ID NO 95
<211> LENGTH: 60
<212> TYPE: DNA
<213> ORGANISM: Homo sapiens

<400> SEQUENCE: 95
tccaggaaaa gtgtcttctc agaaacaacc agctgagaag gctacaagtg acgacaaaga    60

<210> SEQ ID NO 96
<211> LENGTH: 60
<212> TYPE: DNA
<213> ORGANISM: Homo sapiens

<400> SEQUENCE: 96
gttgagaaaa ttatgcaaag ttcctcagaa gttggttatg atactatgtt aggagatgtc    60

<210> SEQ ID NO 97
<211> LENGTH: 60
<212> TYPE: DNA
<213> ORGANISM: Homo sapiens

<400> SEQUENCE: 97
taaaagtcag gttgcagttt ccattgcatt caagaaaatc agaaaaataa atacaacttt    60

<210> SEQ ID NO 98
<211> LENGTH: 60
<212> TYPE: DNA
<213> ORGANISM: Homo sapiens

<400> SEQUENCE: 98
tcaggatgat tcctaacaag tcagtcattt gtgaacttag tggactttt ggttacttta    60

<210> SEQ ID NO 99
<211> LENGTH: 60
<212> TYPE: DNA
<213> ORGANISM: Homo sapiens

<400> SEQUENCE: 99
ctttgaaata acaccaccag tagtcttacg gttgaagtgt ggttcagggc cagtgcatat    60

<210> SEQ ID NO 100
<211> LENGTH: 60
<212> TYPE: DNA
<213> ORGANISM: Homo sapiens

<400> SEQUENCE: 100
gggcaactag tcatctacta gttagcttag taagctaagc attaaatcta agaaatagca    60

```
<210> SEQ ID NO 101
<211> LENGTH: 60
<212> TYPE: DNA
<213> ORGANISM: Homo sapiens

<400> SEQUENCE: 101
agtgtgttgt cgttattaat ttgctattcc ttgtcctatt cagaaaggat ttcaagaggc        60

<210> SEQ ID NO 102
<211> LENGTH: 60
<212> TYPE: DNA
<213> ORGANISM: Homo sapiens

<400> SEQUENCE: 102
gccccatttc aagtataacc aggagggaaa atggtgcttg aaataagcat gccacaaagg        60

<210> SEQ ID NO 103
<211> LENGTH: 60
<212> TYPE: DNA
<213> ORGANISM: Homo sapiens

<400> SEQUENCE: 103
ccacggattg tgttcatctg aaccatttta ttttttattt accaaagtac tgtacttggc        60

<210> SEQ ID NO 104
<211> LENGTH: 60
<212> TYPE: DNA
<213> ORGANISM: Homo sapiens

<400> SEQUENCE: 104
tcctgcatag tctatctttg tatatctttg aacttttcaa gaataaaaaa gcttaaaaag        60

<210> SEQ ID NO 105
<211> LENGTH: 60
<212> TYPE: DNA
<213> ORGANISM: Homo sapiens

<400> SEQUENCE: 105
cagaactcta cttcagcaga cactcaactc aaaaagactg gcaaatggac atgtatttac        60

<210> SEQ ID NO 106
<211> LENGTH: 60
<212> TYPE: DNA
<213> ORGANISM: Homo sapiens

<400> SEQUENCE: 106
tcaagagaga tcctaaagaa agcaaaatca ctgtggactg aaatgagcag acaaggtttt        60

<210> SEQ ID NO 107
<211> LENGTH: 60
<212> TYPE: DNA
<213> ORGANISM: Homo sapiens

<400> SEQUENCE: 107
ttctggattg ttttttacat tcagtgttat aatatttgat tatgctgatt ggttttggtg        60

<210> SEQ ID NO 108
<211> LENGTH: 60
<212> TYPE: DNA
<213> ORGANISM: Homo sapiens

<400> SEQUENCE: 108
tgcaaacaat gttggagctg taatagtaag agctttctta caaagctttg tattactgtg        60
```

<210> SEQ ID NO 109
<211> LENGTH: 60
<212> TYPE: DNA
<213> ORGANISM: Homo sapiens

<400> SEQUENCE: 109
aaataaaagc atgtctttca acatgcatcc aaaacagtgt tcaatttaac gtggcaaagg    60

<210> SEQ ID NO 110
<211> LENGTH: 60
<212> TYPE: DNA
<213> ORGANISM: Homo sapiens

<400> SEQUENCE: 110
gctgacaaag atgatcactt taaggtggat aatgatgaaa atgagcacca gttatcttta    60

<210> SEQ ID NO 111
<211> LENGTH: 60
<212> TYPE: DNA
<213> ORGANISM: Homo sapiens

<400> SEQUENCE: 111
atattcttcc aatatgtagg ggaaaagaca tatgaataag acaaatgaaa aattgcatat    60

<210> SEQ ID NO 112
<211> LENGTH: 60
<212> TYPE: DNA
<213> ORGANISM: Homo sapiens

<400> SEQUENCE: 112
attcacatga gtaaaatgat ggaagaactc tttaaggtaa tcctttggga taaaggatcc    60

<210> SEQ ID NO 113
<211> LENGTH: 60
<212> TYPE: DNA
<213> ORGANISM: Homo sapiens

<400> SEQUENCE: 113
gacttgtact ggtgttgtaa ctttccaagt aaaagtatcc ctaaaggcca cttcctatct    60

<210> SEQ ID NO 114
<211> LENGTH: 60
<212> TYPE: DNA
<213> ORGANISM: Homo sapiens

<400> SEQUENCE: 114
ttaccgaaaa agtccaggat acaagtaaca caggtttagg agaagacatt atacatcagt    60

<210> SEQ ID NO 115
<211> LENGTH: 60
<212> TYPE: DNA
<213> ORGANISM: Homo sapiens

<400> SEQUENCE: 115
aagcacttca tgggccagaa tgttgcagat tacatgcgct acttaatgga agaagatgac    60

<210> SEQ ID NO 116
<211> LENGTH: 60
<212> TYPE: DNA
<213> ORGANISM: Homo sapiens

<400> SEQUENCE: 116
tgaagactta aggcccagta ttttttaata gaatactcat ctaggatgta acagtgaagc    60

<210> SEQ ID NO 117
<211> LENGTH: 60
<212> TYPE: DNA
<213> ORGANISM: Homo sapiens

<400> SEQUENCE: 117
aaacaggaaa aaactcctaa aacacctaaa aggacctagt tctgtagaag acattaaagc    60

<210> SEQ ID NO 118
<211> LENGTH: 60
<212> TYPE: DNA
<213> ORGANISM: Homo sapiens

<400> SEQUENCE: 118
cccgggagtg ttgcaagtta aactgatgaa aagacgttta gtatttaatt gctcctcatg    60

<210> SEQ ID NO 119
<211> LENGTH: 60
<212> TYPE: DNA
<213> ORGANISM: Homo sapiens

<400> SEQUENCE: 119
tgaactgcac attgttgaag cagaggccat gaattacgaa ggcagtccaa ttaaagtaac    60

<210> SEQ ID NO 120
<211> LENGTH: 60
<212> TYPE: DNA
<213> ORGANISM: Homo sapiens

<400> SEQUENCE: 120
atcttcctaa tctcgtggga tcacaatatg aataacaagg atgaacataa gacacatctg    60

<210> SEQ ID NO 121
<211> LENGTH: 60
<212> TYPE: DNA
<213> ORGANISM: Homo sapiens

<400> SEQUENCE: 121
tttaaaaact ggaacggtga aggtgacagc agtcggttgg agcgagcatc ccccaaagtt    60

<210> SEQ ID NO 122
<211> LENGTH: 60
<212> TYPE: DNA
<213> ORGANISM: Homo sapiens

<400> SEQUENCE: 122
gattattctc gaatcacctc ctgtgttgtg ctgggagcag gactgattga attacggaaa    60

<210> SEQ ID NO 123
<211> LENGTH: 60
<212> TYPE: DNA
<213> ORGANISM: Homo sapiens

<400> SEQUENCE: 123
tgatttcaga ctcagaagcc gacgttcgag aggaagattc ttacctcttt gatctcgaca    60

<210> SEQ ID NO 124
<211> LENGTH: 60
<212> TYPE: DNA
<213> ORGANISM: Homo sapiens

<400> SEQUENCE: 124
tttggtcact tttgataagt ttgcatgaaa ccattttggt gcattttag ttgggaatgg    60

```
<210> SEQ ID NO 125
<211> LENGTH: 60
<212> TYPE: DNA
<213> ORGANISM: Homo sapiens

<400> SEQUENCE: 125
gatgtcctgt gctgcttgtg atgagagcct ccacactgta ctgttcaagt caatgttaat      60

<210> SEQ ID NO 126
<211> LENGTH: 60
<212> TYPE: DNA
<213> ORGANISM: Homo sapiens

<400> SEQUENCE: 126
aatgttgcct ttttctagga actgtcagaa atcctcatgc ctttcaagac ttctgtgaat      60

<210> SEQ ID NO 127
<211> LENGTH: 60
<212> TYPE: DNA
<213> ORGANISM: Homo sapiens

<400> SEQUENCE: 127
agaaaaaggc ttttcgagtg tgggacaagg tctgatgtca gtgaacggaa ttgaagagca      60

<210> SEQ ID NO 128
<211> LENGTH: 60
<212> TYPE: DNA
<213> ORGANISM: Homo sapiens

<400> SEQUENCE: 128
tgcaactgag gaaataattt attttttcaca tgaggaaatg cgtagcttgt agagacggct     60

<210> SEQ ID NO 129
<211> LENGTH: 60
<212> TYPE: DNA
<213> ORGANISM: Homo sapiens

<400> SEQUENCE: 129
gggatgcctt actttgcact taatttaata agggcattct cggaggagta gacgtttaat     60

<210> SEQ ID NO 130
<211> LENGTH: 60
<212> TYPE: DNA
<213> ORGANISM: Homo sapiens

<400> SEQUENCE: 130
accctggttt caatgaacct aacctcattc tttgtgtctt cagtgttggc ttgttttagc     60

<210> SEQ ID NO 131
<211> LENGTH: 60
<212> TYPE: DNA
<213> ORGANISM: Homo sapiens

<400> SEQUENCE: 131
agataattaa gagtgaagga gttgaaactt ttcttgttag tgtacaactc attttgcgcc     60

<210> SEQ ID NO 132
<211> LENGTH: 60
<212> TYPE: DNA
<213> ORGANISM: Homo sapiens

<400> SEQUENCE: 132
cagcagccta aaactgttgt gttttttctta tggtttaaaa aacgccatgt cattgataac    60
```

```
<210> SEQ ID NO 133
<211> LENGTH: 60
<212> TYPE: DNA
<213> ORGANISM: Homo sapiens

<400> SEQUENCE: 133
atatattgaa aagagcaatt ttaaattatt tttggcttat gttgcaatat ttattttctt    60

<210> SEQ ID NO 134
<211> LENGTH: 60
<212> TYPE: DNA
<213> ORGANISM: Homo sapiens

<400> SEQUENCE: 134
tccctggtaa tctgtagaac cttctcctag gaaatggtga agtctattag gagccacttg    60

<210> SEQ ID NO 135
<211> LENGTH: 60
<212> TYPE: DNA
<213> ORGANISM: Homo sapiens

<400> SEQUENCE: 135
aatgtgatca cttcctctga ataccttcct acattatggg tcaagcttta caaaagcgaa    60

<210> SEQ ID NO 136
<211> LENGTH: 60
<212> TYPE: DNA
<213> ORGANISM: Homo sapiens

<400> SEQUENCE: 136
ggatgctata acaaaagaca ataaactata tttacaggaa caagagttga atgctcgagc    60

<210> SEQ ID NO 137
<211> LENGTH: 60
<212> TYPE: DNA
<213> ORGANISM: Homo sapiens

<400> SEQUENCE: 137
tatcatcatc gtctataaac tagctttagg atagtgccag acaaacatat gatatcatgg    60

<210> SEQ ID NO 138
<211> LENGTH: 60
<212> TYPE: DNA
<213> ORGANISM: Homo sapiens

<400> SEQUENCE: 138
gaagctttca gtattagtga tgtcatctgt cactataggt catacaatcc attcttaaag    60

<210> SEQ ID NO 139
<211> LENGTH: 60
<212> TYPE: DNA
<213> ORGANISM: Homo sapiens

<400> SEQUENCE: 139
accaggaaga tttctggaaa gtgaaggagt tcctgcataa ccaggggaag cagaagtata    60

<210> SEQ ID NO 140
<211> LENGTH: 60
<212> TYPE: DNA
<213> ORGANISM: Homo sapiens

<400> SEQUENCE: 140
aaagagaggg aagaactaca ctaatgttag agataaggta tgttttggct caaaatgtgt    60
```

<210> SEQ ID NO 141
<211> LENGTH: 60
<212> TYPE: DNA
<213> ORGANISM: Homo sapiens

<400> SEQUENCE: 141
ttctacagct tctgataatc aaccaactgt tacaatcaag gtctatgaag gtgaaagacc    60

<210> SEQ ID NO 142
<211> LENGTH: 60
<212> TYPE: DNA
<213> ORGANISM: Homo sapiens

<400> SEQUENCE: 142
ccagttttct ctgtacctgt gtgtatagaa atagatcaga gcacagttga aattcatgga    60

<210> SEQ ID NO 143
<211> LENGTH: 60
<212> TYPE: DNA
<213> ORGANISM: Homo sapiens

<400> SEQUENCE: 143
gaagtgtgat gtggacatct gcaaagactt atatgccaac gtgctgtctg gcggcaccac    60

<210> SEQ ID NO 144
<211> LENGTH: 60
<212> TYPE: DNA
<213> ORGANISM: Homo sapiens

<400> SEQUENCE: 144
gctggtaaaa gcctctatta cgactgtaag taagttggat gttggcaaaa ttaaattgtt    60

<210> SEQ ID NO 145
<211> LENGTH: 60
<212> TYPE: DNA
<213> ORGANISM: Homo sapiens

<400> SEQUENCE: 145
catgttctca tgatttatgg gaatgaagca agtactgaaa tcaaattaaa tactccctgg    60

<210> SEQ ID NO 146
<211> LENGTH: 60
<212> TYPE: DNA
<213> ORGANISM: Homo sapiens

<400> SEQUENCE: 146
agaaatacca caatgttggt cttagtaaat gtgaaataaa agtagccatg tcgaaggaac    60

<210> SEQ ID NO 147
<211> LENGTH: 60
<212> TYPE: DNA
<213> ORGANISM: Homo sapiens

<400> SEQUENCE: 147
gcacccagca caatgaagat caagatcatt gctcctcctg agcgcaagta ctccgtgtgg    60

<210> SEQ ID NO 148
<211> LENGTH: 60
<212> TYPE: DNA
<213> ORGANISM: Homo sapiens

<400> SEQUENCE: 148
tgtggcatcc acgaaactac cttcaactcc atcatgaagt cggatgtgga catctacaaa    60

<210> SEQ ID NO 149
<211> LENGTH: 60
<212> TYPE: DNA
<213> ORGANISM: Homo sapiens

<400> SEQUENCE: 149
gtcctcctgg gagaagagct atgagctgtc agatggccag gtcatcacca gcagcaacaa    60

<210> SEQ ID NO 150
<211> LENGTH: 60
<212> TYPE: DNA
<213> ORGANISM: Homo sapiens

<400> SEQUENCE: 150
aacttccttt tgctaaatgc attctttctg cttttagaaa tgtagacata aacactcccc    60

<210> SEQ ID NO 151
<211> LENGTH: 60
<212> TYPE: DNA
<213> ORGANISM: Homo sapiens

<400> SEQUENCE: 151
ccccgagtga ttttgcgaaa ccccctttc ccttcagctt gcttagatgt tccaaattta    60

<210> SEQ ID NO 152
<211> LENGTH: 60
<212> TYPE: DNA
<213> ORGANISM: Homo sapiens

<400> SEQUENCE: 152
acctaacctc attctttgta tcttcagtgt tgaattgttt tagctgatcc atctttaacg    60

<210> SEQ ID NO 153
<211> LENGTH: 60
<212> TYPE: DNA
<213> ORGANISM: Homo sapiens

<400> SEQUENCE: 153
acttctacac agataagctt tcaaagttga caaactttt tgactctttc tggaaaaggg    60

<210> SEQ ID NO 154
<211> LENGTH: 60
<212> TYPE: DNA
<213> ORGANISM: Homo sapiens

<400> SEQUENCE: 154
cctacataca gatcactttt gtggagccct actttgatga gtatgagatg aaagacaggg    60

<210> SEQ ID NO 155
<211> LENGTH: 60
<212> TYPE: DNA
<213> ORGANISM: Homo sapiens

<400> SEQUENCE: 155
ggccatacgc catgccatag cttgtgctat ctgtaaatat gagacttgta aagaactgcc    60

<210> SEQ ID NO 156
<211> LENGTH: 60
<212> TYPE: DNA
<213> ORGANISM: Homo sapiens

<400> SEQUENCE: 156
aatattgctt cgatcatggt cttcaaagat gtaaatacaa gagaaccaaa gttattccgg    60

```
<210> SEQ ID NO 157
<211> LENGTH: 60
<212> TYPE: DNA
<213> ORGANISM: Homo sapiens

<400> SEQUENCE: 157
gacaatatta tgcaagtgtg gcaaatggca gagaacattt acaacaatga agaccctgaa    60

<210> SEQ ID NO 158
<211> LENGTH: 60
<212> TYPE: DNA
<213> ORGANISM: Homo sapiens

<400> SEQUENCE: 158
catgtaccct ggcatcacca acaggatgca gaagaagatc accgccctag cacccagcat    60

<210> SEQ ID NO 159
<211> LENGTH: 60
<212> TYPE: DNA
<213> ORGANISM: Homo sapiens

<400> SEQUENCE: 159
ggctttggcc agtagctaaa gtgcaagact gaattaatga gaagatatat taaatgtagt    60

<210> SEQ ID NO 160
<211> LENGTH: 60
<212> TYPE: DNA
<213> ORGANISM: Homo sapiens

<400> SEQUENCE: 160
aagaaatctt atcattcgcc atctaccctg tagaataaag aaatcttatc attcaccgtc    60

<210> SEQ ID NO 161
<211> LENGTH: 60
<212> TYPE: DNA
<213> ORGANISM: Homo sapiens

<400> SEQUENCE: 161
ttttctacag cttttgataa tcaagttaca atcaaggtct atgaaggtaa acaacccctg    60

<210> SEQ ID NO 162
<211> LENGTH: 60
<212> TYPE: DNA
<213> ORGANISM: Homo sapiens

<400> SEQUENCE: 162
ctggtctaca ctggttgccg aatttacttg tattcctaac tgttttgtat atgctgcatt    60

<210> SEQ ID NO 163
<211> LENGTH: 60
<212> TYPE: DNA
<213> ORGANISM: Homo sapiens

<400> SEQUENCE: 163
atgaaactac cttcaactcc atcatgaagt ctgatgtgga catccgcaaa gacctgtaca    60

<210> SEQ ID NO 164
<211> LENGTH: 60
<212> TYPE: DNA
<213> ORGANISM: Homo sapiens

<400> SEQUENCE: 164
catcctatac tgtgacttct tctacttgta cattacaaaa gtactcaagg gaaagaagct    60
```

<210> SEQ ID NO 165
<211> LENGTH: 60
<212> TYPE: DNA
<213> ORGANISM: Homo sapiens

<400> SEQUENCE: 165
atggggttca agagagtaat gggtttcata tttcttatca ccacagtaag ttcctactag    60

<210> SEQ ID NO 166
<211> LENGTH: 60
<212> TYPE: DNA
<213> ORGANISM: Homo sapiens

<400> SEQUENCE: 166
actgactact tcatgaagat cctcatggag tgcagctacc gtttcaccac catggctgag    60

<210> SEQ ID NO 167
<211> LENGTH: 60
<212> TYPE: DNA
<213> ORGANISM: Homo sapiens

<400> SEQUENCE: 167
tagtttttgc acggaagaca gaaagagatg aactcttaaa ggacttgcaa caaagcattg    60

<210> SEQ ID NO 168
<211> LENGTH: 60
<212> TYPE: DNA
<213> ORGANISM: Homo sapiens

<400> SEQUENCE: 168
atgccagatt ttcttggtat ctcccataat acgacctaca gtccatggtc tacagatgtt    60

<210> SEQ ID NO 169
<211> LENGTH: 60
<212> TYPE: DNA
<213> ORGANISM: Homo sapiens

<400> SEQUENCE: 169
caacttcaac taaaatggtt aatggcagaa aaatcactac aaagagaatt gtcgagaacg    60

<210> SEQ ID NO 170
<211> LENGTH: 60
<212> TYPE: DNA
<213> ORGANISM: Homo sapiens

<400> SEQUENCE: 170
gctctgtaat aacagtaata aatagctctg aaataacagt cctaagaact cctaaagtcc    60

<210> SEQ ID NO 171
<211> LENGTH: 60
<212> TYPE: DNA
<213> ORGANISM: Homo sapiens

<400> SEQUENCE: 171
gtgttaatcc atgttaatct gtgtgaaaat tattgcgtgc aacagtattt tctcgtgtac    60

<210> SEQ ID NO 172
<211> LENGTH: 60
<212> TYPE: DNA
<213> ORGANISM: Homo sapiens

<400> SEQUENCE: 172
gcaacaggag agaagctttt tggacccttat gtttggggaa ggtatgactt gctcttcatg    60

<210> SEQ ID NO 173
<211> LENGTH: 60
<212> TYPE: DNA
<213> ORGANISM: Homo sapiens

<400> SEQUENCE: 173
atcacaacta tgccaaataa tcaatcctac aatgtccaaa attttacttt aaaactggaa    60

<210> SEQ ID NO 174
<211> LENGTH: 60
<212> TYPE: DNA
<213> ORGANISM: Homo sapiens

<400> SEQUENCE: 174
agagtgcata aaattatcct tgatcttata tctgagtctc ctacagagga tgtgcacaga    60

<210> SEQ ID NO 175
<211> LENGTH: 60
<212> TYPE: DNA
<213> ORGANISM: Homo sapiens

<400> SEQUENCE: 175
tgaactatct gaaattgacc agtaatcaaa gttccaatca tctgaatgct tttccttgag    60

<210> SEQ ID NO 176
<211> LENGTH: 60
<212> TYPE: DNA
<213> ORGANISM: Homo sapiens

<400> SEQUENCE: 176
tgaaaatgaa aagtcttgat gtagtcagat ggttactctc ttaacattag gtattacccc    60

<210> SEQ ID NO 177
<211> LENGTH: 60
<212> TYPE: DNA
<213> ORGANISM: Homo sapiens

<400> SEQUENCE: 177
gttgctttat gtagcaaatt ctccgtttgg agcttttaaa ataggattat ttgccagaac    60

<210> SEQ ID NO 178
<211> LENGTH: 60
<212> TYPE: DNA
<213> ORGANISM: Homo sapiens

<400> SEQUENCE: 178
ggaaaagaca aagattctca ccactgaagg gtgtaatgca cttatccaca aatcatctgt    60

<210> SEQ ID NO 179
<211> LENGTH: 60
<212> TYPE: DNA
<213> ORGANISM: Homo sapiens

<400> SEQUENCE: 179
cccagggttt tgtaatacat aattgaaaat aaaagtccct gaaactaaat gtttgcagcc    60

<210> SEQ ID NO 180
<211> LENGTH: 60
<212> TYPE: DNA
<213> ORGANISM: Homo sapiens

<400> SEQUENCE: 180
aactaaaaag cattaattaa aaagtactta actcagaaat tataaaaata ggagacatca    60

<210> SEQ ID NO 181
<211> LENGTH: 60
<212> TYPE: DNA
<213> ORGANISM: Homo sapiens

<400> SEQUENCE: 181
ttgagtttga attgtgtaac atctttgatc agtgggtgta tctgtaatga aggaggttca    60

<210> SEQ ID NO 182
<211> LENGTH: 60
<212> TYPE: DNA
<213> ORGANISM: Homo sapiens

<400> SEQUENCE: 182
atagtgaagt ctgatgtgga catccgcaaa gacctgtaca ccaacacagt gctgtctggc    60

<210> SEQ ID NO 183
<211> LENGTH: 60
<212> TYPE: DNA
<213> ORGANISM: Homo sapiens

<400> SEQUENCE: 183
atgggaaaaa taaggataac tcagaatttc aaaaggaaat cacaaattca gctagtaata    60

<210> SEQ ID NO 184
<211> LENGTH: 60
<212> TYPE: DNA
<213> ORGANISM: Homo sapiens

<400> SEQUENCE: 184
gcagaagtac aagctttagg gtgtatctat tcatctattc ctagtacata aaatttagcc    60

<210> SEQ ID NO 185
<211> LENGTH: 60
<212> TYPE: DNA
<213> ORGANISM: Homo sapiens

<400> SEQUENCE: 185
tctctacatg gtattgtaat gaatatctgc tttaatatag ctatcatttc ttttccaaaa    60

<210> SEQ ID NO 186
<211> LENGTH: 60
<212> TYPE: DNA
<213> ORGANISM: Homo sapiens

<400> SEQUENCE: 186
ggtctgcaga ttaaacaaat ccgtcatgag tcgggagctt cgatcaaaat tgatgagcct    60

<210> SEQ ID NO 187
<211> LENGTH: 60
<212> TYPE: DNA
<213> ORGANISM: Homo sapiens

<400> SEQUENCE: 187
agacgctgga cgaagatggg gatggggagt gtgacttcca ggagtttatg gccttcgtct    60

<210> SEQ ID NO 188
<211> LENGTH: 60
<212> TYPE: DNA
<213> ORGANISM: Homo sapiens

<400> SEQUENCE: 188
tccatcaccg gatcagtttt tcctcttagg aaagctgcag gaacctcgtg ggctccaggg    60

<210> SEQ ID NO 189
<211> LENGTH: 60
<212> TYPE: DNA
<213> ORGANISM: Homo sapiens

<400> SEQUENCE: 189
caataagcag cattggcctg gagtgccaga gcgtcacctc caggggggac ctggctactt    60

<210> SEQ ID NO 190
<211> LENGTH: 60
<212> TYPE: DNA
<213> ORGANISM: Homo sapiens

<400> SEQUENCE: 190
gaaatagaga ttgtctgtag ttgattgaaa cgagggcagt tatgaattga tttgggcaat    60

<210> SEQ ID NO 191
<211> LENGTH: 60
<212> TYPE: DNA
<213> ORGANISM: Homo sapiens

<400> SEQUENCE: 191
tggacattcg aacagagttc aagaagcatt atggctattc cctatattca gcaattaaat    60

<210> SEQ ID NO 192
<211> LENGTH: 60
<212> TYPE: DNA
<213> ORGANISM: Homo sapiens

<400> SEQUENCE: 192
aaacatcatc aaaaggaca ttcagaacat gatcgtggag gagtgtgggt gctcatagag    60

<210> SEQ ID NO 193
<211> LENGTH: 60
<212> TYPE: DNA
<213> ORGANISM: Homo sapiens

<400> SEQUENCE: 193
aatggttttg tgcagtgaac aacacatggc gaggtactaa ctgagaaact ttttcatgct    60

<210> SEQ ID NO 194
<211> LENGTH: 60
<212> TYPE: DNA
<213> ORGANISM: Homo sapiens

<400> SEQUENCE: 194
gggccaccaa acagagaatc caggatcaga aggtgcccta catcttccgg gacaaccagt    60

<210> SEQ ID NO 195
<211> LENGTH: 60
<212> TYPE: DNA
<213> ORGANISM: Homo sapiens

<400> SEQUENCE: 195
aacggctacg accccgtaaa cttgctcaac gacatcgtga ttctccagct caacgggtcg    60

<210> SEQ ID NO 196
<211> LENGTH: 60
<212> TYPE: DNA
<213> ORGANISM: Homo sapiens

<400> SEQUENCE: 196
gactcagatt cagaaatgat ctaaacacga ggaaacatta ttcattggaa aagtgcatgg    60

<210> SEQ ID NO 197
<211> LENGTH: 60
<212> TYPE: DNA
<213> ORGANISM: Homo sapiens

<400> SEQUENCE: 197
tgtgactgac tcttcttctc ggggacacag gccagctcca cagtgttgcc agagccttaa    60

<210> SEQ ID NO 198
<211> LENGTH: 60
<212> TYPE: DNA
<213> ORGANISM: Homo sapiens

<400> SEQUENCE: 198
cctgttctgg gtgcagctga gaaaatgagt gactagacgt tcatttgtgt gctcatgtat    60

<210> SEQ ID NO 199
<211> LENGTH: 60
<212> TYPE: DNA
<213> ORGANISM: Homo sapiens

<400> SEQUENCE: 199
ggcgcgcgac aacaagaaga cgcgcatcat cccgcgccac ctgcagctgg ccatccgcaa    60

<210> SEQ ID NO 200
<211> LENGTH: 60
<212> TYPE: DNA
<213> ORGANISM: Homo sapiens

<400> SEQUENCE: 200
gtggtaaccc aaatatgacc tgtcctagta acaaaactcg caaaaattgt caccacagtg    60

<210> SEQ ID NO 201
<211> LENGTH: 60
<212> TYPE: DNA
<213> ORGANISM: Homo sapiens

<400> SEQUENCE: 201
aaacaagaga ctcaatggag acagaagaaa atcccaaggt tctaataact gcattctgaa    60

<210> SEQ ID NO 202
<211> LENGTH: 60
<212> TYPE: DNA
<213> ORGANISM: Homo sapiens

<400> SEQUENCE: 202
aatccttgtg accacaccga tggagataca gaaaaagtta acgactggat tctatcttca    60

<210> SEQ ID NO 203
<211> LENGTH: 60
<212> TYPE: DNA
<213> ORGANISM: Homo sapiens

<400> SEQUENCE: 203
agccacagct cagagactgg gaaacatggt tccaaaactg ttcacttccc aaatttgtct    60

<210> SEQ ID NO 204
<211> LENGTH: 60
<212> TYPE: DNA
<213> ORGANISM: Homo sapiens

<400> SEQUENCE: 204
atatttggga ccacagtatg tcgcaggcat tactaatctg aaaaagtgct caacctcccc    60

<210> SEQ ID NO 205
<211> LENGTH: 60
<212> TYPE: DNA
<213> ORGANISM: Homo sapiens

<400> SEQUENCE: 205
tgaggagctc aacaagcttc tgggcaaagt caccatcgca cagggtggcg tcctgcccaa    60

<210> SEQ ID NO 206
<211> LENGTH: 60
<212> TYPE: DNA
<213> ORGANISM: Homo sapiens

<400> SEQUENCE: 206
gctatggtgt tcttcaagaa agtttctcaa aacagggagt acttcaagat caccctctac    60

<210> SEQ ID NO 207
<211> LENGTH: 60
<212> TYPE: DNA
<213> ORGANISM: Homo sapiens

<400> SEQUENCE: 207
aactggctac tgagtcatga tccttgctga taaatataac catcaataaa gaagcattct    60

<210> SEQ ID NO 208
<211> LENGTH: 60
<212> TYPE: DNA
<213> ORGANISM: Homo sapiens

<400> SEQUENCE: 208
ctgtcaaatt gccacgatct cactaaagga tttctatttg ctgtcagtta aaataaagc     60

<210> SEQ ID NO 209
<211> LENGTH: 60
<212> TYPE: DNA
<213> ORGANISM: Homo sapiens

<400> SEQUENCE: 209
tggttgaagt cagcctacac tacagtgcac agttgaggag ccagagactt cttaaatcat    60

<210> SEQ ID NO 210
<211> LENGTH: 60
<212> TYPE: DNA
<213> ORGANISM: Homo sapiens

<400> SEQUENCE: 210
gataagatgt ggtttgaagc tgatgggtgc cagccctgca ttgctgagtc aatcaataaa    60

<210> SEQ ID NO 211
<211> LENGTH: 60
<212> TYPE: DNA
<213> ORGANISM: Homo sapiens

<400> SEQUENCE: 211
acactcatct gactcattct ttattctatt ttagttggtt tgtatcttgc ctaaggtgcg    60

<210> SEQ ID NO 212
<211> LENGTH: 60
<212> TYPE: DNA
<213> ORGANISM: Homo sapiens

<400> SEQUENCE: 212
gagctggtgc gaaaagatct gcaaaatttt ctcaagaagg agaataagaa tgaaaaggtc    60

<210> SEQ ID NO 213
<211> LENGTH: 60
<212> TYPE: DNA
<213> ORGANISM: Homo sapiens

<400> SEQUENCE: 213
catttaaccc acgcagagta ttctggcata agaatgaacc cgacaactct cagggagaaa    60

<210> SEQ ID NO 214
<211> LENGTH: 60
<212> TYPE: DNA
<213> ORGANISM: Homo sapiens

<400> SEQUENCE: 214
gaattgtcca gagaatcaag gatttttttgc ggaatcttgt acccaggaca gagtcctagt    60

<210> SEQ ID NO 215
<211> LENGTH: 60
<212> TYPE: DNA
<213> ORGANISM: Homo sapiens

<400> SEQUENCE: 215
aatattaacc taatcaccat gtaagcactc tggatgatgg attccacaaa acttggtttt    60

<210> SEQ ID NO 216
<211> LENGTH: 60
<212> TYPE: DNA
<213> ORGANISM: Homo sapiens

<400> SEQUENCE: 216
tgggattcta gattaatggg ggttgctact gtttaattca gtgacttgat cttttttaatg    60

<210> SEQ ID NO 217
<211> LENGTH: 60
<212> TYPE: DNA
<213> ORGANISM: Homo sapiens

<400> SEQUENCE: 217
tgtctaagtc acaaatctga agaaataaga gattgtctgt agttgattga aacgagggca    60

<210> SEQ ID NO 218
<211> LENGTH: 60
<212> TYPE: DNA
<213> ORGANISM: Homo sapiens

<400> SEQUENCE: 218
ccatgggact tttgtgagtc aggcgggaga ccattttatg tttattttct ttagtgtata    60

<210> SEQ ID NO 219
<211> LENGTH: 60
<212> TYPE: DNA
<213> ORGANISM: Homo sapiens

<400> SEQUENCE: 219
cgactttccc gatcgccagg caggagtttc tctcggtgac tactatcgct gtcatgtctg    60

<210> SEQ ID NO 220
<211> LENGTH: 60
<212> TYPE: DNA
<213> ORGANISM: Homo sapiens

<400> SEQUENCE: 220
ggctatggct tcggctatgg ctacaacggc tgtggggctt tcggctacag gagatactcg    60

```
<210> SEQ ID NO 221
<211> LENGTH: 60
<212> TYPE: DNA
<213> ORGANISM: Homo sapiens

<400> SEQUENCE: 221
gagaacgtcg ctatggaacc tgcatctacc agggaagact ctgggcattc tgctgctgag      60

<210> SEQ ID NO 222
<211> LENGTH: 60
<212> TYPE: DNA
<213> ORGANISM: Homo sapiens

<400> SEQUENCE: 222
agagctacag gaaatggttg tttctcctat actttgtcct taacatcttt cttgatccta      60

<210> SEQ ID NO 223
<211> LENGTH: 60
<212> TYPE: DNA
<213> ORGANISM: Homo sapiens

<400> SEQUENCE: 223
ctgtctccct gtttgtgtaa acatactaga gtatactgcg gcgtgttttc tgtctaccca      60

<210> SEQ ID NO 224
<211> LENGTH: 60
<212> TYPE: DNA
<213> ORGANISM: Homo sapiens

<400> SEQUENCE: 224
ctttctgctt gcaaagccta tagacccttc tcagagcggt cctcatggct gggttttctg      60

<210> SEQ ID NO 225
<211> LENGTH: 60
<212> TYPE: DNA
<213> ORGANISM: Homo sapiens

<400> SEQUENCE: 225
cctatgagga ttatgtcgaa ggacttcggg tgtttgacaa ggaaggaaat ggcaccgtca      60

<210> SEQ ID NO 226
<211> LENGTH: 60
<212> TYPE: DNA
<213> ORGANISM: Homo sapiens

<400> SEQUENCE: 226
ttgttcctaa atggtatttt caagtgtaat attgtgagaa cgctactgca gtagttgatg      60

<210> SEQ ID NO 227
<211> LENGTH: 60
<212> TYPE: DNA
<213> ORGANISM: Homo sapiens

<400> SEQUENCE: 227
accagactaa gtgccagtat atatatgact gatattttcg tgactcatag aaggtgtcca      60

<210> SEQ ID NO 228
<211> LENGTH: 60
<212> TYPE: DNA
<213> ORGANISM: Homo sapiens

<400> SEQUENCE: 228
tagtccaccc aatggctgac agtaacagca tctttaacac aactctttgt tcaaatgtac      60
```

<210> SEQ ID NO 229
<211> LENGTH: 60
<212> TYPE: DNA
<213> ORGANISM: Homo sapiens

<400> SEQUENCE: 229 aagggcatt tgtgagcttt gctgtaaatg gattcccagt gttgcttgta ctgtatgttt    60

<210> SEQ ID NO 230
<211> LENGTH: 60
<212> TYPE: DNA
<213> ORGANISM: Homo sapiens

<400> SEQUENCE: 230
taatatcccc aaacctgaga tgagcactac gatggcagag agcagcctgt tggacctgct    60

<210> SEQ ID NO 231
<211> LENGTH: 60
<212> TYPE: DNA
<213> ORGANISM: Homo sapiens

<400> SEQUENCE: 231
aaacaaatga gacttatgga aaattggaag ctgtgcagta taaaactcaa gttgttgctg    60

<210> SEQ ID NO 232
<211> LENGTH: 60
<212> TYPE: DNA
<213> ORGANISM: Homo sapiens

<400> SEQUENCE: 232
ggggacaaag tgacaacttt aaacttactg accatctgaa gtatgtcatg ctgcctgtgg    60

<210> SEQ ID NO 233
<211> LENGTH: 60
<212> TYPE: DNA
<213> ORGANISM: Homo sapiens

<400> SEQUENCE: 233
aaagccatga agaaagccac aaagagtagc tgagttactg ggcccagagg ctgggcccct    60

<210> SEQ ID NO 234
<211> LENGTH: 60
<212> TYPE: DNA
<213> ORGANISM: Homo sapiens

<400> SEQUENCE: 234
ggacaaaagg tgggtgaatt ttctggagcc aataaggaaa agcttgaagc caccattaat    60

<210> SEQ ID NO 235
<211> LENGTH: 60
<212> TYPE: DNA
<213> ORGANISM: Homo sapiens

<400> SEQUENCE: 235
tttagtgaac actgttctct gggtgacaat acgtaaagaa ctgaaaagaa agaaaaagtg    60

<210> SEQ ID NO 236
<211> LENGTH: 60
<212> TYPE: DNA
<213> ORGANISM: Homo sapiens

<400> SEQUENCE: 236
aagccttctt tttcactagg ccaggactac attgagagat gaagaatgga ggttgtttcc    60

<210> SEQ ID NO 237
<211> LENGTH: 60
<212> TYPE: DNA
<213> ORGANISM: Homo sapiens

<400> SEQUENCE: 237
tgaaggcttt ttacccagca atgtcctcaa tgagggtctt ttctttccct caccaaaacc    60

<210> SEQ ID NO 238
<211> LENGTH: 60
<212> TYPE: DNA
<213> ORGANISM: Homo sapiens

<400> SEQUENCE: 238
ctgcctcgac acacataaac cttttaaaa atagacactc cccgaagtct tttgtttgta    60

<210> SEQ ID NO 239
<211> LENGTH: 60
<212> TYPE: DNA
<213> ORGANISM: Homo sapiens

<400> SEQUENCE: 239
aacagtagaa agatcgtttg tcttgtgagc agacacttcc ttagagatgg ctggtgcctt    60

<210> SEQ ID NO 240
<211> LENGTH: 60
<212> TYPE: DNA
<213> ORGANISM: Homo sapiens

<400> SEQUENCE: 240
tgaagctatt tctgggagcc cagaagaaat gctcttttgc ttggagtttg tcatcctaca    60

<210> SEQ ID NO 241
<211> LENGTH: 60
<212> TYPE: DNA
<213> ORGANISM: Homo sapiens

<400> SEQUENCE: 241
ttgagggaaa gctacttgat caaacatccg atagtcacaa atttgaaacc gtgcttcaga    60

<210> SEQ ID NO 242
<211> LENGTH: 60
<212> TYPE: DNA
<213> ORGANISM: Homo sapiens

<400> SEQUENCE: 242
tagctagaac agttgaagtc ttcaactgag gttttatagc agattagaca tgggtaaatg    60

<210> SEQ ID NO 243
<211> LENGTH: 60
<212> TYPE: DNA
<213> ORGANISM: Homo sapiens

<400> SEQUENCE: 243
tttttccttt gatgttcaag tcctagtcta taggattggc agtttaaatg ctttactccc    60

<210> SEQ ID NO 244
<211> LENGTH: 60
<212> TYPE: DNA
<213> ORGANISM: Homo sapiens

<400> SEQUENCE: 244
cctgcaaaag caactggcac aaaggctgga attggacctc aggattaat gagtgtccgg    60

<210> SEQ ID NO 245
<211> LENGTH: 60
<212> TYPE: DNA
<213> ORGANISM: Homo sapiens

<400> SEQUENCE: 245
acaggaagct ctatgacaca cttgatcgaa tatgacagac accgaaaatc acgactcagc    60

<210> SEQ ID NO 246
<211> LENGTH: 60
<212> TYPE: DNA
<213> ORGANISM: Homo sapiens

<400> SEQUENCE: 246
tgcattgata gggacctttg tctcttcctc cctttgatta attgcccggc atcacagttt    60

<210> SEQ ID NO 247
<211> LENGTH: 60
<212> TYPE: DNA
<213> ORGANISM: Homo sapiens

<400> SEQUENCE: 247
ctgttagagc caaaattgtg atgagcaata ctgataattg tccagtttat gtcatctttc    60

<210> SEQ ID NO 248
<211> LENGTH: 60
<212> TYPE: DNA
<213> ORGANISM: Homo sapiens

<400> SEQUENCE: 248
caggaagctc tatgacacac ttgatcgaat atgacagaca ctgaaaatca cgactcatcc    60

<210> SEQ ID NO 249
<211> LENGTH: 60
<212> TYPE: DNA
<213> ORGANISM: Homo sapiens

<400> SEQUENCE: 249
ggaggagccc caccttctgc tactattatg ttcttcagat gagtagaaga gagtggggag    60

<210> SEQ ID NO 250
<211> LENGTH: 60
<212> TYPE: DNA
<213> ORGANISM: Homo sapiens

<400> SEQUENCE: 250
atctagcagg cgactgagtg ccgagaaaat acctggcaga ggtgggcaca aggcggggtc    60

<210> SEQ ID NO 251
<211> LENGTH: 60
<212> TYPE: DNA
<213> ORGANISM: Homo sapiens

<400> SEQUENCE: 251
cttggtaaag ttaccatcgc tcagggcggt gttctgccta acatccaggc cgtactgctc    60

<210> SEQ ID NO 252
<211> LENGTH: 60
<212> TYPE: DNA
<213> ORGANISM: Homo sapiens

<400> SEQUENCE: 252
cgtgggaggt gttgatgatg gtctctatgt tgcgttccag ctgcgacatt ttgcaagtca    60

<210> SEQ ID NO 253
<211> LENGTH: 60
<212> TYPE: DNA
<213> ORGANISM: Homo sapiens

<400> SEQUENCE: 253
cagtctcttc ctctctggga gctggctgga gctgggatgg acacctgaca gaaggaaatt    60

<210> SEQ ID NO 254
<211> LENGTH: 60
<212> TYPE: DNA
<213> ORGANISM: Homo sapiens

<400> SEQUENCE: 254
agcttggatg gtagcagaga cttcagggtg ctccagccaa acgtatttgg gcatcaccat    60

<210> SEQ ID NO 255
<211> LENGTH: 60
<212> TYPE: DNA
<213> ORGANISM: Homo sapiens

<400> SEQUENCE: 255
taccttttgc atatgctttt cttggcctta ggatagtact ggactttgtt gtcctctgct    60

<210> SEQ ID NO 256
<211> LENGTH: 60
<212> TYPE: DNA
<213> ORGANISM: Homo sapiens

<400> SEQUENCE: 256
caggaatcac gggagtgaat cacattccag acacttgctt ggacttcatc acatcctcag    60

<210> SEQ ID NO 257
<211> LENGTH: 60
<212> TYPE: DNA
<213> ORGANISM: Homo sapiens

<400> SEQUENCE: 257
agttacttgc ctccagatat cttggtgtgt gagaacatta aatctgtatg tgtctaaatc    60

<210> SEQ ID NO 258
<211> LENGTH: 60
<212> TYPE: DNA
<213> ORGANISM: Homo sapiens

<400> SEQUENCE: 258
gatctggaaa atacttgttt ggggatcaat aatatgtttg ggctattatc taatgctgtg    60

<210> SEQ ID NO 259
<211> LENGTH: 60
<212> TYPE: DNA
<213> ORGANISM: Homo sapiens

<400> SEQUENCE: 259
ttcacgtcaa cttctggctc ctcagtttgg cagtaaggca gggaagttgt tttcctattt    60

<210> SEQ ID NO 260
<211> LENGTH: 60
<212> TYPE: DNA
<213> ORGANISM: Homo sapiens

<400> SEQUENCE: 260
attggatagg aagaggaata aaatataaaa atcagagaac tgctgaaatt ctgtgacccc    60

```
<210> SEQ ID NO 261
<211> LENGTH: 60
<212> TYPE: DNA
<213> ORGANISM: Homo sapiens

<400> SEQUENCE: 261
ggagagaaca catggtacaa tcgtaacaca tgaaggacaa gtaagtgctg cagtaaaggt    60

<210> SEQ ID NO 262
<211> LENGTH: 60
<212> TYPE: DNA
<213> ORGANISM: Homo sapiens

<400> SEQUENCE: 262
tgaggtaggt gcggtattaa agtgaaaggg aaggtgatgc atttattctg ggttatgctt    60

<210> SEQ ID NO 263
<211> LENGTH: 60
<212> TYPE: DNA
<213> ORGANISM: Homo sapiens

<400> SEQUENCE: 263 actttttgcta agatctgggg gtttcttcat attcctgctg ttggaagcag ttgaccagaa    60

<210> SEQ ID NO 264
<211> LENGTH: 60
<212> TYPE: DNA
<213> ORGANISM: Homo sapiens

<400> SEQUENCE: 264
atttggggac aaaaaggcag gcttcatttt tcatatgttt gatgaaaact ggctcaagat    60

<210> SEQ ID NO 265
<211> LENGTH: 60
<212> TYPE: DNA
<213> ORGANISM: Homo sapiens

<400> SEQUENCE: 265
tgtagtatcc atatgttgct taaatttcct tatgagcccc atgatggaaa gacttaaaga    60

<210> SEQ ID NO 266
<211> LENGTH: 60
<212> TYPE: DNA
<213> ORGANISM: Homo sapiens

<400> SEQUENCE: 266
ctactagctc tttgagataa tacattccga ggggctcagt tctgccttat ctaaatcacc    60

<210> SEQ ID NO 267
<211> LENGTH: 60
<212> TYPE: DNA
<213> ORGANISM: Homo sapiens

<400> SEQUENCE: 267
catgccattt caaggacttg ggaatagatt agggatatcc gtacttcatt acagtcatga    60

<210> SEQ ID NO 268
<211> LENGTH: 60
<212> TYPE: DNA
<213> ORGANISM: Homo sapiens

<400> SEQUENCE: 268
tctttagtga atatcatctg catatctctg taagttcaat tgtgtttctt acagtccctg    60
```

<210> SEQ ID NO 269
<211> LENGTH: 60
<212> TYPE: DNA
<213> ORGANISM: Homo sapiens

<400> SEQUENCE: 269
agaatgcctg gttttcgttt gcaatttgct tgtgtaaatc aggttgtaaa aaggcagata    60

<210> SEQ ID NO 270
<211> LENGTH: 60
<212> TYPE: DNA
<213> ORGANISM: Homo sapiens

<400> SEQUENCE: 270
ggatagtaaa acttgagaag cttttggggt cagatctctg aacatcatg tgatgaagct    60

<210> SEQ ID NO 271
<211> LENGTH: 60
<212> TYPE: DNA
<213> ORGANISM: Homo sapiens

<400> SEQUENCE: 271
agagcaagag cagtatgaaa gtaccatcgg attcaaactt cccagttacc gagcagctaa    60

<210> SEQ ID NO 272
<211> LENGTH: 60
<212> TYPE: DNA
<213> ORGANISM: Homo sapiens

<400> SEQUENCE: 272
gtccaactac taaactgggg gatattatga agggccttga gcatctggat tctgcctaat    60

<210> SEQ ID NO 273
<211> LENGTH: 60
<212> TYPE: DNA
<213> ORGANISM: Homo sapiens

<400> SEQUENCE: 273
agaaaatgtt gtgctgtatg ttcttgattt gacataaatg aatagacttt ggcaagggag    60

<210> SEQ ID NO 274
<211> LENGTH: 60
<212> TYPE: DNA
<213> ORGANISM: Homo sapiens

<400> SEQUENCE: 274
acggtaacat catgcctatg gacattaaag gaatagcaag gacttgctcc cacgacttca    60

<210> SEQ ID NO 275
<211> LENGTH: 60
<212> TYPE: DNA
<213> ORGANISM: Homo sapiens

<400> SEQUENCE: 275
ggacccggga cggtgggcac tggactcggg gggactgcag aggatccagg tgtgatagcc    60

<210> SEQ ID NO 276
<211> LENGTH: 60
<212> TYPE: DNA
<213> ORGANISM: Homo sapiens

<400> SEQUENCE: 276
gtattaaaaa ttaaccccc ataaacccaa cctaagccta tggaatccac agtcacaaaa    60

<210> SEQ ID NO 277
<211> LENGTH: 60
<212> TYPE: DNA
<213> ORGANISM: Homo sapiens

<400> SEQUENCE: 277
ggggctttac aatcctaagg ttggcgttgt aatgaagttc acttggttca aggtttcttt    60

<210> SEQ ID NO 278
<211> LENGTH: 60
<212> TYPE: DNA
<213> ORGANISM: Homo sapiens

<400> SEQUENCE: 278
gctttcgttg actgcttctc tgcagtcgtt gatgctaata atattgtcc tgtttcttca    60

<210> SEQ ID NO 279
<211> LENGTH: 60
<212> TYPE: DNA
<213> ORGANISM: Homo sapiens

<400> SEQUENCE: 279
ctttagtggg tagaacaaat ggaaatttgg tttcagaatg gctgacagaa atcgacataa    60

<210> SEQ ID NO 280
<211> LENGTH: 60
<212> TYPE: DNA
<213> ORGANISM: Homo sapiens

<400> SEQUENCE: 280
tttagcatct gacaggtgtt tacaaaaaag tggttgtcgc actgggaagt ggagtgatgg    60

<210> SEQ ID NO 281
<211> LENGTH: 60
<212> TYPE: DNA
<213> ORGANISM: Homo sapiens

<400> SEQUENCE: 281
aacacctgtt tgtgacagtg agttgaaata tgcattccta tttcttttac cgatacattc    60

<210> SEQ ID NO 282
<211> LENGTH: 60
<212> TYPE: DNA
<213> ORGANISM: Homo sapiens

<400> SEQUENCE: 282
cggagaaatg gaaacatatc actcaagggg gatgctgtgg aaacctggct tattcttcta    60

<210> SEQ ID NO 283
<211> LENGTH: 60
<212> TYPE: DNA
<213> ORGANISM: Homo sapiens

<400> SEQUENCE: 283
atttgtgtct tactaaagca gcttattgta ggtgttggcg ttctaaaacg tttcctgcct    60

<210> SEQ ID NO 284
<211> LENGTH: 60
<212> TYPE: DNA
<213> ORGANISM: Homo sapiens

<400> SEQUENCE: 284
tagtagaatt cctctttggc cacaagaata agcagcaaat aaacaactat ggctgttgag    60

<210> SEQ ID NO 285
<211> LENGTH: 60
<212> TYPE: DNA
<213> ORGANISM: Homo sapiens

<400> SEQUENCE: 285
gggtgttaga acctagattc aaaatggctt gtctttgcta cttttgttcc acattctctc     60

<210> SEQ ID NO 286
<211> LENGTH: 60
<212> TYPE: DNA
<213> ORGANISM: Homo sapiens

<400> SEQUENCE: 286
atgatactaa cacggtgtag gttttacagt ctcctaattt gtactggtaa tgcatattcc     60

<210> SEQ ID NO 287
<211> LENGTH: 60
<212> TYPE: DNA
<213> ORGANISM: Homo sapiens

<400> SEQUENCE: 287
aaggtatttt tccttttccc tcttactgga ttttttcaatt ttcaaaccat atggcctagg    60

<210> SEQ ID NO 288
<211> LENGTH: 60
<212> TYPE: DNA
<213> ORGANISM: Homo sapiens

<400> SEQUENCE: 288
ctagggatct aattaaggac attaaagtac aattcttgag ctactaacca tcagctcttc     60

<210> SEQ ID NO 289
<211> LENGTH: 60
<212> TYPE: DNA
<213> ORGANISM: Homo sapiens

<400> SEQUENCE: 289
tttcagtcgt tgtgcttttt tgttttgtgc taacgtctta ctaatttaaa gatgctgtcg     60

<210> SEQ ID NO 290
<211> LENGTH: 60
<212> TYPE: DNA
<213> ORGANISM: Homo sapiens

<400> SEQUENCE: 290
aaacagaaac agtctcaact tcaaaactta ttctacagca aattgccttc aagaacctgg     60

<210> SEQ ID NO 291
<211> LENGTH: 60
<212> TYPE: DNA
<213> ORGANISM: Homo sapiens

<400> SEQUENCE: 291
tatacctttt cacattaaaa aaggtattta tattattact ttgtagtgat tgtcttaaga     60

<210> SEQ ID NO 292
<211> LENGTH: 60
<212> TYPE: DNA
<213> ORGANISM: Homo sapiens

<400> SEQUENCE: 292
tctcagaaga cagagggttt tcttttgagg taaatttgat agtacatttt gatagtacgg     60

<210> SEQ ID NO 293
<211> LENGTH: 60
<212> TYPE: DNA
<213> ORGANISM: Homo sapiens

<400> SEQUENCE: 293
ggcggaaaac aagtttagtc acagaagact actccatgtt tgagcttctg tttcaaggga      60

<210> SEQ ID NO 294
<211> LENGTH: 60
<212> TYPE: DNA
<213> ORGANISM: Homo sapiens

<400> SEQUENCE: 294
gtctataaca aacagtctgt tcatttattt ctgttgataa accatttgga cagagtgagg      60

<210> SEQ ID NO 295
<211> LENGTH: 60
<212> TYPE: DNA
<213> ORGANISM: Homo sapiens

<400> SEQUENCE: 295
gaactcagat ttgcaaacca ggtttctgaa actttgggta aggtgtatgc ttttaacttt      60

<210> SEQ ID NO 296
<211> LENGTH: 60
<212> TYPE: DNA
<213> ORGANISM: Homo sapiens

<400> SEQUENCE: 296
cgttgcctgt cttgctggat aactgcatat attgtgttca gttgtgtatt tgttttgctt      60

<210> SEQ ID NO 297
<211> LENGTH: 60
<212> TYPE: DNA
<213> ORGANISM: Homo sapiens

<400> SEQUENCE: 297
gaataaacag aaatagggaa gtaaacctac aaatatttta gggagaagct cacttcttcc      60

<210> SEQ ID NO 298
<211> LENGTH: 60
<212> TYPE: DNA
<213> ORGANISM: Homo sapiens

<400> SEQUENCE: 298
ttcacatgca agttctaatc taaagttaag cagtctctta tttgtttcgg gactctgatt      60

<210> SEQ ID NO 299
<211> LENGTH: 60
<212> TYPE: DNA
<213> ORGANISM: Homo sapiens

<400> SEQUENCE: 299
tgtggtttgg tattccaagt ggggtctttt tcagaatctc tgcactagtg tgagatgcaa      60

<210> SEQ ID NO 300
<211> LENGTH: 60
<212> TYPE: DNA
<213> ORGANISM: Homo sapiens

<400> SEQUENCE: 300
ggcatgctgt cccaggaaac tagggctccc actaacttat gaggttttta aacacattga      60

```
<210> SEQ ID NO 301
<211> LENGTH: 60
<212> TYPE: DNA
<213> ORGANISM: Homo sapiens

<400> SEQUENCE: 301
gaaagttcac atacagggga aagtgtacga tttcatctac tgtttatctt ctaacctcac      60

<210> SEQ ID NO 302
<211> LENGTH: 60
<212> TYPE: DNA
<213> ORGANISM: Homo sapiens

<400> SEQUENCE: 302
cttccattcc atttagcctt tggatcatcc tggctgggag aagtgggacc gagccaccca      60

<210> SEQ ID NO 303
<211> LENGTH: 60
<212> TYPE: DNA
<213> ORGANISM: Homo sapiens

<400> SEQUENCE: 303
gagtggtgtc tagatttcta atgaagaatc atgatacagt ttggattaag tatcttggac      60

<210> SEQ ID NO 304
<211> LENGTH: 60
<212> TYPE: DNA
<213> ORGANISM: Homo sapiens

<400> SEQUENCE: 304
gaggggtatt tagggccact gtattttgg tgccacaatt ttctacattg ttggcatttt       60

<210> SEQ ID NO 305
<211> LENGTH: 60
<212> TYPE: DNA
<213> ORGANISM: Homo sapiens

<400> SEQUENCE: 305
tccaggtgcc tttaatgtac tgtaacctca caactccaag tccacagaat atttcaaact     60

<210> SEQ ID NO 306
<211> LENGTH: 60
<212> TYPE: DNA
<213> ORGANISM: Homo sapiens

<400> SEQUENCE: 306
cagtcaagct gtggatgaaa tgaccaggaa cggagaatga agtatgtaaa tcccagcttc     60

<210> SEQ ID NO 307
<211> LENGTH: 60
<212> TYPE: DNA
<213> ORGANISM: Homo sapiens

<400> SEQUENCE: 307
ttgccagcat tttttgaagt aatacactgc tgctacctgg aagatgtcta acttcatttt     60

<210> SEQ ID NO 308
<211> LENGTH: 60
<212> TYPE: DNA
<213> ORGANISM: Homo sapiens

<400> SEQUENCE: 308
tagtgctgta gtgcttgttt atgtttaaaa gtgcacatta tgcagctcat tttagtatgc     60
```

```
<210> SEQ ID NO 309
<211> LENGTH: 60
<212> TYPE: DNA
<213> ORGANISM: Homo sapiens

<400> SEQUENCE: 309
gggtgggaaa gcataagatg gggactaaga ctttgccttt aaccttcatg acatgaagaa      60

<210> SEQ ID NO 310
<211> LENGTH: 60
<212> TYPE: DNA
<213> ORGANISM: Homo sapiens

<400> SEQUENCE: 310
gatgaagaat ttgccttact ttgttgttcg ctcagttcct aagactgtga gttgtcaaat      60

<210> SEQ ID NO 311
<211> LENGTH: 60
<212> TYPE: DNA
<213> ORGANISM: Homo sapiens

<400> SEQUENCE: 311
caggtaagga tgggaatatt ttgttatact gtgtatagtg aatgtattgt actgtgtctg      60

<210> SEQ ID NO 312
<211> LENGTH: 60
<212> TYPE: DNA
<213> ORGANISM: Homo sapiens

<400> SEQUENCE: 312
ttcctatgga cttttgcatt atttcattgt gcatgcatcc agtgattata cataagcaac      60

<210> SEQ ID NO 313
<211> LENGTH: 60
<212> TYPE: DNA
<213> ORGANISM: Homo sapiens

<400> SEQUENCE: 313
cgagagctgc gtgaccgagc ccgagtgccg cgagggcttt caccgccgcg cccgcgccag      60

<210> SEQ ID NO 314
<211> LENGTH: 60
<212> TYPE: DNA
<213> ORGANISM: Homo sapiens

<400> SEQUENCE: 314
tgccaggaca acctttctcc cagatgtaaa cagagagaca tgtacaaacc tggattttt       60

<210> SEQ ID NO 315
<211> LENGTH: 60
<212> TYPE: DNA
<213> ORGANISM: Homo sapiens

<400> SEQUENCE: 315
agctatgaca acagcaagag ttggcggcgg cgctcgtgct ggaggaaatg gaagcaactg      60

<210> SEQ ID NO 316
<211> LENGTH: 60
<212> TYPE: DNA
<213> ORGANISM: Homo sapiens

<400> SEQUENCE: 316
agcctatgga tggatggact tcggccgccg cagtgctgag gatgagaact aacaatccta      60
```

<210> SEQ ID NO 317
<211> LENGTH: 60
<212> TYPE: DNA
<213> ORGANISM: Homo sapiens

<400> SEQUENCE: 317
ccgtggcctc gtgctccgca gggcgcccag cgccgtccgg cggccccgcc gcagaccagc    60

<210> SEQ ID NO 318
<211> LENGTH: 60
<212> TYPE: DNA
<213> ORGANISM: Homo sapiens

<400> SEQUENCE: 318
gggtctccga ggtgccggtt aggagtttga acccccccca ctctgcagag ggaagcgggg    60

<210> SEQ ID NO 319
<211> LENGTH: 60
<212> TYPE: DNA
<213> ORGANISM: Homo sapiens

<400> SEQUENCE: 319
tgtagatact gtagatactg tagataccgc cccggcgccg acttgataaa cggtttcgcc    60

<210> SEQ ID NO 320
<211> LENGTH: 60
<212> TYPE: DNA
<213> ORGANISM: Homo sapiens

<400> SEQUENCE: 320
cgagacgtgt tgccccgggc ccgggtgtcg cgccagccca gaccccccgg ccccgccgac    60

<210> SEQ ID NO 321
<211> LENGTH: 60
<212> TYPE: DNA
<213> ORGANISM: Homo sapiens

<400> SEQUENCE: 321
gccgacgcgc cgaccgcgcg ctcgaacggt gagtgcggcc gtggcggccc ggggccggtg    60

<210> SEQ ID NO 322
<211> LENGTH: 60
<212> TYPE: DNA
<213> ORGANISM: Homo sapiens

<400> SEQUENCE: 322
cccgcgcgga cccggcgaga ggcggcggcg ggagcggcgg tgatggacgg gtccggggag    60

<210> SEQ ID NO 323
<211> LENGTH: 60
<212> TYPE: DNA
<213> ORGANISM: Homo sapiens

<400> SEQUENCE: 323
cattcaaaga atactagaat ggtagcacta cccggccgga gccgcccacc gtcttgggtc    60

<210> SEQ ID NO 324
<211> LENGTH: 60
<212> TYPE: DNA
<213> ORGANISM: Homo sapiens

<400> SEQUENCE: 324
gcagcgactc agagaacgtc tacgaggtca tccaggactt gcacgtcccg ccgccggagg    60

```
<210> SEQ ID NO 325
<211> LENGTH: 60
<212> TYPE: DNA
<213> ORGANISM: Homo sapiens

<400> SEQUENCE: 325
ccccaaacca gacaagttat acggggacaa atccggcagc agccgccgca atttgaagat      60

<210> SEQ ID NO 326
<211> LENGTH: 60
<212> TYPE: DNA
<213> ORGANISM: Homo sapiens

<400> SEQUENCE: 326
cagggtgcag gcgcgcaccg cccaaccccc acctcccggt gtatgcagtg gtgatgccta      60

<210> SEQ ID NO 327
<211> LENGTH: 60
<212> TYPE: DNA
<213> ORGANISM: Homo sapiens

<400> SEQUENCE: 327
cagcgccgct gcagctggcc gtgcgccctc accaccgccg ccaggctccg aggccgcgcc      60

<210> SEQ ID NO 328
<211> LENGTH: 60
<212> TYPE: DNA
<213> ORGANISM: Homo sapiens

<400> SEQUENCE: 328
gctgggctct ctggtgaagt cggagcccag cggcagcccg cccgcccag cgcactcgcg       60

<210> SEQ ID NO 329
<211> LENGTH: 60
<212> TYPE: DNA
<213> ORGANISM: Homo sapiens

<400> SEQUENCE: 329
gccgcccgcc atcgcatcgc actctcagcg cgcgtgcctc ggcgacctgc gcgacatgat      60

<210> SEQ ID NO 330
<211> LENGTH: 60
<212> TYPE: DNA
<213> ORGANISM: Homo sapiens

<400> SEQUENCE: 330
gtgagaagtt ctgcagatgt atgtggcgca cagcctctac agccgccgac tccgactcct      60

<210> SEQ ID NO 331
<211> LENGTH: 60
<212> TYPE: DNA
<213> ORGANISM: Homo sapiens

<400> SEQUENCE: 331
cttcaagcac taccgctgcc gccagtgcga caagagcttc gcgctcaagt cctacctcca      60

<210> SEQ ID NO 332
<211> LENGTH: 60
<212> TYPE: DNA
<213> ORGANISM: Homo sapiens

<400> SEQUENCE: 332
gttcgaggtg aagaaggagc ctcccgaggc cgagcgcttc tgccaccgcc tgccgccagg      60
```

```
<210> SEQ ID NO 333
<211> LENGTH: 60
<212> TYPE: DNA
<213> ORGANISM: Homo sapiens

<400> SEQUENCE: 333
cagactgaac tccttctgga cctggtggct gaagcccagt cccgccgcct ggaggagcag       60

<210> SEQ ID NO 334
<211> LENGTH: 60
<212> TYPE: DNA
<213> ORGANISM: Homo sapiens

<400> SEQUENCE: 334
gcgaggtggg aaccgccgcg gcccaggaga agtgcggcgc ccctccagcc gccgcctgcc       60

<210> SEQ ID NO 335
<211> LENGTH: 60
<212> TYPE: DNA
<213> ORGANISM: Homo sapiens

<400> SEQUENCE: 335
ccgggccgcc ccccaggatg agctgggggg taggggcagc agcagcagcg aaagccagaa       60

<210> SEQ ID NO 336
<211> LENGTH: 60
<212> TYPE: DNA
<213> ORGANISM: Homo sapiens

<400> SEQUENCE: 336
gaggggtgcc agcccctggt gtcctcagct gtggatcgca gagctccagc gggcaggcgt       60

<210> SEQ ID NO 337
<211> LENGTH: 60
<212> TYPE: DNA
<213> ORGANISM: Homo sapiens

<400> SEQUENCE: 337
tcaggagtcc aggaagagca ggagccgccc ccgcgctcct acggagtcgg caatgcaga        60

<210> SEQ ID NO 338
<211> LENGTH: 60
<212> TYPE: DNA
<213> ORGANISM: Homo sapiens

<400> SEQUENCE: 338
acggagcctc gggctacggt cccgccggct cacttgcccc gctgccggc agctccggag        60

<210> SEQ ID NO 339
<211> LENGTH: 60
<212> TYPE: DNA
<213> ORGANISM: Homo sapiens

<400> SEQUENCE: 339
aacagcaatg gtgccgccgc cggacgggac tttaagatga agttatggga tgtcgtggct       60

<210> SEQ ID NO 340
<211> LENGTH: 60
<212> TYPE: DNA
<213> ORGANISM: Homo sapiens

<400> SEQUENCE: 340
ttatttgaac aagggtcccc cgccatcatg cagcctccaa ggtgccaaga ggactcccta       60
```

```
<210> SEQ ID NO 341
<211> LENGTH: 60
<212> TYPE: DNA
<213> ORGANISM: Homo sapiens

<400> SEQUENCE: 341 aggggcgcg gccggggagg atggagacct ggggctgggc tccgccaggg cgtgcctggc      60

<210> SEQ ID NO 342
<211> LENGTH: 60
<212> TYPE: DNA
<213> ORGANISM: Homo sapiens

<400> SEQUENCE: 342
caagctggcc acgcaccgct tagcacacgg aggcgcccga ccccacccat gcccagactg      60

<210> SEQ ID NO 343
<211> LENGTH: 60
<212> TYPE: DNA
<213> ORGANISM: Homo sapiens

<400> SEQUENCE: 343
tgcaggtttt tgccccgcc gttgcggctg ttttcccccc gtcagcgagg cttttgttg       60

<210> SEQ ID NO 344
<211> LENGTH: 60
<212> TYPE: DNA
<213> ORGANISM: Homo sapiens

<400> SEQUENCE: 344
aggaggcccg ccctccacgc gccgaaggcc tcaataaacg gagctggcgc tgcgggtccg      60

<210> SEQ ID NO 345
<211> LENGTH: 60
<212> TYPE: DNA
<213> ORGANISM: Homo sapiens

<400> SEQUENCE: 345 ggggtttcc ccccgggag gacccccct ggggggccccc ctgtttgtta cacggcgggt      60

<210> SEQ ID NO 346
<211> LENGTH: 60
<212> TYPE: DNA
<213> ORGANISM: Homo sapiens

<400> SEQUENCE: 346
tcagcggcta cgcggtgcgg tacttgaagc ccgacgtgac ccagacctgg cggtactgcc      60

<210> SEQ ID NO 347
<211> LENGTH: 60
<212> TYPE: DNA
<213> ORGANISM: Homo sapiens

<400> SEQUENCE: 347
aggcagccgc cgggccaggt cgaggccgcc gccgcccggc cagagcacgc cagggagcag      60

<210> SEQ ID NO 348
<211> LENGTH: 60
<212> TYPE: DNA
<213> ORGANISM: Homo sapiens

<400> SEQUENCE: 348
caagtggaaa aaaatattaa aaaactgata atggcctcgg ttggcctcag cggcggaact      60
```

```
<210> SEQ ID NO 349
<211> LENGTH: 60
<212> TYPE: DNA
<213> ORGANISM: Homo sapiens

<400> SEQUENCE: 349
tgcggctccg ctgccggtag cgccgtcccc cgggaccacc cttcggctgg cgccctccca      60

<210> SEQ ID NO 350
<211> LENGTH: 60
<212> TYPE: DNA
<213> ORGANISM: Homo sapiens

<400> SEQUENCE: 350
agccccaagg gcgaggtcct cagtgagcac cggatcccac gccgcgagac tccggccccg      60

<210> SEQ ID NO 351
<211> LENGTH: 60
<212> TYPE: DNA
<213> ORGANISM: Homo sapiens

<400> SEQUENCE: 351
ccccgcctgg ccttggctgc gctccggaat tcttgggtcg aagaagcagg gatggacgag      60

<210> SEQ ID NO 352
<211> LENGTH: 60
<212> TYPE: DNA
<213> ORGANISM: Homo sapiens

<400> SEQUENCE: 352
atgcatgagg ctctgcacaa ccactacacg cagaagagcc tctccctgtc tccgggtaaa      60

<210> SEQ ID NO 353
<211> LENGTH: 60
<212> TYPE: DNA
<213> ORGANISM: Homo sapiens

<400> SEQUENCE: 353
acaccttcta cggtatggac gtctggggcc aagggaccac ggtcaccgtc tcctcagcat      60

<210> SEQ ID NO 354
<211> LENGTH: 60
<212> TYPE: DNA
<213> ORGANISM: Homo sapiens

<400> SEQUENCE: 354
atacgcaagg ggatgtggat acttggccca aagtaactgg tggtaggaat cttagaaaca      60

<210> SEQ ID NO 355
<211> LENGTH: 60
<212> TYPE: DNA
<213> ORGANISM: Homo sapiens

<400> SEQUENCE: 355
taggagacag agtcaccatc acttgccggg caagtcagac cattagcagc tatttaaatt      60

<210> SEQ ID NO 356
<211> LENGTH: 60
<212> TYPE: DNA
<213> ORGANISM: Homo sapiens

<400> SEQUENCE: 356
gcagcctgca gcctgaagat attgcaacat attactgtca acagtatgat aatctccctc      60
```

```
<210> SEQ ID NO 357
<211> LENGTH: 60
<212> TYPE: DNA
<213> ORGANISM: Homo sapiens

<400> SEQUENCE: 357
tcagggtatt agcagctggt tagcctggta tcagcagaaa ccagagaaag cccctaagtc      60

<210> SEQ ID NO 358
<211> LENGTH: 60
<212> TYPE: DNA
<213> ORGANISM: Homo sapiens

<400> SEQUENCE: 358
agacagcact ggttcttatt tgctgttcgg cggagggacc aagctgaccg tcctaggtca      60

<210> SEQ ID NO 359
<211> LENGTH: 60
<212> TYPE: DNA
<213> ORGANISM: Homo sapiens

<400> SEQUENCE: 359
agctcctgat ctacgatgca tccactttgg aaaccggggt cccatcaagg ttcagtgcac      60

<210> SEQ ID NO 360
<211> LENGTH: 60
<212> TYPE: DNA
<213> ORGANISM: Homo sapiens

<400> SEQUENCE: 360
gagttgaaga ccccactaac cgccaacatc acaaaatccg gaaacacatt ccggcccgag      60

<210> SEQ ID NO 361
<211> LENGTH: 60
<212> TYPE: DNA
<213> ORGANISM: Homo sapiens

<400> SEQUENCE: 361
gcctgaagat cttgcagtat attactgtca gcagtatagt agtccacctc ggacttttgg      60

<210> SEQ ID NO 362
<211> LENGTH: 60
<212> TYPE: DNA
<213> ORGANISM: Homo sapiens

<400> SEQUENCE: 362
agatggtgca gccacagttc gtttgatctc cagctcgagc cgctgcgtgt tttcctcttg      60

<210> SEQ ID NO 363
<211> LENGTH: 60
<212> TYPE: DNA
<213> ORGANISM: Homo sapiens

<400> SEQUENCE: 363
ggacatgttt gcactacttg ggggagtttg gagaagacca gatctatgaa gcccaccaac      60

<210> SEQ ID NO 364
<211> LENGTH: 60
<212> TYPE: DNA
<213> ORGANISM: Homo sapiens

<400> SEQUENCE: 364
atggtatgat ggaagtaata aatactatgc agactccgtg aagggccgat tcaccatctc      60
```

<210> SEQ ID NO 365
<211> LENGTH: 60
<212> TYPE: DNA
<213> ORGANISM: Homo sapiens

<400> SEQUENCE: 365
gtggcacata ctatgcagac tccgtgaagg gccgattcac catctccaga gacaatgcca      60

<210> SEQ ID NO 366
<211> LENGTH: 60
<212> TYPE: DNA
<213> ORGANISM: Homo sapiens

<400> SEQUENCE: 366
gccaagaaca cgctgtatct gcaaatgaac agtctgagag ccgaggacac ggctgtgtat      60

<210> SEQ ID NO 367
<211> LENGTH: 60
<212> TYPE: DNA
<213> ORGANISM: Homo sapiens

<400> SEQUENCE: 367
gcagggtgga ggctgaggat gttggggttt attactgcat gcaaggtaca cactggcctc      60

<210> SEQ ID NO 368
<211> LENGTH: 60
<212> TYPE: DNA
<213> ORGANISM: Homo sapiens

<400> SEQUENCE: 368
catagttata accaccaacg tcactgctgg ttccagtgca ggagatggtg atcgactgtc      60

<210> SEQ ID NO 369
<211> LENGTH: 60
<212> TYPE: DNA
<213> ORGANISM: Homo sapiens

<400> SEQUENCE: 369
gtaaacccac ccacatcaat gtgtctgttg tcatggcgga ggcggatggc acctgctact      60

<210> SEQ ID NO 370
<211> LENGTH: 60
<212> TYPE: DNA
<213> ORGANISM: Homo sapiens

<400> SEQUENCE: 370
agcctgatgc ctgaacagtg gagatcccgc agcagctaca actgctgggc catgcataaa      60

<210> SEQ ID NO 371
<211> LENGTH: 60
<212> TYPE: DNA
<213> ORGANISM: Homo sapiens

<400> SEQUENCE: 371
gaggatgagg ctgattatta ctgtgcagca tgggatgaca gcctgagtgg tcccacagtg      60

<210> SEQ ID NO 372
<211> LENGTH: 60
<212> TYPE: DNA
<213> ORGANISM: Homo sapiens

<400> SEQUENCE: 372
tgatctatgc tgcatccagt ttgcagtcgg gggtcccatc tcggttcagt ggcagtggat      60

<210> SEQ ID NO 373
<211> LENGTH: 60
<212> TYPE: DNA
<213> ORGANISM: Homo sapiens

<400> SEQUENCE: 373
aacaaggcca cactggtgtg tctcatgaat gacttctatc tgggaatctt gacggtgacc    60

<210> SEQ ID NO 374
<211> LENGTH: 60
<212> TYPE: DNA
<213> ORGANISM: Homo sapiens

<400> SEQUENCE: 374
cacaagccca gcaacaccaa ggtggacaag agagttgagt ccaaatatgg tcccccatgc    60

<210> SEQ ID NO 375
<211> LENGTH: 60
<212> TYPE: DNA
<213> ORGANISM: Homo sapiens

<400> SEQUENCE: 375
tcactatcag cagcctgcag cctgaagatt ttgcaactta ctattgtcaa caggctaaca    60

<210> SEQ ID NO 376
<211> LENGTH: 60
<212> TYPE: DNA
<213> ORGANISM: Homo sapiens

<400> SEQUENCE: 376
atcagtagac acgtccaaga accagttctc cctgaagctg agctctgtga ccgctgcgga    60

<210> SEQ ID NO 377
<211> LENGTH: 60
<212> TYPE: DNA
<213> ORGANISM: Homo sapiens

<400> SEQUENCE: 377
ccgtatctgc aaatgaacag cttgagagct gaggacacgg ctgtgtatta ctgtgtgaaa    60

<210> SEQ ID NO 378
<211> LENGTH: 60
<212> TYPE: DNA
<213> ORGANISM: Homo sapiens

<400> SEQUENCE: 378
ccatcagcag cctgcagtct gaagattttg cagtttatta ctgtcagcag tataataact    60

<210> SEQ ID NO 379
<211> LENGTH: 60
<212> TYPE: DNA
<213> ORGANISM: Homo sapiens

<400> SEQUENCE: 379
ctgtcaggtg tgggatagta ctagtgatca ttatgtcttc ggaactggga ccaaggtcgc    60

<210> SEQ ID NO 380
<211> LENGTH: 60
<212> TYPE: DNA
<213> ORGANISM: Homo sapiens

<400> SEQUENCE: 380
caattccaag aacacgctgt atctgcaagt gaacagcctg agagtcgagg acacggccct    60

```
<210> SEQ ID NO 381
<211> LENGTH: 60
<212> TYPE: DNA
<213> ORGANISM: Homo sapiens

<400> SEQUENCE: 381
agcagcctgc agcctgaaga ttttgcaacc tattactgtc aacagagtga caacacaaga    60

<210> SEQ ID NO 382
<211> LENGTH: 60
<212> TYPE: DNA
<213> ORGANISM: Homo sapiens

<400> SEQUENCE: 382
catcactggt ctccaggctg aggacgaggc tgattattac tgcagctcat atacaagcag    60

<210> SEQ ID NO 383
<211> LENGTH: 60
<212> TYPE: DNA
<213> ORGANISM: Homo sapiens

<400> SEQUENCE: 383
aagatagcag ccccgtcaag cgggagtgga gaccaccaca ccctccaaac aaagcaacaa    60

<210> SEQ ID NO 384
<211> LENGTH: 60
<212> TYPE: DNA
<213> ORGANISM: Homo sapiens

<400> SEQUENCE: 384
ccagagatga ttccaagaac acggcgtatc tgcaaatgaa cagcctgaaa accgaggaca    60

<210> SEQ ID NO 385
<211> LENGTH: 60
<212> TYPE: DNA
<213> ORGANISM: Homo sapiens

<400> SEQUENCE: 385
gacagagtca ccatcacttg tcgggcgagt cagggaatta gcaattattt agcctggttt    60

<210> SEQ ID NO 386
<211> LENGTH: 60
<212> TYPE: DNA
<213> ORGANISM: Homo sapiens

<400> SEQUENCE: 386
gcagattaca ctctcaccat ccgcagcctg cagcctgaag attttgcaaa ttattactgt    60

<210> SEQ ID NO 387
<211> LENGTH: 60
<212> TYPE: DNA
<213> ORGANISM: Homo sapiens

<400> SEQUENCE: 387
atgcagactc cgtgaagggc cgattcacca tctccagaga caattccaag aacacggtgt    60

<210> SEQ ID NO 388
<211> LENGTH: 60
<212> TYPE: DNA
<213> ORGANISM: Homo sapiens

<400> SEQUENCE: 388
tgggcatcac cggactccag actggggacg aggccgatta ttactgcgga acatggaata    60
```

<210> SEQ ID NO 389
<211> LENGTH: 60
<212> TYPE: DNA
<213> ORGANISM: Homo sapiens

<400> SEQUENCE: 389
tccaagccaa caaggctaca ctggtgtgtc tcatgaatga cttttatccg ggaatcttga    60

<210> SEQ ID NO 390
<211> LENGTH: 60
<212> TYPE: DNA
<213> ORGANISM: Homo sapiens

<400> SEQUENCE: 390
agtttgggct gagctgcctt tttcttgtgg ctattttaaa aggtgtccag tgtgaggtgc    60

<210> SEQ ID NO 391
<211> LENGTH: 60
<212> TYPE: DNA
<213> ORGANISM: Homo sapiens

<400> SEQUENCE: 391
cagcagcctg cagcctgaag attttgcagc ttattactgt caacagagtg acagtacccc    60

<210> SEQ ID NO 392
<211> LENGTH: 60
<212> TYPE: DNA
<213> ORGANISM: Homo sapiens

<400> SEQUENCE: 392
ggccaccatc aactgcaagt ccagccagag tgttttatac agctccaaca ataagaacta    60

<210> SEQ ID NO 393
<211> LENGTH: 60
<212> TYPE: DNA
<213> ORGANISM: Homo sapiens

<400> SEQUENCE: 393
agcagcctgc agcctgaaga ttttgcagtt tattactgtc agcaggatta taacttacct    60

<210> SEQ ID NO 394
<211> LENGTH: 60
<212> TYPE: DNA
<213> ORGANISM: Homo sapiens

<400> SEQUENCE: 394
cgtgaggatg cttggcacgt accccgtgta catacttccc aggcacccag catggaaata    60

<210> SEQ ID NO 395
<211> LENGTH: 60
<212> TYPE: DNA
<213> ORGANISM: Homo sapiens

<400> SEQUENCE: 395
gtgggtctgg gacagagttc actctcacca tcagcagcct gcagtctgaa gattttgcag    60

<210> SEQ ID NO 396
<211> LENGTH: 60
<212> TYPE: DNA
<213> ORGANISM: Homo sapiens

<400> SEQUENCE: 396
tctgtcataa gtgtagcagg tctctgtagc actgtcttca tcacagatat tgctctgggt    60

<210> SEQ ID NO 397
<211> LENGTH: 60
<212> TYPE: DNA
<213> ORGANISM: Homo sapiens

<400> SEQUENCE: 397
gattttacac tgaaaatcag cagagtggag gctgaggatg ttggggttta ttactgcatg      60

<210> SEQ ID NO 398
<211> LENGTH: 60
<212> TYPE: DNA
<213> ORGANISM: Homo sapiens

<400> SEQUENCE: 398
ctttcctgtt tgcattggaa gccgtggtta tctctgttgg ctccatggga ttgattatca      60

<210> SEQ ID NO 399
<211> LENGTH: 60
<212> TYPE: DNA
<213> ORGANISM: Homo sapiens

<400> SEQUENCE: 399
atttcctgaa cctgcgacgg atgctggtgc agacacacct gcaggacctg aaagaggtga      60

<210> SEQ ID NO 400
<211> LENGTH: 60
<212> TYPE: DNA
<213> ORGANISM: Homo sapiens

<400> SEQUENCE: 400
gttggaggat actttggcat tcagcgatgc aagactttgg actgctacga tccaacatta      60

<210> SEQ ID NO 401
<211> LENGTH: 60
<212> TYPE: DNA
<213> ORGANISM: Homo sapiens

<400> SEQUENCE: 401
tttactccaa ccatgtcatc cattgaagag cttgaaaaca agggccaagt gatgaagact      60

<210> SEQ ID NO 402
<211> LENGTH: 60
<212> TYPE: DNA
<213> ORGANISM: Homo sapiens

<400> SEQUENCE: 402
ctgtgaggga tgtttgggag atgtaagaaa tgttcttgca gttaagggtt agtttacaat      60

<210> SEQ ID NO 403
<211> LENGTH: 60
<212> TYPE: DNA
<213> ORGANISM: Homo sapiens

<400> SEQUENCE: 403
ctacgttgta gcccacttcc actatgtcct atcaatagga gctgtatttg ccatcatagg      60

<210> SEQ ID NO 404
<211> LENGTH: 60
<212> TYPE: DNA
<213> ORGANISM: Homo sapiens

<400> SEQUENCE: 404
catcgctggg tcaatagtac ttgccgcagt actcttaaaa ctaggcggct atggtataat      60

<210> SEQ ID NO 405
<211> LENGTH: 60
<212> TYPE: DNA
<213> ORGANISM: Homo sapiens

<400> SEQUENCE: 405
catggccatc cccttatgag cgggcacagt gattataggc tttcgctcta agattaaaaa    60

<210> SEQ ID NO 406
<211> LENGTH: 60
<212> TYPE: DNA
<213> ORGANISM: Homo sapiens

<400> SEQUENCE: 406
gactccttga cgttgacaat cgagtagtac tcccgattga agcccccatt cgtataataa    60

<210> SEQ ID NO 407
<211> LENGTH: 60
<212> TYPE: DNA
<213> ORGANISM: Homo sapiens

<400> SEQUENCE: 407
aagatcagaa gccagtcatg gatgaccagc gcgaccttat ctccaacaat gagcaactgc    60

<210> SEQ ID NO 408
<211> LENGTH: 60
<212> TYPE: DNA
<213> ORGANISM: Homo sapiens

<400> SEQUENCE: 408
gctaggctgg agtgatttgt tacaaatgag caaaagatga gtccttgctt ccctcagaaa    60

<210> SEQ ID NO 409
<211> LENGTH: 60
<212> TYPE: DNA
<213> ORGANISM: Homo sapiens

<400> SEQUENCE: 409
ttccagatga gctcttcttt cctacaagtt ttcataatta gggaatgcca gggtttaggg    60

<210> SEQ ID NO 410
<211> LENGTH: 60
<212> TYPE: DNA
<213> ORGANISM: Homo sapiens

<400> SEQUENCE: 410
caacttctac cagctgagga acttcctgaa gtgctccgaa gacaacccgc tctttgccgg    60

<210> SEQ ID NO 411
<211> LENGTH: 60
<212> TYPE: DNA
<213> ORGANISM: Homo sapiens

<400> SEQUENCE: 411
ctagccatgg ccatccccctt aagcggggtg attataggct ttcgctctaa gattaaaaat    60

<210> SEQ ID NO 412
<211> LENGTH: 60
<212> TYPE: DNA
<213> ORGANISM: Homo sapiens

<400> SEQUENCE: 412
aaggccacca cacaccaccct gtccagaaag gccttcgata cgggataatc ctatttatta    60

<210> SEQ ID NO 413
<211> LENGTH: 60
<212> TYPE: DNA
<213> ORGANISM: Homo sapiens

<400> SEQUENCE: 413
aagtttagaa ttggaattac ttccttacta gtgtcttttg gcttaaattt tgtcttttga    60

<210> SEQ ID NO 414
<211> LENGTH: 60
<212> TYPE: DNA
<213> ORGANISM: Homo sapiens

<400> SEQUENCE: 414
acggcttgaa catcgagatg cacaaacagg ctgagatcgt caaaaggctg aacgggattt    60

<210> SEQ ID NO 415
<211> LENGTH: 60
<212> TYPE: DNA
<213> ORGANISM: Homo sapiens

<400> SEQUENCE: 415
ctccgatccg tccctaaaca aactaggagg cgtcctttgc cctattatat ccatcctcat    60

<210> SEQ ID NO 416
<211> LENGTH: 60
<212> TYPE: DNA
<213> ORGANISM: Homo sapiens

<400> SEQUENCE: 416
acggctgaac atcatctcta acctggactg tgtgaacgag gtgattggca tccggtcagc    60

<210> SEQ ID NO 417
<211> LENGTH: 60
<212> TYPE: DNA
<213> ORGANISM: Homo sapiens

<400> SEQUENCE: 417
ttagcatcat ccctctacta tttttagcc aaatcaacaa caacctattt tagctgttcc    60

<210> SEQ ID NO 418
<211> LENGTH: 60
<212> TYPE: DNA
<213> ORGANISM: Homo sapiens

<400> SEQUENCE: 418
aatatgacta gcttacacaa tagctcacat agtacagata ctctttacgg actccactta    60

<210> SEQ ID NO 419
<211> LENGTH: 60
<212> TYPE: DNA
<213> ORGANISM: Homo sapiens

<400> SEQUENCE: 419
ttacatgggt tttcatgatc agccgcgaaa ctgagaacgt caggtcagcg aggagattgg    60

<210> SEQ ID NO 420
<211> LENGTH: 60
<212> TYPE: DNA
<213> ORGANISM: Homo sapiens

<400> SEQUENCE: 420
cttagaagct tcgaactcaa aatcatggaa aggttttaag atttgaggtt ggttttaggg    60

```
<210> SEQ ID NO 421
<211> LENGTH: 60
<212> TYPE: DNA
<213> ORGANISM: Homo sapiens

<400> SEQUENCE: 421
tacatgccag tgacacttcc agtccccttt gtattcctta aataaactca atgagctctt      60

<210> SEQ ID NO 422
<211> LENGTH: 60
<212> TYPE: DNA
<213> ORGANISM: Homo sapiens

<400> SEQUENCE: 422
gagctcacac accatatatt aacatataca actgtgaacc agctaatccc tctgagaaaa      60

<210> SEQ ID NO 423
<211> LENGTH: 60
<212> TYPE: DNA
<213> ORGANISM: Homo sapiens

<400> SEQUENCE: 423
ggcagaacat ttgactggca ctgatttgca ataagctaag ctcagaaact ttcctactgt      60

<210> SEQ ID NO 424
<211> LENGTH: 60
<212> TYPE: DNA
<213> ORGANISM: Homo sapiens

<400> SEQUENCE: 424
tgcatgcctg cccactgaag tttggaagct atgcctatac aacagctgaa gtggtttatt      60

<210> SEQ ID NO 425
<211> LENGTH: 60
<212> TYPE: DNA
<213> ORGANISM: Homo sapiens

<400> SEQUENCE: 425
aaacaagatg gaataaaaga aattgggatc ttgggttgga gggacagtga agcttagagc      60

<210> SEQ ID NO 426
<211> LENGTH: 60
<212> TYPE: DNA
<213> ORGANISM: Homo sapiens

<400> SEQUENCE: 426
tctagaaaag tctcttattt tcaagctgtt ctaaatagct tcgtctcagt ttccccaaaa      60

<210> SEQ ID NO 427
<211> LENGTH: 60
<212> TYPE: DNA
<213> ORGANISM: Homo sapiens

<400> SEQUENCE: 427
gaggaatcag aagggaagat caacagcaag gatggggcat cattaagact tgctataaaa      60

<210> SEQ ID NO 428
<211> LENGTH: 60
<212> TYPE: DNA
<213> ORGANISM: Homo sapiens

<400> SEQUENCE: 428
cgctgaagga tggtatcatc atgatccaga cgctgctgat catcctcttc atcatcgtgc      60
```

<210> SEQ ID NO 429
<211> LENGTH: 60
<212> TYPE: DNA
<213> ORGANISM: Homo sapiens

<400> SEQUENCE: 429
gcctcaggca caagaaaatg tggactatgt gatcctcaaa cattgacact ggatgggctg    60

<210> SEQ ID NO 430
<211> LENGTH: 60
<212> TYPE: DNA
<213> ORGANISM: Homo sapiens

<400> SEQUENCE: 430
tgctcaaagc tcaaaatgta acaaggtaca taaaacttgg tcatggtgga cactggagtc    60

<210> SEQ ID NO 431
<211> LENGTH: 60
<212> TYPE: DNA
<213> ORGANISM: Homo sapiens

<400> SEQUENCE: 431
ccagcttgcc tgccggtttt caggaatcta aactctcatc ttgtgcaatt tatcaggtgt    60

<210> SEQ ID NO 432
<211> LENGTH: 60
<212> TYPE: DNA
<213> ORGANISM: Homo sapiens

<400> SEQUENCE: 432
tcgcacggtc atccggagta ctaagcccca gtaaggtgtt caggactggt aagcgactgt    60

<210> SEQ ID NO 433
<211> LENGTH: 60
<212> TYPE: DNA
<213> ORGANISM: Homo sapiens

<400> SEQUENCE: 433
tttcccccct ttatagatgg tcacgcacct gggtgttaca aagttgtatg tggcatgaat    60

<210> SEQ ID NO 434
<211> LENGTH: 60
<212> TYPE: DNA
<213> ORGANISM: Homo sapiens

<400> SEQUENCE: 434
gttagcattt cctcctgaag tgttctgttg gcaataaaat gcactttgac tgtttgttgt    60

<210> SEQ ID NO 435
<211> LENGTH: 60
<212> TYPE: DNA
<213> ORGANISM: Homo sapiens

<400> SEQUENCE: 435
gctttggtta tagaagtgaa gtggactaaa tacggatccc tgctgaatcc acaggccaaa    60

<210> SEQ ID NO 436
<211> LENGTH: 60
<212> TYPE: DNA
<213> ORGANISM: Homo sapiens

<400> SEQUENCE: 436
catcgtcaga gagtgtttgt atgacagaat agcacaagaa actgtggatg aaactgaaat    60

<210> SEQ ID NO 437
<211> LENGTH: 60
<212> TYPE: DNA
<213> ORGANISM: Homo sapiens

<400> SEQUENCE: 437
tcgccaagaa cctggttaga ggcataaaga ccttttttca ccgttaccta attttttccc    60

<210> SEQ ID NO 438
<211> LENGTH: 60
<212> TYPE: DNA
<213> ORGANISM: Homo sapiens

<400> SEQUENCE: 438
ttttcttttt aataaaaagg cacctataaa acaggtcaat acagtacagg cagcacagag    60

<210> SEQ ID NO 439
<211> LENGTH: 60
<212> TYPE: DNA
<213> ORGANISM: Homo sapiens

<400> SEQUENCE: 439
aacactattg taggtagtga tatgtgtgtt aggaaaaaaa taaggccgag agaggggagt    60

<210> SEQ ID NO 440
<211> LENGTH: 60
<212> TYPE: DNA
<213> ORGANISM: Homo sapiens

<400> SEQUENCE: 440
gatcaactca aactatgtcg accccaagtt ccctccatgc gaggaatatt cacagagcga    60

<210> SEQ ID NO 441
<211> LENGTH: 60
<212> TYPE: DNA
<213> ORGANISM: Homo sapiens

<400> SEQUENCE: 441
agatggtgca gtggttagag ctgaggctta tcccacagag aaccctggcg ccttggtcaa    60

<210> SEQ ID NO 442
<211> LENGTH: 60
<212> TYPE: DNA
<213> ORGANISM: Homo sapiens

<400> SEQUENCE: 442
aagaaactgc ttgttgtgta tcagtaatca ttagtggcaa tgatgacatt ctgaaaagct    60

<210> SEQ ID NO 443
<211> LENGTH: 60
<212> TYPE: DNA
<213> ORGANISM: Homo sapiens

<400> SEQUENCE: 443
tgaccaccta tgacagcgtg accatctcct ggacccgcca gaatggcgaa gctgtgaaaa    60

<210> SEQ ID NO 444
<211> LENGTH: 60
<212> TYPE: DNA
<213> ORGANISM: Homo sapiens

<400> SEQUENCE: 444
tggtaagttt ctctctcttt agagactcca caataaagtt ttcaacatgg taaggttttc    60

<210> SEQ ID NO 445
<211> LENGTH: 60
<212> TYPE: DNA
<213> ORGANISM: Homo sapiens

<400> SEQUENCE: 445
taagcgagta tataatattc ctgtgcgatt tattgaagca acaaaacaat atgccttggg    60

<210> SEQ ID NO 446
<211> LENGTH: 60
<212> TYPE: DNA
<213> ORGANISM: Homo sapiens

<400> SEQUENCE: 446
gggtgaatgt ttgaaaatca tgaatcagcc accattatta attgaagagc tgggaatacc    60

<210> SEQ ID NO 447
<211> LENGTH: 60
<212> TYPE: DNA
<213> ORGANISM: Homo sapiens

<400> SEQUENCE: 447
agacaagctt ttaccgactt cctctgcttg ccagcaaagt catctgctaa ctggatattg    60

<210> SEQ ID NO 448
<211> LENGTH: 60
<212> TYPE: DNA
<213> ORGANISM: Homo sapiens

<400> SEQUENCE: 448
ccattttaaa gatggctact taggaccata tggatgttgt actgatgtca tttgaccacg    60

<210> SEQ ID NO 449
<211> LENGTH: 60
<212> TYPE: DNA
<213> ORGANISM: Homo sapiens

<400> SEQUENCE: 449
tgtgaaaagc atcgatgatg aagatgtgga tgaaaacgaa gatgacgtgt atggaaactc    60

<210> SEQ ID NO 450
<211> LENGTH: 60
<212> TYPE: DNA
<213> ORGANISM: Homo sapiens

<400> SEQUENCE: 450
atcctccatg gtatctgaat cccagaatcc tacaatcctg catggtatct gaaacatact    60

<210> SEQ ID NO 451
<211> LENGTH: 60
<212> TYPE: DNA
<213> ORGANISM: Homo sapiens

<400> SEQUENCE: 451
ctgcagatct ttattactgg caagaaagtc ccagaagttc ttttctctaa cttatgacta    60

<210> SEQ ID NO 452
<211> LENGTH: 60
<212> TYPE: DNA
<213> ORGANISM: Homo sapiens

<400> SEQUENCE: 452
tggaaaggtg tttctctcat ctctgtccta aggcttgata aagtcattaa aattgtgttc    60

<210> SEQ ID NO 453
<211> LENGTH: 60
<212> TYPE: DNA
<213> ORGANISM: Homo sapiens

<400> SEQUENCE: 453
ataatacaaa gatggcgcag ggaagatgaa ttgtgggaga gccgtcatgg cttttttta      60

<210> SEQ ID NO 454
<211> LENGTH: 60
<212> TYPE: DNA
<213> ORGANISM: Homo sapiens

<400> SEQUENCE: 454
ctctgaggct aagattactg gtgtactcat tgggaccagt ttggtctcag tgactgaaaa      60

<210> SEQ ID NO 455
<211> LENGTH: 60
<212> TYPE: DNA
<213> ORGANISM: Homo sapiens

<400> SEQUENCE: 455
gaagtttgaa cttctttgta ttgtatgatc atccctttac cttaatactc acatgaaatg      60

<210> SEQ ID NO 456
<211> LENGTH: 60
<212> TYPE: DNA
<213> ORGANISM: Homo sapiens

<400> SEQUENCE: 456
gacgggacat catgctgggc aacacagcta aaatgcgggt gaagaccaga tttcttgcac      60

<210> SEQ ID NO 457
<211> LENGTH: 60
<212> TYPE: DNA
<213> ORGANISM: Homo sapiens

<400> SEQUENCE: 457
attgtcggca tcttccatgc tctgagtcag ttagcattta cagtgaatct gcccttctgt      60

<210> SEQ ID NO 458
<211> LENGTH: 60
<212> TYPE: DNA
<213> ORGANISM: Homo sapiens

<400> SEQUENCE: 458
tacaccggag gctgatggcg ctgcgggagc gcaacgtgct gcagcagatt gtgaatctga      60

<210> SEQ ID NO 459
<211> LENGTH: 60
<212> TYPE: DNA
<213> ORGANISM: Homo sapiens

<400> SEQUENCE: 459
tggccccaga ggatgaggtc attgtgaatc agtacgtgat tcggcctggc ccctcggcct      60

<210> SEQ ID NO 460
<211> LENGTH: 60
<212> TYPE: DNA
<213> ORGANISM: Homo sapiens

<400> SEQUENCE: 460
ttcgggcctg tcatgatcat ctctcggttt gctgatgggg acttggatgc cgtgctgtct      60

```
<210> SEQ ID NO 461
<211> LENGTH: 60
<212> TYPE: DNA
<213> ORGANISM: Homo sapiens

<400> SEQUENCE: 461
aagcgccagg gccgcaccct ctacggtttc ggtggttgag cgtcccttte tatcaataaa      60

<210> SEQ ID NO 462
<211> LENGTH: 60
<212> TYPE: DNA
<213> ORGANISM: Homo sapiens

<400> SEQUENCE: 462
ccttccagcc agtctctgta ccgcacgtcc ggagctttcg tctacgactg tagcaagttt      60

<210> SEQ ID NO 463
<211> LENGTH: 60
<212> TYPE: DNA
<213> ORGANISM: Homo sapiens

<400> SEQUENCE: 463
agcggacctc agggcggagg cttcccacgg ggaggcagga agaaataaag gtctttggct      60

<210> SEQ ID NO 464
<211> LENGTH: 60
<212> TYPE: DNA
<213> ORGANISM: Homo sapiens

<400> SEQUENCE: 464
gtggggaggg tttcttgggt ttcttgaagc cagtatttcc catagtatct tacgtcccag      60

<210> SEQ ID NO 465
<211> LENGTH: 60
<212> TYPE: DNA
<213> ORGANISM: Homo sapiens

<400> SEQUENCE: 465
tagcctcctc ggcagaaaaa cttcaacgaa tagtaaagaa ccttgacttc attgtctata      60

<210> SEQ ID NO 466
<211> LENGTH: 60
<212> TYPE: DNA
<213> ORGANISM: Homo sapiens

<400> SEQUENCE: 466
gccgggctgg ggctgcgtag gtgaaaaggc agaacactcc gcgcttctta gaagaggagt      60

<210> SEQ ID NO 467
<211> LENGTH: 59
<212> TYPE: DNA
<213> ORGANISM: Homo sapiens

<400> SEQUENCE: 467
ctcgtgccct tcgtcaccgt gaacgcccag tgggcatcc tcagcaagtg cctgaccta       59

<210> SEQ ID NO 468
<211> LENGTH: 60
<212> TYPE: DNA
<213> ORGANISM: Homo sapiens

<400> SEQUENCE: 468
tcagttccca taaaaccttc attacacata aagatacacg tggggggtcag tgaatctgct     60
```

```
<210> SEQ ID NO 469
<211> LENGTH: 60
<212> TYPE: DNA
<213> ORGANISM: Homo sapiens

<400> SEQUENCE: 469
agtgaacttc tcctattacg gcctgagtct ggatgtgtcg gggctgggc tgaacgtgta    60

<210> SEQ ID NO 470
<211> LENGTH: 60
<212> TYPE: DNA
<213> ORGANISM: Homo sapiens

<400> SEQUENCE: 470
acgaatatgc gttcgacaag ccggtcccga aagacatggt catctggaat cgtgaacggg    60

<210> SEQ ID NO 471
<211> LENGTH: 60
<212> TYPE: DNA
<213> ORGANISM: Homo sapiens

<400> SEQUENCE: 471
ttgtctttta aattaagcct cggttgagcc cttgtatatt aaataaatgc attttgtcc    60

<210> SEQ ID NO 472
<211> LENGTH: 60
<212> TYPE: DNA
<213> ORGANISM: Homo sapiens

<400> SEQUENCE: 472
cccattcaaa ttgtcctagg tctatcagaa attagggaag gtagtcctgc tttataatag    60

<210> SEQ ID NO 473
<211> LENGTH: 60
<212> TYPE: DNA
<213> ORGANISM: Homo sapiens

<400> SEQUENCE: 473
tgggggaagg gtcgtgggtg gggaatttat caccaacatc cattgtaggg ggaatctatg    60

<210> SEQ ID NO 474
<211> LENGTH: 60
<212> TYPE: DNA
<213> ORGANISM: Homo sapiens

<400> SEQUENCE: 474
agctttgctt tgcaaagatt gatgacagac tggttcctca gaggcctagg ctacccgtca    60

<210> SEQ ID NO 475
<211> LENGTH: 60
<212> TYPE: DNA
<213> ORGANISM: Homo sapiens

<400> SEQUENCE: 475
gcgggctggg cgctctggcg gtgtgcgctg aggtgggcag agcggcaggt gggggcgttg    60

<210> SEQ ID NO 476
<211> LENGTH: 60
<212> TYPE: DNA
<213> ORGANISM: Homo sapiens

<400> SEQUENCE: 476
gtgggagggg ccggtgtgag gcaaggctca cgctgacctc tctcggcgtg ggaggggccg    60
```

<210> SEQ ID NO 477
<211> LENGTH: 60
<212> TYPE: DNA
<213> ORGANISM: Homo sapiens

<400> SEQUENCE: 477
cacagaaaca tacaaggaag gcaccccgc tctgtgggcg agacaaagca gcaatcctct    60

<210> SEQ ID NO 478
<211> LENGTH: 60
<212> TYPE: DNA
<213> ORGANISM: Homo sapiens

<400> SEQUENCE: 478
ggaattggct cttcctattt ccctacttca tgaaaactcc agtagaagac cttagaacct    60

<210> SEQ ID NO 479
<211> LENGTH: 60
<212> TYPE: DNA
<213> ORGANISM: Homo sapiens

<400> SEQUENCE: 479
tttaaacaca cgtggtcccc cgtctagaag cctctgcatt taagcacacg tggtcccccg    60

<210> SEQ ID NO 480
<211> LENGTH: 60
<212> TYPE: DNA
<213> ORGANISM: Homo sapiens

<400> SEQUENCE: 480
atggctaagt tgggagacca aaagaagaa tgtacttcat ctggttgggc tggattccct    60

<210> SEQ ID NO 481
<211> LENGTH: 60
<212> TYPE: DNA
<213> ORGANISM: Homo sapiens

<400> SEQUENCE: 481
tgtgactcga ctgctgggat gtatctgctt ttgggagcag actgagtttc ttttgcaatt    60

<210> SEQ ID NO 482
<211> LENGTH: 60
<212> TYPE: DNA
<213> ORGANISM: Homo sapiens

<400> SEQUENCE: 482
tccccgtcca cgttaccgca ttcagagctt gggtcacctg gacactgaac tcaggtgaat    60

<210> SEQ ID NO 483
<211> LENGTH: 60
<212> TYPE: DNA
<213> ORGANISM: Homo sapiens

<400> SEQUENCE: 483
tacagagcag tcgccgggca gttgaagatc agctaaagat atgtggccac aggagggatg    60

<210> SEQ ID NO 484
<211> LENGTH: 60
<212> TYPE: DNA
<213> ORGANISM: Homo sapiens

<400> SEQUENCE: 484
aaatgtggcg ctctcgccaa gaaaaagctt ggggactgaa ttcttgagat ttatggtgca    60

<210> SEQ ID NO 485
<211> LENGTH: 60
<212> TYPE: DNA
<213> ORGANISM: Homo sapiens

<400> SEQUENCE: 485
aagattttat tgtaaaacag agctgaagtc acaggaagta gggaactttg cacccaacat    60

<210> SEQ ID NO 486
<211> LENGTH: 60
<212> TYPE: DNA
<213> ORGANISM: Homo sapiens

<400> SEQUENCE: 486
tattaagaaa gatgctcaag tcccatggca cagagcaagg cgggcaggga acggttattt    60

<210> SEQ ID NO 487
<211> LENGTH: 60
<212> TYPE: DNA
<213> ORGANISM: Homo sapiens

<400> SEQUENCE: 487
aagatgatga accagctgta aaactacaac tactaccaca taaacatgat atcatcacac    60

<210> SEQ ID NO 488
<211> LENGTH: 60
<212> TYPE: DNA
<213> ORGANISM: Homo sapiens

<400> SEQUENCE: 488
tcctttggag taaaactagt gcttaccagt ttccaattgt atttagcttc tggttggaat    60

<210> SEQ ID NO 489
<211> LENGTH: 60
<212> TYPE: DNA
<213> ORGANISM: Homo sapiens

<400> SEQUENCE: 489
aagcatatct acccatggcg gaaaatgaag tcagaaagat ttgtagtgac attaggcaga    60

<210> SEQ ID NO 490
<211> LENGTH: 60
<212> TYPE: DNA
<213> ORGANISM: Homo sapiens

<400> SEQUENCE: 490
actgcaatga acacatatac atatacatcc aaacattcct ccattcgtct attaatctgc    60

<210> SEQ ID NO 491
<211> LENGTH: 60
<212> TYPE: DNA
<213> ORGANISM: Homo sapiens

<400> SEQUENCE: 491
catcaactgg taaacaaaaa actgtgagaa cggatcctga atcttgcgct taccagggga    60

<210> SEQ ID NO 492
<211> LENGTH: 60
<212> TYPE: DNA
<213> ORGANISM: Homo sapiens

<400> SEQUENCE: 492
tgtgcctcca aggactgtct ggcaatgact tgtattggcc accaactgta gatgtatata    60

<210> SEQ ID NO 493
<211> LENGTH: 60
<212> TYPE: DNA
<213> ORGANISM: Homo sapiens

<400> SEQUENCE: 493
actcccctag tctgtagacg gaattggcat acggtctaat ttgtgtagta agcacctttg    60

<210> SEQ ID NO 494
<211> LENGTH: 60
<212> TYPE: DNA
<213> ORGANISM: Homo sapiens

<400> SEQUENCE: 494
ccatctgacg ctacagtcac cacgaccttc aatatcctgg ttattgacat caatgacaat    60

<210> SEQ ID NO 495
<211> LENGTH: 60
<212> TYPE: DNA
<213> ORGANISM: Homo sapiens

<400> SEQUENCE: 495
tcctcctgaa aagagaattt ttacaaccac ccatacacca aattgtttgt tccaggatgt    60

<210> SEQ ID NO 496
<211> LENGTH: 60
<212> TYPE: DNA
<213> ORGANISM: Homo sapiens

<400> SEQUENCE: 496
agaatctgga aaccatacaa gaaacgtgag actcctgatt gcttctggaa atactgtgtc    60

<210> SEQ ID NO 497
<211> LENGTH: 60
<212> TYPE: DNA
<213> ORGANISM: Homo sapiens

<400> SEQUENCE: 497
cttccctcat ggtaccaaag gtgcaattta tgactccaga aggaaatcaa aacacatcgg    60

<210> SEQ ID NO 498
<211> LENGTH: 60
<212> TYPE: DNA
<213> ORGANISM: Homo sapiens

<400> SEQUENCE: 498
agaaagtttc aggatttctc tggacaagat cctaacattt tactgagtca tcttttggcc    60

<210> SEQ ID NO 499
<211> LENGTH: 60
<212> TYPE: DNA
<213> ORGANISM: Homo sapiens

<400> SEQUENCE: 499
ccttcctcat tttggaactt aaggttgtgt acagaacagt cttacaatga cagtgtttag    60

<210> SEQ ID NO 500
<211> LENGTH: 60
<212> TYPE: DNA
<213> ORGANISM: Homo sapiens

<400> SEQUENCE: 500
ttctatacct ctaagctgtt cttttctgaa ccatgaatcg ggagaattat tgtcactcat    60

<210> SEQ ID NO 501
<211> LENGTH: 60
<212> TYPE: DNA
<213> ORGANISM: Homo sapiens

<400> SEQUENCE: 501
tctctaccgc ttcttgctag aaacaatggc ctatgttaaa ataacttgt caagaatcag    60

<210> SEQ ID NO 502
<211> LENGTH: 60
<212> TYPE: DNA
<213> ORGANISM: Homo sapiens

<400> SEQUENCE: 502
ccctcctagt ccacctgaaa acaccaaatt caaccatcat ctgtcaagaa attaaaagaa    60

<210> SEQ ID NO 503
<211> LENGTH: 60
<212> TYPE: DNA
<213> ORGANISM: Homo sapiens

<400> SEQUENCE: 503
acctccttct cttctggaca tgtccaggag tggccgttgc tacaagtcac ctggtgctac    60

<210> SEQ ID NO 504
<211> LENGTH: 60
<212> TYPE: DNA
<213> ORGANISM: Homo sapiens

<400> SEQUENCE: 504
agcaagatat cctcctcatg gtccctttag ctctcaaaag caatgaaatc ctcctgttct    60

<210> SEQ ID NO 505
<211> LENGTH: 60
<212> TYPE: DNA
<213> ORGANISM: Homo sapiens

<400> SEQUENCE: 505
cctcctgtga ctctggaaag caaaggattg gctgtgtatt gtccattgat tcctgattga    60

<210> SEQ ID NO 506
<211> LENGTH: 60
<212> TYPE: DNA
<213> ORGANISM: Homo sapiens

<400> SEQUENCE: 506
tcctcctgca actgtggttt gaaactgcgc attctctagt agtatatatc gtgcctgtct    60

<210> SEQ ID NO 507
<211> LENGTH: 60
<212> TYPE: DNA
<213> ORGANISM: Homo sapiens

<400> SEQUENCE: 507
cctcctcgac ttaaatagaa aaaacttgac attttttatc aacgatgaac aacaaggtcc    60

<210> SEQ ID NO 508
<211> LENGTH: 60
<212> TYPE: DNA
<213> ORGANISM: Homo sapiens

<400> SEQUENCE: 508
gcacctctgt ggcttctgtg taccatggga aaattctcat aggcaccgta tttcacaaaa    60

<210> SEQ ID NO 509
<211> LENGTH: 60
<212> TYPE: DNA
<213> ORGANISM: Homo sapiens

<400> SEQUENCE: 509
actggtcctt tttctaatac ttgcttatat catgtgctgc cgacgggaag gcgtggaaaa    60

<210> SEQ ID NO 510
<211> LENGTH: 60
<212> TYPE: DNA
<213> ORGANISM: Homo sapiens

<400> SEQUENCE: 510
ttgtactgac ctcttgtcct gtatagcaac ctatttgact gcttcacgga ctctttgctg    60

<210> SEQ ID NO 511
<211> LENGTH: 60
<212> TYPE: DNA
<213> ORGANISM: Homo sapiens

<400> SEQUENCE: 511
cagctcgagt cactttataa gaacctcagg ataccgttat taggagatga agaagagggc    60

<210> SEQ ID NO 512
<211> LENGTH: 60
<212> TYPE: DNA
<213> ORGANISM: Homo sapiens

<400> SEQUENCE: 512
ctcccttgcc acccaaatgt tagaaaaata gctgtgaaca gagagcgctt ttgtctgcaa    60

<210> SEQ ID NO 513
<211> LENGTH: 60
<212> TYPE: DNA
<213> ORGANISM: Homo sapiens

<400> SEQUENCE: 513
actcctggtc ttgtacttcg aagtctgggt gccttgacgg gaccacagct tctgtccctt    60

<210> SEQ ID NO 514
<211> LENGTH: 60
<212> TYPE: DNA
<213> ORGANISM: Homo sapiens

<400> SEQUENCE: 514
cagacctcca gaattcaaaa aatgcaacca gcaggcctgc aagaaaagtg ccgatttact    60

<210> SEQ ID NO 515
<211> LENGTH: 60
<212> TYPE: DNA
<213> ORGANISM: Homo sapiens

<400> SEQUENCE: 515
atcctcccat catgaaacaa actctgccta catgttatct ccaaagccac agaagaaatt    60

<210> SEQ ID NO 516
<211> LENGTH: 60
<212> TYPE: DNA
<213> ORGANISM: Homo sapiens

<400> SEQUENCE: 516
cctcccagac cagaataata tgtggattcg agaccatgag gatagtgggt ctgtacattt    60

<210> SEQ ID NO 517
<211> LENGTH: 60
<212> TYPE: DNA
<213> ORGANISM: Homo sapiens

<400> SEQUENCE: 517
cctggtagcc tttcctacta gagtagcagg tggtgttgga attacctgtt ggattttagt    60

<210> SEQ ID NO 518
<211> LENGTH: 60
<212> TYPE: DNA
<213> ORGANISM: Homo sapiens

<400> SEQUENCE: 518
gctcctacag gagatgacct ccagagtaaa acaaacaaat tcatcttaaa tcaggaacct    60

<210> SEQ ID NO 519
<211> LENGTH: 60
<212> TYPE: DNA
<213> ORGANISM: Homo sapiens

<400> SEQUENCE: 519
tcaattgctt cctcctcaat ctggcagcca ctgacctgca gtttgtgcta acgctgccct    60

<210> SEQ ID NO 520
<211> LENGTH: 60
<212> TYPE: DNA
<213> ORGANISM: Homo sapiens

<400> SEQUENCE: 520
ccttccatta gcaactactc tgtaccaccc ttcccaagag tatgtctgga ggactagtgt    60

<210> SEQ ID NO 521
<211> LENGTH: 60
<212> TYPE: DNA
<213> ORGANISM: Homo sapiens

<400> SEQUENCE: 521
ttcttccctc catacatttg cttccaagtg aatttgcata agcagtgctc agactgcacc    60

<210> SEQ ID NO 522
<211> LENGTH: 60
<212> TYPE: DNA
<213> ORGANISM: Homo sapiens

<400> SEQUENCE: 522
ctccttcaac cctacatggt cgatcacatc attcacacca gagaagacat agacggtatt    60

<210> SEQ ID NO 523
<211> LENGTH: 60
<212> TYPE: DNA
<213> ORGANISM: Homo sapiens

<400> SEQUENCE: 523
cttcctggtg atgactttcc acacggaaac aggaagcatg cttttctgg agaagattgt     60

<210> SEQ ID NO 524
<211> LENGTH: 60
<212> TYPE: DNA
<213> ORGANISM: Homo sapiens

<400> SEQUENCE: 524
cctggctctg ttatttaccg tgtatcatat gtaaatatcg acagaaactt caataaactt    60

```
<210> SEQ ID NO 525
<211> LENGTH: 60
<212> TYPE: DNA
<213> ORGANISM: Homo sapiens

<400> SEQUENCE: 525
aagaactatc ctcctgtctg cgaaatcttc cggctacact tcaggcaatt gtgttaccac      60

<210> SEQ ID NO 526
<211> LENGTH: 60
<212> TYPE: DNA
<213> ORGANISM: Homo sapiens

<400> SEQUENCE: 526
tcctggtttt tgagactcaa ccactttgaa agcatttgtg tagcatcaca ggtgctccag      60

<210> SEQ ID NO 527
<211> LENGTH: 60
<212> TYPE: DNA
<213> ORGANISM: Homo sapiens

<400> SEQUENCE: 527
ccttcttggg tcagttaggc cattggtttc tttttaaagg ttttcaaatt tatttgcatc      60

<210> SEQ ID NO 528
<211> LENGTH: 60
<212> TYPE: DNA
<213> ORGANISM: Homo sapiens

<400> SEQUENCE: 528
agttgtactg tcaaggggca gcatttctgg tatttctata ataatttttt ctgtgatctc      60

<210> SEQ ID NO 529
<211> LENGTH: 60
<212> TYPE: DNA
<213> ORGANISM: Homo sapiens

<400> SEQUENCE: 529
agaaaccgag acccaaactc actgctccta agatcccaga aggggagaaa gtggacttcg      60

<210> SEQ ID NO 530
<211> LENGTH: 60
<212> TYPE: DNA
<213> ORGANISM: Homo sapiens

<400> SEQUENCE: 530
ggcattcact gatcccagca ggtctccatc tatttgtacc agcctcctct attcctccca      60

<210> SEQ ID NO 531
<211> LENGTH: 60
<212> TYPE: DNA
<213> ORGANISM: Homo sapiens

<400> SEQUENCE: 531
gccctttttt gtcactcact gttgtgacag atcctccgat ttcttacata agttatgcag      60

<210> SEQ ID NO 532
<211> LENGTH: 60
<212> TYPE: DNA
<213> ORGANISM: Homo sapiens

<400> SEQUENCE: 532
gagcccaact acccttctgt ctttcaacga gaaaagcgaa tttctggcag gcgtgtagcc      60
```

<210> SEQ ID NO 533
<211> LENGTH: 60
<212> TYPE: DNA
<213> ORGANISM: Homo sapiens

<400> SEQUENCE: 533
ctaatggact agattgctga ccttttaata cctttggttt tcattgaaca tacaatcacc    60

<210> SEQ ID NO 534
<211> LENGTH: 60
<212> TYPE: DNA
<213> ORGANISM: Homo sapiens

<400> SEQUENCE: 534
aatcctggtt tcctaacctc ctcttgtagt aattctcaac tcaactcaaa gtcccaagaa    60

<210> SEQ ID NO 535
<211> LENGTH: 60
<212> TYPE: DNA
<213> ORGANISM: Homo sapiens

<400> SEQUENCE: 535
ccctcctgat gatgaaggac ctgtcattgg agaatcgacc aaaactgaca gtgataactt    60

<210> SEQ ID NO 536
<211> LENGTH: 60
<212> TYPE: DNA
<213> ORGANISM: Homo sapiens

<400> SEQUENCE: 536
ccctgaacct acatagacat tttatatcag catacagaaa agtaaaatcc tccttcagtc    60

<210> SEQ ID NO 537
<211> LENGTH: 60
<212> TYPE: DNA
<213> ORGANISM: Homo sapiens

<400> SEQUENCE: 537
attcctttct ggtctccatc ctctctgtag atatgtagat ctctttgaaa cgaagtaagc    60

<210> SEQ ID NO 538
<211> LENGTH: 60
<212> TYPE: DNA
<213> ORGANISM: Homo sapiens

<400> SEQUENCE: 538
ggctgagcac tctgtgctga aaacctttga acctcacggt gtcctgatga aggaagcaga    60

<210> SEQ ID NO 539
<211> LENGTH: 60
<212> TYPE: DNA
<213> ORGANISM: Homo sapiens

<400> SEQUENCE: 539
caaggtgccc ccacgactgc aggctgtgac tgatgaccac atccggatgc acaaggtgct    60

<210> SEQ ID NO 540
<211> LENGTH: 60
<212> TYPE: DNA
<213> ORGANISM: Homo sapiens

<400> SEQUENCE: 540
agttctcctc ctcagccttt tcctcctcag ttttctcttt aaaactgtga agtactaact    60

<210> SEQ ID NO 541
<211> LENGTH: 60
<212> TYPE: DNA
<213> ORGANISM: Homo sapiens

<400> SEQUENCE: 541
tcctgcccca ttatcttgat ccggtgcgcc atgttgaatc cccctaaccg ctgcttgaaa     60

<210> SEQ ID NO 542
<211> LENGTH: 60
<212> TYPE: DNA
<213> ORGANISM: Homo sapiens

<400> SEQUENCE: 542
ctccctcacc tgtacctcag aggccttctc cagttacttc aacaaagtcg gggtggcaca     60

<210> SEQ ID NO 543
<211> LENGTH: 60
<212> TYPE: DNA
<213> ORGANISM: Homo sapiens

<400> SEQUENCE: 543
ggcgcagaag tcttgtgacc tccttctctt cctgagggac aagattgctt cctacagcag     60

<210> SEQ ID NO 544
<211> LENGTH: 60
<212> TYPE: DNA
<213> ORGANISM: Homo sapiens

<400> SEQUENCE: 544
acctcccctg cagacaccaa tgtgctccgc tacatccagc tgactcagct gaagatgaat     60

<210> SEQ ID NO 545
<211> LENGTH: 60
<212> TYPE: DNA
<213> ORGANISM: Homo sapiens

<400> SEQUENCE: 545
tccttccccc tgaccctgac tccttgaacg tcactgaaaa cggcagctat tgcaaggagt     60

<210> SEQ ID NO 546
<211> LENGTH: 60
<212> TYPE: DNA
<213> ORGANISM: Homo sapiens

<400> SEQUENCE: 546 tttttctcc ttcccctttc tttaagagag gctgacagat ctaggtgtca atcaattgga     60

<210> SEQ ID NO 547
<211> LENGTH: 60
<212> TYPE: DNA
<213> ORGANISM: Homo sapiens

<400> SEQUENCE: 547 cctcccttc tggtagtcat aggcaggatt gagtgacggt tgggaagggg gctcagaagc     60

<210> SEQ ID NO 548
<211> LENGTH: 60
<212> TYPE: DNA
<213> ORGANISM: Homo sapiens

<400> SEQUENCE: 548
tcccctactc cccgcatctt tggggaatcg gttccccata tgtcttcctt actagactgt     60

```
<210> SEQ ID NO 549
<211> LENGTH: 60
<212> TYPE: DNA
<213> ORGANISM: Homo sapiens

<400> SEQUENCE: 549
gcttcctgca ccctgaagtg actgagacaa tggagaaggg cttctccaaa tagaattctc      60

<210> SEQ ID NO 550
<211> LENGTH: 60
<212> TYPE: DNA
<213> ORGANISM: Homo sapiens

<400> SEQUENCE: 550
accaccctcc agcagataga cgccggcacc ccttcctctt cctagggtgg aaggggccct      60

<210> SEQ ID NO 551
<211> LENGTH: 60
<212> TYPE: DNA
<213> ORGANISM: Homo sapiens

<400> SEQUENCE: 551
tcccttcagc ccattccccc tcggttttat ccatttcctt gcctcctttt tgtgtcttca      60

<210> SEQ ID NO 552
<211> LENGTH: 60
<212> TYPE: DNA
<213> ORGANISM: Homo sapiens

<400> SEQUENCE: 552
aggttcctcc cagacctgaa tccctctctg caactcctgt ttgcaagcgc tgggcctgcc      60

<210> SEQ ID NO 553
<211> LENGTH: 60
<212> TYPE: DNA
<213> ORGANISM: Homo sapiens

<400> SEQUENCE: 553
tccctcagct tcctccttgg tcaaccttga ctcgttggtc aaggcacccc aggttgcaaa      60

<210> SEQ ID NO 554
<211> LENGTH: 60
<212> TYPE: DNA
<213> ORGANISM: Homo sapiens

<400> SEQUENCE: 554
gcccacctca tttacatgtt cactcccgac cctggaaacc cggatttcgc ctccggacag      60

<210> SEQ ID NO 555
<211> LENGTH: 60
<212> TYPE: DNA
<213> ORGANISM: Homo sapiens

<400> SEQUENCE: 555
attttcacct cccctggtcc atgctcagga agtctggtca ccctggcaaa ctgcacctga      60

<210> SEQ ID NO 556
<211> LENGTH: 60
<212> TYPE: DNA
<213> ORGANISM: Homo sapiens

<400> SEQUENCE: 556
tctgacacct cagcctccct ggccatcact ggactccagg ctgaagatga ggctgattat      60
```

<210> SEQ ID NO 557
<211> LENGTH: 60
<212> TYPE: DNA
<213> ORGANISM: Homo sapiens

<400> SEQUENCE: 557
cctcctacta ccaggggtg tactcccggc ccattatgaa ctcctcttaa gaagacgacg    60

<210> SEQ ID NO 558
<211> LENGTH: 60
<212> TYPE: DNA
<213> ORGANISM: Homo sapiens

<400> SEQUENCE: 558
tcgccacgcc agccccttc ctcagaacgc cgaggcctca ggagcgtgtg cgcgccggga    60

<210> SEQ ID NO 559
<211> LENGTH: 60
<212> TYPE: DNA
<213> ORGANISM: Homo sapiens

<400> SEQUENCE: 559
cttccttccc taggatctca gcacccttt agatcccgtg cagattgtct ttctgttaaa    60

<210> SEQ ID NO 560
<211> LENGTH: 60
<212> TYPE: DNA
<213> ORGANISM: Homo sapiens

<400> SEQUENCE: 560
ctccttcccc atcttctggt aacacaacct ttatttattt gtggggaacc tattccctgt    60

<210> SEQ ID NO 561
<211> LENGTH: 60
<212> TYPE: DNA
<213> ORGANISM: Homo sapiens

<400> SEQUENCE: 561
aattgccatg ctgcccacct cccgaagtgt taggaggtaa catctcatcg tctcatcgca    60

<210> SEQ ID NO 562
<211> LENGTH: 60
<212> TYPE: DNA
<213> ORGANISM: Homo sapiens

<400> SEQUENCE: 562
tcagaagatc tcgtatttgt cttagcagct tctaacctgc cgtggtaaga gaccaagaga    60

<210> SEQ ID NO 563
<211> LENGTH: 60
<212> TYPE: DNA
<213> ORGANISM: Homo sapiens

<400> SEQUENCE: 563
tttttctttt aaaaaagcgg tttctacctc tctatgtgcc tgagtgatga tacaatcgct    60

<210> SEQ ID NO 564
<211> LENGTH: 60
<212> TYPE: DNA
<213> ORGANISM: Homo sapiens

<400> SEQUENCE: 564
tgggagtgga ccatgcttat gtcaccagta ttggcagact cattggaatc gttactctaa    60

<210> SEQ ID NO 565
<211> LENGTH: 60
<212> TYPE: DNA
<213> ORGANISM: Homo sapiens

<400> SEQUENCE: 565
gacattgtgt ttgcaacatg ggcctcttat cacattccac ctgaatctga ctcaaggcaa    60

<210> SEQ ID NO 566
<211> LENGTH: 60
<212> TYPE: DNA
<213> ORGANISM: Homo sapiens

<400> SEQUENCE: 566
gtctacaggc caaaatgcgc acagttgatt ttcggtgtgt tcctgtataa cggcttgaaa    60

<210> SEQ ID NO 567
<211> LENGTH: 60
<212> TYPE: DNA
<213> ORGANISM: Homo sapiens

<400> SEQUENCE: 567
ggcaaatagc aaaagttgtt gcactcctga aattctatta acatttccgc agaagatgag    60

<210> SEQ ID NO 568
<211> LENGTH: 60
<212> TYPE: DNA
<213> ORGANISM: Homo sapiens

<400> SEQUENCE: 568
aaatgttttt accgtagccc tcatctaact tacacgtggt gcatattaaa ataagcagag    60

<210> SEQ ID NO 569
<211> LENGTH: 60
<212> TYPE: DNA
<213> ORGANISM: Homo sapiens

<400> SEQUENCE: 569
ctcccagcag agtcatcact acctttgggg ccgcaggatc acccagcttg gaactagata    60

<210> SEQ ID NO 570
<211> LENGTH: 60
<212> TYPE: DNA
<213> ORGANISM: Homo sapiens

<400> SEQUENCE: 570
acaactgccc agagtgtaat tcccaccgat aagcgcggat ccttatcttt gaaacacaaa    60

<210> SEQ ID NO 571
<211> LENGTH: 60
<212> TYPE: DNA
<213> ORGANISM: Homo sapiens

<400> SEQUENCE: 571
ctgtacttca gaccaaatca ggacaatccg taatgtatat gcccattctc tctttctgga    60

<210> SEQ ID NO 572
<211> LENGTH: 60
<212> TYPE: DNA
<213> ORGANISM: Homo sapiens

<400> SEQUENCE: 572
atattcctca gactcaacaa ttcttgttct ttagaactgt gttctcacct tcccaacact    60

<210> SEQ ID NO 573
<211> LENGTH: 60
<212> TYPE: DNA
<213> ORGANISM: Homo sapiens

<400> SEQUENCE: 573
tcctcttcta tggcagattc tcatccccat agatgcaatt agtctgtcac tccatttaga    60

<210> SEQ ID NO 574
<211> LENGTH: 60
<212> TYPE: DNA
<213> ORGANISM: Homo sapiens

<400> SEQUENCE: 574
ataacctaca tcaaccgaga taccaaaatc atcctggaga ccaagagcaa gaccatttac    60

<210> SEQ ID NO 575
<211> LENGTH: 60
<212> TYPE: DNA
<213> ORGANISM: Homo sapiens

<400> SEQUENCE: 575
cacaaattcc tcactcatct tgcagaagct cccagttttc aatattctcc taaatgctgt    60

<210> SEQ ID NO 576
<211> LENGTH: 60
<212> TYPE: DNA
<213> ORGANISM: Homo sapiens

<400> SEQUENCE: 576
gttcctagta gaaaaacaga agacattacc caaactacct aaatctgctc caagcattag    60

<210> SEQ ID NO 577
<211> LENGTH: 60
<212> TYPE: DNA
<213> ORGANISM: Homo sapiens

<400> SEQUENCE: 577
gaaaaatctc attcccagag tcagaggaga agagacatgt accttgacca tcgtccttcc    60

<210> SEQ ID NO 578
<211> LENGTH: 60
<212> TYPE: DNA
<213> ORGANISM: Homo sapiens

<400> SEQUENCE: 578
gacatcccag cttgcggtaa atagaagtca ttgcccctaa tgtattcaat catctttaaa    60

<210> SEQ ID NO 579
<211> LENGTH: 60
<212> TYPE: DNA
<213> ORGANISM: Homo sapiens

<400> SEQUENCE: 579
tcaaagacaa gagaaagcaa aagcctccaa gctctccaaa aagaaagcat ctgccctgtt    60

<210> SEQ ID NO 580
<211> LENGTH: 60
<212> TYPE: DNA
<213> ORGANISM: Homo sapiens

<400> SEQUENCE: 580
agacacagga tgttcctgtt ggtccagata cttgagctaa aaggtgatgg atacctggat    60

```
<210> SEQ ID NO 581
<211> LENGTH: 60
<212> TYPE: DNA
<213> ORGANISM: Homo sapiens

<400> SEQUENCE: 581
ctacttccca aaatagtatt tctctcagca gatatttctt tggtactacc atgtattgtg      60

<210> SEQ ID NO 582
<211> LENGTH: 60
<212> TYPE: DNA
<213> ORGANISM: Homo sapiens

<400> SEQUENCE: 582
tacttcaaag gctcatcaag tcccgaggaa agtctcagtc caaacacctc aatgtccaaa      60

<210> SEQ ID NO 583
<211> LENGTH: 60
<212> TYPE: DNA
<213> ORGANISM: Homo sapiens

<400> SEQUENCE: 583
tcgcggtgag actgaacatt tcatgagctc atgttgcctt tgaccaccat ttcttaagga      60

<210> SEQ ID NO 584
<211> LENGTH: 60
<212> TYPE: DNA
<213> ORGANISM: Homo sapiens

<400> SEQUENCE: 584
atgggagatt ttccaccagt cctgtgcaaa caaggatatc tgagtctttc ccagcgaaaa      60

<210> SEQ ID NO 585
<211> LENGTH: 60
<212> TYPE: DNA
<213> ORGANISM: Homo sapiens

<400> SEQUENCE: 585
ttctcttgag ggttgagaga gtctgttttc ctaagaatct ggttctctcc atcagtctct      60

<210> SEQ ID NO 586
<211> LENGTH: 60
<212> TYPE: DNA
<213> ORGANISM: Homo sapiens

<400> SEQUENCE: 586
atgtctcttt caaccatatg atcaatcagt tggacgactt ctggttttc ctgaataaat      60

<210> SEQ ID NO 587
<211> LENGTH: 60
<212> TYPE: DNA
<213> ORGANISM: Homo sapiens

<400> SEQUENCE: 587
ctcttcatag ctcagttctc agtgcataca gagattcaat atagccccat cgctctcagt      60

<210> SEQ ID NO 588
<211> LENGTH: 60
<212> TYPE: DNA
<213> ORGANISM: Homo sapiens

<400> SEQUENCE: 588
catagagcag ttgctcccca ttgacaccaa gtaattccag tccacatttg cctttaagca      60
```

```
<210> SEQ ID NO 589
<211> LENGTH: 60
<212> TYPE: DNA
<213> ORGANISM: Homo sapiens

<400> SEQUENCE: 589
acccagcgag gagccaacta tcccaaatat acctggggtg aaatatacca aattctgcat      60

<210> SEQ ID NO 590
<211> LENGTH: 60
<212> TYPE: DNA
<213> ORGANISM: Homo sapiens

<400> SEQUENCE: 590
acccagcgag gagccaacta tcccaaatat acctggggtg aaatatacca aattctgcat      60

<210> SEQ ID NO 591
<211> LENGTH: 60
<212> TYPE: DNA
<213> ORGANISM: Homo sapiens

<400> SEQUENCE: 591
acccagcgag gagccaacta tcccaaatat acctggggtg aaatatacca aattctgcat      60

<210> SEQ ID NO 592
<211> LENGTH: 60
<212> TYPE: DNA
<213> ORGANISM: Homo sapiens

<400> SEQUENCE: 592
acccagcgag gagccaacta tcccaaatat acctggggtg aaatatacca aattctgcat      60

<210> SEQ ID NO 593
<211> LENGTH: 60
<212> TYPE: DNA
<213> ORGANISM: Homo sapiens

<400> SEQUENCE: 593
acccagcgag gagccaacta tcccaaatat acctggggtg aaatatacca aattctgcat      60

<210> SEQ ID NO 594
<211> LENGTH: 60
<212> TYPE: DNA
<213> ORGANISM: Homo sapiens

<400> SEQUENCE: 594
acccagcgag gagccaacta tcccaaatat acctggggtg aaatatacca aattctgcat      60

<210> SEQ ID NO 595
<211> LENGTH: 60
<212> TYPE: DNA
<213> ORGANISM: Homo sapiens

<400> SEQUENCE: 595
acccagcgag gagccaacta tcccaaatat acctggggtg aaatatacca aattctgcat      60

<210> SEQ ID NO 596
<211> LENGTH: 60
<212> TYPE: DNA
<213> ORGANISM: Homo sapiens

<400> SEQUENCE: 596
acccagcgag gagccaacta tcccaaatat acctggggtg aaatatacca aattctgcat      60
```

<210> SEQ ID NO 597
<211> LENGTH: 60
<212> TYPE: DNA
<213> ORGANISM: Homo sapiens

<400> SEQUENCE: 597
tgaaatatac caaattctgc atctccagag gaaaataaga aataaagatg aattgttgca    60

<210> SEQ ID NO 598
<211> LENGTH: 60
<212> TYPE: DNA
<213> ORGANISM: Homo sapiens

<400> SEQUENCE: 598
acccagcgag gagccaacta tcccaaatat acctggggtg aaatatacca aattctgcat    60

<210> SEQ ID NO 599
<211> LENGTH: 60
<212> TYPE: DNA
<213> ORGANISM: Homo sapiens

<400> SEQUENCE: 599
acccagcgag gagccaacta tcccaaatat acctggggtg aaatatacca aattctgcat    60

<210> SEQ ID NO 600
<211> LENGTH: 60
<212> TYPE: DNA
<213> ORGANISM: Homo sapiens

<400> SEQUENCE: 600
cacggtcctg ctggtggtgg acaaatgcga cgaacctctg agcatcctgg tgaggaataa    60

<210> SEQ ID NO 601
<211> LENGTH: 60
<212> TYPE: DNA
<213> ORGANISM: Homo sapiens

<400> SEQUENCE: 601
ttgttcgttt tgccttctgt ccttggaaca gtcatatctc aagttcaaag gccaaaacct    60

<210> SEQ ID NO 602
<211> LENGTH: 60
<212> TYPE: DNA
<213> ORGANISM: Homo sapiens

<400> SEQUENCE: 602
agacttgtat actggctgaa tatcagtgct gtttgtaatt tttcactttg agaaccaaca    60

<210> SEQ ID NO 603
<211> LENGTH: 60
<212> TYPE: DNA
<213> ORGANISM: Homo sapiens

<400> SEQUENCE: 603
actctgagtc agttgaaata gggtaccatc taggtcagtt taagaagagt cagctcagag    60

<210> SEQ ID NO 604
<211> LENGTH: 60
<212> TYPE: DNA
<213> ORGANISM: Homo sapiens

<400> SEQUENCE: 604
tgcagtcagt gggggcagct ggactctctg tgacatctaa agttatcggg ggctttgctg    60

```
<210> SEQ ID NO 605
<211> LENGTH: 60
<212> TYPE: DNA
<213> ORGANISM: Homo sapiens

<400> SEQUENCE: 605
accaggatgt tcagaggttc gtcgcatttg tccaccacca gcaggaccgt gctgccgggg      60

<210> SEQ ID NO 606
<211> LENGTH: 60
<212> TYPE: DNA
<213> ORGANISM: Homo sapiens

<400> SEQUENCE: 606
cgctcccaga tgtaaagaac gcgacttcca caaacctgga ttttttatgt acaaccctga      60

<210> SEQ ID NO 607
<211> LENGTH: 60
<212> TYPE: DNA
<213> ORGANISM: Homo sapiens

<400> SEQUENCE: 607
attctggatg aatatatgcg ctttctgaac tgtagaaagg gacggaagga cccttccaag      60

<210> SEQ ID NO 608
<211> LENGTH: 60
<212> TYPE: DNA
<213> ORGANISM: Homo sapiens

<400> SEQUENCE: 608
ctctgcatct actggacaaa gtattatgac tttaaaaacc ccattattga aaagtacctg      60

<210> SEQ ID NO 609
<211> LENGTH: 60
<212> TYPE: DNA
<213> ORGANISM: Homo sapiens

<400> SEQUENCE: 609
caaccctgac cgtgaccgtt tgctatattc cttttttctat gaaataatgt gaatgataat     60

<210> SEQ ID NO 610
<211> LENGTH: 60
<212> TYPE: DNA
<213> ORGANISM: Homo sapiens

<400> SEQUENCE: 610
aaggatgttc taattctttc tgctctgaga cgaatgctat gggctgcaga tgacttctta      60

<210> SEQ ID NO 611
<211> LENGTH: 60
<212> TYPE: DNA
<213> ORGANISM: Homo sapiens

<400> SEQUENCE: 611
ctgaccgtga ccgtttgcta tattcctttt tctatgaaat aatgtgaata ataattaaac      60

<210> SEQ ID NO 612
<211> LENGTH: 60
<212> TYPE: DNA
<213> ORGANISM: Homo sapiens

<400> SEQUENCE: 612
agtagccagc agctcccaga acctcttctt ccttcttggc ctaactcttc cagttaggat      60
```

<210> SEQ ID NO 613
<211> LENGTH: 60
<212> TYPE: DNA
<213> ORGANISM: Homo sapiens

<400> SEQUENCE: 613
agaagagaag catttagaga gcatcagcaa tacaaaaccg ctgagttctt gagcaaactg    60

<210> SEQ ID NO 614
<211> LENGTH: 60
<212> TYPE: DNA
<213> ORGANISM: Homo sapiens

<400> SEQUENCE: 614
tgggggagct tcctacaagg agagactcct gctgctttgg aaaactgaga aaaatagggg    60

<210> SEQ ID NO 615
<211> LENGTH: 60
<212> TYPE: DNA
<213> ORGANISM: Homo sapiens

<400> SEQUENCE: 615
ctgaagatca gaggctcagt tagcaacctg tgttgtagca gtgatgtcag tccattgatt    60

<210> SEQ ID NO 616
<211> LENGTH: 60
<212> TYPE: DNA
<213> ORGANISM: Homo sapiens

<400> SEQUENCE: 616
caaaataatc tgaaacttta ctggccaaag tgggactcct ttaaaattcc aaaacttgcc    60

<210> SEQ ID NO 617
<211> LENGTH: 60
<212> TYPE: DNA
<213> ORGANISM: Homo sapiens

<400> SEQUENCE: 617
acagtggatc ttggagtggg atttcttggg taaattatct ttgcccttttg aaatgtctcc    60

<210> SEQ ID NO 618
<211> LENGTH: 60
<212> TYPE: DNA
<213> ORGANISM: Homo sapiens

<400> SEQUENCE: 618
agaaggcaga gaaagtgaag accaagtcca gaactgaatc ctaagaaatg caggactgca    60

<210> SEQ ID NO 619
<211> LENGTH: 60
<212> TYPE: DNA
<213> ORGANISM: Homo sapiens

<400> SEQUENCE: 619
tctttggcaa tggccaccct ggtgttggca tattggcccc actgtaactt ttgggggctt    60

<210> SEQ ID NO 620
<211> LENGTH: 60
<212> TYPE: DNA
<213> ORGANISM: Homo sapiens

<400> SEQUENCE: 620
aaccaaatat ctatgtaggc agaggtaacc aggagagaag caagacttgc tgcctaaagg    60

```
<210> SEQ ID NO 621
<211> LENGTH: 60
<212> TYPE: DNA
<213> ORGANISM: Homo sapiens

<400> SEQUENCE: 621
ctgtcatttt ccatttccgt tcctggatct acggagtctt ctaagagatt ttgcaatgag      60

<210> SEQ ID NO 622
<211> LENGTH: 60
<212> TYPE: DNA
<213> ORGANISM: Homo sapiens

<400> SEQUENCE: 622
gtttccagcc agttagtttt ctctgggaga cttctctgta catttctgcc atgtactcca      60

<210> SEQ ID NO 623
<211> LENGTH: 60
<212> TYPE: DNA
<213> ORGANISM: Homo sapiens

<400> SEQUENCE: 623
caaataaacc aacgggaaaa aagaaaggtt ccagttttgt ctgaaaattc tgattaagcc      60

<210> SEQ ID NO 624
<211> LENGTH: 60
<212> TYPE: DNA
<213> ORGANISM: Homo sapiens

<400> SEQUENCE: 624
ggcatcggag aagtgcagct gctgtgcctg atgtgggaac agctcttctc ccagatgtaa      60

<210> SEQ ID NO 625
<211> LENGTH: 60
<212> TYPE: DNA
<213> ORGANISM: Homo sapiens

<400> SEQUENCE: 625
actttgagaa ctctgtgaga caaggtcctt aggcacccag atatcagcca ctttcacatt      60

<210> SEQ ID NO 626
<211> LENGTH: 60
<212> TYPE: DNA
<213> ORGANISM: Homo sapiens

<400> SEQUENCE: 626
ctgctgtgcc tgatgtgggg acagacctgc tcccagatgt aaacagagca acctgcacaa      60

<210> SEQ ID NO 627
<211> LENGTH: 60
<212> TYPE: DNA
<213> ORGANISM: Homo sapiens

<400> SEQUENCE: 627
cagcttattt cctcattttt ataatgtccc ttcacaaacc cagtgtttta ggagcatgag      60

<210> SEQ ID NO 628
<211> LENGTH: 60
<212> TYPE: DNA
<213> ORGANISM: Homo sapiens

<400> SEQUENCE: 628
tgccaagtgt gcccagggct gcatctgcaa agggacgtca gacaagtgca gctgctgtgt      60
```

<210> SEQ ID NO 629
<211> LENGTH: 60
<212> TYPE: DNA
<213> ORGANISM: Homo sapiens

<400> SEQUENCE: 629
tgtgccaagt gtgcccacgg ctgcatctgc aaagggacgt cggagaagtg cagctgctgt    60

<210> SEQ ID NO 630
<211> LENGTH: 60
<212> TYPE: DNA
<213> ORGANISM: Homo sapiens

<400> SEQUENCE: 630
agctgctgtg cctgatgtcg ggacagccct gctcccaagt acaaatagag tgacccgtaa    60

<210> SEQ ID NO 631
<211> LENGTH: 60
<212> TYPE: DNA
<213> ORGANISM: Homo sapiens

<400> SEQUENCE: 631
caagcaggat caagtttgta gaataaacac tggtttccta gccatcctct gaaaacagta    60

<210> SEQ ID NO 632
<211> LENGTH: 60
<212> TYPE: DNA
<213> ORGANISM: Homo sapiens

<400> SEQUENCE: 632
ctactgcgtg actgtgtctg ctagtgccgg cattgggaat ctcgtgacat ttggccacag    60

<210> SEQ ID NO 633
<211> LENGTH: 60
<212> TYPE: DNA
<213> ORGANISM: Homo sapiens

<400> SEQUENCE: 633
tttaacactg gcattcctgc ctacttgctg tggtggtctt gtgaaaggtg atgggtttta    60

<210> SEQ ID NO 634
<211> LENGTH: 60
<212> TYPE: DNA
<213> ORGANISM: Homo sapiens

<400> SEQUENCE: 634
tttgcactat ggtagatttc aggaatttca aaagaaatct gatgtcagtg caattatccg    60

<210> SEQ ID NO 635
<211> LENGTH: 60
<212> TYPE: DNA
<213> ORGANISM: Homo sapiens

<400> SEQUENCE: 635
tcaacttgac ttcatgttaa aaaccctcaa caaaccaggc gtcgaaggaa catacctcaa    60

<210> SEQ ID NO 636
<211> LENGTH: 60
<212> TYPE: DNA
<213> ORGANISM: Homo sapiens

<400> SEQUENCE: 636
tcttcaaagc aaagctcttt actttcccct tggttctcat aactctgtga tcttgctctc    60

<210> SEQ ID NO 637
<211> LENGTH: 60
<212> TYPE: DNA
<213> ORGANISM: Homo sapiens

<400> SEQUENCE: 637
tgtcctgaaa gttggaatga aagagaccct ataagagcac tgacatgttt cagtgtcctc    60

<210> SEQ ID NO 638
<211> LENGTH: 60
<212> TYPE: DNA
<213> ORGANISM: Homo sapiens

<400> SEQUENCE: 638
ggaaggtcaa ttacaacttt gaagatgaga ccgtgaggaa gtttctactg agccagttgc    60

<210> SEQ ID NO 639
<211> LENGTH: 60
<212> TYPE: DNA
<213> ORGANISM: Homo sapiens

<400> SEQUENCE: 639
attcgaataa agctcttgag aagggactga atcctctgaa tgcatactcc gatctcgctg    60

<210> SEQ ID NO 640
<211> LENGTH: 60
<212> TYPE: DNA
<213> ORGANISM: Homo sapiens

<400> SEQUENCE: 640
catactgtac tcagaatcac gacattcctt ccctaccaag gccacttcta tttttttgagg   60

<210> SEQ ID NO 641
<211> LENGTH: 60
<212> TYPE: DNA
<213> ORGANISM: Homo sapiens

<400> SEQUENCE: 641
ttcacctcag tctctaattg gctgtgagtc agtctttcat ttacataggg tgtaaccatc    60

<210> SEQ ID NO 642
<211> LENGTH: 60
<212> TYPE: DNA
<213> ORGANISM: Homo sapiens

<400> SEQUENCE: 642
tcatcagaga agtgccgctg ctgtgcctga tgttgggaga gccctgctcc cagacataaa    60

<210> SEQ ID NO 643
<211> LENGTH: 60
<212> TYPE: DNA
<213> ORGANISM: Homo sapiens

<400> SEQUENCE: 643
caacagcctc tatgacgaca tcgagtgctt ccttatggag ctggagcagc ccgcctagaa    60

<210> SEQ ID NO 644
<211> LENGTH: 60
<212> TYPE: DNA
<213> ORGANISM: Homo sapiens

<400> SEQUENCE: 644
ccagggctgc atctgcaaag ggacgtcaga caagtgcagc tgctgtgcct gatgccagga    60

-continued

<210> SEQ ID NO 645
<211> LENGTH: 60
<212> TYPE: DNA
<213> ORGANISM: Homo sapiens

<400> SEQUENCE: 645
cggaagtgcc taagtcttta gtttccaatt tgcggatcca ctgccctctg cttgcgggct    60

<210> SEQ ID NO 646
<211> LENGTH: 60
<212> TYPE: DNA
<213> ORGANISM: Homo sapiens

<400> SEQUENCE: 646
taaagagctt tgctttgaag acacagagga ttccttttt agactggaag gaaaaggag    60

<210> SEQ ID NO 647
<211> LENGTH: 60
<212> TYPE: DNA
<213> ORGANISM: Homo sapiens

<400> SEQUENCE: 647
aatgtggctt ctctaatgta gtttctttga ttaccgacta cacaattatg taccatcaca    60

<210> SEQ ID NO 648
<211> LENGTH: 60
<212> TYPE: DNA
<213> ORGANISM: Homo sapiens

<400> SEQUENCE: 648
agtcacagtt accgcgtgta ctacaatgcc ggccccaagg atgaggacca ggactacatc    60

<210> SEQ ID NO 649
<211> LENGTH: 60
<212> TYPE: DNA
<213> ORGANISM: Homo sapiens

<400> SEQUENCE: 649
aagatagatc cagaaaatgc agaattcctg actgctctct gtgagctccg actttccatt    60

<210> SEQ ID NO 650
<211> LENGTH: 60
<212> TYPE: DNA
<213> ORGANISM: Homo sapiens

<400> SEQUENCE: 650
atccccccac caggataaaa gtcctgacct ttgttctctt gacggaataa aagcttgctt    60

<210> SEQ ID NO 651
<211> LENGTH: 60
<212> TYPE: DNA
<213> ORGANISM: Homo sapiens

<400> SEQUENCE: 651
accatgttga ctttcctcat gtgtttcctt atgactcagt aagttggcaa ggtcctgact    60

<210> SEQ ID NO 652
<211> LENGTH: 60
<212> TYPE: DNA
<213> ORGANISM: Homo sapiens

<400> SEQUENCE: 652
atgagcggat gggcaaaaag ttgacagagt tgtctatgca ggatgaagag ctgatgaaga    60

<210> SEQ ID NO 653
<211> LENGTH: 60
<212> TYPE: DNA
<213> ORGANISM: Homo sapiens

<400> SEQUENCE: 653
tgctcggctt tcgcttgaa cattcccttg atctcatcag ttctgagcgg gtcatggggc    60

<210> SEQ ID NO 654
<211> LENGTH: 60
<212> TYPE: DNA
<213> ORGANISM: Homo sapiens

<400> SEQUENCE: 654
tggaagttca gttttggtgt ctgcttcaag aggggttttt acactctgat tccaggacaa    60

<210> SEQ ID NO 655
<211> LENGTH: 60
<212> TYPE: DNA
<213> ORGANISM: Homo sapiens

<400> SEQUENCE: 655
ggactggcta tcccaagacc tggcagatgt ggctgctcaa taaacacttg ttgaaccatc    60

<210> SEQ ID NO 656
<211> LENGTH: 60
<212> TYPE: DNA
<213> ORGANISM: Homo sapiens

<400> SEQUENCE: 656
agaacagatt tcttcgcaag actatggaaa ggaagtggac ctctacgctt tggggctaat    60

<210> SEQ ID NO 657
<211> LENGTH: 60
<212> TYPE: DNA
<213> ORGANISM: Homo sapiens

<400> SEQUENCE: 657
atgtttgagt cccaacaaaa ttcatatcaa aacataatcc caactgggtg cagtggctca    60

<210> SEQ ID NO 658
<211> LENGTH: 60
<212> TYPE: DNA
<213> ORGANISM: Homo sapiens

<400> SEQUENCE: 658
atatgatccg gatgaaggac tccttgattt gccttgactg tgccatggag agtagcagaa    60

<210> SEQ ID NO 659
<211> LENGTH: 60
<212> TYPE: DNA
<213> ORGANISM: Homo sapiens

<400> SEQUENCE: 659
gtgaaaatga agacgacaac gttgtcttag cctttgaaca actgagtaca acttttggg    60

<210> SEQ ID NO 660
<211> LENGTH: 60
<212> TYPE: DNA
<213> ORGANISM: Homo sapiens

<400> SEQUENCE: 660
gacaacattt gatcccaaga aaaccagaat ggaacccttt cacttcaaaa actcagttat    60

```
<210> SEQ ID NO 661
<211> LENGTH: 60
<212> TYPE: DNA
<213> ORGANISM: Homo sapiens

<400> SEQUENCE: 661
tgaccagagt gttctcttca ggggactggc tcctttccca gtgtccttaa aataaagaaa      60

<210> SEQ ID NO 662
<211> LENGTH: 60
<212> TYPE: DNA
<213> ORGANISM: Homo sapiens

<400> SEQUENCE: 662
cagccttgga gagagcaggg gtaccaagga tcttcctcca gtgaaggacc ctggagccct      60

<210> SEQ ID NO 663
<211> LENGTH: 60
<212> TYPE: DNA
<213> ORGANISM: Homo sapiens

<400> SEQUENCE: 663
gtgtgtctca tccaggagcc aaaagtccat gaaccagttc gaattgccta tgacaggcct      60

<210> SEQ ID NO 664
<211> LENGTH: 60
<212> TYPE: DNA
<213> ORGANISM: Homo sapiens

<400> SEQUENCE: 664
tgagtggaga agaaacaaac atagtgggta taatcatgga tcgcttgtac ccctgtgaaa      60

<210> SEQ ID NO 665
<211> LENGTH: 60
<212> TYPE: DNA
<213> ORGANISM: Homo sapiens

<400> SEQUENCE: 665
aattaattgt taagctgcag ttgagttgtt caagtgagag ttttgataag ccacttatgg      60

<210> SEQ ID NO 666
<211> LENGTH: 60
<212> TYPE: DNA
<213> ORGANISM: Homo sapiens

<400> SEQUENCE: 666
cattgatatc cactggtcac atcataactg tctatagggc aataaaatct gtgttaaact      60

<210> SEQ ID NO 667
<211> LENGTH: 60
<212> TYPE: DNA
<213> ORGANISM: Homo sapiens

<400> SEQUENCE: 667
agttctttac gctttctgat tgaactgatt tgaagttctt atttcgtgtg ttggggaaca      60

<210> SEQ ID NO 668
<211> LENGTH: 60
<212> TYPE: DNA
<213> ORGANISM: Homo sapiens

<400> SEQUENCE: 668
ctacgtcctg gttgctcaca gtggttcagg agttatcgaa cgtgagacag ttaatgattt      60
```

<210> SEQ ID NO 669
<211> LENGTH: 60
<212> TYPE: DNA
<213> ORGANISM: Homo sapiens

<400> SEQUENCE: 669
atgagggcct cgtttattaa gatctttaaa ctgctttata cactgtcacg tggcttcatc    60

<210> SEQ ID NO 670
<211> LENGTH: 60
<212> TYPE: DNA
<213> ORGANISM: Homo sapiens

<400> SEQUENCE: 670
ggaagaggtg atcactctca cactaagact gaggaaataa aaaggtttg gtgttttcct    60

<210> SEQ ID NO 671
<211> LENGTH: 60
<212> TYPE: DNA
<213> ORGANISM: Homo sapiens

<400> SEQUENCE: 671
cgatttttct tcatgacctt aacctgtgtg ggctaacaga ggacccagat cttacaggtt    60

<210> SEQ ID NO 672
<211> LENGTH: 60
<212> TYPE: DNA
<213> ORGANISM: Homo sapiens

<400> SEQUENCE: 672
tgattcggtt tctcagagtc tcatggcatc atagttttc cagaatgaca cagtagccac    60

<210> SEQ ID NO 673
<211> LENGTH: 60
<212> TYPE: DNA
<213> ORGANISM: Homo sapiens

<400> SEQUENCE: 673
tctaagagag aatggaatgt atgggaaaag aaagttactg gaactaatag gacacgctgt    60

<210> SEQ ID NO 674
<211> LENGTH: 60
<212> TYPE: DNA
<213> ORGANISM: Homo sapiens

<400> SEQUENCE: 674
tcagccggga gctgtgctgg cgagaaggcc caggcacgga ccagactgag gcagaggccc    60

<210> SEQ ID NO 675
<211> LENGTH: 60
<212> TYPE: DNA
<213> ORGANISM: Homo sapiens

<400> SEQUENCE: 675
aagtgcaaat gcacctcctg caagaagagc tgctgctcct gttgccccct gggctgtgcc    60

<210> SEQ ID NO 676
<211> LENGTH: 60
<212> TYPE: DNA
<213> ORGANISM: Homo sapiens

<400> SEQUENCE: 676
caacagtgga acaatgccac atggacagag gtctcctaca ccttctcaga ctaccccgg    60

<210> SEQ ID NO 677
<211> LENGTH: 60
<212> TYPE: DNA
<213> ORGANISM: Homo sapiens

<400> SEQUENCE: 677
ttcgtttcag tcaagacaat gcttagttca gatactcaaa aatgtcttca ctctgtctta    60

<210> SEQ ID NO 678
<211> LENGTH: 60
<212> TYPE: DNA
<213> ORGANISM: Homo sapiens

<400> SEQUENCE: 678
gtttagctct tacactctat ccttcctaga aaatggtaat tgagattact cagatattaa    60

<210> SEQ ID NO 679
<211> LENGTH: 60
<212> TYPE: DNA
<213> ORGANISM: Homo sapiens

<400> SEQUENCE: 679
gtacataaga atctatcact aagtaatgta tccttcagaa tgtgttggtt taccagtgac    60

<210> SEQ ID NO 680
<211> LENGTH: 60
<212> TYPE: DNA
<213> ORGANISM: Homo sapiens

<400> SEQUENCE: 680
accagtcctg cccccaaaac tgaccatgaa ccccaactgg actgtgaggt ctgattccga    60

<210> SEQ ID NO 681
<211> LENGTH: 60
<212> TYPE: DNA
<213> ORGANISM: Homo sapiens

<400> SEQUENCE: 681
taacagggcc ttgctaatcg ggttgtcact caacaaaagt gctttggatt taagttacta    60

<210> SEQ ID NO 682
<211> LENGTH: 60
<212> TYPE: DNA
<213> ORGANISM: Homo sapiens

<400> SEQUENCE: 682
gagattgtcc agagtcctat gacagacctt caaggtttta agttccacag acttggactt    60

<210> SEQ ID NO 683
<211> LENGTH: 60
<212> TYPE: DNA
<213> ORGANISM: Homo sapiens

<400> SEQUENCE: 683
tattcctgca tttgtgaaat gatggtgaaa gtaagtggta gcttttccct tcttttttctt   60

<210> SEQ ID NO 684
<211> LENGTH: 60
<212> TYPE: DNA
<213> ORGANISM: Homo sapiens

<400> SEQUENCE: 684
tccccgtacc ggaaacaggt ggagaaaatc cgttactgca tcaccaaact tgacagggag    60

<210> SEQ ID NO 685
<211> LENGTH: 60
<212> TYPE: DNA
<213> ORGANISM: Homo sapiens

<400> SEQUENCE: 685
gtcgtcgtcc cgcagacaca caatccagaa gtcactttcc tcgagacatt ggtcagccca    60

<210> SEQ ID NO 686
<211> LENGTH: 60
<212> TYPE: DNA
<213> ORGANISM: Homo sapiens

<400> SEQUENCE: 686
ccttacacct aaataataca agagattaat gaatagtggt tagaagtagt tgagggagag    60

<210> SEQ ID NO 687
<211> LENGTH: 60
<212> TYPE: DNA
<213> ORGANISM: Homo sapiens

<400> SEQUENCE: 687
tgccccttaa aagattgaag aaagagaaac ttgtcaactc atatccacgt tatctagcaa    60

<210> SEQ ID NO 688
<211> LENGTH: 60
<212> TYPE: DNA
<213> ORGANISM: Homo sapiens

<400> SEQUENCE: 688
cgccaagcat gtgaacatct gggccctgac tgtgggcatc ctcatgacca ttctgctcat    60

<210> SEQ ID NO 689
<211> LENGTH: 60
<212> TYPE: DNA
<213> ORGANISM: Homo sapiens

<400> SEQUENCE: 689
gctcagggaa ggggctggga tcggaacttc ctgctcttgt ttctggacaa ctttcccctt    60

<210> SEQ ID NO 690
<211> LENGTH: 60
<212> TYPE: DNA
<213> ORGANISM: Homo sapiens

<400> SEQUENCE: 690
aatagaccga atatcaggga gccctgcgg atggacctcg ctgacctgct gacacagaat     60

<210> SEQ ID NO 691
<211> LENGTH: 60
<212> TYPE: DNA
<213> ORGANISM: Homo sapiens

<400> SEQUENCE: 691
aggtgatgta gcacttccaa gatggcacca gcatttggtt cttctcaaga gttgaccatt    60

<210> SEQ ID NO 692
<211> LENGTH: 60
<212> TYPE: DNA
<213> ORGANISM: Homo sapiens

<400> SEQUENCE: 692
aggggacaca ggcttcttaa aacaacccgg cttcctcacc ctatgtcctt tatttacaaa    60

```
<210> SEQ ID NO 693
<211> LENGTH: 60
<212> TYPE: DNA
<213> ORGANISM: Homo sapiens

<400> SEQUENCE: 693
cccagccttt ccaaccgtgc ctgggatctg ggctttaatg cagaggccat gtccttatct    60

<210> SEQ ID NO 694
<211> LENGTH: 60
<212> TYPE: DNA
<213> ORGANISM: Homo sapiens

<400> SEQUENCE: 694
ccgcctgggg gtgggcgcag agctgctggt cgacgtgggt cagaggctgc gccgtgggac    60

<210> SEQ ID NO 695
<211> LENGTH: 60
<212> TYPE: DNA
<213> ORGANISM: Homo sapiens

<400> SEQUENCE: 695
ttctcttcct cacctgaaat tatgcttcct aaaatctcaa gccaaactca agaatgggg     60

<210> SEQ ID NO 696
<211> LENGTH: 60
<212> TYPE: DNA
<213> ORGANISM: Homo sapiens

<400> SEQUENCE: 696
gccatcaacc tactgaagtt gtgtggaggg atggaaagtg ggtcagtgga gaagggattc    60

<210> SEQ ID NO 697
<211> LENGTH: 60
<212> TYPE: DNA
<213> ORGANISM: Homo sapiens

<400> SEQUENCE: 697
agctgaccca gcatcagcca cactctgggt tggaaaatgt ttgcctgttg gaattaattt    60

<210> SEQ ID NO 698
<211> LENGTH: 60
<212> TYPE: DNA
<213> ORGANISM: Homo sapiens

<400> SEQUENCE: 698
tgagccctac atcaagtggg aagacaagga cgccaagatc ttccgagttg tggatccaaa    60

<210> SEQ ID NO 699
<211> LENGTH: 60
<212> TYPE: DNA
<213> ORGANISM: Homo sapiens

<400> SEQUENCE: 699
gctatccggg tgttagctga ccaaaatgtc attcctaatg tggctaatgt cacttgctat    60

<210> SEQ ID NO 700
<211> LENGTH: 60
<212> TYPE: DNA
<213> ORGANISM: Homo sapiens

<400> SEQUENCE: 700
atctgttgtg tttctgagtc tagggtctgt acacttgttt ataataaatg caatcgtttg    60
```

<210> SEQ ID NO 701
<211> LENGTH: 60
<212> TYPE: DNA
<213> ORGANISM: Homo sapiens

<400> SEQUENCE: 701
atagccagaa agcggcagtt tcagtccata tcaattgtgt gaccagggct agtcactttt    60

<210> SEQ ID NO 702
<211> LENGTH: 60
<212> TYPE: DNA
<213> ORGANISM: Homo sapiens

<400> SEQUENCE: 702
atacagcagt ttatacccac acacctgtct acagtgtcat tcaataaagt gcacgtgctt    60

<210> SEQ ID NO 703
<211> LENGTH: 60
<212> TYPE: DNA
<213> ORGANISM: Homo sapiens

<400> SEQUENCE: 703
aaatattaac atttccctgg accataagag acctttgatt aaggttttgg gaattagcag    60

<210> SEQ ID NO 704
<211> LENGTH: 60
<212> TYPE: DNA
<213> ORGANISM: Homo sapiens

<400> SEQUENCE: 704
aggacatagc accctcatct gggaataggg aaggcacctt gcagaaaata tgagcaattt    60

<210> SEQ ID NO 705
<211> LENGTH: 60
<212> TYPE: DNA
<213> ORGANISM: Homo sapiens

<400> SEQUENCE: 705
aaactgtgag gcaaataaaa tgcttctcaa atctgtgtgg ctcttatggg gttaatttga    60

<210> SEQ ID NO 706
<211> LENGTH: 60
<212> TYPE: DNA
<213> ORGANISM: Homo sapiens

<400> SEQUENCE: 706
atgagggcct cgtttattaa gatctttaaa ctgctttata cactgtcacg tggcttcatc    60

<210> SEQ ID NO 707
<211> LENGTH: 60
<212> TYPE: DNA
<213> ORGANISM: Homo sapiens

<400> SEQUENCE: 707
tgtcgacctg gacttgaact aaaggaaggg cctctgctga ctcctaccag agcatccgtc    60

<210> SEQ ID NO 708
<211> LENGTH: 60
<212> TYPE: DNA
<213> ORGANISM: Homo sapiens

<400> SEQUENCE: 708
ggtactgagc agagtcttag gtaaaagtct tgggaaatat ttgggcattg gtctggccaa    60

<210> SEQ ID NO 709
<211> LENGTH: 60
<212> TYPE: DNA
<213> ORGANISM: Homo sapiens

<400> SEQUENCE: 709
atgagggcct cgtttattaa gatctttaaa ctgctttata cactgtcacg tggcttcatc    60

<210> SEQ ID NO 710
<211> LENGTH: 60
<212> TYPE: DNA
<213> ORGANISM: Homo sapiens

<400> SEQUENCE: 710
gcgtgatgtt ccttagccca aagacggtga gacagggctg aaatcaggtg gcttctgcca    60

<210> SEQ ID NO 711
<211> LENGTH: 60
<212> TYPE: DNA
<213> ORGANISM: Homo sapiens

<400> SEQUENCE: 711
atgagggcct cgtttattaa gatctttaaa ctgctttata cactgtcacg tggcttcatc    60

<210> SEQ ID NO 712
<211> LENGTH: 60
<212> TYPE: DNA
<213> ORGANISM: Homo sapiens

<400> SEQUENCE: 712
cccagaagat cgttgcgacc taccgcctgt gctcggaaca actgtcctct cagcatcatt    60

<210> SEQ ID NO 713
<211> LENGTH: 60
<212> TYPE: DNA
<213> ORGANISM: Homo sapiens

<400> SEQUENCE: 713
atgagggcct cgtttattaa gatctttaaa ctgctttata cactgtcacg tggcttcatc    60

<210> SEQ ID NO 714
<211> LENGTH: 60
<212> TYPE: DNA
<213> ORGANISM: Homo sapiens

<400> SEQUENCE: 714
tgccaggaca acctttctcc cagatgtaaa cagagagaca tgtacaaacc tggattttt    60

<210> SEQ ID NO 715
<211> LENGTH: 60
<212> TYPE: DNA
<213> ORGANISM: Homo sapiens

<400> SEQUENCE: 715
cttttcaagt tgggtgatat gttggtagat tctaatggct ttattgcagc gattaataac    60

<210> SEQ ID NO 716
<211> LENGTH: 60
<212> TYPE: DNA
<213> ORGANISM: Homo sapiens

<400> SEQUENCE: 716
ctgagtgggt atcctgataa atctgggctt gtcttcctaa tgctaccttt gttggtcctt    60

```
<210> SEQ ID NO 717
<211> LENGTH: 60
<212> TYPE: DNA
<213> ORGANISM: Homo sapiens

<400> SEQUENCE: 717 ttgaaccta cacgaagaaa gaactttctg ctgttacttt ccctgacatc attcgcaatt    60

<210> SEQ ID NO 718
<211> LENGTH: 60
<212> TYPE: DNA
<213> ORGANISM: Homo sapiens

<400> SEQUENCE: 718
atgagggcct cgtttattaa gatctttaaa ctgctttata cactgtcacg tggcttcatc    60

<210> SEQ ID NO 719
<211> LENGTH: 60
<212> TYPE: DNA
<213> ORGANISM: Homo sapiens

<400> SEQUENCE: 719
tcccatagaa gttccctccc tttgaaatta atatataatg tataaattct gcactgagcc    60

<210> SEQ ID NO 720
<211> LENGTH: 60
<212> TYPE: DNA
<213> ORGANISM: Homo sapiens

<400> SEQUENCE: 720
tgaagacctg atcgagtgta ttgattttag tattgcttcg tgtcctccac acaggaggag    60

<210> SEQ ID NO 721
<211> LENGTH: 60
<212> TYPE: DNA
<213> ORGANISM: Homo sapiens

<400> SEQUENCE: 721
tttataataa ccgtagccca cattgtagta gttttcagc tctttactaa gtcccaccaa    60

<210> SEQ ID NO 722
<211> LENGTH: 60
<212> TYPE: DNA
<213> ORGANISM: Homo sapiens

<400> SEQUENCE: 722
acagtgaatt ttgatgcatt taaaataaga ttctgatgcc agactgttaa aacaggcgct    60

<210> SEQ ID NO 723
<211> LENGTH: 60
<212> TYPE: DNA
<213> ORGANISM: Homo sapiens

<400> SEQUENCE: 723
tatgaagaaa tcgggagtgc acttttgac tgtagattgt tcgaagacac atttgtaaat    60

<210> SEQ ID NO 724
<211> LENGTH: 60
<212> TYPE: DNA
<213> ORGANISM: Homo sapiens

<400> SEQUENCE: 724
tcactggagg aagattttcc cttgcttctg cataaaattt taactccata acttataagc    60
```

<210> SEQ ID NO 725
<211> LENGTH: 60
<212> TYPE: DNA
<213> ORGANISM: Homo sapiens

<400> SEQUENCE: 725
tttttagtgg catgcaggct atacctcagt atttgtggac atgcacccag gaatatgtac    60

<210> SEQ ID NO 726
<211> LENGTH: 60
<212> TYPE: DNA
<213> ORGANISM: Homo sapiens

<400> SEQUENCE: 726
aggcagagga acgcgttgtg gtgatcagca gctcggaaga ctcagatgcc gaaaactcgt    60

<210> SEQ ID NO 727
<211> LENGTH: 60
<212> TYPE: DNA
<213> ORGANISM: Homo sapiens

<400> SEQUENCE: 727
aaatcttaac tctgctacat ggctctgact gctgtggggg attgaaaaga atatgcttat    60

<210> SEQ ID NO 728
<211> LENGTH: 60
<212> TYPE: DNA
<213> ORGANISM: Homo sapiens

<400> SEQUENCE: 728
tctgggtcaa attcttcttt tgtatgtcca gtctcctgca cagcacctgc agcattgtaa    60

<210> SEQ ID NO 729
<211> LENGTH: 60
<212> TYPE: DNA
<213> ORGANISM: Homo sapiens

<400> SEQUENCE: 729
gcctgatgaa cgtaggcacg tgatgcgtaa tagtcttcaa tggtacactt aactagtctc    60

<210> SEQ ID NO 730
<211> LENGTH: 60
<212> TYPE: DNA
<213> ORGANISM: Homo sapiens

<400> SEQUENCE: 730
atgagggcct cgtttattaa gatctttaaa ctgctttata cactgtcacg tggcttcatc    60

<210> SEQ ID NO 731
<211> LENGTH: 60
<212> TYPE: DNA
<213> ORGANISM: Homo sapiens

<400> SEQUENCE: 731
aactattttt gtttgtattc actgtccccct gcaaggggga cggggcggga gcactggtca    60

<210> SEQ ID NO 732
<211> LENGTH: 60
<212> TYPE: DNA
<213> ORGANISM: Homo sapiens

<400> SEQUENCE: 732
atcctcatga gcattctgct catcttcatc ccagtgttga tctttcaagt ctatcaatag    60

-continued

<210> SEQ ID NO 733
<211> LENGTH: 60
<212> TYPE: DNA
<213> ORGANISM: Homo sapiens

<400> SEQUENCE: 733
gaagggtttc acaatgaaga tgtgtagcag gcgttatccc attgttatca ctgggcagaa    60

<210> SEQ ID NO 734
<211> LENGTH: 60
<212> TYPE: DNA
<213> ORGANISM: Homo sapiens

<400> SEQUENCE: 734
aaattcaggt gaaatacttt ggacgtgacc cagccgatgg aagaatgagg ctttctcgaa    60

<210> SEQ ID NO 735
<211> LENGTH: 60
<212> TYPE: DNA
<213> ORGANISM: Homo sapiens

<400> SEQUENCE: 735
ccaatgcaga caaaccaccc cttttttgttg ggaaaggaat tacctttgac agtggtggta    60

<210> SEQ ID NO 736
<211> LENGTH: 60
<212> TYPE: DNA
<213> ORGANISM: Homo sapiens

<400> SEQUENCE: 736
cttttatgtg gttcctgccc ctgagaataa agaagcccca gcgtggctgc gaggcaccat    60

<210> SEQ ID NO 737
<211> LENGTH: 60
<212> TYPE: DNA
<213> ORGANISM: Homo sapiens

<400> SEQUENCE: 737
agtgtggatc ttgtgtgaag ctcactgcct caaggtggcc gtggatggtc agcacctgtt    60

<210> SEQ ID NO 738
<211> LENGTH: 60
<212> TYPE: DNA
<213> ORGANISM: Homo sapiens

<400> SEQUENCE: 738
gggccctgat tctgggcatc ctcatgacca ttctgctcat cgtcatccca gtgctgatct    60

<210> SEQ ID NO 739
<211> LENGTH: 60
<212> TYPE: DNA
<213> ORGANISM: Homo sapiens

<400> SEQUENCE: 739
gacatctgac gtagagacct gcgaatggat ctgagatgag tagtaacgca ggttgtccgg    60

<210> SEQ ID NO 740
<211> LENGTH: 60
<212> TYPE: DNA
<213> ORGANISM: Homo sapiens

<400> SEQUENCE: 740
gcagattctg agaacaataa ctccacaatg gcgtcggcct cggagggtga aatggagtgt    60

<210> SEQ ID NO 741
<211> LENGTH: 60
<212> TYPE: DNA
<213> ORGANISM: Homo sapiens

<400> SEQUENCE: 741
tcctggtgct ctcagcgcaa cagattcttc acgtgaaaca agaaaagcca tatggtcgcc    60

<210> SEQ ID NO 742
<211> LENGTH: 60
<212> TYPE: DNA
<213> ORGANISM: Homo sapiens

<400> SEQUENCE: 742
atcctgagcc tactcgaatc caacaaagac ttgctgttga ctagctcata cctgtctgat    60

<210> SEQ ID NO 743
<211> LENGTH: 60
<212> TYPE: DNA
<213> ORGANISM: Homo sapiens

<400> SEQUENCE: 743
cttctgcccc ccagaccata gccccttttta gttggtttta gttgctctgg ggggaggaga   60

<210> SEQ ID NO 744
<211> LENGTH: 60
<212> TYPE: DNA
<213> ORGANISM: Homo sapiens

<400> SEQUENCE: 744
gggattcata gcattcacct actccctgaa gtctagggac aggaagatgg ttggagacct    60

<210> SEQ ID NO 745
<211> LENGTH: 60
<212> TYPE: DNA
<213> ORGANISM: Homo sapiens

<400> SEQUENCE: 745
caaagatgca tttacctctg tatcaactca ggaaatctca taagctggta ccactcagga    60

<210> SEQ ID NO 746
<211> LENGTH: 60
<212> TYPE: DNA
<213> ORGANISM: Homo sapiens

<400> SEQUENCE: 746
aaattgcttg cagatatttt taaatgacag caattttcta atatttggtt taataaaatg    60

<210> SEQ ID NO 747
<211> LENGTH: 60
<212> TYPE: DNA
<213> ORGANISM: Homo sapiens

<400> SEQUENCE: 747
gaatccgagc cctttttccca tatcatctgt ttgttctgtt gtctaaaagc acactgcaag    60

<210> SEQ ID NO 748
<211> LENGTH: 60
<212> TYPE: DNA
<213> ORGANISM: Homo sapiens

<400> SEQUENCE: 748
atgagggcct cgtttattaa gatctttaaa ctgctttata cactgtcacg tggcttcatc    60

<210> SEQ ID NO 749
<211> LENGTH: 60
<212> TYPE: DNA
<213> ORGANISM: Homo sapiens

<400> SEQUENCE: 749
tctgaagcaa agaaaggatc aaaatttgat actgggagct ttgttggtgg tattgtatta    60

<210> SEQ ID NO 750
<211> LENGTH: 60
<212> TYPE: DNA
<213> ORGANISM: Homo sapiens

<400> SEQUENCE: 750
actcagtaag gaagtcgggt tggaccttaa catctgcatt ggacaactcc accccttcct    60

<210> SEQ ID NO 751
<211> LENGTH: 60
<212> TYPE: DNA
<213> ORGANISM: Homo sapiens

<400> SEQUENCE: 751
tcgccggcct cagtttacca cgtctgaggt cgggggggacc ccctccgagt cccgcgctgt    60

<210> SEQ ID NO 752
<211> LENGTH: 60
<212> TYPE: DNA
<213> ORGANISM: Homo sapiens

<400> SEQUENCE: 752
acagttgttt tgtcttcaag ccactgactt ctggaatttg cagattttgc aatccatgca    60

<210> SEQ ID NO 753
<211> LENGTH: 60
<212> TYPE: DNA
<213> ORGANISM: Homo sapiens

<400> SEQUENCE: 753
aaatcagcct ccatcagtat cactgcagtt atatatgatg tatgccttat tgctcaagac    60

<210> SEQ ID NO 754
<211> LENGTH: 60
<212> TYPE: DNA
<213> ORGANISM: Homo sapiens

<400> SEQUENCE: 754
aaacaaagtg actgtttggc ttataaacac attgaatgcg ctttattgcc catgggatat    60

<210> SEQ ID NO 755
<211> LENGTH: 60
<212> TYPE: DNA
<213> ORGANISM: Homo sapiens

<400> SEQUENCE: 755
atgagggcct cgtttattaa gatctttaaa ctgctttata cactgtcacg tggcttcatc    60

<210> SEQ ID NO 756
<211> LENGTH: 60
<212> TYPE: DNA
<213> ORGANISM: Homo sapiens

<400> SEQUENCE: 756
aaagtgggaa ataacttgca acgtctgtta gagatggttg ctacacatgt tgggtctgta    60

<210> SEQ ID NO 757
<211> LENGTH: 60
<212> TYPE: DNA
<213> ORGANISM: Homo sapiens

<400> SEQUENCE: 757
ccatgctgtg ctgtgttatt taattttttcc tggctaagat catgtctgaa ttatgtatga    60

<210> SEQ ID NO 758
<211> LENGTH: 60
<212> TYPE: DNA
<213> ORGANISM: Homo sapiens

<400> SEQUENCE: 758
ccaaaagagt taaaggcacg actgggattt cttctgagac tgtggtgaaa ctccttccaa    60

<210> SEQ ID NO 759
<211> LENGTH: 60
<212> TYPE: DNA
<213> ORGANISM: Homo sapiens

<400> SEQUENCE: 759
ccataaactg actgtgaccc tgtcatgtgg cagaccttcc atccgaacca cggcttggga    60

<210> SEQ ID NO 760
<211> LENGTH: 60
<212> TYPE: DNA
<213> ORGANISM: Homo sapiens

<400> SEQUENCE: 760
ccagttatct ctccaaaaca cgacccacac gaggacctcg cattaaagta ttttcggaaa    60

<210> SEQ ID NO 761
<211> LENGTH: 60
<212> TYPE: DNA
<213> ORGANISM: Homo sapiens

<400> SEQUENCE: 761
agtgatgtac ctcaatgaga gtgttcacat tgataaagag acggcgagtc gactgaagtc    60

<210> SEQ ID NO 762
<211> LENGTH: 60
<212> TYPE: DNA
<213> ORGANISM: Homo sapiens

<400> SEQUENCE: 762
tgccaatgta ctggcagatt aacatacaac ctatgttttg aacaaaaaca accagcgata    60

<210> SEQ ID NO 763
<211> LENGTH: 60
<212> TYPE: DNA
<213> ORGANISM: Homo sapiens

<400> SEQUENCE: 763
gatgtcaata gcattgtttt tgtcatgtag ctgttttaag aaatctggcc cagggtgttt    60

<210> SEQ ID NO 764
<211> LENGTH: 60
<212> TYPE: DNA
<213> ORGANISM: Homo sapiens

<400> SEQUENCE: 764
caccaaaaga tcaacagaca aatgctccag aaatctatgc tgactgtgac acaagagcct    60

```
<210> SEQ ID NO 765
<211> LENGTH: 60
<212> TYPE: DNA
<213> ORGANISM: Homo sapiens

<400> SEQUENCE: 765
ccagatggat acgaattcaa gttccccaac cgcctcaacc tggaggccat caactacatg       60

<210> SEQ ID NO 766
<211> LENGTH: 60
<212> TYPE: DNA
<213> ORGANISM: Homo sapiens

<400> SEQUENCE: 766
aagattttat tgtaaaacag agctgaagtc acaggaagta gggaactttg cacccaacat       60

<210> SEQ ID NO 767
<211> LENGTH: 60
<212> TYPE: DNA
<213> ORGANISM: Homo sapiens

<400> SEQUENCE: 767
ggggtatcct gggggaccca atgtaggagc tgccttggct cagacatgtt ttccgtgaaa       60

<210> SEQ ID NO 768
<211> LENGTH: 60
<212> TYPE: DNA
<213> ORGANISM: Homo sapiens

<400> SEQUENCE: 768
ctggtctgaa gggtcacggg gctgtcaaca ggtgttcctt actcataatt gattattcaa       60

<210> SEQ ID NO 769
<211> LENGTH: 60
<212> TYPE: DNA
<213> ORGANISM: Homo sapiens

<400> SEQUENCE: 769
tccaggatga gttacttgaa atttgccttg agtgtgttac ctccttttcca agctcctcgt      60

<210> SEQ ID NO 770
<211> LENGTH: 60
<212> TYPE: DNA
<213> ORGANISM: Homo sapiens

<400> SEQUENCE: 770
ccgaccatgt cctggtccct gttcaacacc cacttcatga atgctgcctg ggcttcatag       60

<210> SEQ ID NO 771
<211> LENGTH: 60
<212> TYPE: DNA
<213> ORGANISM: Homo sapiens

<400> SEQUENCE: 771
tgggtcttta gggtaggaca ggctgtggta tgagaggcag gagtctccac aaggcttcat       60

<210> SEQ ID NO 772
<211> LENGTH: 60
<212> TYPE: DNA
<213> ORGANISM: Homo sapiens

<400> SEQUENCE: 772
gaagccagaa acttttccaa aaaatcaaag gagagtgttt cgagctcctg atctgaaagg       60
```

```
<210> SEQ ID NO 773
<211> LENGTH: 60
<212> TYPE: DNA
<213> ORGANISM: Homo sapiens

<400> SEQUENCE: 773
ctgcttgctt ctctggctgc ctggtcagtg cagaggtgcc ccctgcagat gttcaataaa    60

<210> SEQ ID NO 774
<211> LENGTH: 60
<212> TYPE: DNA
<213> ORGANISM: Homo sapiens

<400> SEQUENCE: 774
tatatcgtag gtggctttaa tacgtgttat ttgctcatct gtatttctta ctctttgcac    60

<210> SEQ ID NO 775
<211> LENGTH: 60
<212> TYPE: DNA
<213> ORGANISM: Homo sapiens

<400> SEQUENCE: 775
gataagaact tagtgatgtg gagggactgg gaagagtcac ggcagatggt gggagctcta    60

<210> SEQ ID NO 776
<211> LENGTH: 60
<212> TYPE: DNA
<213> ORGANISM: Homo sapiens

<400> SEQUENCE: 776
ccatcttcag ggttgcacag aatcctccaa gatactttgc agccttttttt cccctggtc     60

<210> SEQ ID NO 777
<211> LENGTH: 60
<212> TYPE: DNA
<213> ORGANISM: Homo sapiens

<400> SEQUENCE: 777
gtgtatgcgg atatccgaaa gaattaagag aatacctaga acatatcctc agcaagaaac    60

<210> SEQ ID NO 778
<211> LENGTH: 60
<212> TYPE: DNA
<213> ORGANISM: Homo sapiens

<400> SEQUENCE: 778
tccgttttta cagcattctc gacctgtgat tcttggtggg ggaaactagt tatgtggata    60

<210> SEQ ID NO 779
<211> LENGTH: 60
<212> TYPE: DNA
<213> ORGANISM: Homo sapiens

<400> SEQUENCE: 779
aaatcaaacc agaaggcggg atggaatgga tgcaccgcaa ataatgcatt ttctgagttt    60

<210> SEQ ID NO 780
<211> LENGTH: 60
<212> TYPE: DNA
<213> ORGANISM: Homo sapiens

<400> SEQUENCE: 780
ttagttgctg ttggttggtt gaactgaaca tatcttgtct tagcacccag gaaacagaac    60
```

<210> SEQ ID NO 781
<211> LENGTH: 60
<212> TYPE: DNA
<213> ORGANISM: Homo sapiens

<400> SEQUENCE: 781
ctggatgctt acttgaagac gaggactttt ctggtgggcg aacgagtgac attggctgac    60

<210> SEQ ID NO 782
<211> LENGTH: 60
<212> TYPE: DNA
<213> ORGANISM: Homo sapiens

<400> SEQUENCE: 782
catgtttgtg gtcaaggcct atctgcccgt caacgagtcc tttggcttca ccgctgacct    60

<210> SEQ ID NO 783
<211> LENGTH: 60
<212> TYPE: DNA
<213> ORGANISM: Homo sapiens

<400> SEQUENCE: 783
tcctgtttgc caggcgcttt ctatacttaa tcccatgtca tgcgacccta ggactttttt    60

<210> SEQ ID NO 784
<211> LENGTH: 60
<212> TYPE: DNA
<213> ORGANISM: Homo sapiens

<400> SEQUENCE: 784
catgagtatt gatgagagca ttcacctcca gcggtgggat aaatacagca acaagatgct    60

<210> SEQ ID NO 785
<211> LENGTH: 60
<212> TYPE: DNA
<213> ORGANISM: Homo sapiens

<400> SEQUENCE: 785
tcgtggaggt ggtttgtgta tcttactggt ctgaagggac caagtgtgtt tgttgtttgt    60

<210> SEQ ID NO 786
<211> LENGTH: 60
<212> TYPE: DNA
<213> ORGANISM: Homo sapiens

<400> SEQUENCE: 786
gaatttcagt cagcctcaga ggttgacttc tacattgata aggacatgat ccacatcgcg    60

<210> SEQ ID NO 787
<211> LENGTH: 60
<212> TYPE: DNA
<213> ORGANISM: Homo sapiens

<400> SEQUENCE: 787
aactcagcag cagcactcca gaatctccat gcctgcacct gcccaaggat ttattcatag    60

<210> SEQ ID NO 788
<211> LENGTH: 60
<212> TYPE: DNA
<213> ORGANISM: Homo sapiens

<400> SEQUENCE: 788
aggttgactt ctacattgat aaggacatga tccacatcgc ggacaccaag gtctccaggc    60

```
<210> SEQ ID NO 789
<211> LENGTH: 60
<212> TYPE: DNA
<213> ORGANISM: Homo sapiens

<400> SEQUENCE: 789
ctcatcactg gatgaagatt ctcctgtgct agatgtgcaa atgcaagcta gtggcttcaa      60

<210> SEQ ID NO 790
<211> LENGTH: 60
<212> TYPE: DNA
<213> ORGANISM: Homo sapiens

<400> SEQUENCE: 790
gctgctgatt gtgaatctca gagtcttaag agagaagcca aatatattcc tcttgtaaat      60

<210> SEQ ID NO 791
<211> LENGTH: 60
<212> TYPE: DNA
<213> ORGANISM: Homo sapiens

<400> SEQUENCE: 791
acactttgca tgctgggtca gggaagattg tggagagagg acagtgcacc tggtttcccc      60

<210> SEQ ID NO 792
<211> LENGTH: 60
<212> TYPE: DNA
<213> ORGANISM: Homo sapiens

<400> SEQUENCE: 792
aaggaagtaa ggtacacctc cttggtcaag tacgactccg agaggcactt catcgacgac      60

<210> SEQ ID NO 793
<211> LENGTH: 60
<212> TYPE: DNA
<213> ORGANISM: Homo sapiens

<400> SEQUENCE: 793
gatggttcgt gttcatactg cagcttaaaa caagcaaaat acacagatga taatatgcta      60

<210> SEQ ID NO 794
<211> LENGTH: 60
<212> TYPE: DNA
<213> ORGANISM: Homo sapiens

<400> SEQUENCE: 794
actatgtgcc agcatttccg tatgtgcaga agttcatcaa tagatataga ctcaaagagc      60

<210> SEQ ID NO 795
<211> LENGTH: 60
<212> TYPE: DNA
<213> ORGANISM: Homo sapiens

<400> SEQUENCE: 795
tggatgaatg tgagcagagt acctttgtgt tggataaatt tcagtgcagg tactctaagg      60

<210> SEQ ID NO 796
<211> LENGTH: 60
<212> TYPE: DNA
<213> ORGANISM: Homo sapiens

<400> SEQUENCE: 796
gctaaggagg aaatacccag acaaaatctt tgggacgaat gaaaatttgt aactcttctg      60
```

```
<210> SEQ ID NO 797
<211> LENGTH: 60
<212> TYPE: DNA
<213> ORGANISM: Homo sapiens

<400> SEQUENCE: 797
tgtggatcat gtccttatca atgtagaagt caacctctga ggctgactga aattcaccat    60

<210> SEQ ID NO 798
<211> LENGTH: 60
<212> TYPE: DNA
<213> ORGANISM: Homo sapiens

<400> SEQUENCE: 798
tagctgtttc tctctttaat ctcacgtagc cttttcagg ttagtacgtg ttcttctgtc    60

<210> SEQ ID NO 799
<211> LENGTH: 60
<212> TYPE: DNA
<213> ORGANISM: Homo sapiens

<400> SEQUENCE: 799
acttaatttg agcgagtacc ttttcatttg acactttcc tgtttctaac cttaggaaac    60

<210> SEQ ID NO 800
<211> LENGTH: 60
<212> TYPE: DNA
<213> ORGANISM: Homo sapiens

<400> SEQUENCE: 800
ccaggctgtg cagtgggtga actttgctga tgatagccag taccagggtg ttcccacctt    60

<210> SEQ ID NO 801
<211> LENGTH: 60
<212> TYPE: DNA
<213> ORGANISM: Homo sapiens

<400> SEQUENCE: 801
actggctttt ctttcatctc tggagagagc ttgattcgtc atcttattgc tttgtctgaa    60

<210> SEQ ID NO 802
<211> LENGTH: 60
<212> TYPE: DNA
<213> ORGANISM: Homo sapiens

<400> SEQUENCE: 802
ggcaatggcg ttgctctcaa acacacagaa tccatcatca ccctcaaatg ctgggacctt    60
```